(12) United States Patent
Lee et al.

(10) Patent No.: US 11,355,711 B2
(45) Date of Patent: Jun. 7, 2022

(54) ORGANIC LIGHT-EMITTING DEVICE

(71) Applicant: Samsung Display Co., Ltd., Yongin-si (KR)

(72) Inventors: Jaeyong Lee, Yongin-si (KR); Gina Yoo, Yongin-si (KR); Sunjin Joo, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 748 days.

(21) Appl. No.: 16/234,306

(22) Filed: Dec. 27, 2018

(65) Prior Publication Data

US 2019/0207118 A1 Jul. 4, 2019

(30) Foreign Application Priority Data

Jan. 2, 2018 (KR) .................. 10-2018-0000335

(51) Int. Cl.
| | | |
|---|---|---|
| *C07D 213/16* | (2006.01) | |
| *C07D 239/26* | (2006.01) | |
| *C07D 251/24* | (2006.01) | |
| *C07D 401/14* | (2006.01) | |
| *H01L 51/00* | (2006.01) | |
| *H01L 51/50* | (2006.01) | |
| *H01L 51/52* | (2006.01) | |
| *H01L 27/32* | (2006.01) | |
| *H01L 51/56* | (2006.01) | |

(52) U.S. Cl.
CPC ........ *H01L 51/0067* (2013.01); *C07D 213/16* (2013.01); *C07D 239/26* (2013.01); *C07D 251/24* (2013.01); *C07D 401/14* (2013.01); *H01L 51/0072* (2013.01); *H01L 27/3248* (2013.01); *H01L 51/001* (2013.01); *H01L 51/5016* (2013.01); *H01L 51/5056* (2013.01); *H01L 51/5072* (2013.01); *H01L 51/5088* (2013.01); *H01L 51/5206* (2013.01); *H01L 51/5221* (2013.01); *H01L 51/56* (2013.01); *H01L 2251/308* (2013.01); *H01L 2251/5384* (2013.01); *H01L 2251/558* (2013.01)

(58) Field of Classification Search
CPC ............ H01L 51/0067; H01L 51/0072; H01L 51/5016

See application file for complete search history.

(56) References Cited

U.S. PATENT DOCUMENTS

| 8,803,137 B2 | 8/2014 | Lee et al. | |
|---|---|---|---|
| 2009/0053488 A1* | 2/2009 | Jinde .................. | C09K 11/06 428/213 |

(Continued)

FOREIGN PATENT DOCUMENTS

| JP | 2009-37981 A | 2/2009 |
|---|---|---|
| KR | 10-2013-0107391 A | 10/2013 |

(Continued)

*Primary Examiner* — Vu A Nguyen
(74) *Attorney, Agent, or Firm* — Lewis Roca Rothgerber Christie LLP

(57) ABSTRACT

An organic light-emitting device includes: a first electrode; a second electrode facing the first electrode; and an organic layer between the first electrode and the second electrode and including an emission layer. The emission layer includes at least one doping layer and at least one non-doping layer. The doping layer comprises a first host, a second host, and a dopant.

20 Claims, 1 Drawing Sheet

(56) References Cited

U.S. PATENT DOCUMENTS

| | | |
|---|---|---|
| 2014/0021449 A1 | 1/2014 | Xia et al. |
| 2014/0361272 A1 | 12/2014 | Joo et al. |
| 2016/0126472 A1* | 5/2016 | Oh .................. C07D 405/04 257/40 |
| 2016/0133844 A1* | 5/2016 | Kim .................. H01L 51/0054 257/40 |
| 2017/0110669 A1 | 4/2017 | Im |

FOREIGN PATENT DOCUMENTS

| | | |
|---|---|---|
| KR | 10-2013-0134728 A | 12/2013 |
| KR | 10-2014-0143545 A | 12/2014 |
| KR | 10-2015-0028579 A | 3/2015 |
| KR | 10-2017-0046251 A | 5/2017 |
| KR | 10-2017-0076148 A | 7/2017 |

* cited by examiner

| 190 |
|-----|
| 150 |
| 110 |

| 190 |  |
|-----|--|
| 170 |  |
| 151-ND2 | ⎫ |
| 151-D | ⎬ 151 |
| 151-ND1 | ⎭ |
| 120 |  |
| 110 |  |

| 190 |  |
|-----|--|
| 170 |  |
| 151-ND2 | ⎫ |
| 151-D2 |  |
| 151-ND3 | ⎬ 151 |
| 151-D1 |  |
| 151-ND1 | ⎭ |
| 120 |  |
| 110 |  |

ORGANIC LIGHT-EMITTING DEVICE

CROSS-REFERENCE TO RELATED APPLICATION

This application claims priority to and the benefit of Korean Patent Application No. 10-2018-0000335, filed on Jan. 2, 2018, in the Korean Intellectual Property Office, the entire content of which is incorporated herein by reference.

BACKGROUND

1. Field

One or more embodiments relate to an organic light-emitting device.

2. Description of the Related Art

Organic light-emitting devices are self-emission devices that produce full-color images, and also have wide viewing angles, high contrast ratios, short response times, and excellent characteristics in terms of brightness, driving voltage, and response speed, as compared to other devices in the art.

An example of such organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit (e.g., transition or relax) from an excited state to a ground state, thereby generating light.

SUMMARY

One or more embodiments include an organic light-emitting device having low driving voltage and high efficiency.

Additional aspects of embodiments will be set forth in part in the description which follows and, in part, will be apparent from the description, or may be learned by practice of the presented embodiments.

According to one or more embodiments, an organic light-emitting device includes: a first electrode; a second electrode facing the first electrode; and an organic layer between the first electrode and the second electrode and including an emission layer.

The emission layer may include at least one doping layer and at least one non-doping layer.

The doping layer may include a first host, a second host, and a dopant, and the non-doping layer may include a third host and a fourth host, and does not include a dopant (e.g., is free or substantially free of a dopant).

The first host and the third host may each independently be represented by Formula 1, and the second host and the fourth host may each independently be represented by one selected from Formulae 2-1 to 2-3:

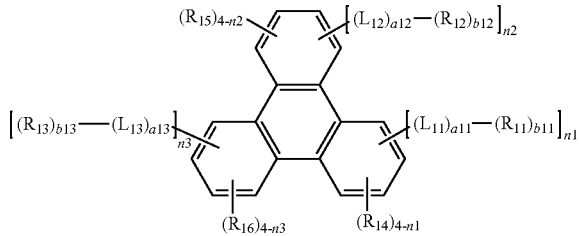

Formula 1

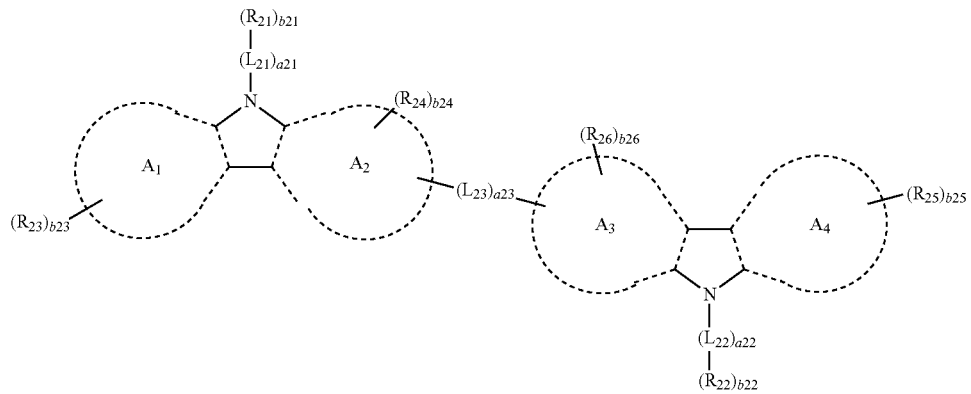

Formula 2-1

-continued

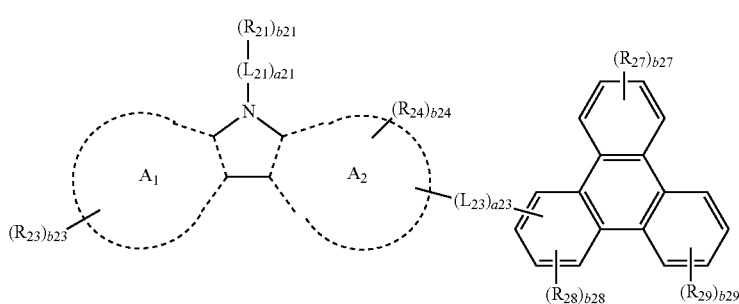

Formula 2-2

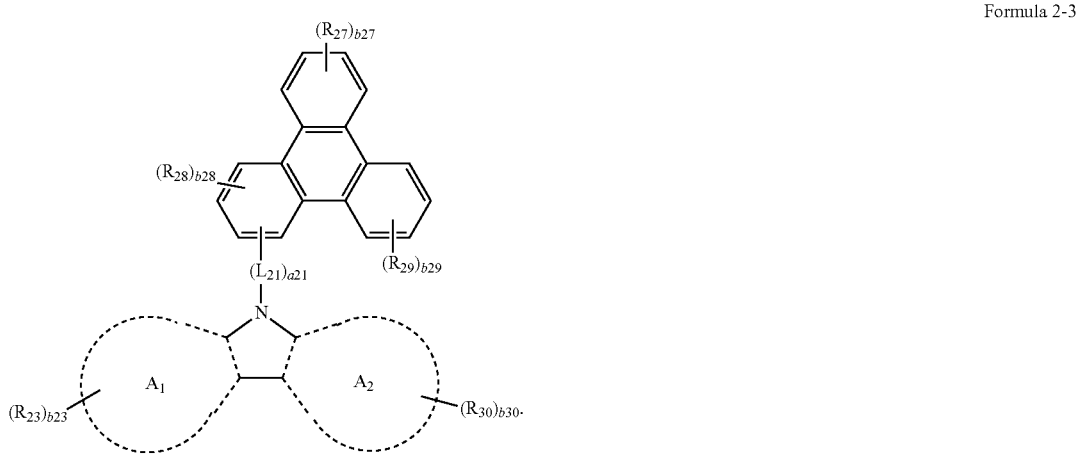

Formula 2-3

In Formulae 1 and 2-1 to 2-3, n1 to n3 may each independently be 0, 1, or 2, the sum of n1, n2, and n3 may be 1, 2, 3, 4, 5, or 6, $L_{11}$ to $L_{13}$ and $L_{21}$ to $L_{23}$ may each independently be selected from a single bond, a substituted or unsubstituted $C_5$-$C_{60}$ carbocyclic group, and a substituted or unsubstituted $C_1$-$C_{60}$ heterocyclic group, a11 to a13 and a21 to a23 may each independently be 1, 2, 3, 4, or 5, $A_1$ to $A_4$ may each independently be selected from a $C_5$-$C_{60}$ carbocyclic group and a $C_1$-$C_{60}$ heterocyclic group, $R_{11}$ to $R_{16}$ and $R_{21}$ to $R_{30}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —C(=O)($Q_1$), —N($Q_1$)($Q_2$), —P(=O)($Q_1$)($Q_2$), and —S(=O)$_2$($Q_1$)($Q_2$), at least one selected from $R_{11}$ to $R_{13}$ may be $R_{ET}$, b11 to b13, b21 to b26, and b30 may each independently be 1, 2, 3, 4, or 5, b27 and b29 may each independently be 1, 2, 3, or 4, b28 may be 1, 2, or 3, $R_{ET}$ may be selected from:

a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbolinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, and a pyrimidobenzothiophenyl group;

a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbolinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, and a pyrimidobenzothiophenyl group, each substituted with at least one selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a pyridinyl group, a pyrazinyl group, a pyrimidinyl group, a pyridazinyl group, a triazinyl group, —N($Q_{31}$)($Q_{32}$), —Si($Q_{31}$)($Q_{32}$)($Q_{33}$), and —B($Q_{31}$)($Q_{32}$); and a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbolinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, and a pyrimidobenzothiophenyl group, each substituted with at least one selected from, a phenyl group, a biphenyl group, a terphenyl group, and a naphthyl group that are each substituted with at least one selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a pyridinyl group, a pyrazinyl group, a pyrimidinyl group, a pyridazinyl group, a triazinyl group, —N($Q_{41}$)($Q_{42}$), —Si($Q_{41}$)($Q_{42}$)($Q_{43}$), and —B($Q_{41}$)($Q_{42}$), at least one substituent selected from the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, $Q_{31}$ to $Q_{33}$, and $Q_{41}$ to $Q_{43}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

According to one or more embodiments, an electronic apparatus includes the organic light-emitting device and a thin film transistor, wherein the first electrode of the organic light-emitting device is electrically coupled to (e.g., electrically connected to) one of a source electrode and a drain electrode of the thin film transistor.

BRIEF DESCRIPTION OF THE DRAWINGS

These and/or other aspects of embodiments will become apparent and more readily appreciated from the following description of the embodiments, taken in conjunction with the accompanying drawings in which:

FIGS. 1-3 are each a schematic view of an organic light-emitting device according to an embodiment.

DETAILED DESCRIPTION

The present disclosure will now be described more fully with reference to exemplary embodiments. The disclosure may, however, be embodied in many different forms and should not be construed as being limited to the embodiments set forth herein; rather, these embodiments are provided so that this disclosure will be thorough and complete, and will fully convey the concept of the disclosure to those skilled in the art. Features of embodiments of the present disclosure, and how to achieve them, will become apparent by reference to the embodiment that will be described herein below in more detail, together with the accompanying drawings. The subject matter of the present disclosure may, however, be embodied in many different forms and should not be limited to the exemplary embodiments.

Hereinafter, embodiments are described in more detail by referring to the attached drawings, and in the drawings, like reference numerals denote like elements, and a redundant explanation thereof will not be provided herein.

As used herein, the singular forms "a," "an" and "the" are intended to include the plural forms as well, unless the context clearly indicates otherwise.

It will be further understood that the terms "comprises" and/or "comprising," as used herein, specify the presence of stated features or components, but do not preclude the presence or addition of one or more other features or components.

It will be understood that when a layer, region, or component is referred to as being "on" or "onto" another layer, region, or component, it may be directly or indirectly formed on the other layer, region, or component. For example, intervening layers, regions, or components may be present.

Sizes of components in the drawings may be exaggerated for convenience of explanation. In other words, since sizes and thicknesses of components in the drawings may be arbitrarily illustrated for convenience of explanation, the following embodiments of the present disclosure are not limited thereto.

An organic light-emitting device according to an embodiment includes: a first electrode; a second electrode facing the first electrode; and an organic layer between the first electrode and the second electrode and including an emission layer, wherein the emission layer includes at least one doping layer and at least one non-doping layer, wherein the doping layer includes a first host, a second host, and a dopant, and the non-doping layer includes a third host and a fourth host, and does not include a dopant (e.g., is free or substantially free of a dopant). As used herein, the statement "substantially free of a dopant" means that a dopant is present, if at all, in an amount that does not materially affect the emission characteristics of the respective emission layer (e.g., the dopant may be present as an incidental impurity).

The first host and the third host may each independently be represented by Formula 1, and the second host and the fourth host may each independently be represented by one selected from Formulae 2-1 to 2-3:

Formula 1

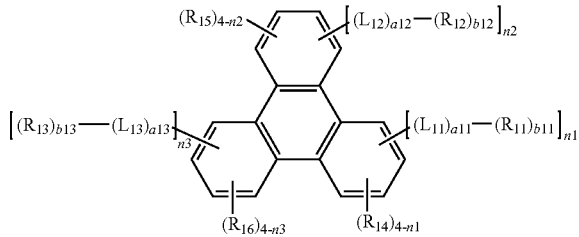

Formula 2-1

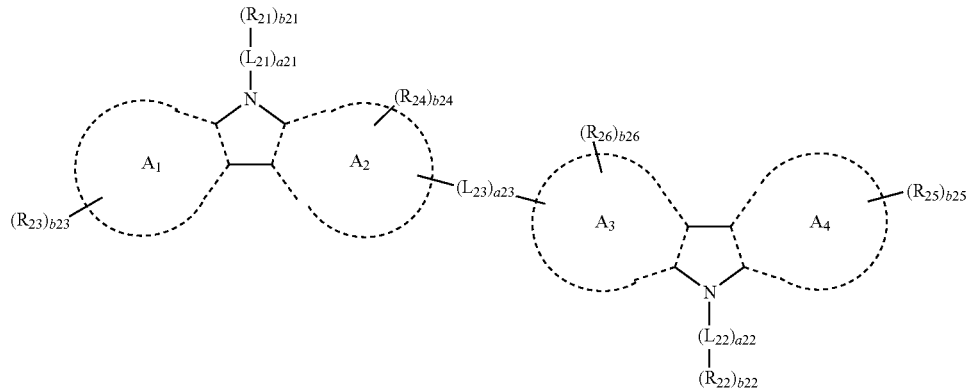

-continued

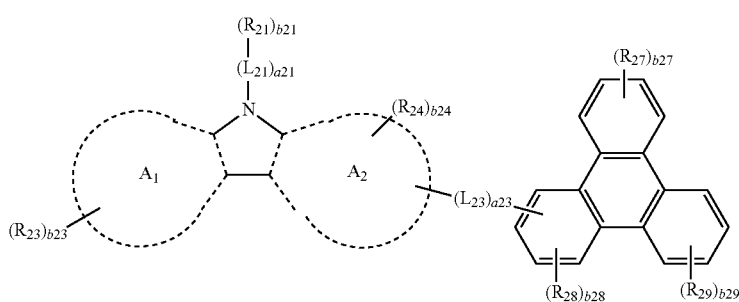

Formula 2-2

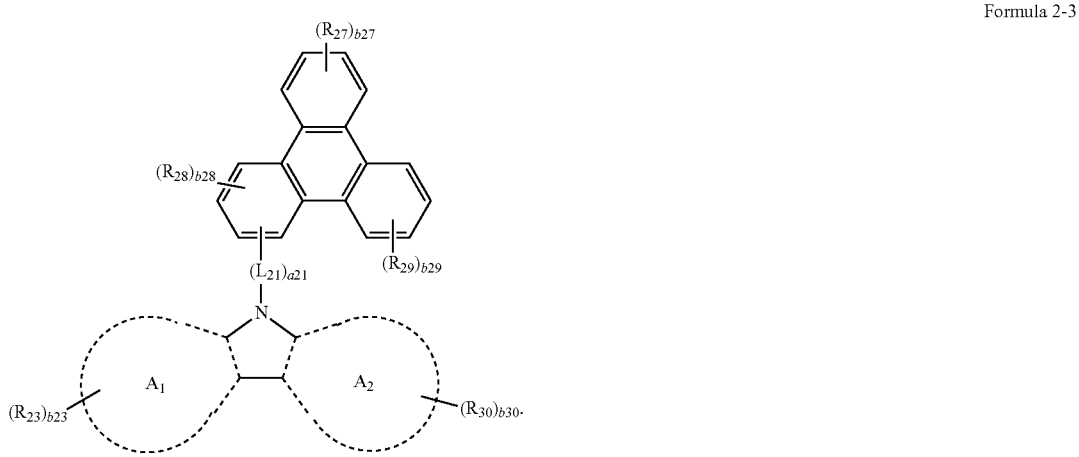

Formula 2-3

In Formula 1, n1 to n3 may each independently be 0, 1, or 2, and the sum of n1, n2, and n3 may be 1, 2, 3, 4, 5, or 6.

In one embodiment, n1 to n3 may each independently be 0 or 1, and the sum of n1, n2, and n3 may be 1, 2, or 3.

In one or more embodiments, n1 to n3 may each independently be 0 or 1, and the sum of n1, n2, and n3 may be 1 or 2.

In one or more embodiments, n1 to n3 may each independently be 0 or 1, and the sum of n1, n2, and n3 may be 1.

In Formulae 1 and 2-1 to 2-3, $L_{11}$ to $L_{13}$ and $L_{21}$ to $L_{23}$ may each independently be selected from a single bond, a substituted or unsubstituted $C_5$-$C_{60}$ carbocyclic group, and a substituted or unsubstituted $C_1$-$C_{60}$ heterocyclic group.

In one embodiment, $L_{11}$ to $L_{13}$ and $L_{21}$ to $L_{23}$ may each independently be selected from:

a single bond, a benzene group, a pentalene group, an indene group, a naphthalene group, an azulene group, a heptalene group, an indacene group, an acenaphthalene group, a fluorene group, a spiro-bifluorene group, a benzofluorene group, a phenalene group, a phenanthrene group, an anthracene group, a fluoranthene group, a triphenylene group, a pyrene group, a chrysene group, a naphthacene group, a picene group, a perylene group, a pentaphenylene group, a hexacene group, a pyrrole group, an imidazole group, a pyrazole group, a pyridine group, a pyrazine group, a pyrimidine group, a pyridazine group, an isoindole group, an indole group, an indazole group, a purine group, a quinoline group, an isoquinoline group, a benzoquinoline group, a phthalazine group, a naphthyridine group, a quinoxaline group, a quinazoline group, a cinnoline group, a carbazole group, a phenanthridine group, an acridine group, a phenanthroline group, a phenazine group, a benzoxazole group, a benzimidazole group, a furan group, a benzofuran group, a thiophene group, a benzothiophene group, a thiazole group, an isothiazole group, a benzothiazole group, an isooxazole group, an oxazole group, a triazole group, a tetrazole group, an oxadiazole group, a triazine group, a benzoxazole group, a dibenzofuran group, a dibenzothiophene group, a benzocarbazole group, and a dibenzocarbazole group; and a benzene group, a pentalene group, an indene group, a naphthalene group, an azulene group, a heptalene group, an indacene group, an acenaphthalene group, a fluorene group, a spiro-fluorene group, a benzofluorene group, a phenalene group, a phenanthrene group, an anthracene group, a fluoranthene group, a triphenylene group, a pyrene group, a chrysene group, a naphthacene group, a picene group, a perylene group, a pentaphenylene group, a hexacene group, a pyrrole group, an imidazole group, a pyrazole group, a pyridine group, a pyrazine group, a pyrimidine group, a pyridazine group, an isoindole group, an indole group, an indazole group, a purine group, a quinoline group, an isoquinoline group, a benzoquinoline group, a phthalazine group, a naphthyridine group, a quinoxaline group, a quinazoline group, a cinnoline group, a carbazole group, a phenanthridine group, an acridine group, a phenanthroline group, a phenazine group, a benzoxazole group, a benzimidazole group, a furan group, a benzofuran group, a thiophene group, a benzothiophene group, a thiazole group, an isothiazole group, a benzothiazole group, an isooxazole group, an oxazole group, a triazole group, a tetrazole group, an oxadiazole group, a triazine group, a benzoxazole group, a dibenzofuran group, a dibenzothiophene group, a benzocarbazole group and a dibenzocarbazole group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a $C_6$-$C_{20}$ aryl group, a $C_1$-$C_{20}$ heteroaryl group, —N($Q_{31}$)($Q_{32}$), —Si($Q_{31}$)($Q_{32}$)($Q_{33}$), and —B($Q_{31}$)($Q_{32}$), and $Q_{31}$ to $Q_{33}$ may each independently be selected from a $C_1$-$C_{20}$ alkyl group, a $C_1$-$C_{20}$ alkoxy group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group.

in one embodiment, $L_{11}$ to $L_{13}$ and $L_{21}$ to $L_{23}$ may each independently be selected from:

a single bond, a benzene group, a pentalene group, an indene group, a naphthalene group, an azulene group, a heptalene group, an indacene group, an acenaphthalene group, a fluorene group, a spiro-bifluorene group, a benzofluorene group, a phenalene group, a phenanthrene group, an anthracene group, a fluoranthene group, a triphenylene group, a pyrene group, a chrysene group, a naphthacene group, a picene group, a perylene group, a pentaphenylene group, a hexacene group, a pyrrole group, an imidazole group, a pyrazole group, a pyridine group, a pyrazine group, a pyrimidine group, a pyridazine group, an isoindole group, an indole group, an indazole group, a purine group, a quinoline group, an isoquinoline group, a benzoquinoline group, a phthalazine group, a naphthyridine group, a quinoxaline group, a quinazoline group, a cinnoline group, a carbazole group, a phenanthridine group, an acridine group, a phenanthroline group, a phenazine group, a benzoxazole group, a benzimidazole group, a furan group, a benzofuran group, a thiophene group, a benzothiophene group, a thiazole group, an isothiazole group, a benzothiazole group, an isooxazole group, an oxazole group, a triazole group, a tetrazole group, an oxadiazole group, a triazine group, a benzoxazole group, a dibenzofuran group, a dibenzothiophene group, a benzocarbazole group, and a dibenzocarbazole group; and a benzene group, a pentalene group, an indene group, a naphthalene group, an azulene group, a heptalene group, an indacene group, an acenaphthalene group, a fluorene group, a spiro-fluorene group, a benzofluorene group, a phenalene group, a phenanthrene group, an anthracene group, a fluoranthene group, a triphenylene group, a pyrene group, a chrysene group, a naphthacene group, a picene group, a perylene group, a pentaphenylene group, a hexacene group, a pyrrole group, an imidazole group, a pyrazole group, a pyridine group, a pyrazine group, a pyrimidine group, a pyridazine group, an isoindole group, an indole group, an indazole group, a purine group, a quinoline group, an isoquinoline group, a benzoquinoline group, a phthalazine group, a naphthyridine group, a quinoxaline group, a quinazoline group, a cinnoline group, a carbazole group, a phenanthridine group, an acridine group, a phenanthroline group, a phenazine group, a benzoxazole group, a benzimidazole group, a furan group, a benzofuran group, a thiophene group, a benzothiophene group, a thiazole group, an isothiazole group, a benzothiazole group, an isooxazole group, an oxazole group, a triazole group, a tetrazole group, an oxadiazole group, a triazine group, a benzoxazole group, a dibenzofuran group, a dibenzothiophene group, a benzocarbazole group and a dibenzocarbazole group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a $C_6$-$C_{20}$ aryl group, a phenyl group, a biphenyl group, a terphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an oxazolyl group, a pyridinyl group, a pyrazinyl group, a pyrimidinyl group, a pyridazinyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a carbazolyl group, a cinnolinyl group, a phenanthridinyl group, an acridinyl group, a phenanthrolinyl group, a phenazinyl group, a benzimidazolyl group, a benzofuranyl group, a benzothiophenyl group, a triazolyl group, a tetrazolyl group, a triazinyl group, a dibenzofuranyl group, a dibenzothiophenyl group, —N($Q_{31}$)($Q_{32}$), —Si($Q_{31}$)($Q_{32}$)($Q_{33}$), and —B($Q_{31}$)($Q_{32}$), and $Q_{31}$ to $Q_{33}$ may each independently be selected from a $C_1$-$C_{20}$ alkyl group, a $C_1$-$C_{20}$ alkoxy group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group.

For example, $L_{11}$ to $L_{13}$ and $L_{21}$ to $L_{23}$ may each independently be selected from:

a single bond, a benzene group, a pyridine group, a pyrimidine group, and a triazine group; and a benzene group, a pyridine group, a pyrimidine group, and a triazine group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a $C_6$-$C_{20}$ aryl group, a $C_1$-$C_{20}$ heteroaryl group, —N($Q_{31}$)($Q_{32}$), —Si($Q_{31}$)($Q_{32}$)($Q_{33}$), and —B($Q_{31}$)($Q_{32}$), $Q_{31}$ to $Q_{33}$ may each independently be selected from a $C_1$-$C_{20}$ alkyl group, a $C_1$-$C_{20}$ alkoxy group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group.

In one or more embodiments, $L_{11}$ to $L_{13}$ and $L_{21}$ to $L_{23}$ may each independently be selected from a single bond and groups represented by Formulae 3-1 to 3-53:
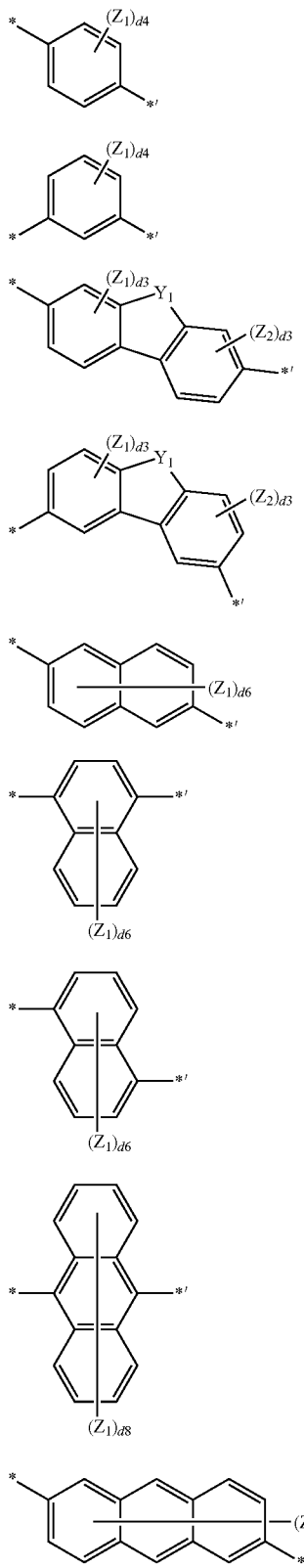
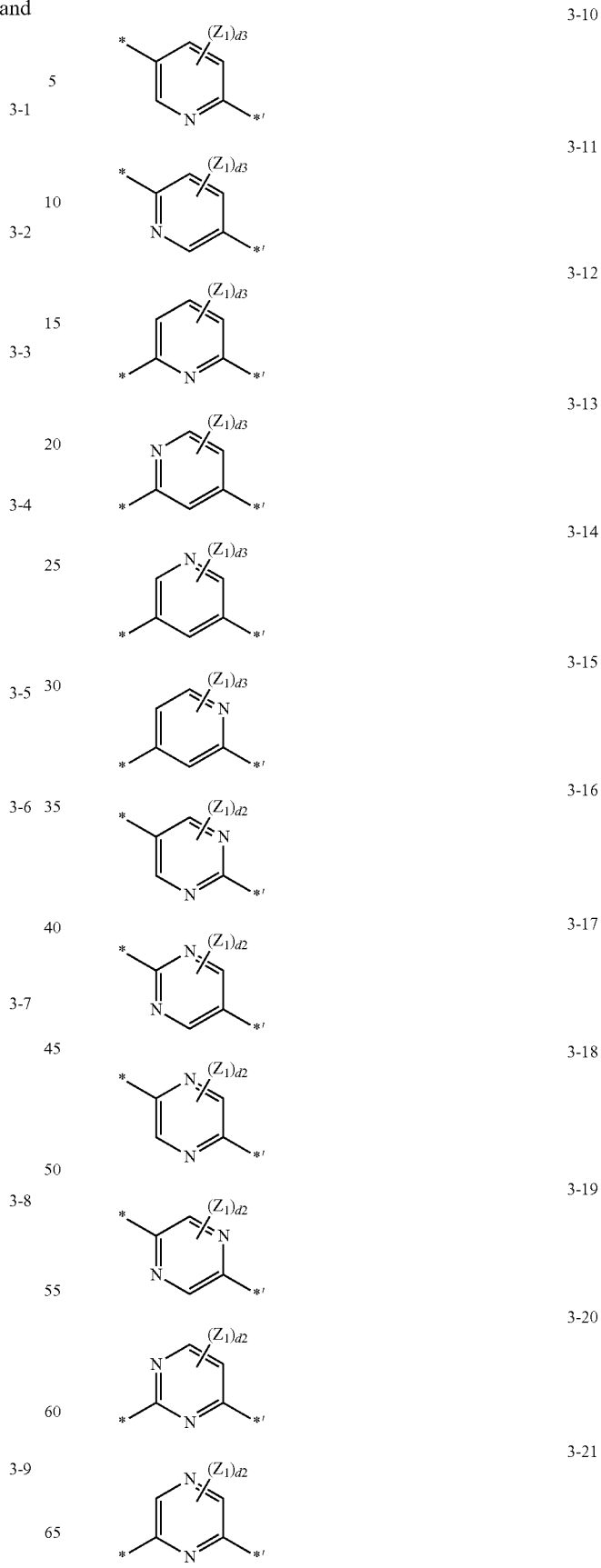

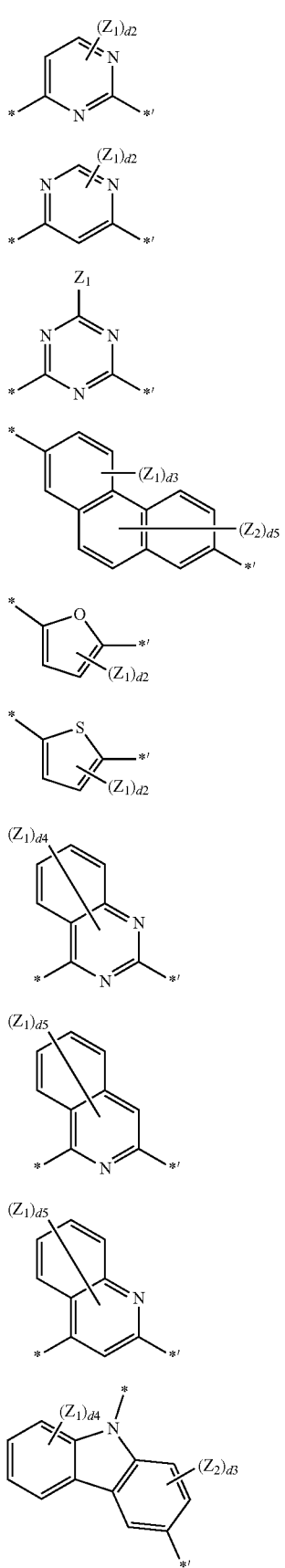
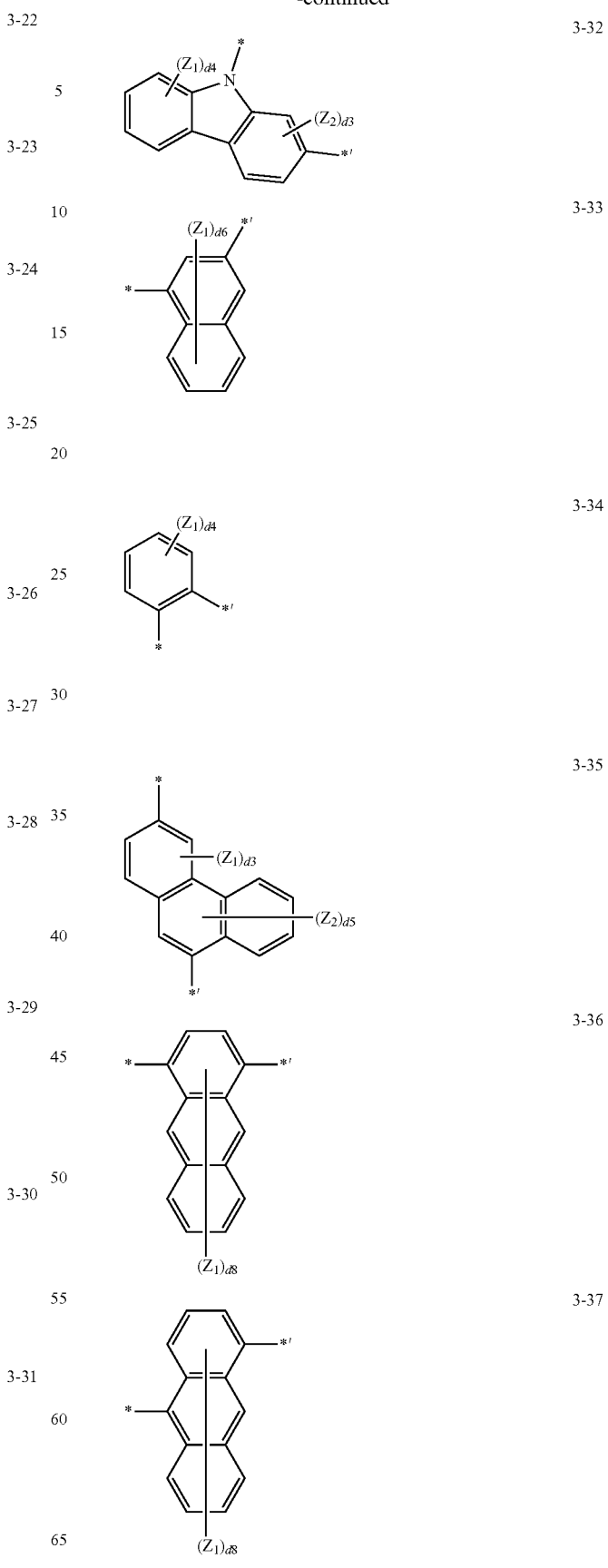

-continued
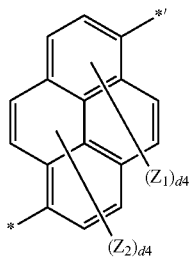
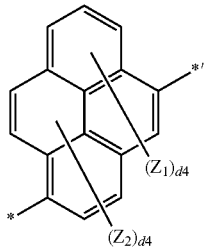
3-39
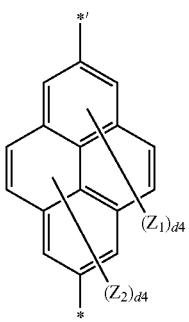
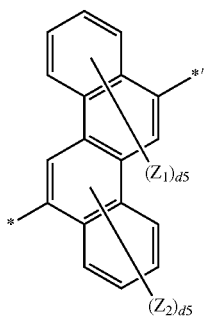
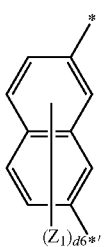
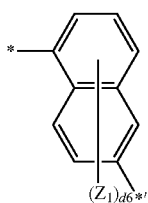
-continued
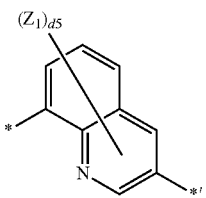
3-38
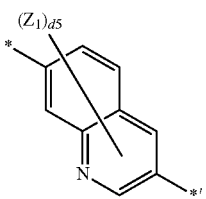
3-39
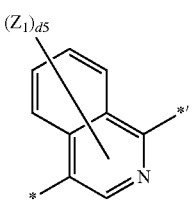
3-40
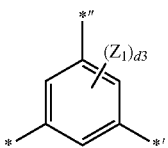
3-41
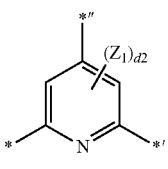
3-42
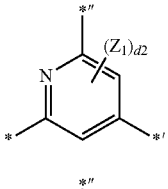
3-43
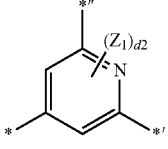
3-44
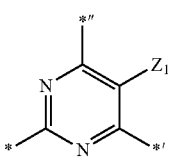
3-45
3-46
3-47
3-48
3-49
3-50
3-51
3-52

-continued 3-53
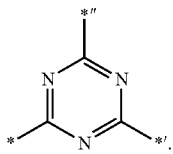

In Formulae 3-1 to 3-53, $Y_1$ may be O, S, $C(Z_3)(Z_4)$, $N(Z_5)$, or $Si(Z_6)(Z_7)$, $Z_1$ to $Z_7$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, a dibenzothiophenyl group, —$N(Q_{31})(Q_{32})$, —$Si(Q_{31})(Q_{32})(Q_{33})$, and —$B(Q_{31})(Q_{32})$, d2 may be an integer of 0 to 2, and when d2 is two, two $Z_1(s)$ may be identical to or different from each other, d3 may be an integer of 0 to 3, and when d3 is two or more, two or more of $Z_1(s)$ may be identical to or different from each other and two or more of $Z_2(s)$ may be identical to or different from each other, d4 may be an integer of 0 to 4, when d4 is two or more, two or more of $Z_1(s)$ may be identical to or different from each other and two or more of $Z_2(s)$ may be identical to or different from each other, d5 may be an integer of 0 to 5, and when d5 is two or more, two or more of $Z_1(s)$ may be identical to or different from each other and two or more of $Z_2(s)$ may be identical to or different from each other, d6 may be an integer of 0 to 6, and when d6 is two or more, two or more of $Z_1(s)$ may be identical to or different from each other, d8 may be an integer of 0 to 8, and when d8 is two or more, two or more of $Z_1(s)$ may be identical to or different from each other, $Q_{31}$ to $Q_{33}$ may each independently be selected from a $C_1$-$C_{20}$ alkyl group, a $C_1$-$C_{20}$ alkoxy group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, and

*, *', and *'' each indicate a binding site to a neighboring atom.

For example, $L_{11}$ to $L_{13}$ and $L_{21}$ to $L_{23}$ may each independently be selected from groups represented by Formulae 3-1, 3-2, 3-10 to 3-24, 3-34, and 3-47 to 3-53, but embodiments of the present disclosure are not limited thereto.

In one embodiment, $L_{11}$ to $L_{13}$ may each independently be selected from groups represented by Formulae 3-1, 3-2, 3-34, and 3-47 to 3-53, and groups represented by Formulae 4-1 to 4-11:

4-1
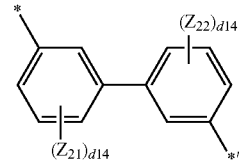

4-2
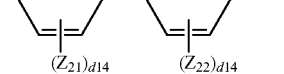

4-3
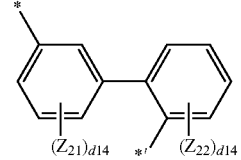

4-4
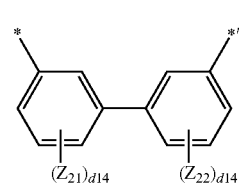

4-5
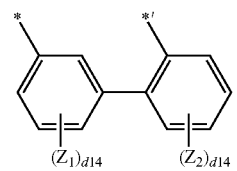

4-6
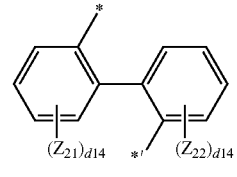

4-7
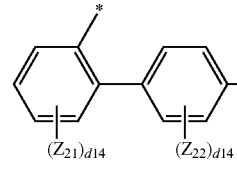

4-8
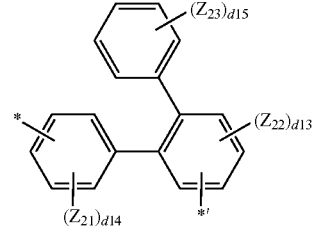

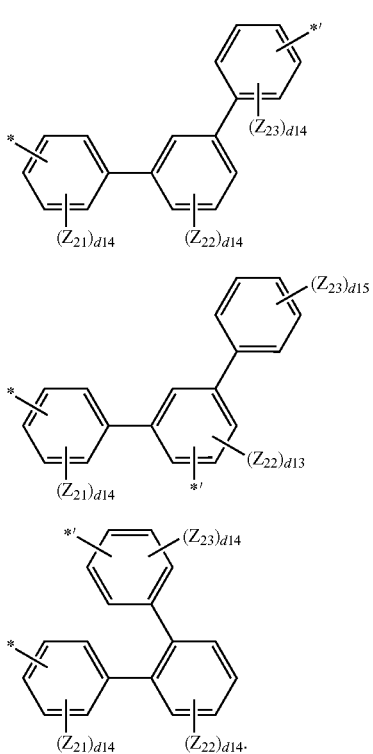

In Formulae 4-1 to 4-11, $Z_{21}$ to $Z_{23}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, a dibenzothiophenyl group, —$N(Q_{31})(Q_{32})$, —$Si(Q_{31})(Q_{32})(Q_{33})$, and —$B(Q_{31})(Q_{32})$, d13 may be an integer of 0 to 3, and when d13 is two or more, two or more of $Z_{22}(S)$ may be identical to or different from each other, d14 may be an integer of 0 to 4, and when d14 is two or more, two or more of $Z_{21}(s)$ may be identical to or different from each other, two or more of $Z_{22}(S)$ may be identical to or different from each other, and two or more of $Z_{23}(S)$ may be identical to or different from each other, d15 may be an integer of 0 to 5, and when d15 is two or more, two or more of $Z_{23}(S)$ may be identical to or different from each other, $Q_{31}$ to $Q_{33}$ may each independently be selected from a $C_1$-$C_{20}$ alkyl group, a $C_1$-$C_{20}$ alkoxy group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, and

* and *' each indicate a binding site to a neighboring atom.

In Formulae 1 and 2-1 to 2-3, a11 to a13, and a21 to a23 may each independently be 1, 2, 3, 4, or 5.

a11 indicates the number of $L_{11}$, and when a11 is two or more, two or more of $L_{11}(s)$ may be identical to or different from each other. a12, a13, and a21 to a23 may each independently be the same as described in connection with a11.

In one embodiment, in Formulae 1, a11 to a13 may each independently be 1, 2, 3, or 4.

In one embodiment, in Formulae 2-1 to 2-3, a21 to a23 may each independently be 1 or 2. For example, in Formula 2-1, a21 to a23 may each independently be 1.

in one embodiment, in Formula 2-1, a21 to a23 may each independently be 1, $L_{21}$ and $L_{22}$ may each independently be selected from a single bond, a substituted or unsubstituted $C_5$-$C_{60}$ carbocyclic group, and a substituted or unsubstituted $C_1$-$C_{60}$ heterocyclic group, and $L_{23}$ may be a single bond.

In Formulae 2-1 to 2-3, $A_1$ to $A_4$ may each independently be selected from a $C_5$-$C_{60}$ carbocyclic group and a $C_1$-$C_{60}$ heterocyclic group.

in one embodiment, $A_1$ to $A_4$ may each independently be selected from a benzene group, an indene group, a naphthalene group, an anthracene group, a fluorene group, a phenanthrene group, a triphenylene group, a pyrene group, a chrysene group, a naphthacene group, a pyrrole group, an imidazole group, a pyrazole group, a pyridine group, a pyrimidine group, a pyrazine group, a pyridazine group, an indole group, an isoindole group, an indazole group, a quinoline group, an isoquinoline group, a benzoquinoline group, a naphthyridine group, a quinoxaline group, a quinazoline group, a cinnoline group, a carbazole group, a phenanthridine group, an acridine group, a phenanthroline group, a phenazine group, a benzimidazole group, a furan group, a benzofuran group, a thiophene group, a benzothiophene group, a thiazole group, an isothiazole group, a benzothiazole group, an isooxazole group, an oxazole group, a triazole group, an oxadiazole group, a triazine group, a benzoxazole group, a dibenzofuran group, a dibenzothiophene group, a benzocarbazole group and a dibenzocarbazole group.

in one embodiment, $A_1$ to $A_4$ may each independently be selected from a benzene group, an indene group, a naphthalene group, an anthracene group, a fluorene group, a phenanthrene group, a pyridine group, a pyrimidine group, a pyrazine group, a pyridazine group, and a carbazole group.

in one embodiment, $A_1$ to $A_4$ may each independently be selected from a benzene group, a naphthalene group, a pyridine group, a pyrimidine group, a pyrazine group, and a pyridazine group.

For example, $A_1$ to $A_4$ may each independently be a benzene group, but embodiments of the present disclosure are not limited thereto.

In Formulae 1 and 2-1 to 2-3, $R_{11}$ to $R_{16}$ and $R_{21}$ to $R_{30}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —C(=O)($Q_1$), —N($Q_1$)($Q_2$), —P(=O)($Q_1$)($Q_2$), and —S(=O)$_2$($Q_1$)($Q_2$).

wherein, at least one selected from $R_{11}$ to $R_{13}$ may be $R_{ET}$, wherein $R_{ET}$ refers to an electron transport substituent.

$R_{ET}$ may be selected from:

a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbolinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, and a pyrimidobenzothiophenyl group;

a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbolinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, and a pyrimidobenzothiophenyl group, each substituted with at least one selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a pyridinyl group, a pyrazinyl group, a pyrimidinyl group, a pyridazinyl group, a triazinyl group, —N($Q_{31}$)($Q_{32}$), —Si($Q_{31}$)($Q_{32}$)($Q_{33}$), and —B($Q_{31}$)($Q_{32}$); and a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbolinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, and a pyrimidobenzothiophenyl group, each substituted with at least one selected from a phenyl group, a biphenyl group, a terphenyl group, and a naphthyl group that are each substituted with at least one selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a pyridinyl group, a pyrazinyl group, a pyrimidinyl group, a pyridazinyl group, a triazinyl group, —N($Q_{41}$)($Q_{42}$), —Si($Q_{41}$)($Q_{42}$)($Q_{43}$), and —B($Q_{41}$)($Q_{42}$), and $Q_{31}$ to $Q_{33}$ and $Q_{41}$ to $Q_{43}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

For example, $R_{ET}$ may be selected from:

a pyridinyl group, a pyrazinyl group, a pyrimidinyl group, a pyridazinyl group, a quinolinyl group, an isoquinolinyl group, a benzoquinolinyl group, a naphthyridinyl group, a quinoxalinyl group, a quinazolinyl group, a phenanthridinyl group, a phenanthrolinyl group, a benzophenanthrolinyl group, a benzimidazolyl group, a naphthoimidazolyl group, a triazinyl group, a carbolinyl group, and an imidazopyridinyl group;

a pyridinyl group, a pyrazinyl group, a pyrimidinyl group, a pyridazinyl group, a quinolinyl group, an isoquinolinyl group, a benzoquinolinyl group, a naphthyridinyl group, a quinoxalinyl group, a quinazolinyl group, a phenanthridinyl group, a phenanthrolinyl group, a benzophenanthrolinyl group, a benzimidazolyl group, a naphthoimidazolyl group, a triazinyl group, a carbolinyl group, and an imidazopyridinyl group, each substituted with at least one selected from deuterium, —F, —Cl, —Br, —I, a methyl group, an ethyl group, an n-propyl group, an isopropyl group, an n-butyl group, a sec-butyl group, an isobutyl group, a tert-butyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, a terphenyl group, a naphthyl group, a pyridinyl group, a pyrazinyl group, a pyrimidinyl group, a pyridazinyl group, a triazinyl group, —N($Q_{31}$)($Q_{32}$), —Si($Q_{31}$)($Q_{32}$)($Q_{33}$), and —B($Q_{31}$)($Q_{32}$); and a pyridinyl group, a pyrazinyl group, a pyrimidinyl group, a pyridazinyl group, a quinolinyl group, an isoquinolinyl group, a benzoquinolinyl group, a naphthyridinyl group, a quinoxalinyl group, a quinazolinyl group, a phenanthridinyl group, a phenanthrolinyl group, a benzophenanthrolinyl group, a benzimidazolyl group, a naphthoimidazolyl group, a triazinyl group, a carbolinyl group, and an imidazopyridinyl group, each substituted with at least one selected from a phenyl group, a biphenyl group, a terphenyl group, and a naphthyl group that are each substituted with at least one selected from deuterium, —F, —Cl, —Br, —I, a methyl group, an ethyl group, an n-propyl group, an isopropyl group, an n-butyl group, a sec-butyl group, an isobutyl group, a tert-butyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, a terphenyl group, a naphthyl group, a pyridinyl group, a pyrazinyl group, a pyrimidinyl group, a pyridazinyl group, a triazinyl group, —N($Q_{41}$)($Q_{42}$), —Si($Q_{41}$)($Q_{42}$)($Q_{43}$), and —B($Q_{41}$)($Q_{42}$), and $Q_{31}$ to $Q_{33}$ and $Q_{41}$ to $Q_{43}$ may each independently be selected from a methyl group, an ethyl group, an n-propyl group, an isopropyl group, an n-butyl group, a sec-butyl group, an isobutyl group, a tert-butyl group, a phenyl group, a biphenyl group, a terphenyl group, and a naphthyl group, but embodiments of the present disclosure are not limited thereto.

In one embodiment, $R_{ET}$ may be selected from:
a pyridinyl group, a pyrazinyl group, a pyrimidinyl group, a pyridazinyl group, and a triazinyl group;

a pyridinyl group, a pyrazinyl group, a pyrimidinyl group, a pyridazinyl group, and a triazinyl group, each substituted with at least one selected from deuterium, —F, —Cl, —Br, —I, a methyl group, an ethyl group, an n-propyl group, an isopropyl group, an n-butyl group, a sec-butyl group, an isobutyl group, a tert-butyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, a terphenyl group, a naphthyl group, a pyridinyl group, a pyrazinyl group, a pyrimidinyl group, a pyridazinyl group, a triazinyl group, —N($Q_{31}$)($Q_{32}$), —Si($Q_{31}$)($Q_{32}$)($Q_{33}$), and —B($Q_{31}$)($Q_{32}$); and a pyridinyl group, a pyrazinyl group, a pyrimidinyl group, a pyridazinyl group, and a triazinyl group, each substituted with at least one selected from a phenyl group, a biphenyl group, a terphenyl group, and a naphthyl group that are each substituted with at least one selected from deuterium, —F, —Cl, —Br, —I, a methyl group, an ethyl group, an n-propyl group, an isopropyl group, an n-butyl group, a sec-butyl group, an isobutyl group, a tert-butyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, a terphenyl group, a naphthyl group, a pyridinyl group, a pyrazinyl group, a pyrimidinyl group, a pyridazinyl group, a triazinyl group, —N($Q_{41}$)($Q_{42}$), —Si($Q_{41}$)($Q_{42}$)($Q_{43}$), and —B($Q_{41}$)($Q_{42}$), and $Q_{31}$ to $Q_{33}$ and $Q_{41}$ to $Q_{43}$ may each independently be selected from a methyl group, an ethyl group, an n-propyl group, an isopropyl group, an n-butyl group, a sec-butyl group, an isobutyl group, a tert-butyl group, a phenyl group, a biphenyl group, a terphenyl group, and a naphthyl group, but embodiments of the present disclosure are not limited thereto.

In one embodiment, $R_{11}$ to $R_{13}$ and $R_{21}$ and $R_{22}$ may each independently be selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one embodiment, $R_{11}$ to $R_{13}$, $R_{21}$, and $R_{22}$ may each independently be selected from groups represented by Formulae 5-1 to 5-81, wherein at least one selected from $R_{11}$ to $R_{13}$ may be selected from groups represented by Formulae 5-21 to 5-79:

5-1

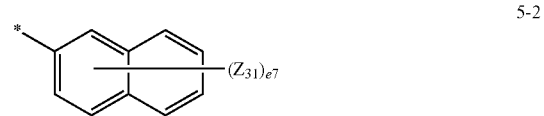

5-2

5-3

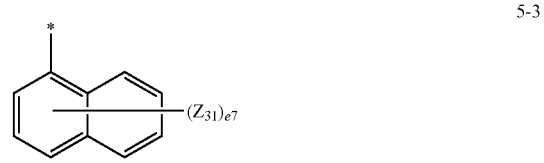

5-4

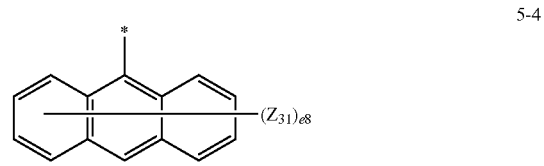

5-5

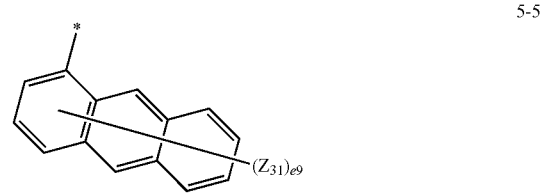

5-6

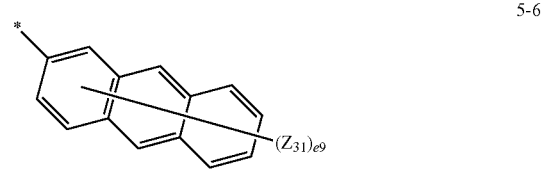

5-7

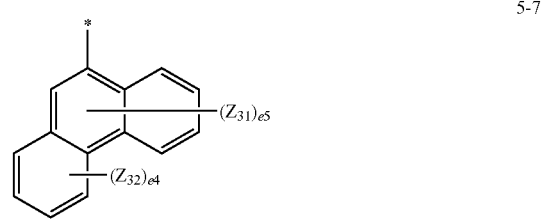

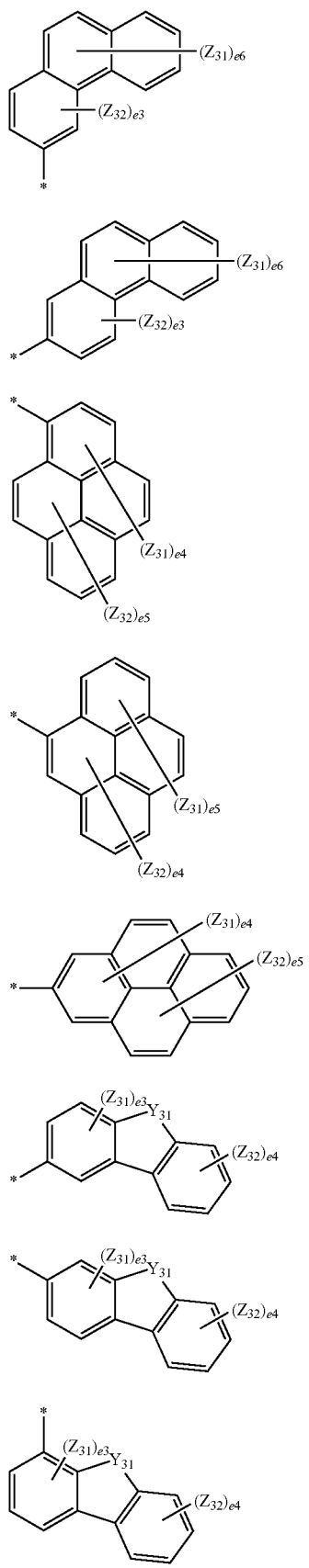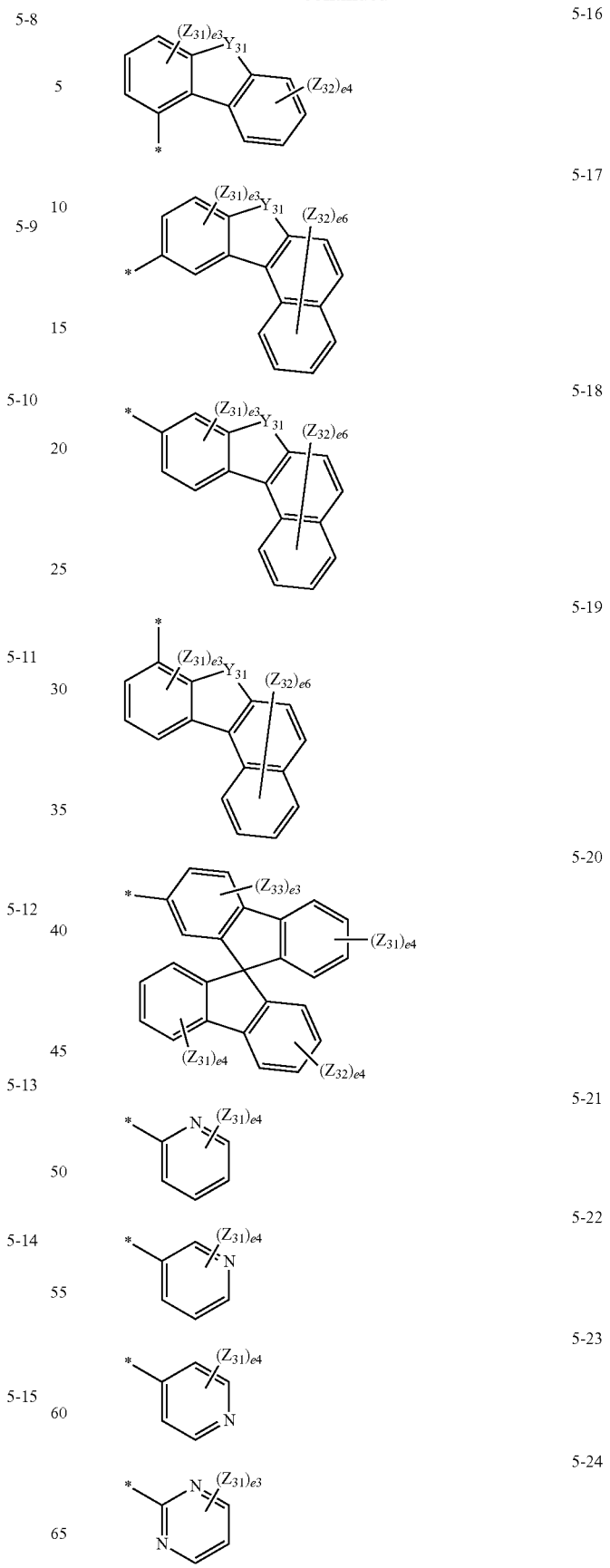

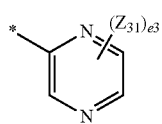
5-25
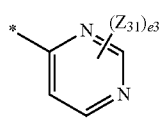
5-26
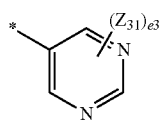
5-27
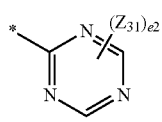
5-78
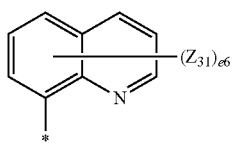
5-29
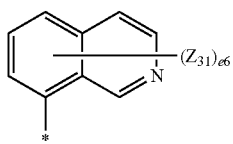
5-30
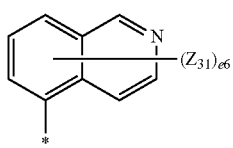
5-31
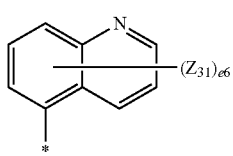
5-32
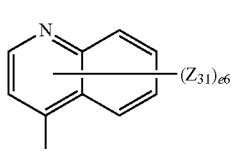
5-33
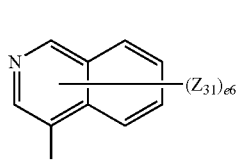
5-34
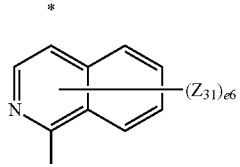
5-35
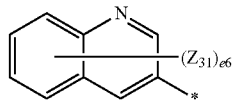
5-36
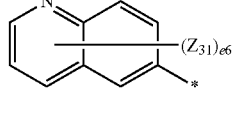
5-37
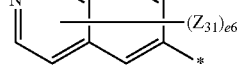
5-38
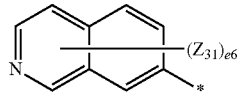
5-39
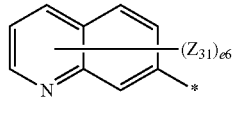
5-40
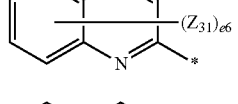
5-41
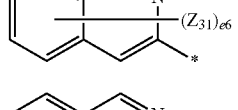
5-42
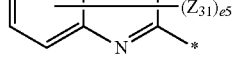
5-43
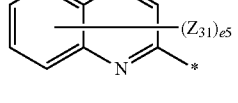
5-44
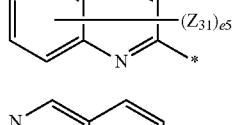
5-45
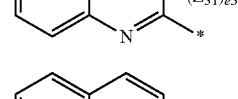
5-46
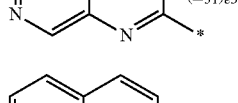
5-47
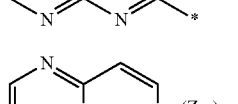
5-48
5-49

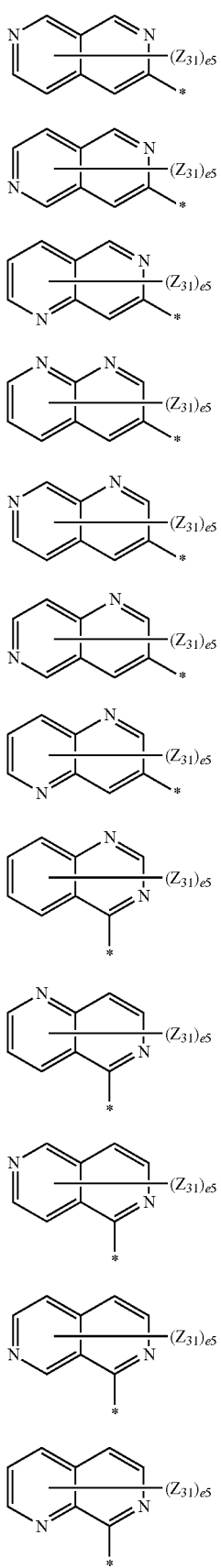
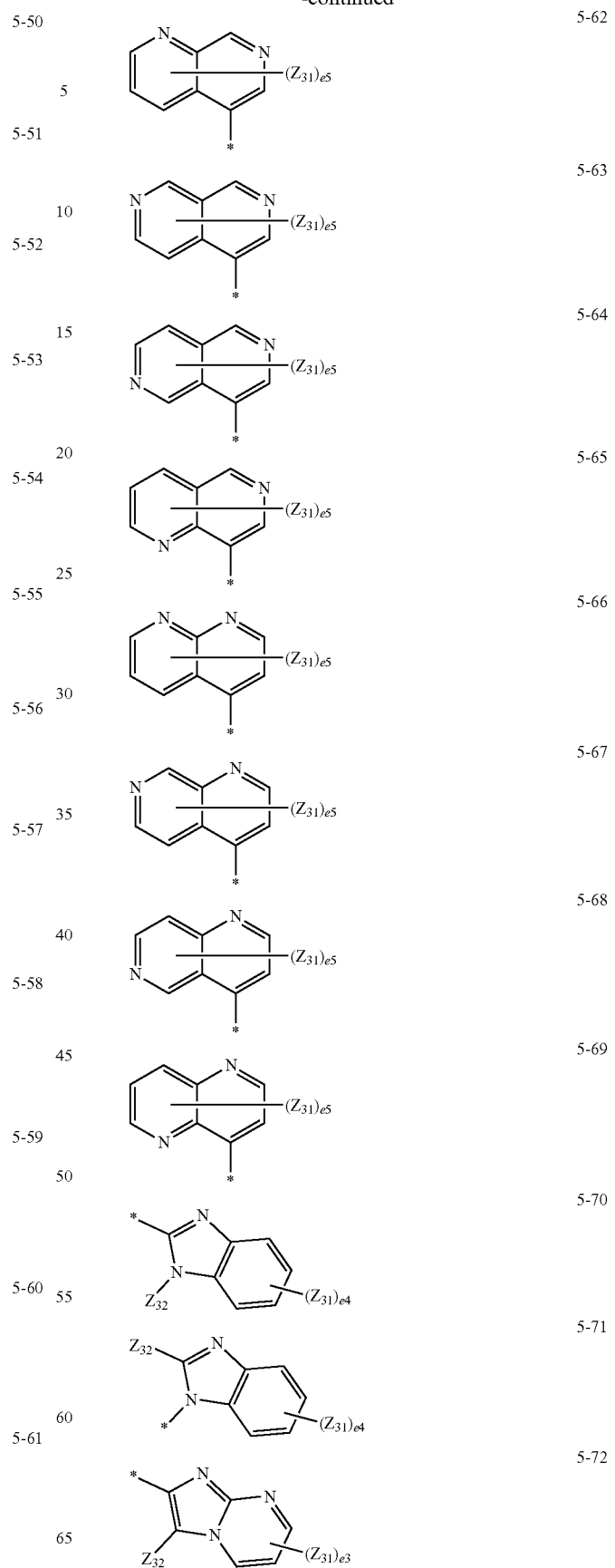

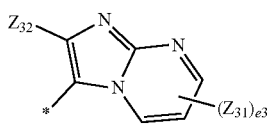

5-73

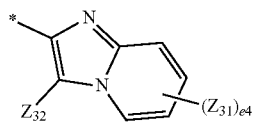

5-74

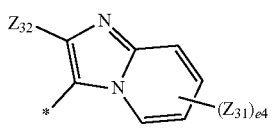

5-75

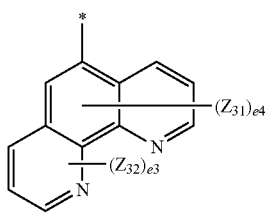

5-76

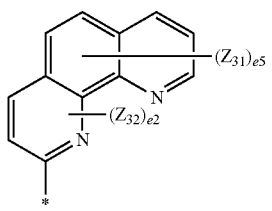

5-77

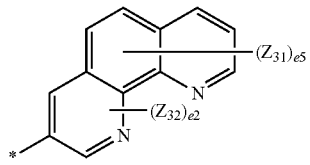

5-78

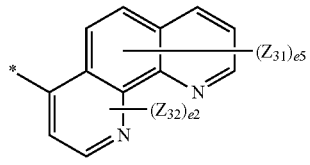

5-79

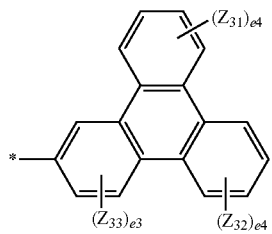

5-80

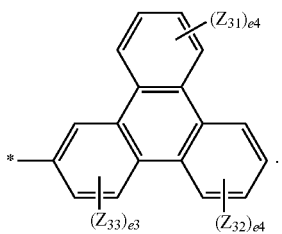

5-81

In Formulae 5-1 to 5-81, $Y_{31}$ may be O, S, $C(Z_{33})(Z_{34})$, $N(Z_{35})$ or $Si(Z_{36})(Z_{37})$, $Z_{31}$ to $Z_{37}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, a dibenzothiophenyl group, —$N(Q_{31})(Q_{32})$, —$Si(Q_{31})(Q_{32})(Q_{33})$, and —$B(Q_{31})(Q_{32})$, e2 may be an integer of 0 to 2, and when e2 is two, two $Z_{31}(s)$ may be identical to or different from each other, and two $Z_{32}(S)$ may be identical to or different from each other, e3 may be an integer of 0 to 3, and when e3 is two or more, two or more of $Z_{31}(s)$ may be identical to or different from each other, two or more of $Z_{32}(s)$ may be identical to or different from each other, and two or more of $Z_{33}(S)$ may be identical to or different from each other, e4 may be an integer of 0 to 4, and when e4 is two or more, two or more of $Z_{31}(s)$ may be identical to or different from each other, and two or more of $Z_{32}(s)$ may be identical to or different from each other, e5 may be an integer of 0 to 5, and when e5 is two or more, two or more of $Z_{31}(s)$ may be identical to or different from each other, and two or more of $Z_{32}(s)$ may be identical to or different from each other, e6 may be an integer of 0 to 6, and when e6 is two or more, two or more of $Z_{31}(s)$ may be identical to or different from each other, and two or more of $Z_{32}(s)$ may be identical to or different from each other, e7 may be an integer of 0 to 7, and when e7 is two or more, two or more of $Z_{31}(s)$ may be identical to or different from each other, e9 may be an integer of 0 to 9, and when e9 is two or more, two or more of $Z_{31}(s)$ may be identical to or different from each other, $Q_{31}$ to $Q_{33}$ may each independently be selected from a $C_1$-$C_{20}$ alkyl group, a $C_1$-$C_{20}$ alkoxy group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, and

* indicates a binding site to a neighboring atom.

In one embodiment, at least one selected from $R_{21}$ and $R_{22}$ in Formula 2-1 may be $R_{ET}$.

For example, in Formula 2-1, at least one selected from $R_{21}$ and $R_{22}$ may be selected from groups represented by Formulae 5-21 to 5-79.

In one embodiment, one of $R_{21}$ and $R_{22}$ in Formula 2-1 may be selected from groups represented by Formulae 5-1 to 5-3, 5-13 to 5-16, 5-80, and 5-81, and the other may be selected from groups represented by Formulae 5-21 to 5-79.

In one or more embodiments, $R_{14}$ to $R_{16}$ and $R_{23}$ to $R_{29}$ may each independently be selected from hydrogen, deuterium, —F, —Cl, —Br, —I, a cyano group, a substituted or unsubstituted $C_1$-$C_{60}$ alkyl group, a substituted or unsubstituted $C_1$-$C_{60}$ alkoxy group, a substituted or unsubstituted $C_6$-$C_{60}$ aryl group, —Si($Q_1$)($Q_2$)($Q_3$), —B($Q_1$)($Q_2$), and —N($Q_1$)($Q_2$), $R_{30}$ may be selected from hydrogen, deuterium, —F, —Cl, —Br, —I, a cyano group, a substituted or unsubstituted $C_1$-$C_{60}$ alkyl group, a substituted or unsubstituted $C_1$-$C_{60}$ alkoxy group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), and —N($Q_1$)($Q_2$), and $Q_1$ to $Q_3$ may each independently be selected from a $C_1$-$C_{60}$ alkyl group, a $C_1$-$C_{60}$ alkoxy group, and a $C_6$-$C_{60}$ aryl group.

In one embodiment, $R_{14}$ to $R_{16}$ and $R_{23}$ to $R_{29}$ may each independently be selected from hydrogen, deuterium, —F, a cyano group, a methyl group, an ethyl group, an n-propyl group, an isopropyl group, an n-butyl group, a sec-butyl group, an isobutyl group, a tert-butyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, a terphenyl group, a naphthyl group, —Si($Q_1$)($Q_2$)($Q_3$), —B($Q_1$)($Q_2$), and —N($Q_1$)($Q_2$), $R_{30}$ may be selected from hydrogen, deuterium, —F, a cyano group, a methyl group, an ethyl group, an n-propyl group, an isopropyl group, an n-butyl group, a sec-butyl group, an isobutyl group, a tert-butyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, a terphenyl group, a naphthyl group, a fluorenyl group, a 9,9-dimethylfluorenyl group, a dibenzofuranyl group, a dibenzothiophenyl group, a carbazolyl group, phenyl-substituted carbazolyl group, —Si($Q_1$)($Q_2$)($Q_3$), —B($Q_1$)($Q_2$), and —N($Q_1$)($Q_2$), $Q_1$ to $Q_3$ may each independently be selected from a methyl group, an ethyl group, an n-propyl group, an isopropyl group, an n-butyl group, a sec-butyl group, an isobutyl group, a tert-butyl group, a phenyl group, a biphenyl group, a terphenyl group, and a naphthyl group.

b11 to b13, b21 to b26, and b30 may each independently be 1, 2, 3, 4, or 5.

b27 and b29 may each independently be 1, 2, 3, or 4, b28 may be 1, 2, or 3, and b11 indicates the number of $R_{11}$(s), wherein, when b11 is two or more, two or more of $R_{11}$(s) may be identical to or different from each other, and wherein b12, b13, and b21 to b30 may each independently be the same as described in connection with b11.

At least one substituent selected from the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, $Q_{31}$ to $Q_{33}$, and $Q_{41}$ to $Q_{43}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

In one embodiment, the first host and the third host may each independently be represented by Formula 1-1:

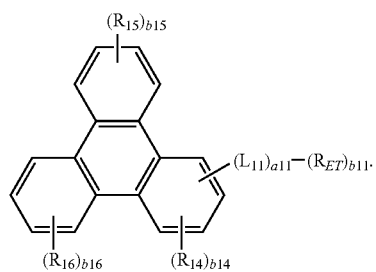

Formula 1-1

In Formula 1-1, $L_{11}$, a11, $R_{ET}$, $R_{14}$ to $R_{16}$, and b11 may be the same as described in connection with Formula 1, b14 may be 1, 2, or 3, and b15 and b16 may each independently be 1, 2, 3, or 4.

In one or more embodiments, the first host and the third host may each independently be represented by Formula 1-1A or 1-1 B:

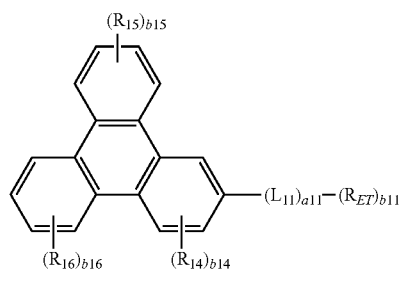

Formula 1-1A

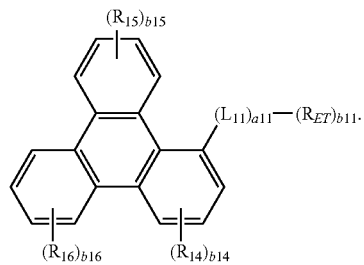

Formula 1-1B

In Formulae 1-1A and 1-1B, $L_{11}$, a11, $R_{ET}$, $R_{14}$ to $R_{16}$, and b11 may be the same as described in connection with Formula 1, b14 may be 1, 2, or 3, and b15 and b16 may each independently be 1, 2, 3, or 4.

In one embodiment, the second host and the fourth host may each independently be one selected from Formulae 2-4 to 2-6:

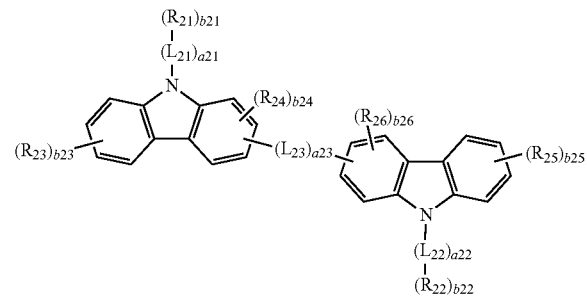

Formula 2-4

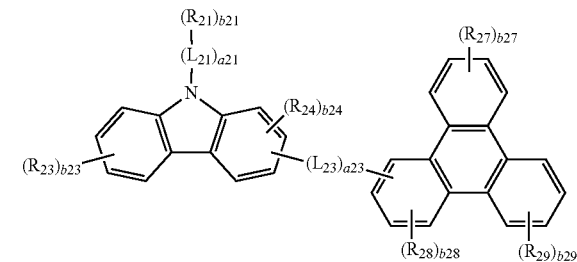

Formula 2-5

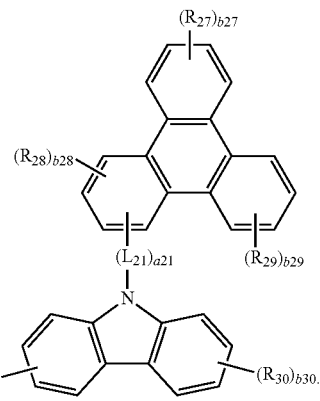

Formula 2-6

In Formulae 2-4 to 2-6, $L_{21}$ to $L_{23}$, a21 to a23, $R_{21}$ to $R_{30}$, b21, b22, and b27 to b29 may be the same as described in connection with Formula 2-1 to 2-3, b23, b25, and b30 may each independently be 1, 2, 3, or 4, and b24 and b26 may each independently be 1, 2, or 3.

In one embodiment, the second host and the fourth host may each independently be represented by one selected from Formulae 2-1A to 2-11, 2-2A to 2-2D, and 2-3A:

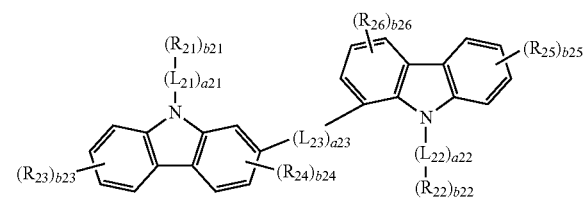

Formula 2-1A

Formula 2-1B
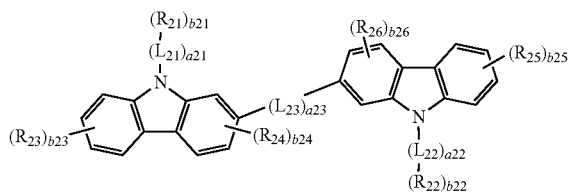
Formula 2-1G
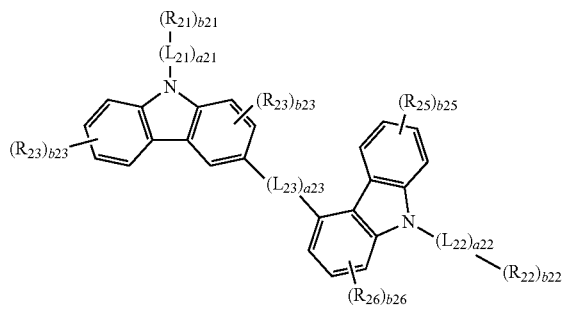
Formula 2-1C
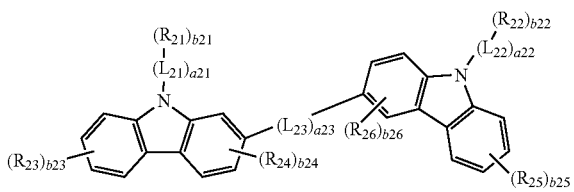
Formula 2-1D
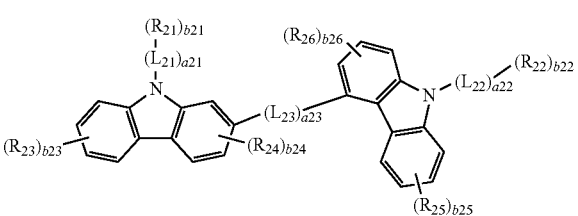
Formula 2-1H
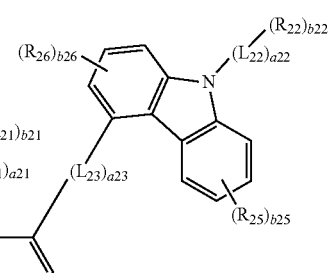
Formula 2-1E
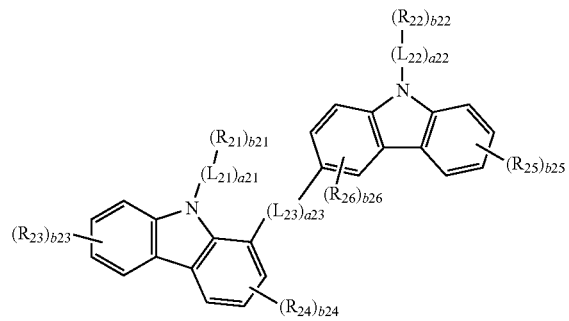
Formula 2-1I
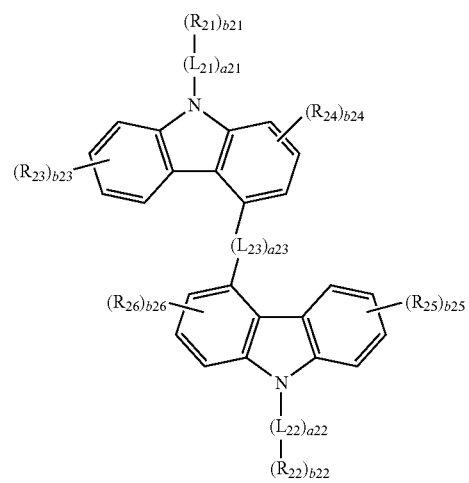
Formula 2-1F
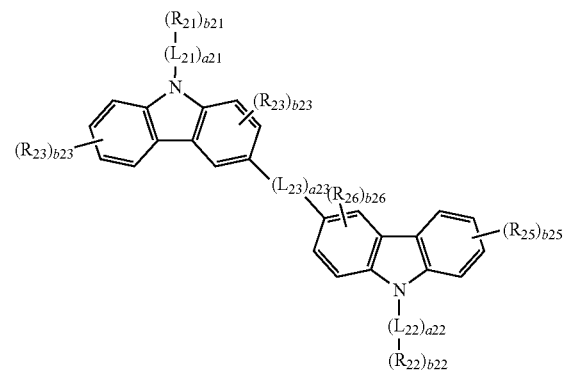
Formula 2-2A
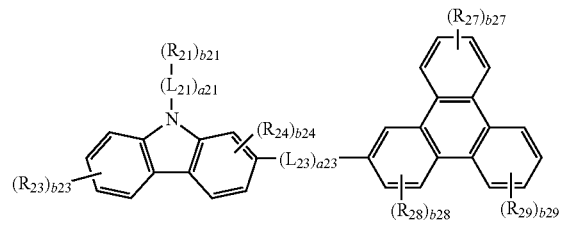

Formula 2-2B
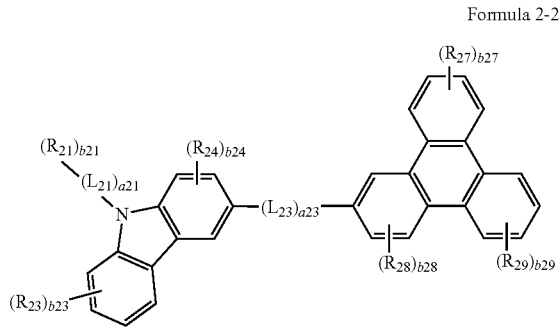

Formula 2-2C
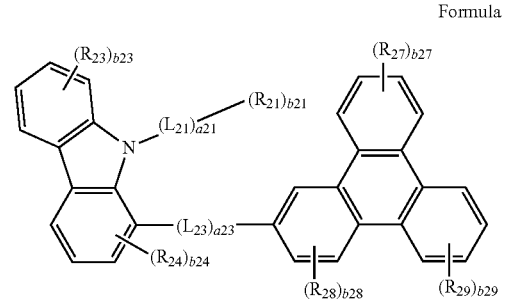

Formula 2-2D
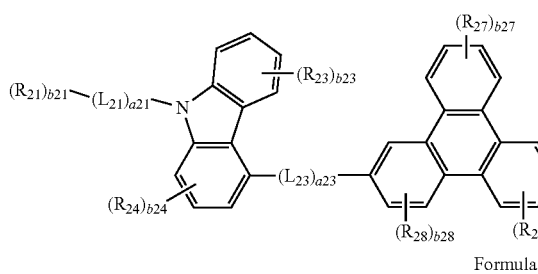

Formula 2-3A
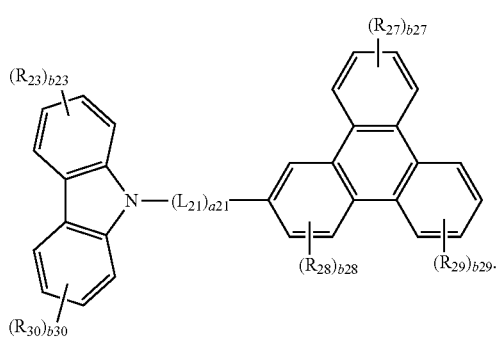

In Formulae 2-1A to 2-1l, 2-2A to 2-2D, and 2-3A, $L_{21}$ to $L_{23}$, a21 to a23, $R_{21}$ to $R_{30}$, b21, b22, and b27 to b29 may be the same as described in connection with Formula 2-1 to 2-3, b23, b25, and b30 may each independently be 1, 2, 3, or 4, and b24 and b26 may each independently be 1, 2, or 3.

In one or more embodiments, the second host and the fourth host may each independently be represented by Formulae 2-1L to 2-3L:

Formula 2-1L
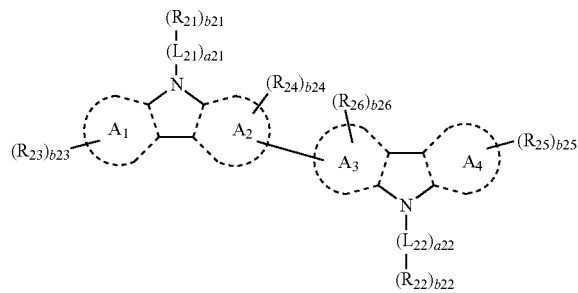

Formula 2-2L
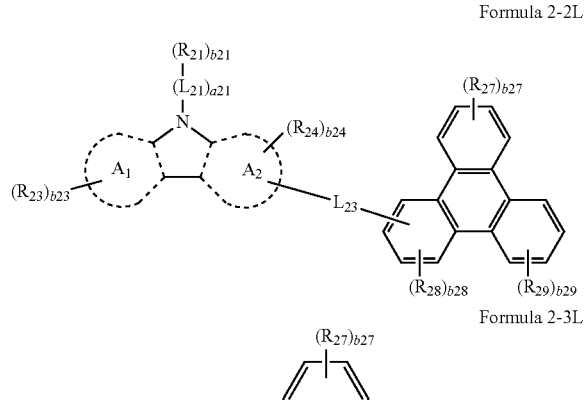

Formula 2-3L
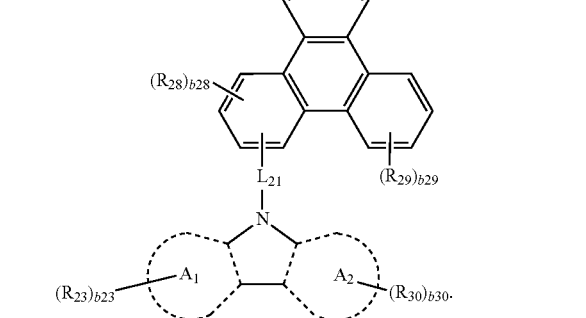

In Formulae 2-1L to 2-3L, $A_1$ to $A_4$, $L_{21}$ to $L_{23}$, a21, a22 and $R_{21}$ to $R_{30}$, and b21 to b30 may be the same as described in connection with Formulae 2-1 to 2-3.

In one embodiment, the first host and the third host may each independently be selected from Compounds A-1 to A-125, but embodiments of the present disclosure are not limited thereto:

A-1
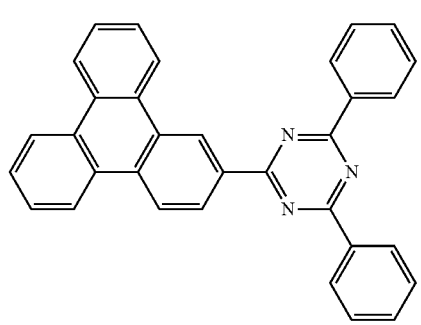

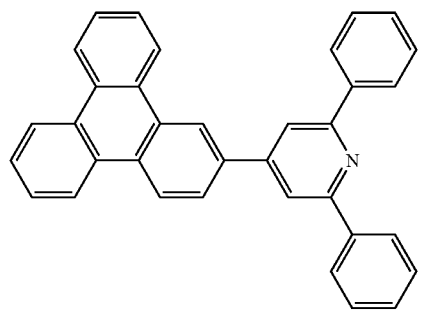 A-2
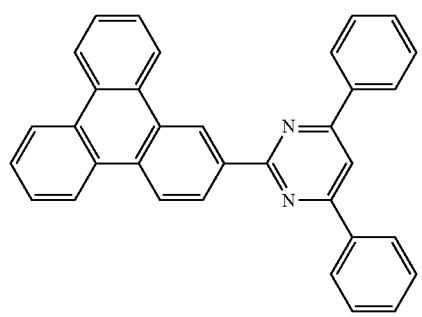 A-3
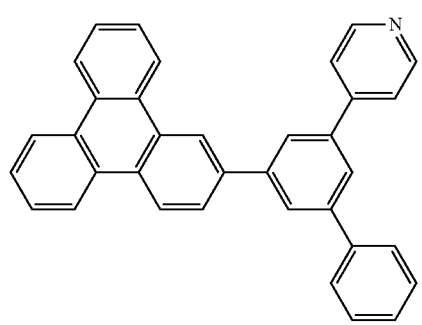 A-4
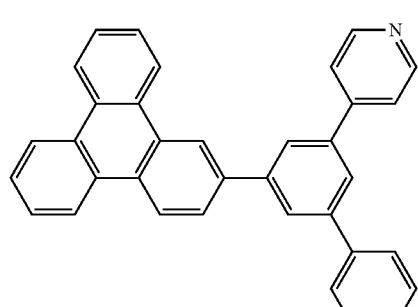 A-5
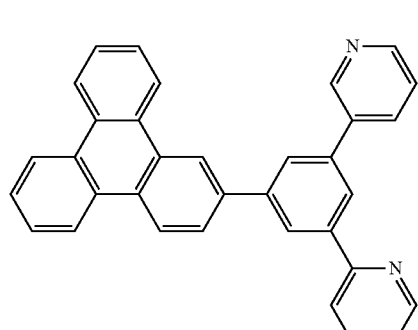 A-6
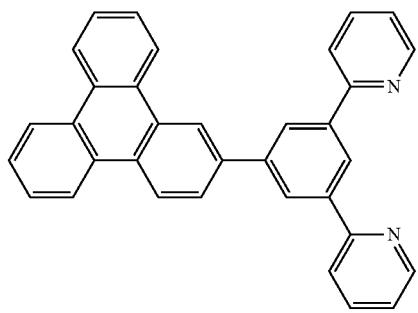 A-7
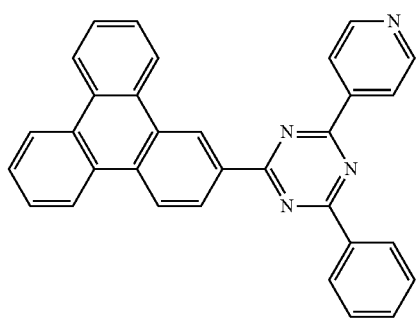 A-8
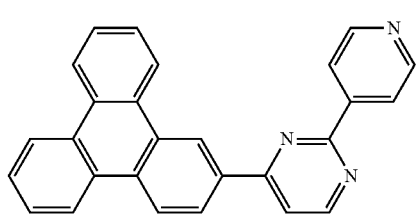 A-9
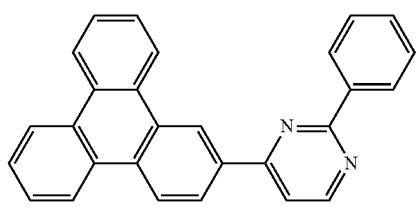 A-10
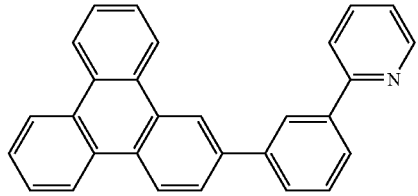 A-11
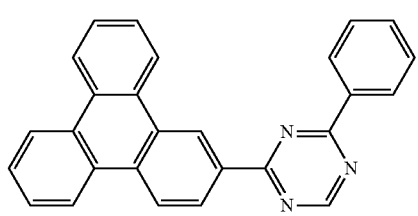 A-12

A-13
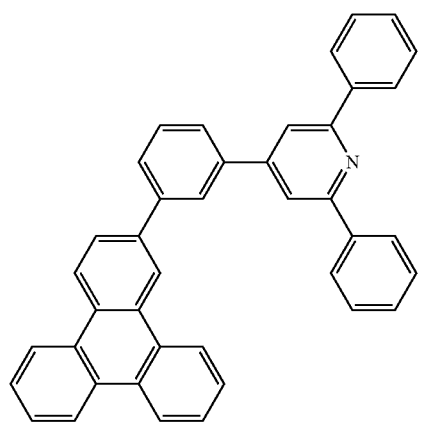
A-14
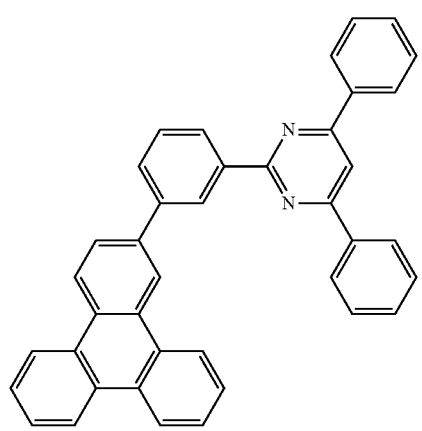
A-15
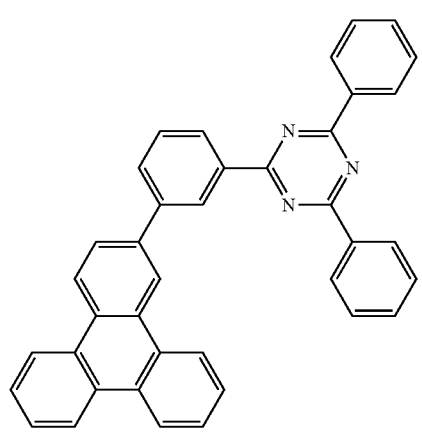
A-16
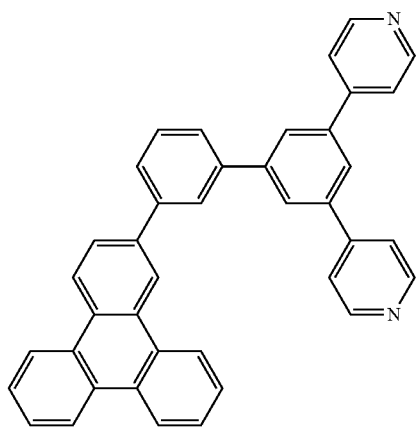
A-17

A-18
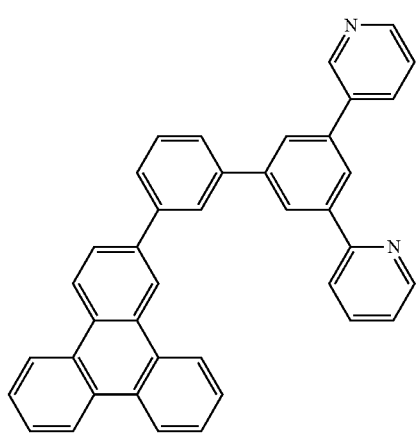

A-19
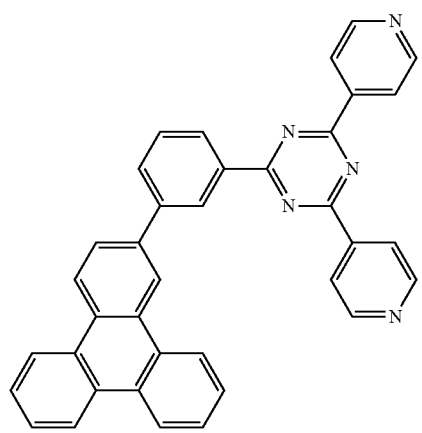
A-20
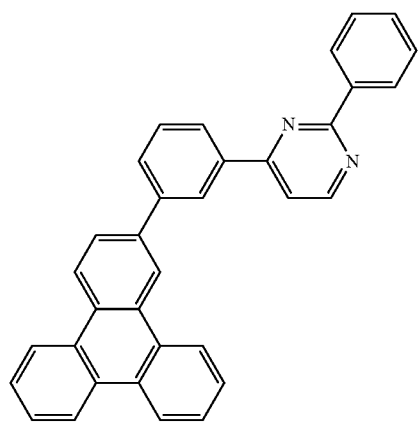
A-21
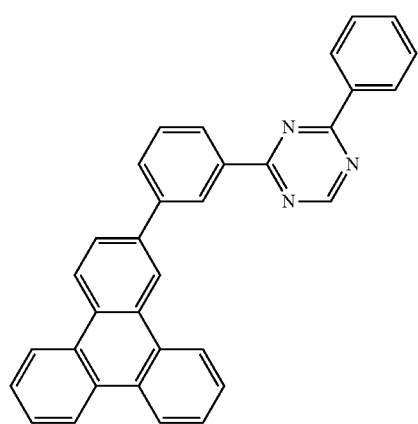
A-22
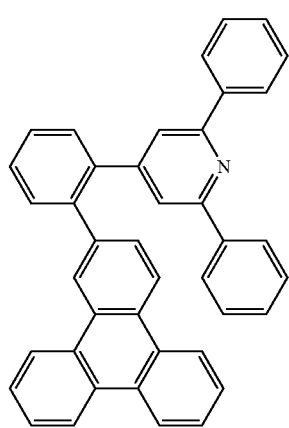
A-23
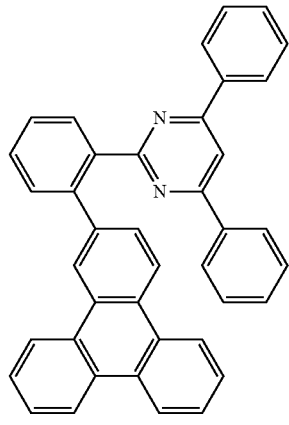
A-24
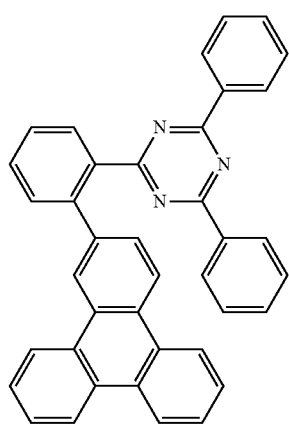

A-25
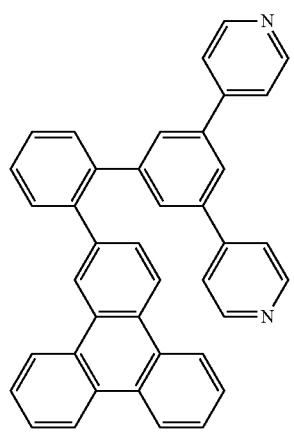
A-26
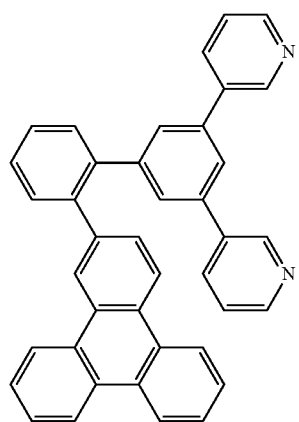
A-27
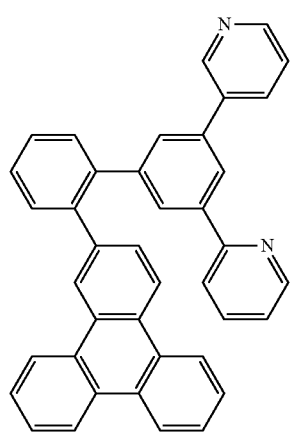
A-28
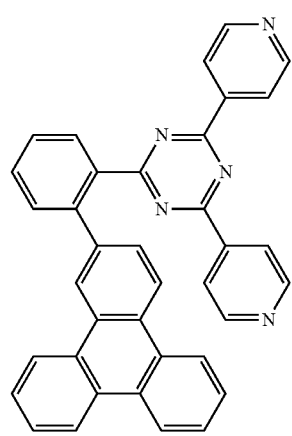
A-29
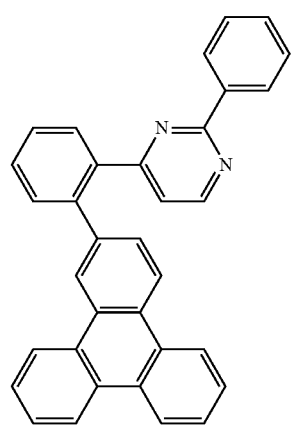
A-30
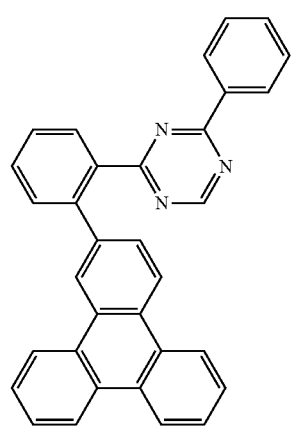

A-31
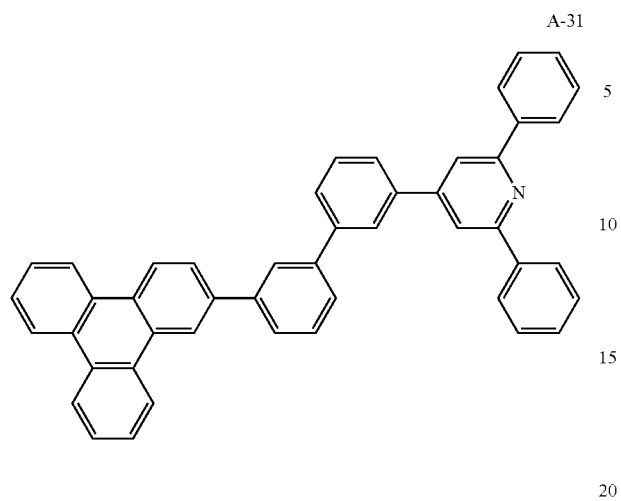
A-34
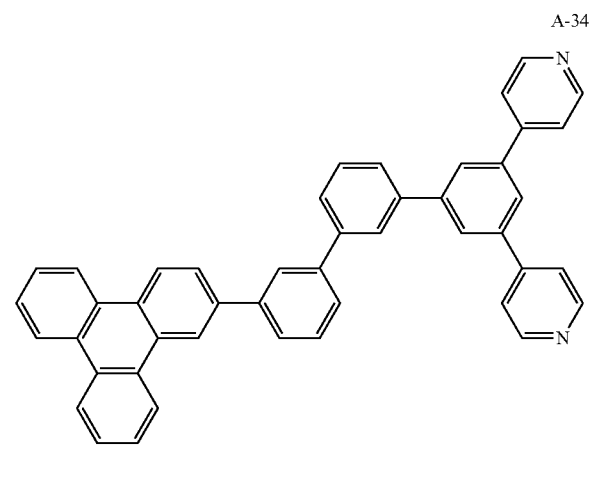
A-32
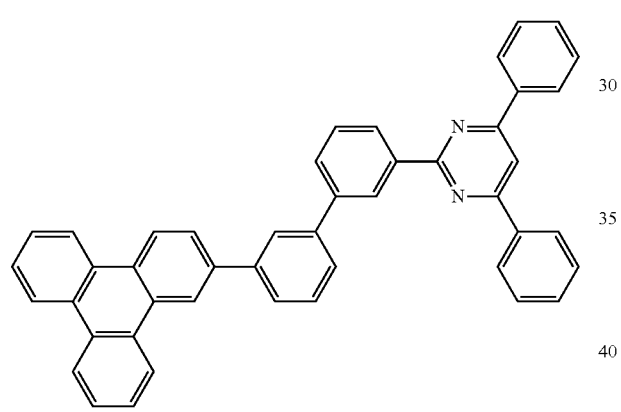
A-35
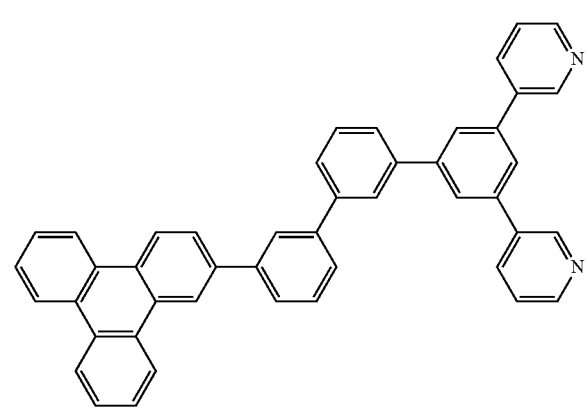
A-33
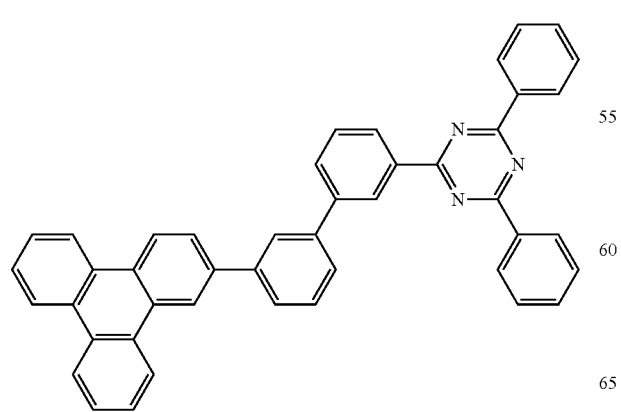
A-36
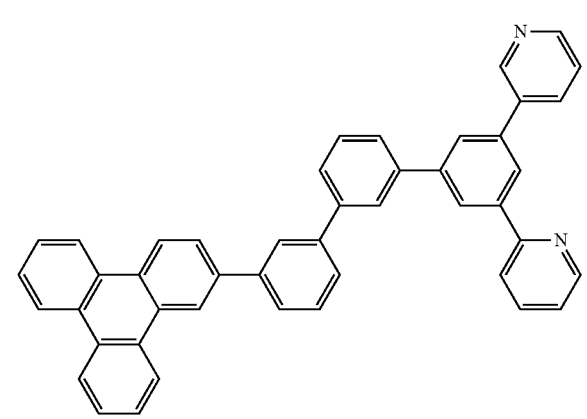

A-37
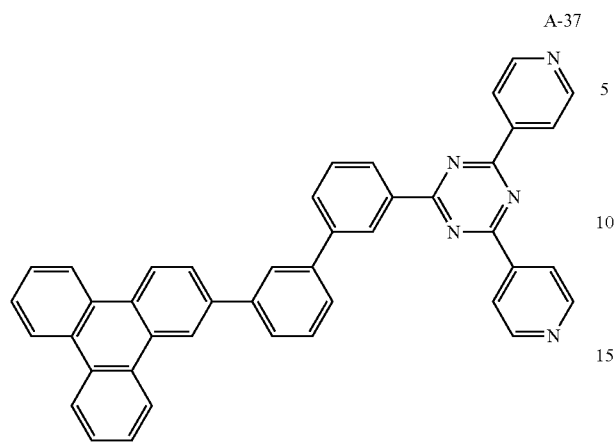
A-41
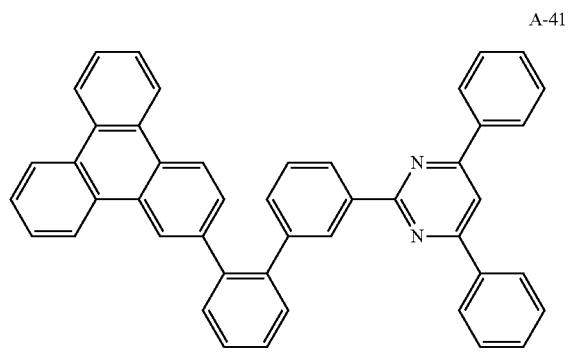
A-38
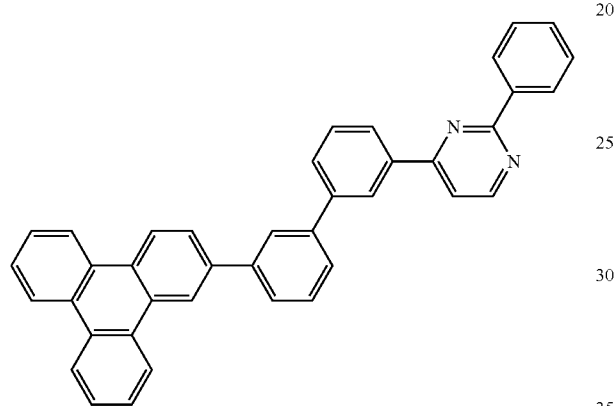
A-42
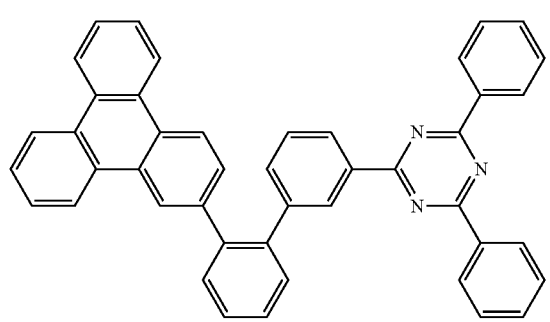
A-39
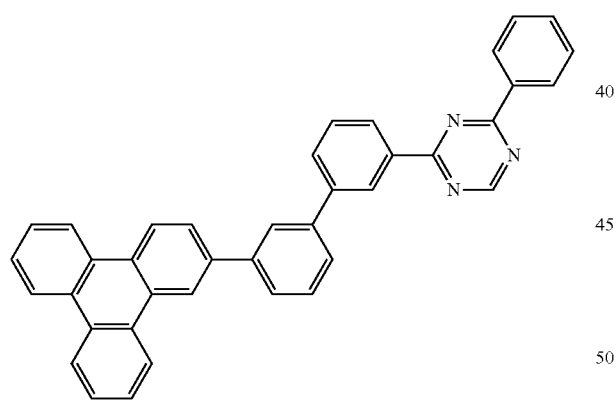
A-43
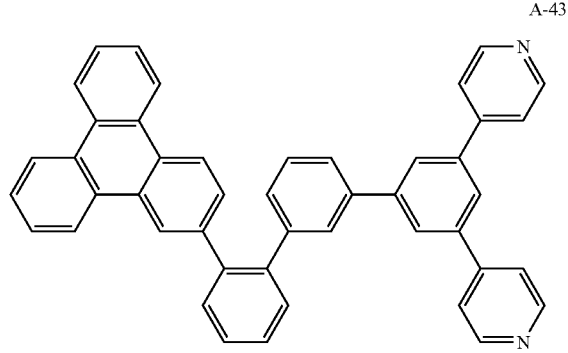
A-40
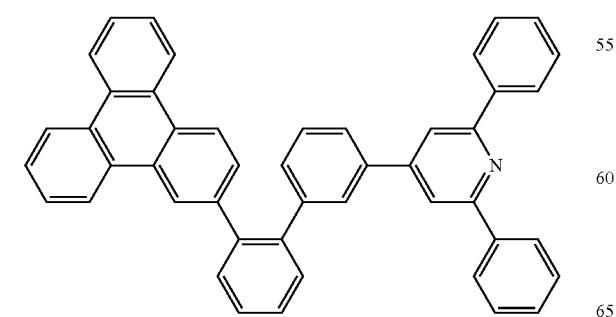
A-44
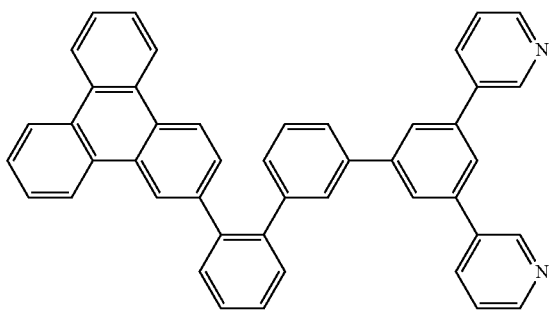

A-45
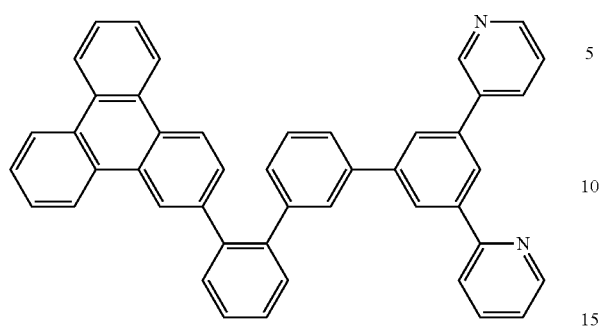
A-46
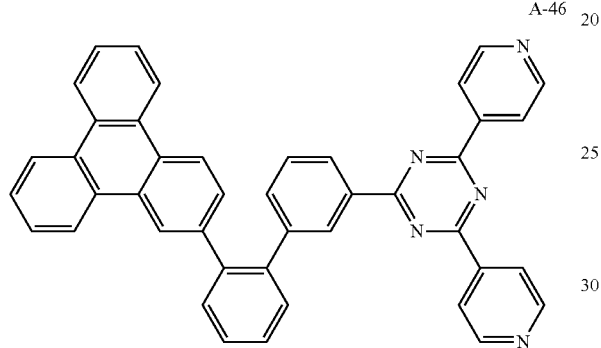
A-47
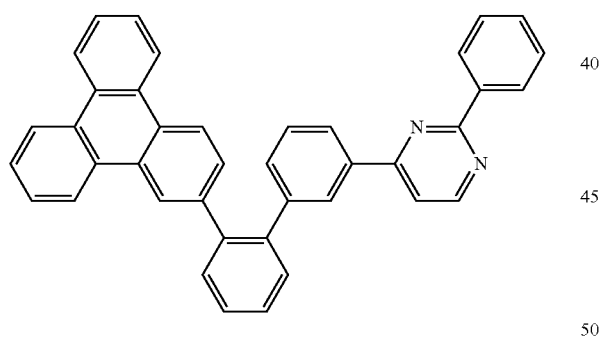
A-48
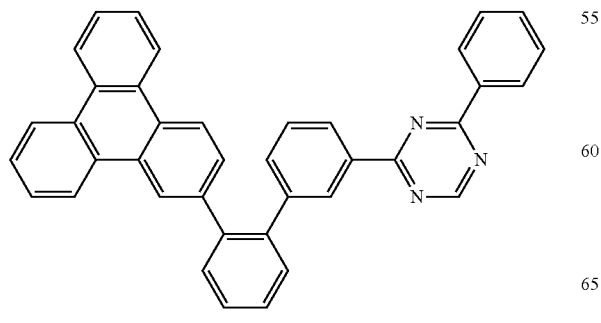
A-49
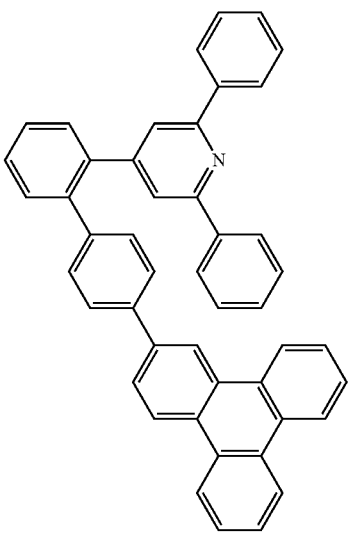
A-50
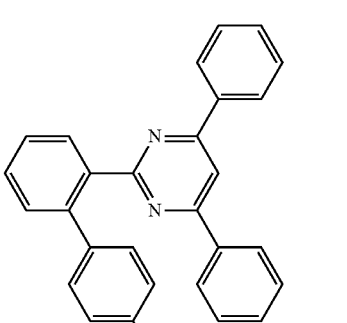
A-51
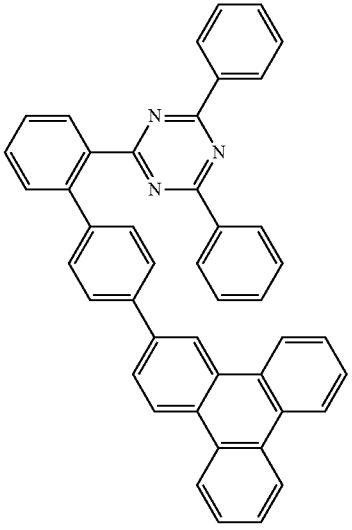

A-52
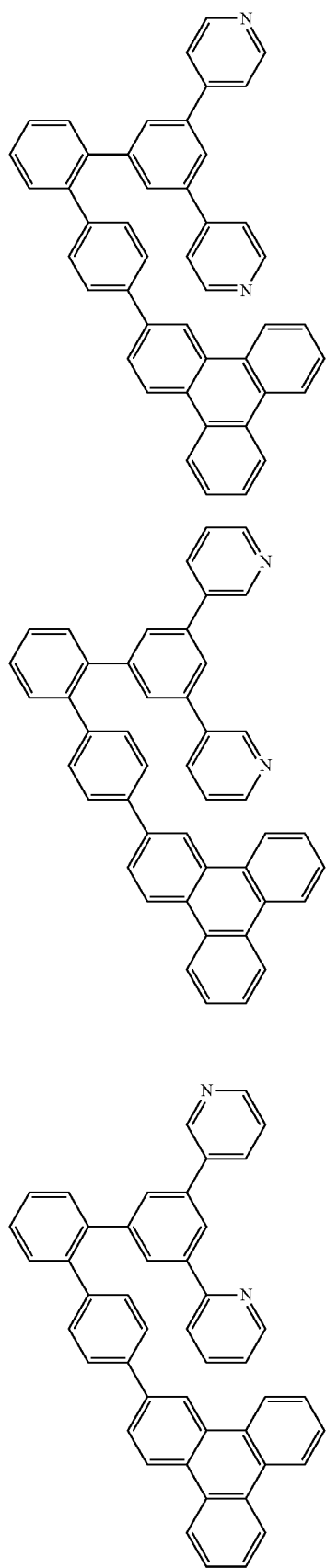
A-53
A-54
A-55
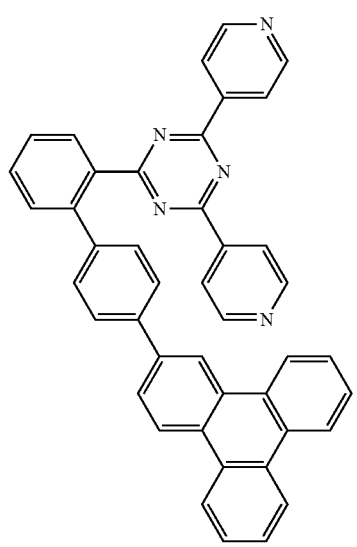
A-56
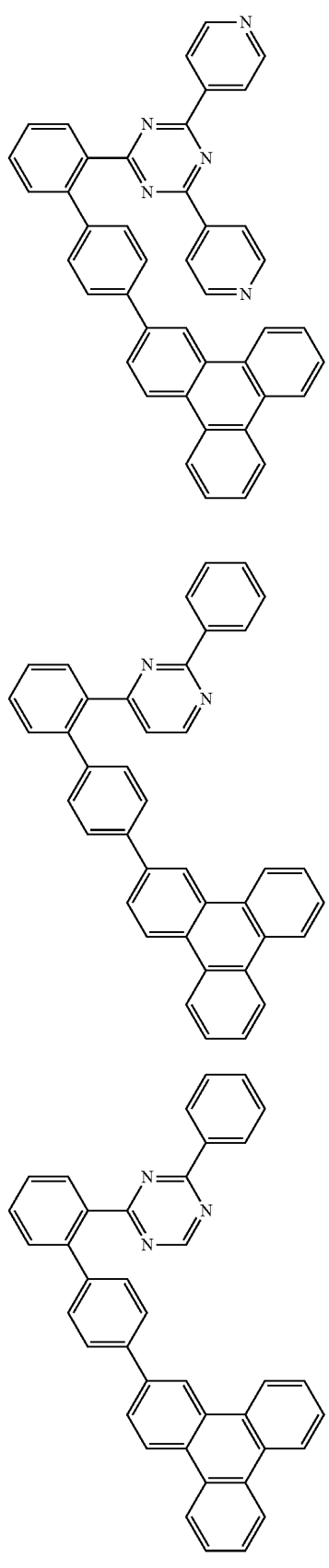
A-57

A-58
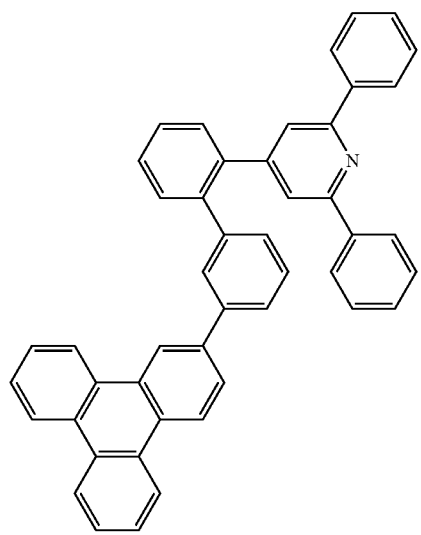
A-59
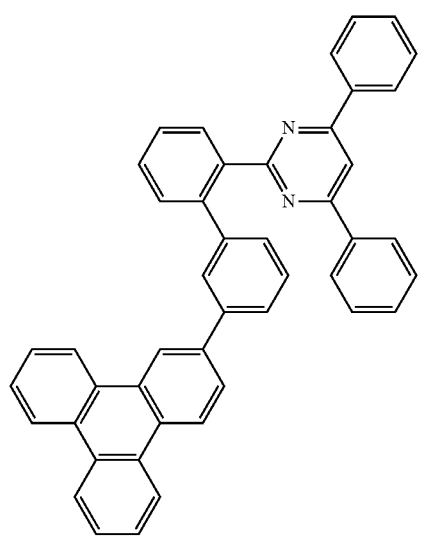
A-60
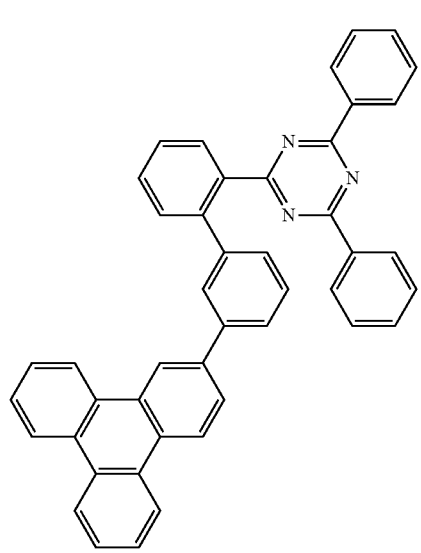
A-61
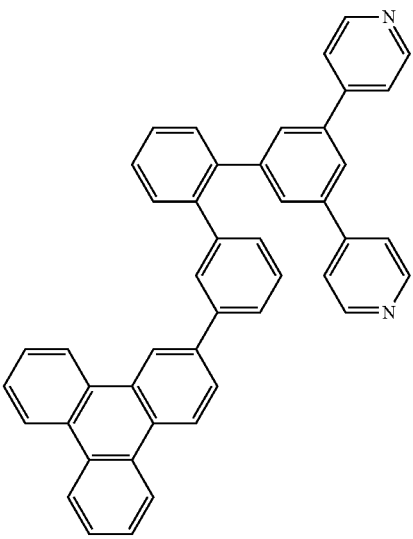
A-62
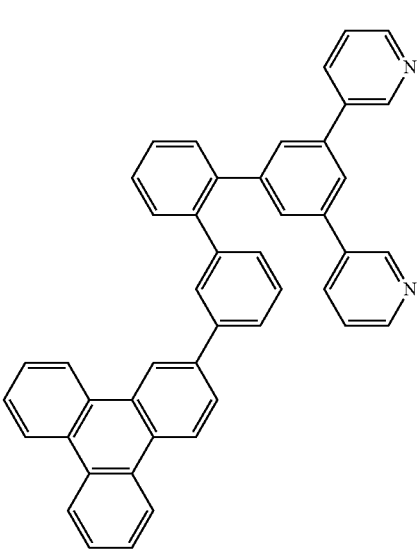
A-63
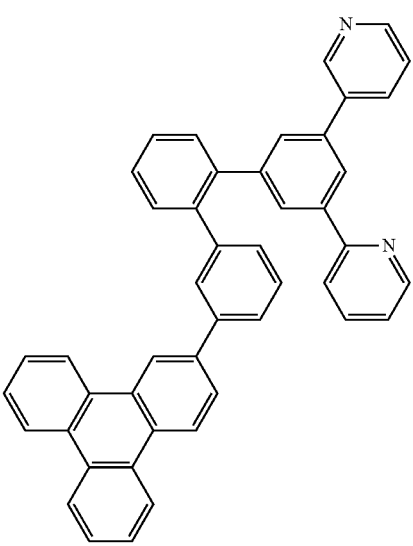

A-64
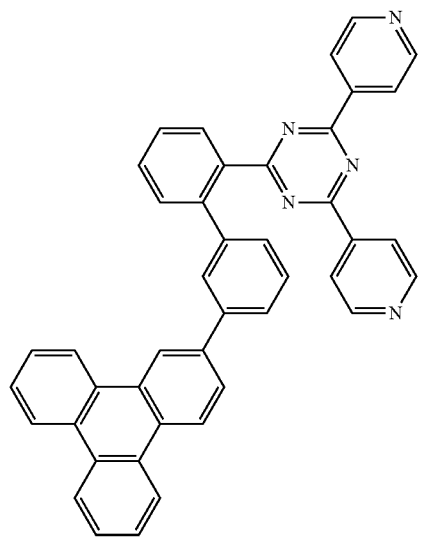
A-65
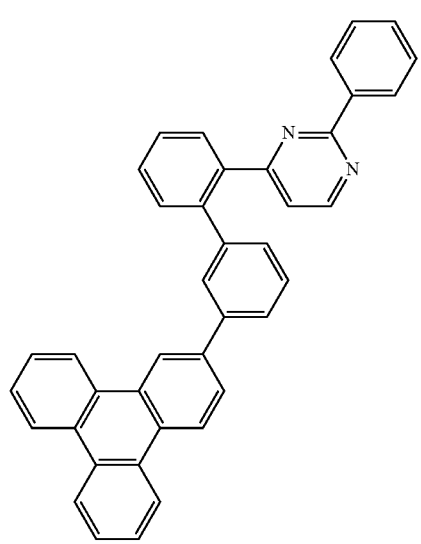
A-66
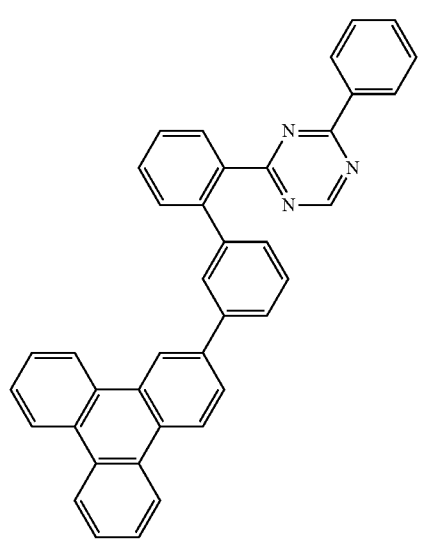
A-67
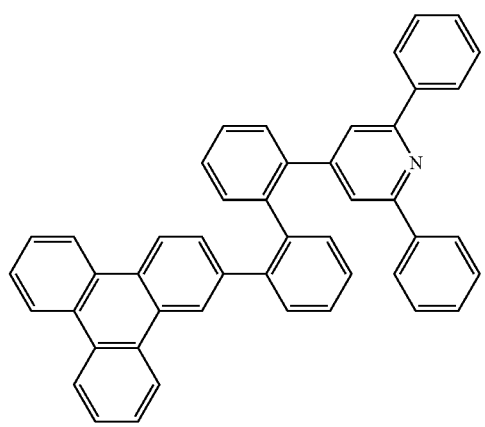
A-68
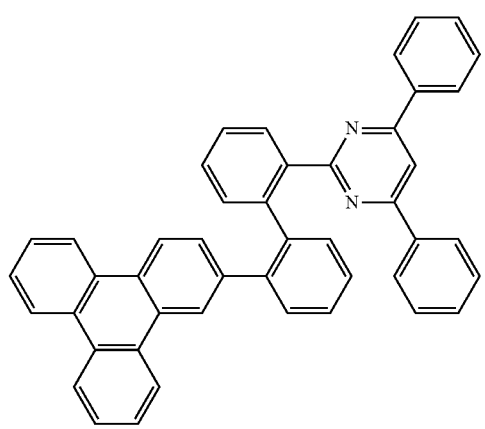
A-69
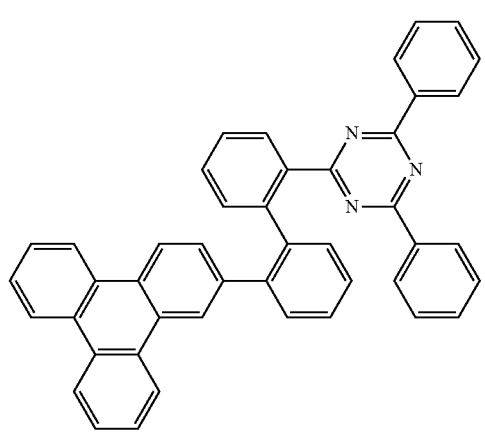

A-70
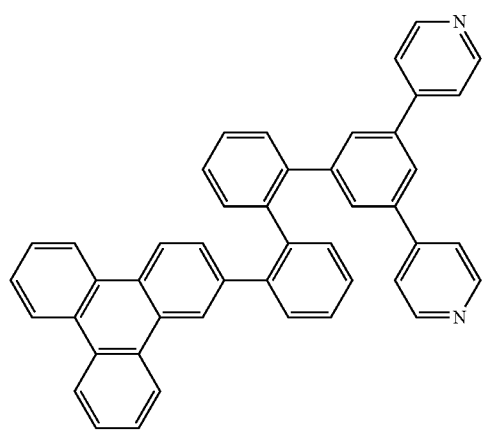
A-71
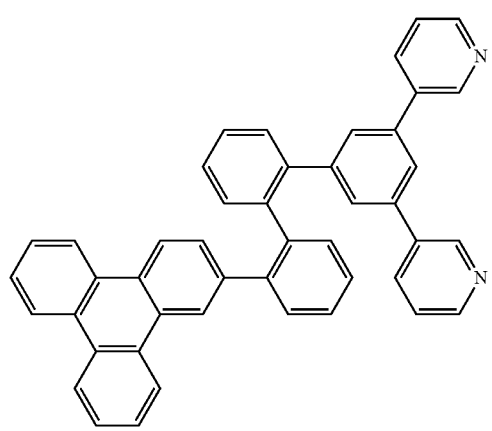
A-72
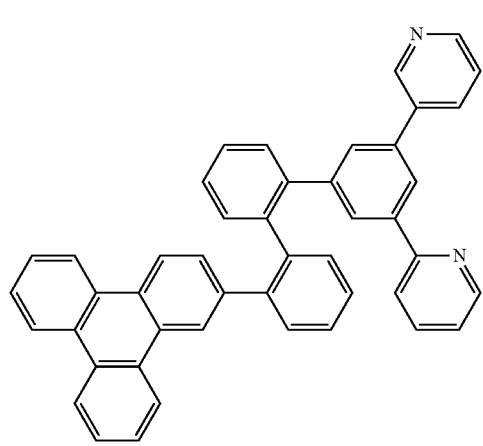
A-73
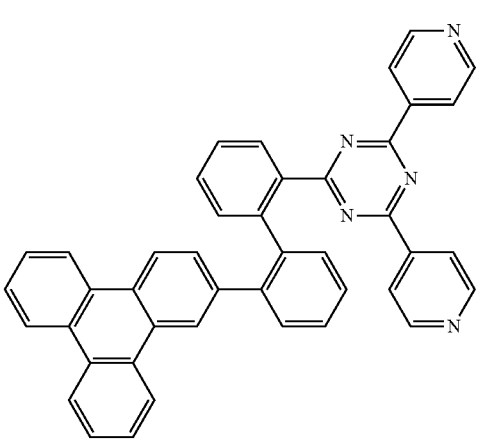
A-74
A-75
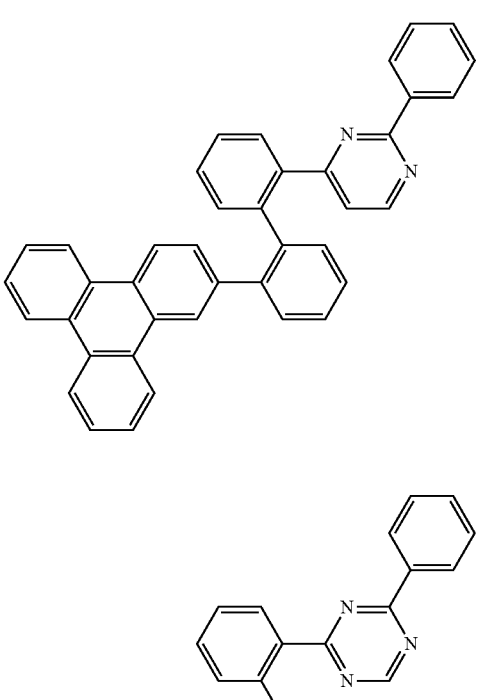
A-76
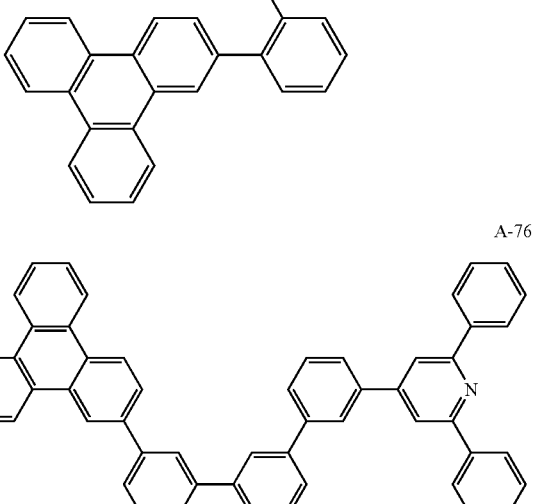

-continued
A-77
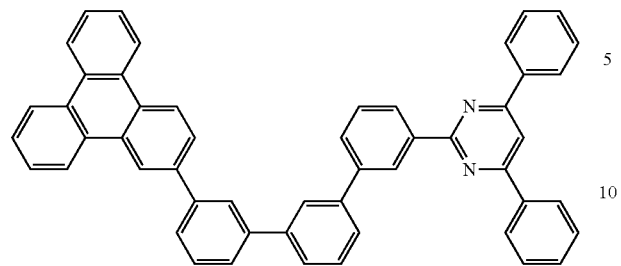
A-78
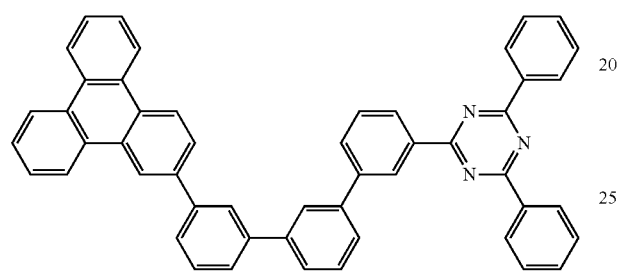
A-79
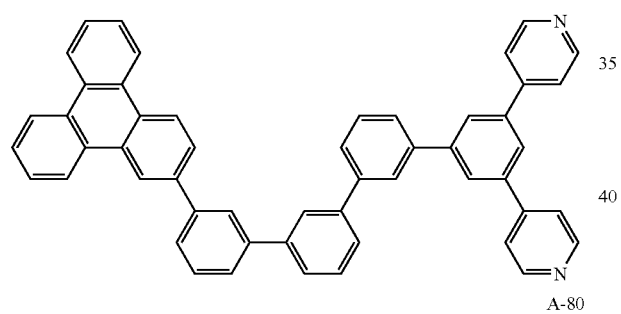
A-80
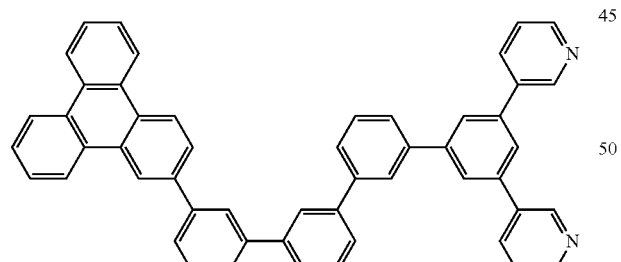
A-81
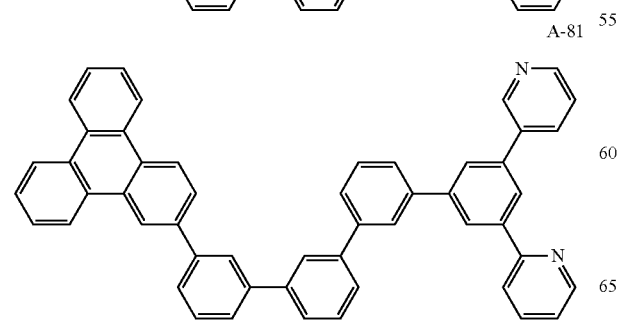
-continued
A-82
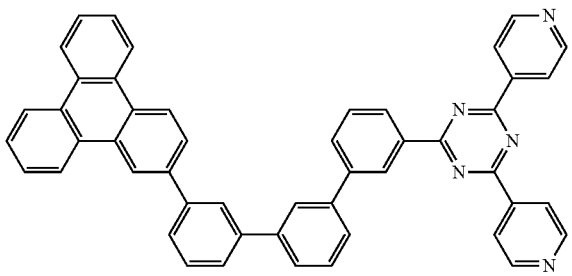
A-83
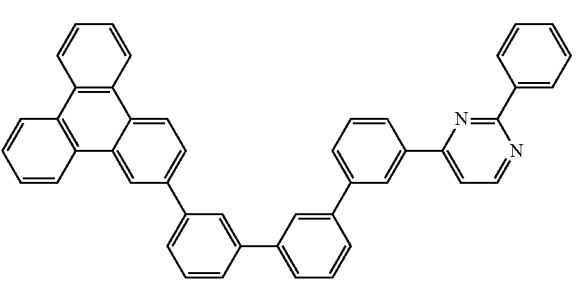
A-84
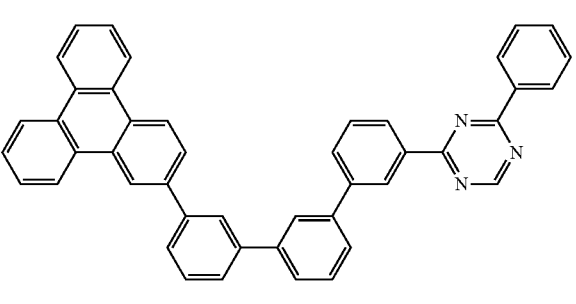
A-85
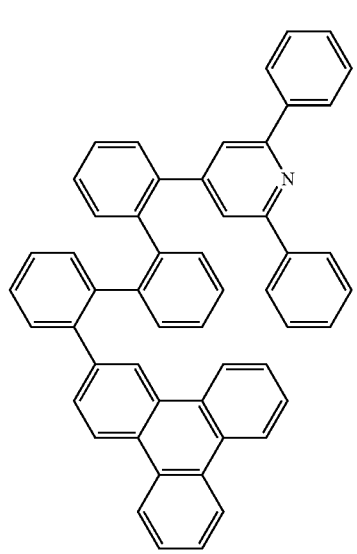

A-86
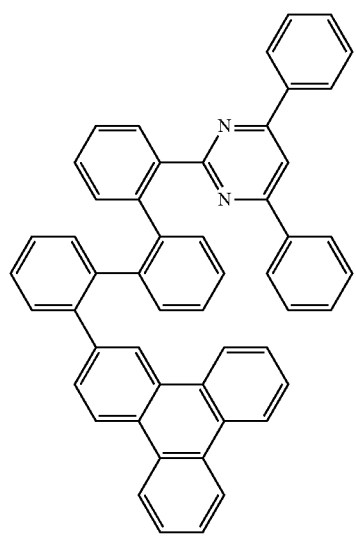
A-87
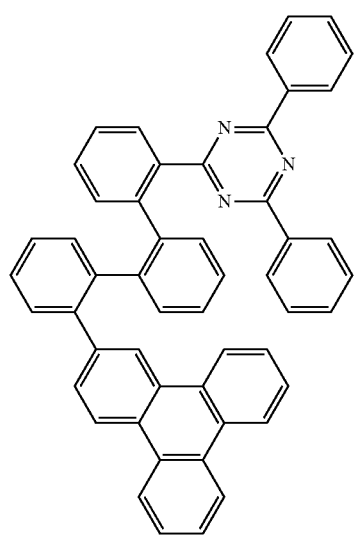
A-88
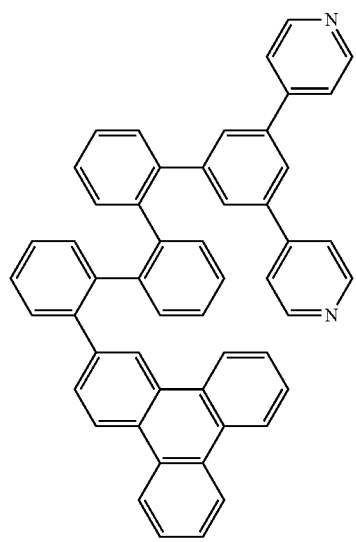
A-89
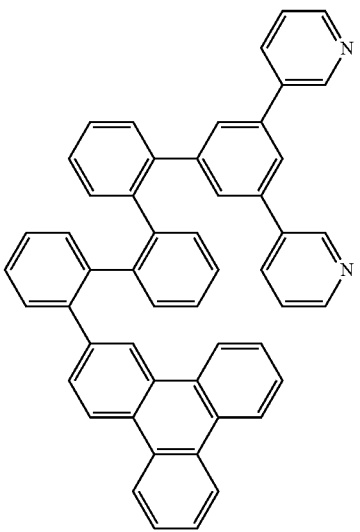
A-90
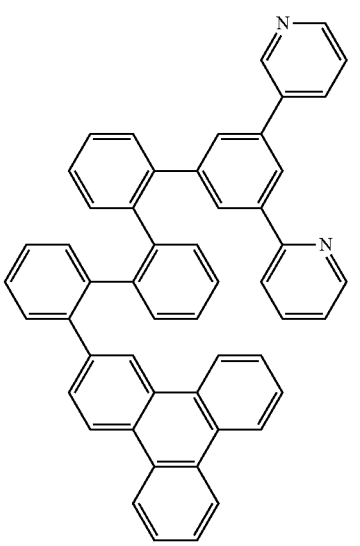
A-91
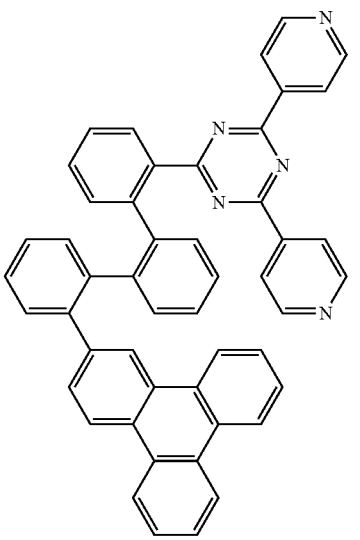

A-92
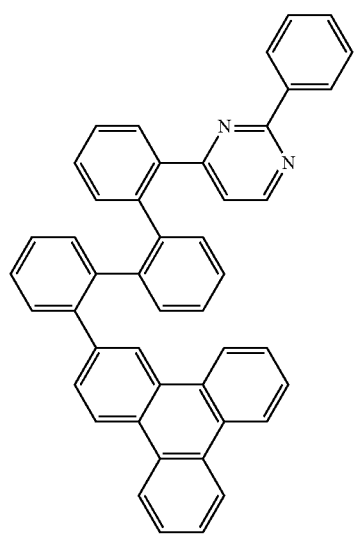
A-93
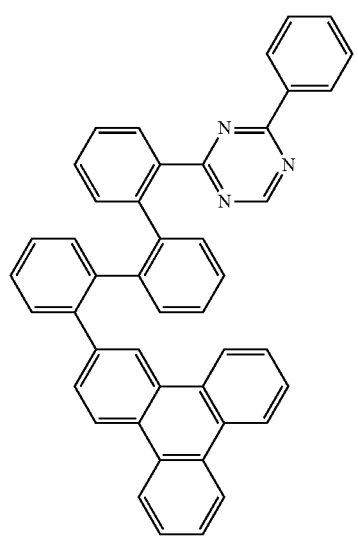
A-94
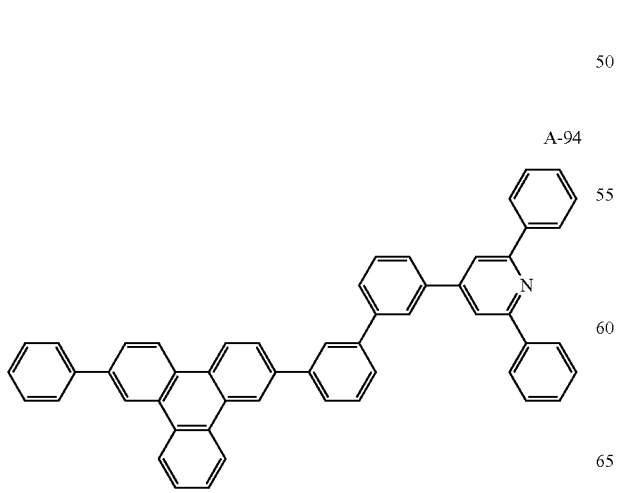
A-95
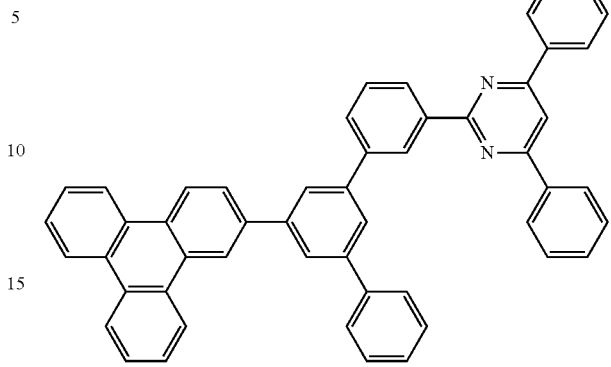
A-96
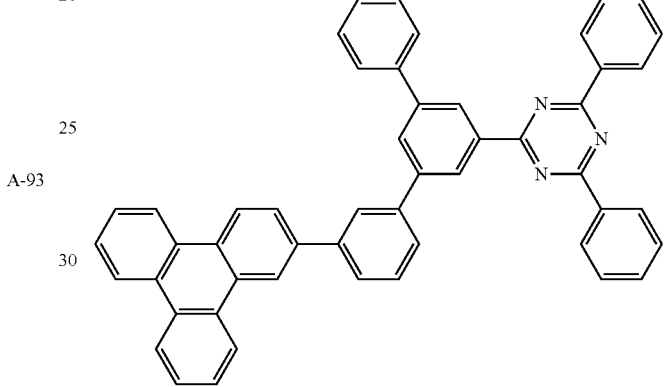
A-97
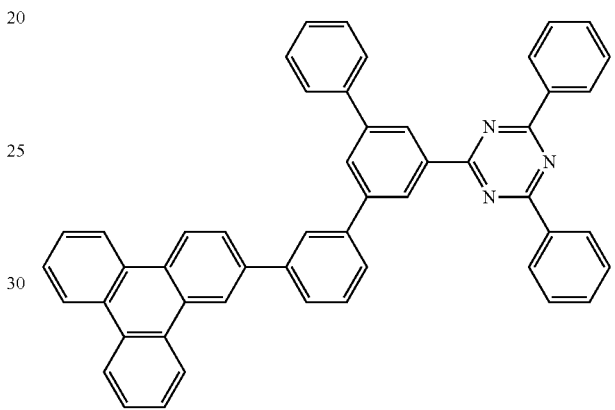
A-98
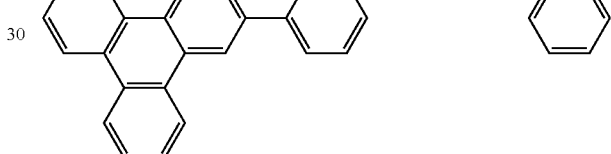

-continued
A-99
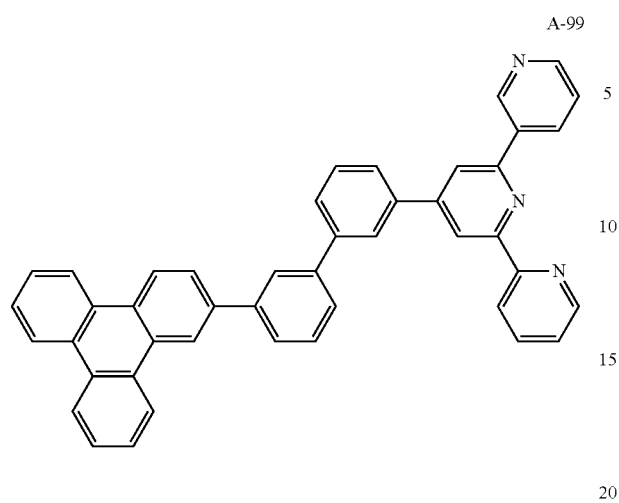
A-100
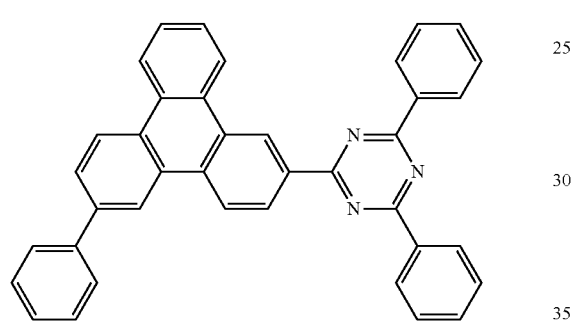
A-101
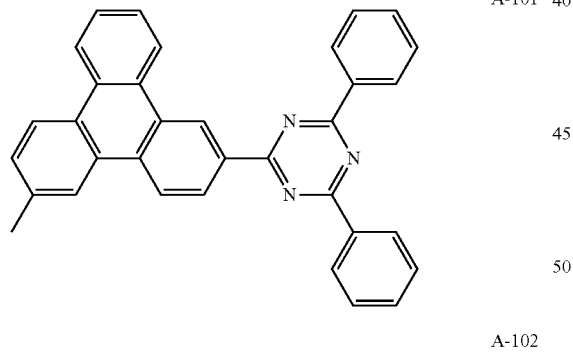
A-102
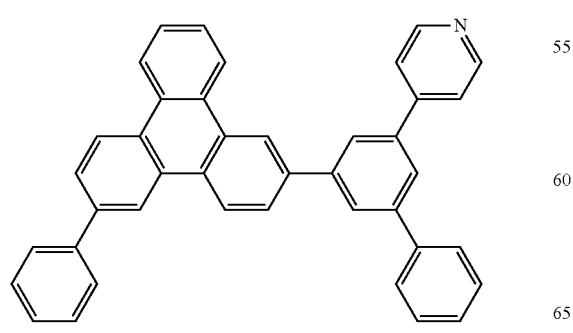
A-103
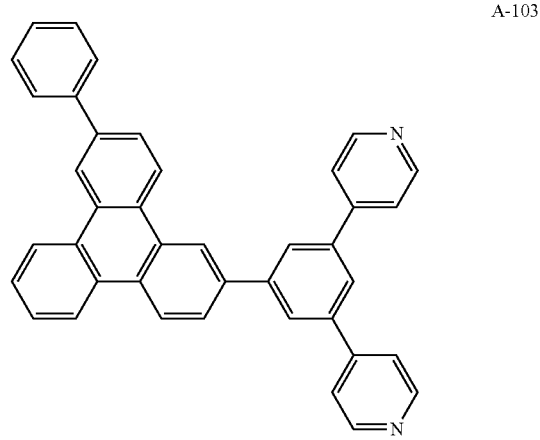
A-104
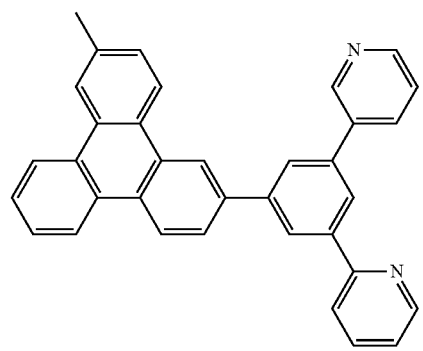
A-105
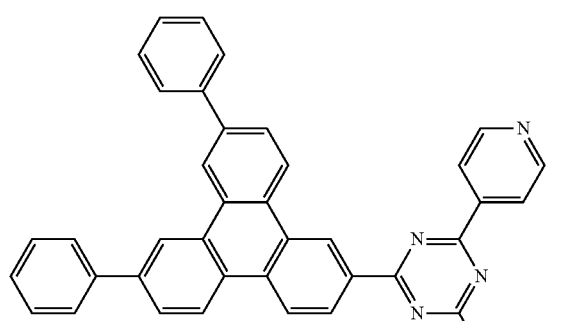
A-106
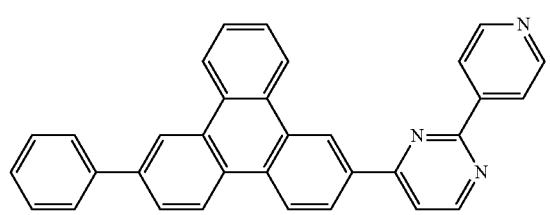

-continued
A-107
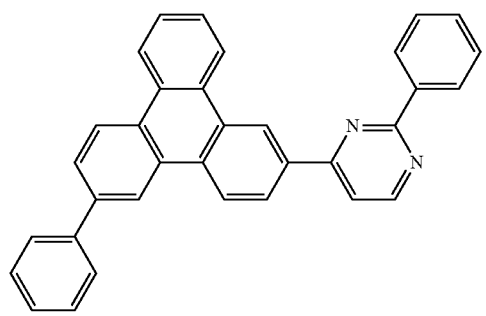
A-108
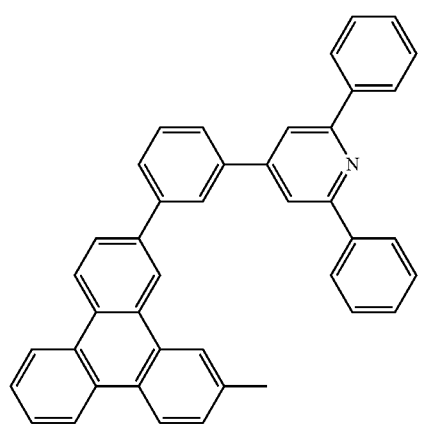
A-109
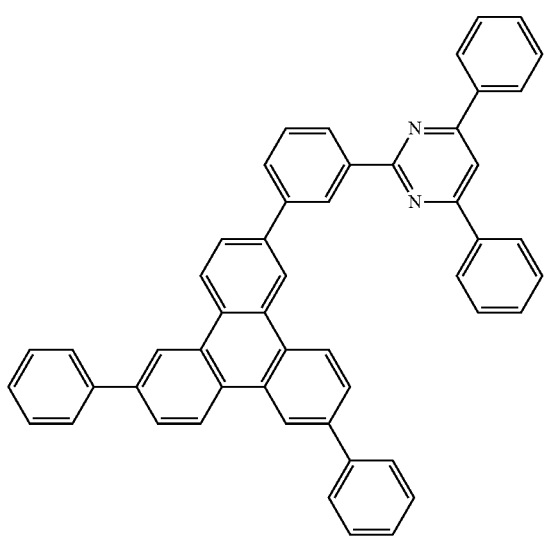
-continued
A-110
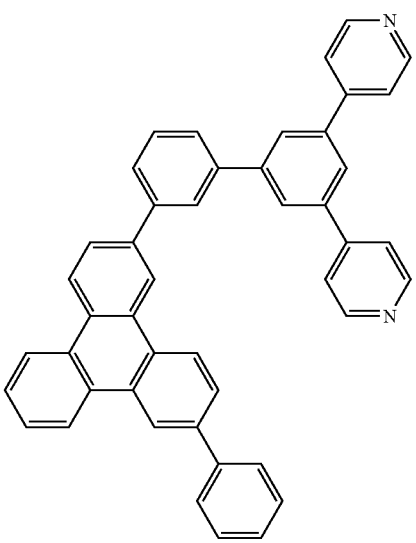
A-111
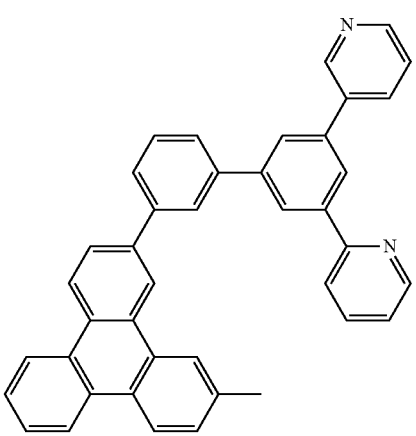
A-112
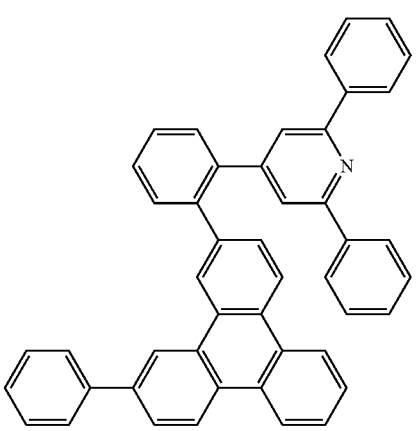

A-113
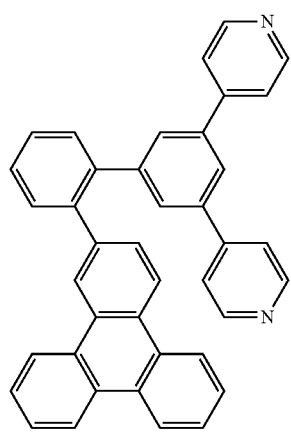
A-114
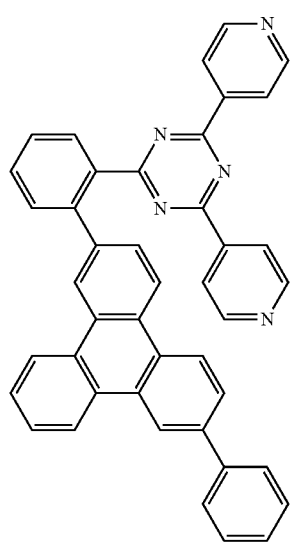
A-115
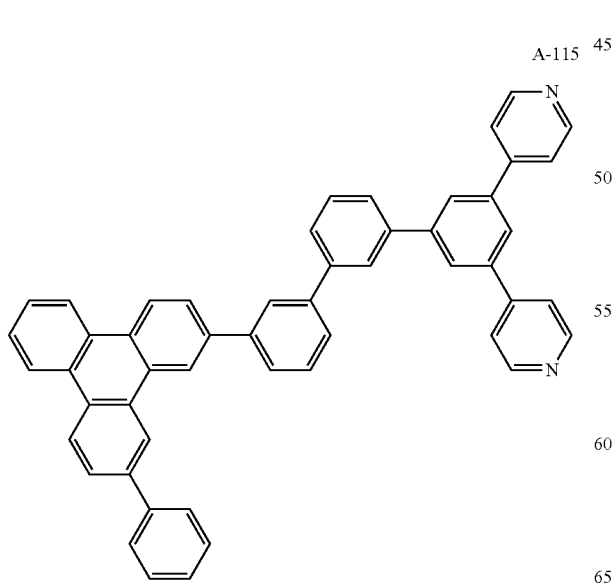
A-116
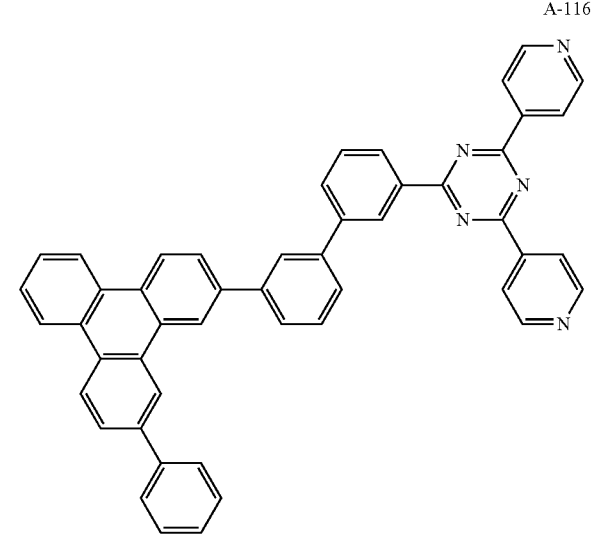
A-117
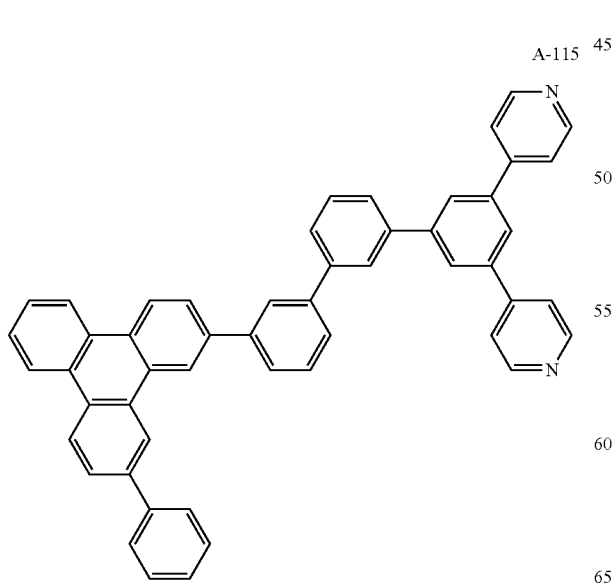
A-118
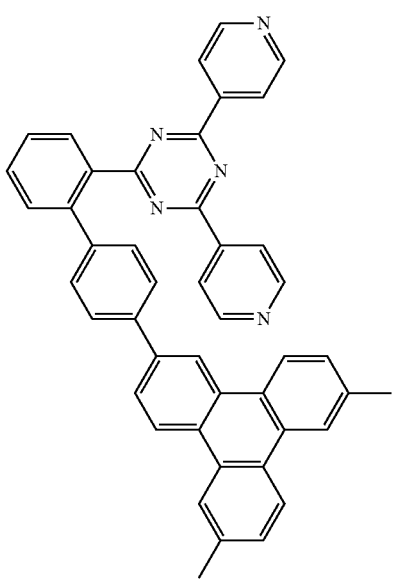

A-119
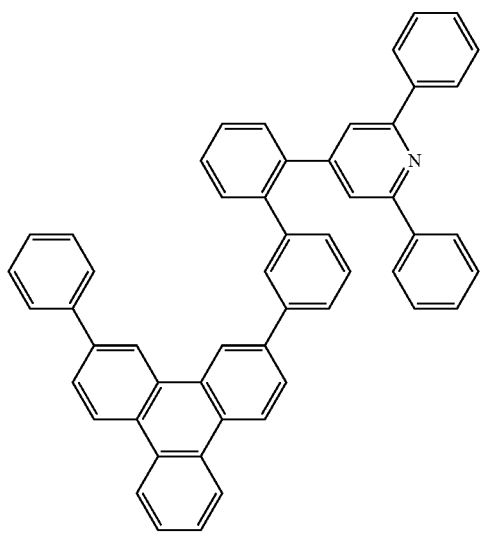
A-120
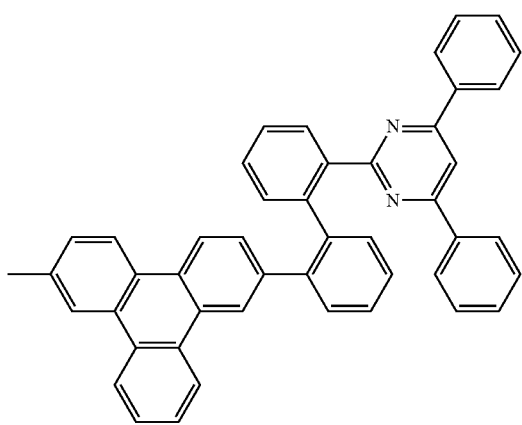
A-121
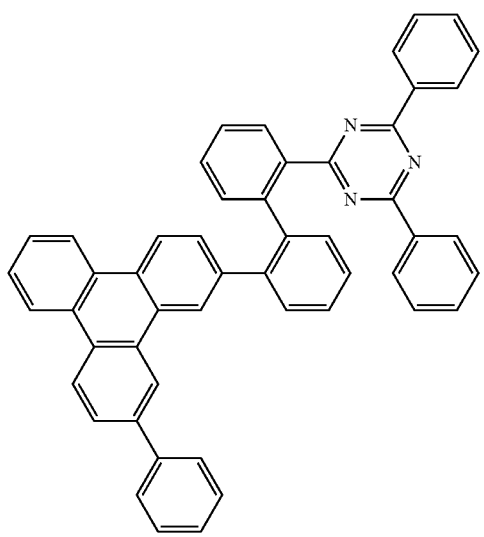
A-122
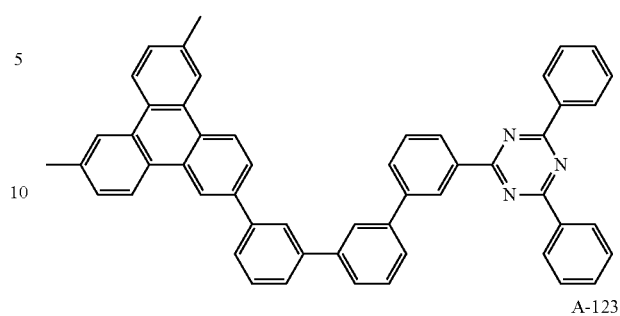
A-123
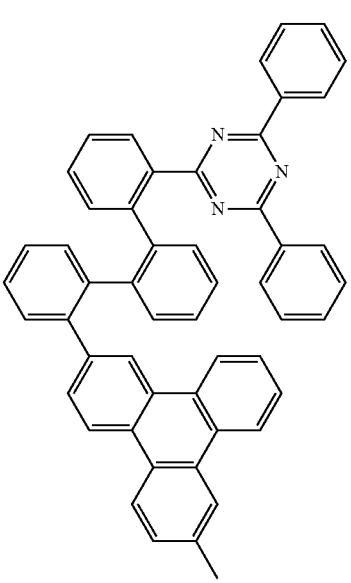
A-124
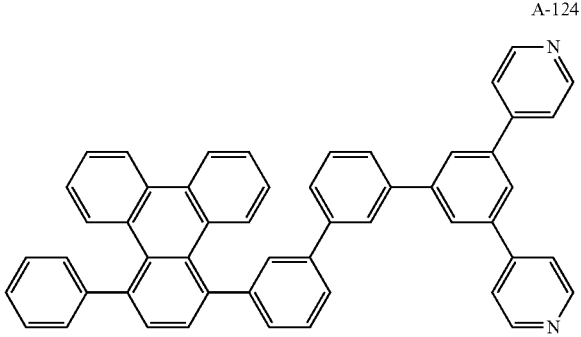
A-125
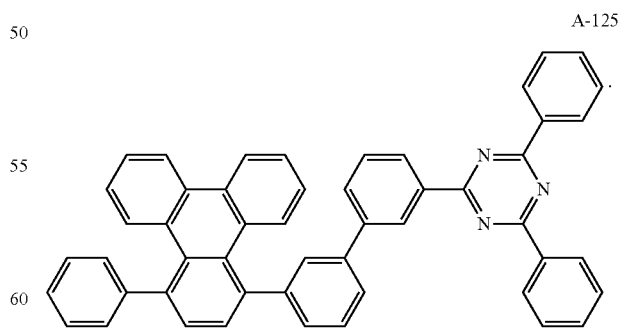
In one embodiment, the second host and the fourth host may each independently be selected from Compounds B-10 to B-35, B-37 to B-38, B-40, B-41, B-43 to B-13, Compounds C-10 to C-33, and Compounds D-10 to D-29, but embodiments of the present disclosure are not limited thereto:
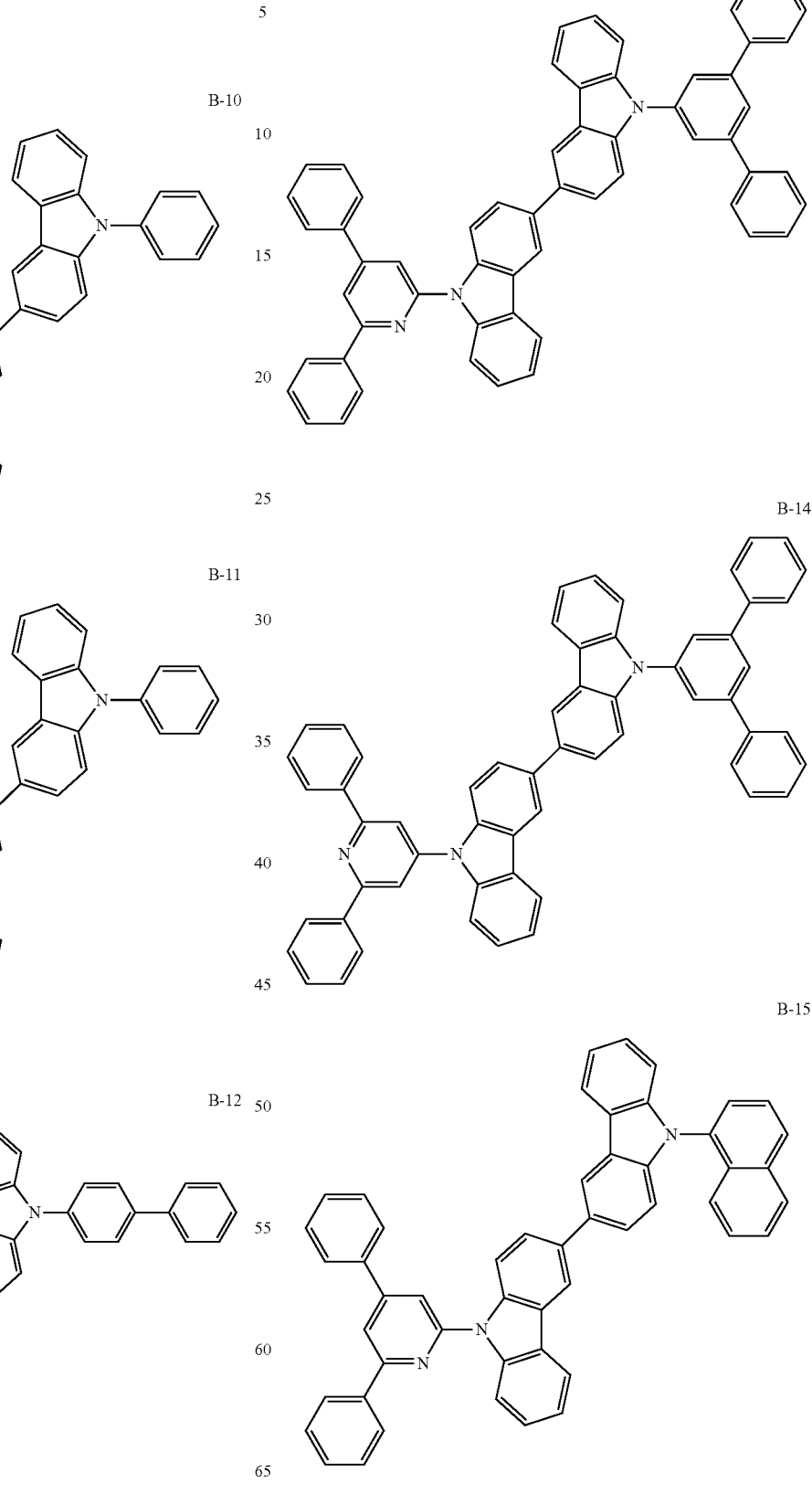

B-16
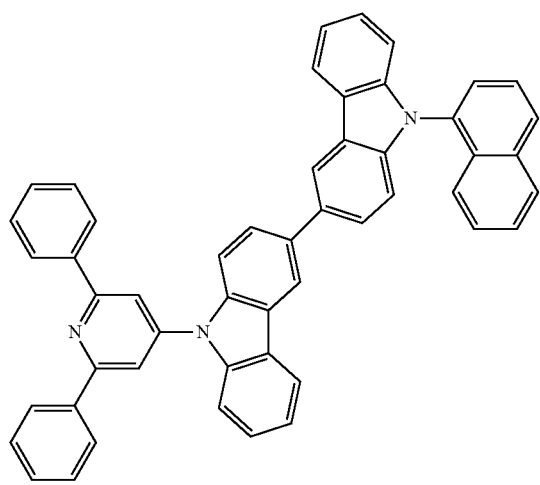
B-17
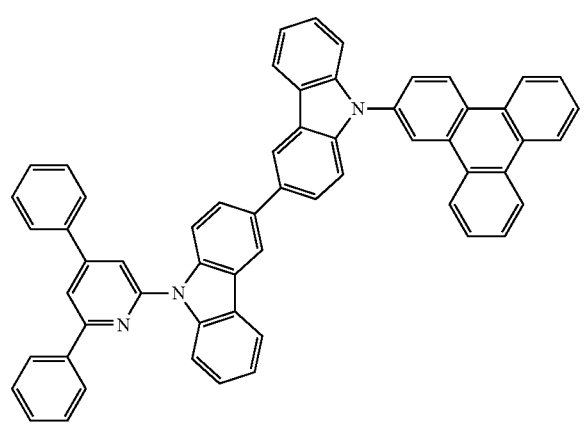
B-18
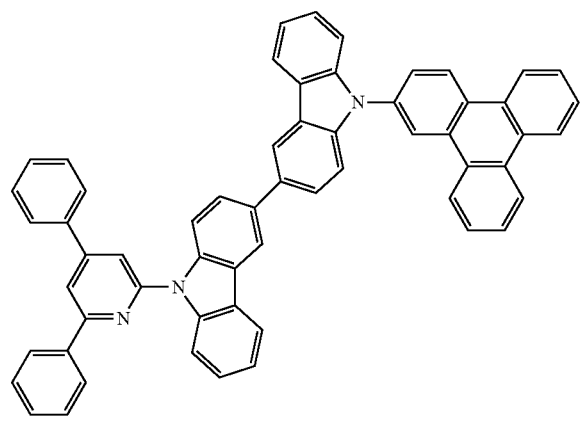
B-19
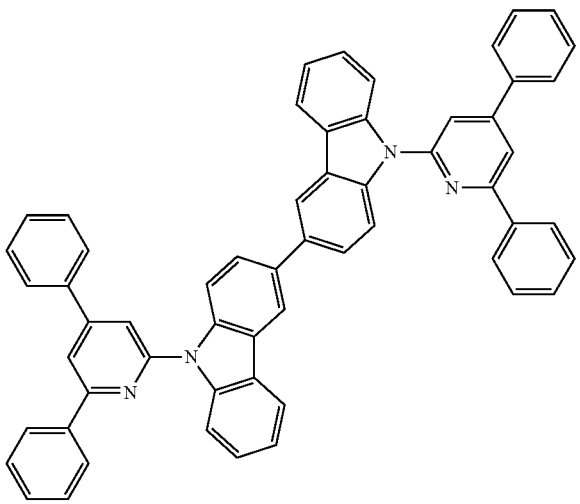
B-20
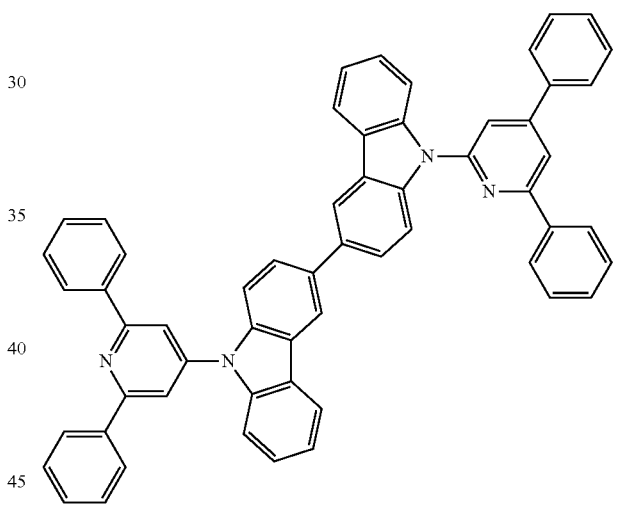
B-21
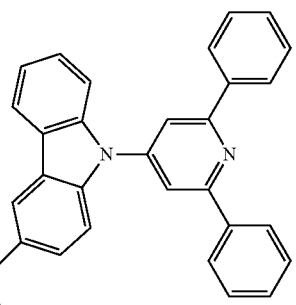

B-22
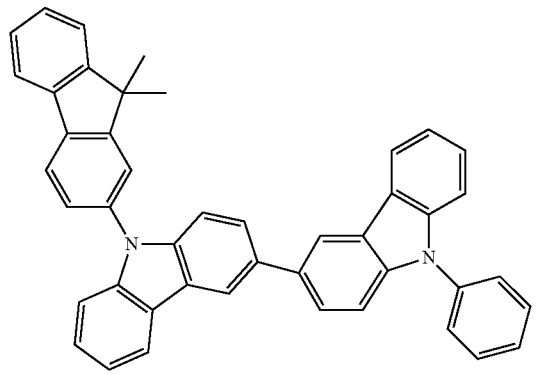
B-25
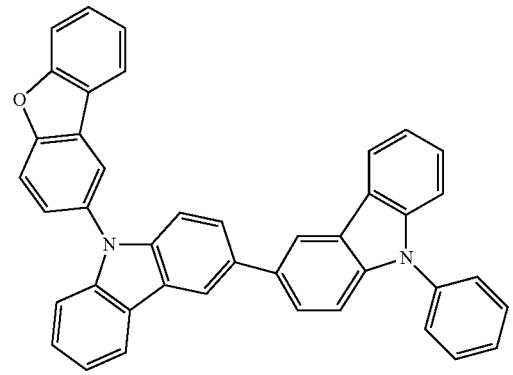
B-23
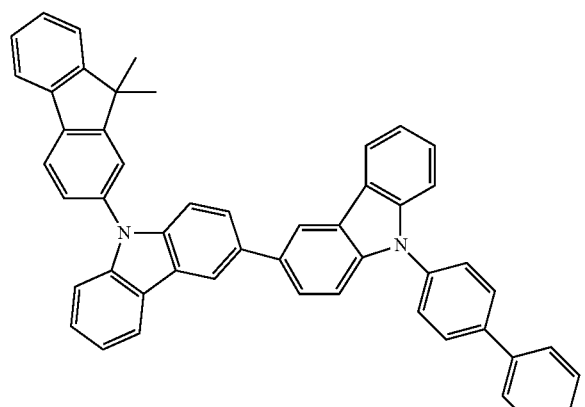
B-26
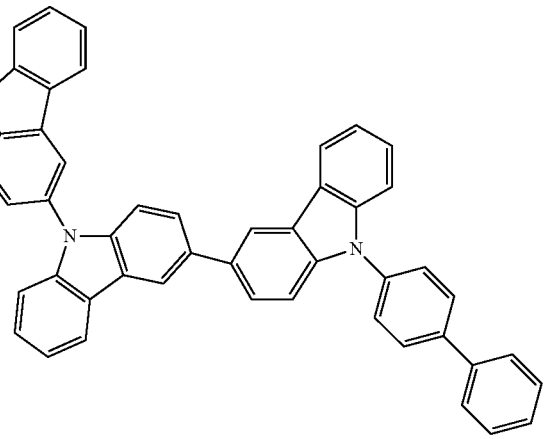
B-24
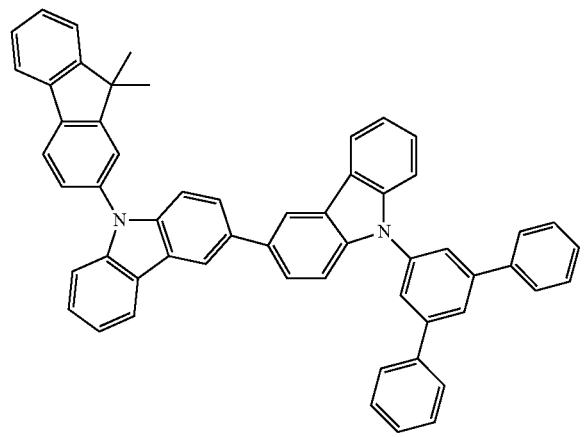
B-27
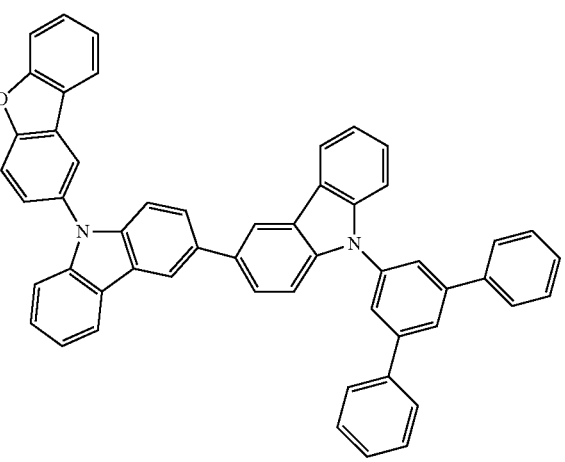

B-28
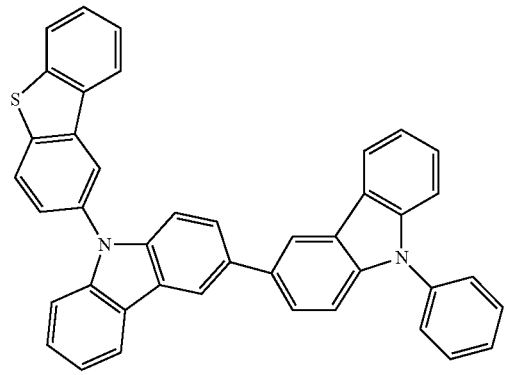
B-31
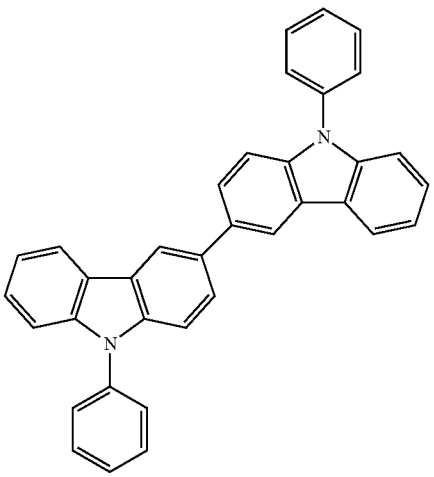
B-29
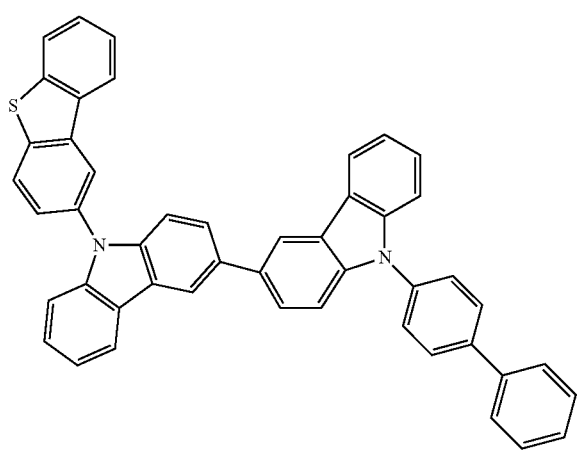
B-32
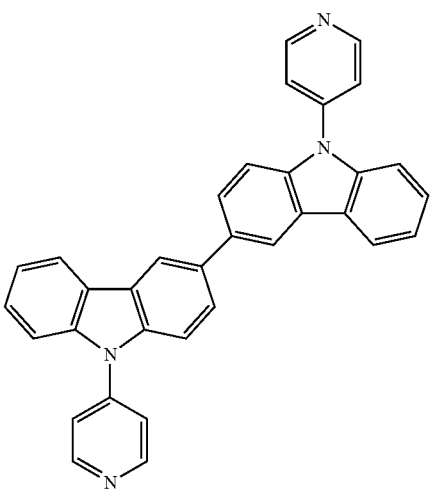
B-30
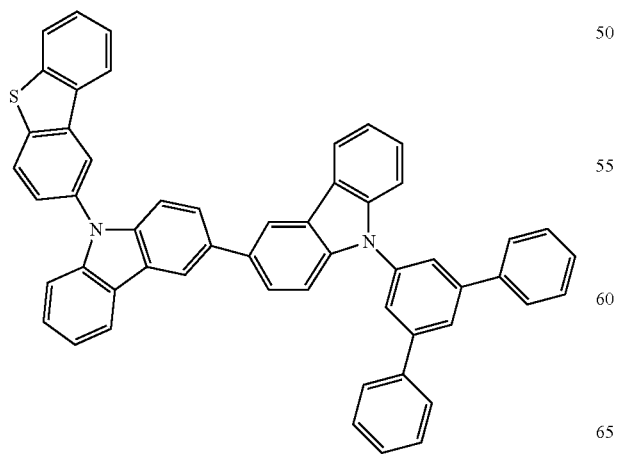
B-33
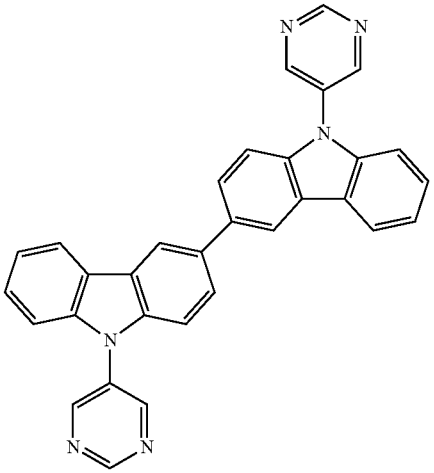

B-34
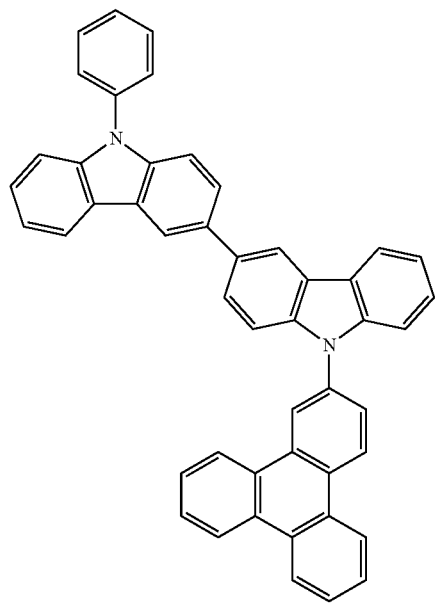
B-37
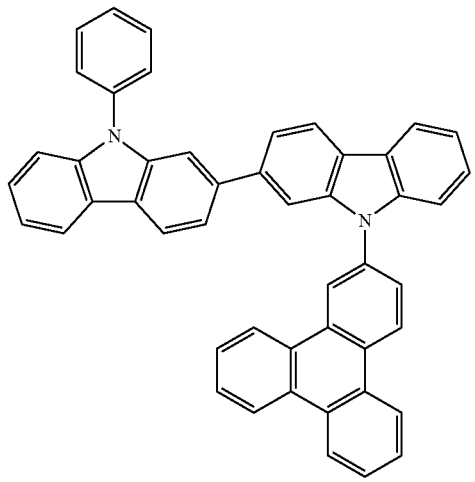
B-38
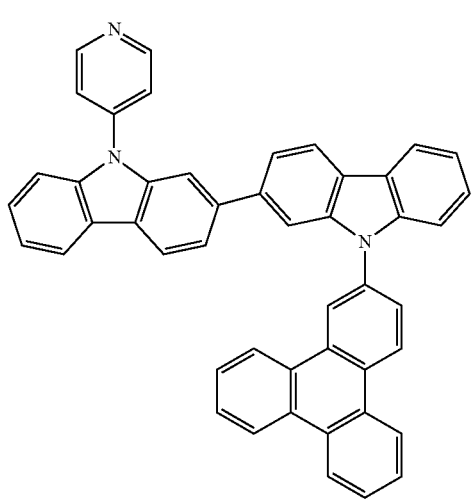
B-35
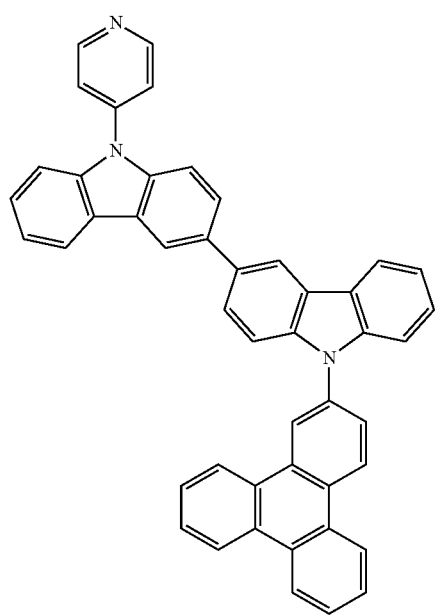
B-40
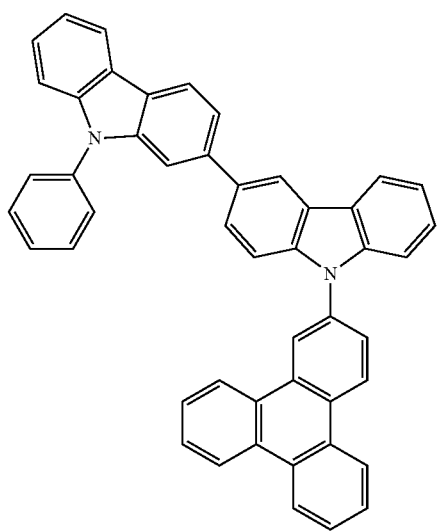

B-41
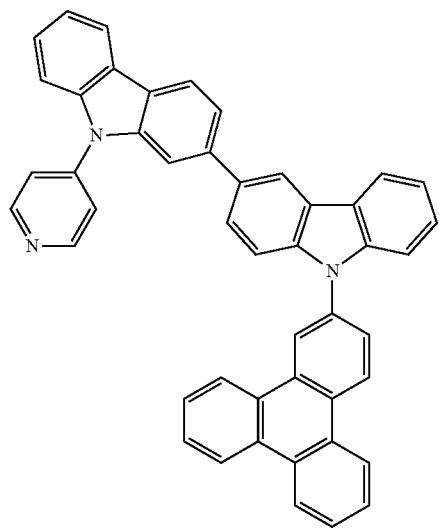
B-44
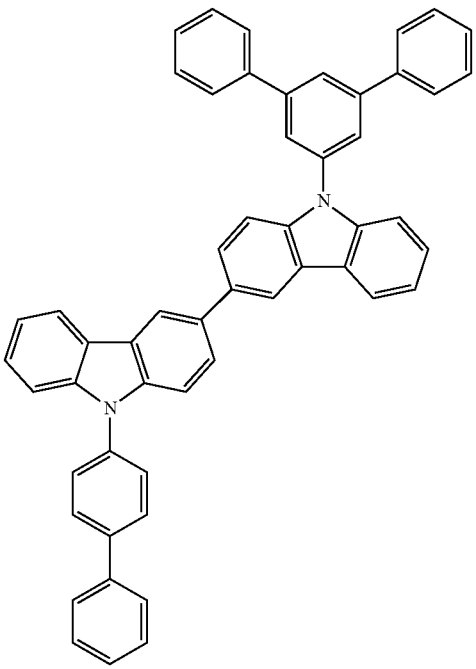
B-43
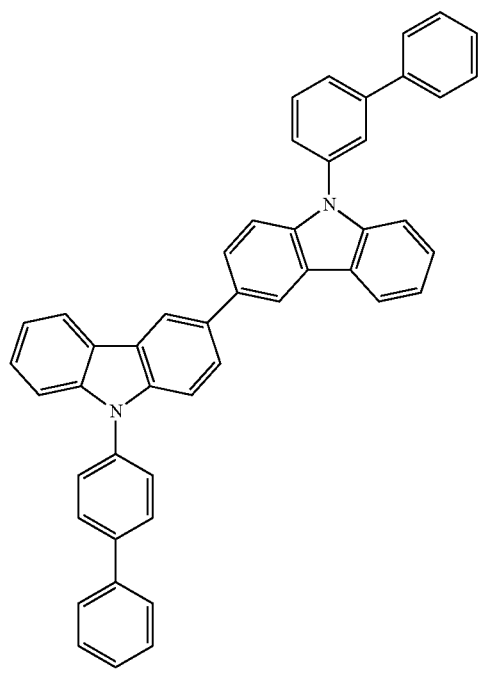
B-45
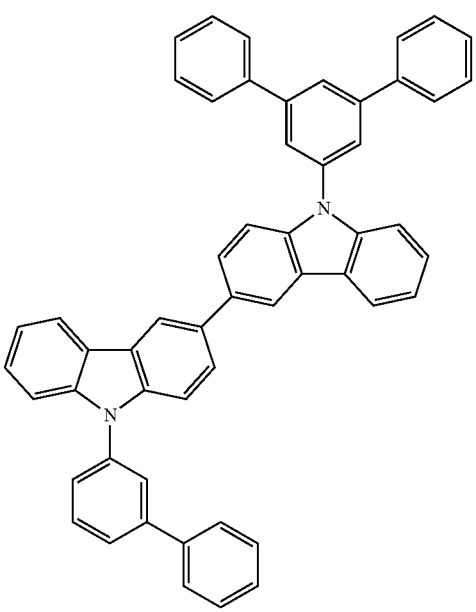

B-46
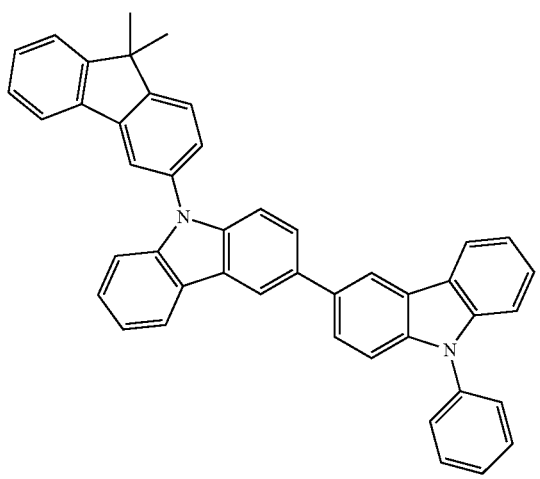
B-47
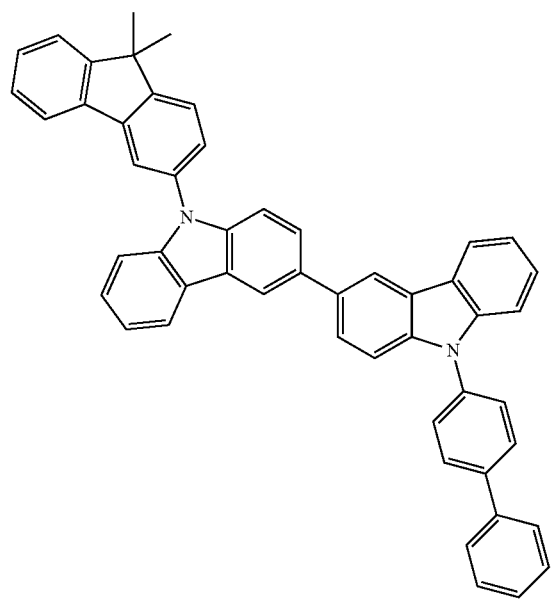
B-48
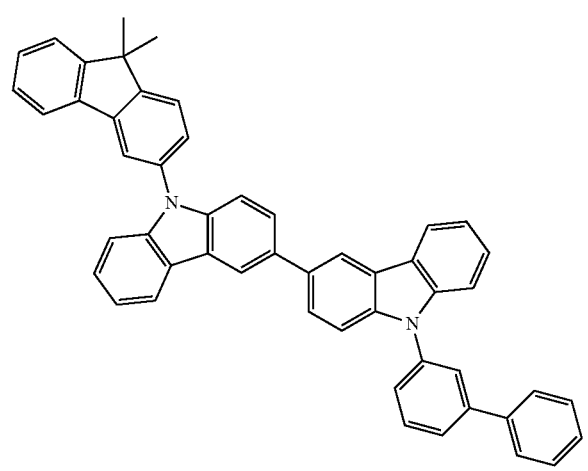
B-49
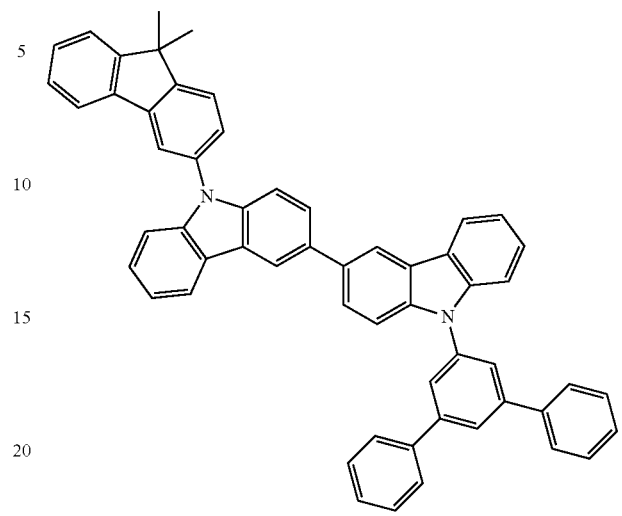
B-50
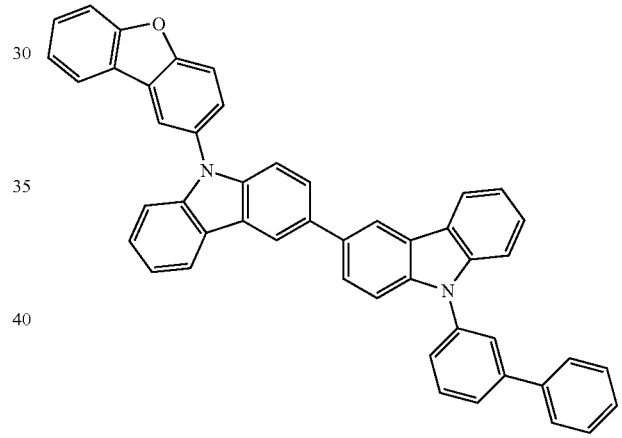
B-51

-continued
B-52
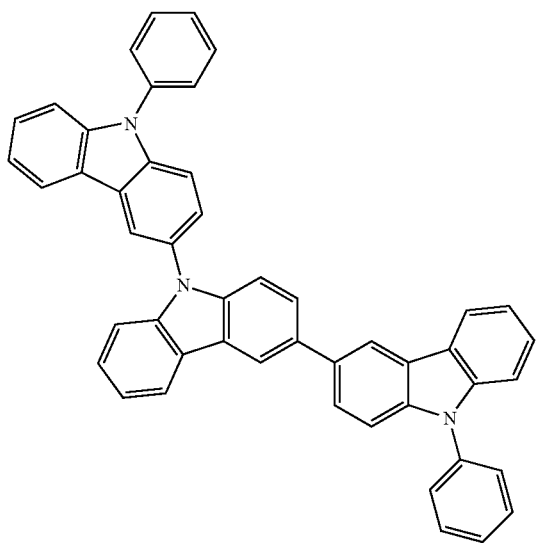
B-53
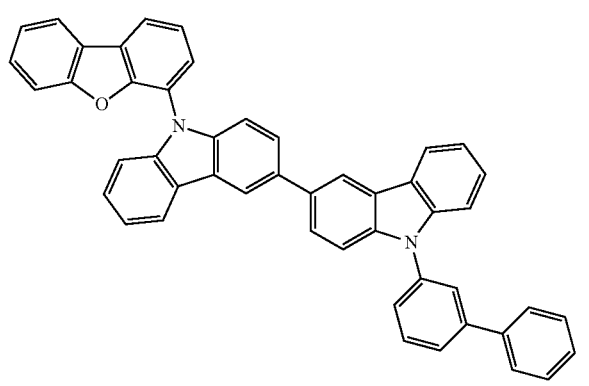
B-54
-continued
B-55
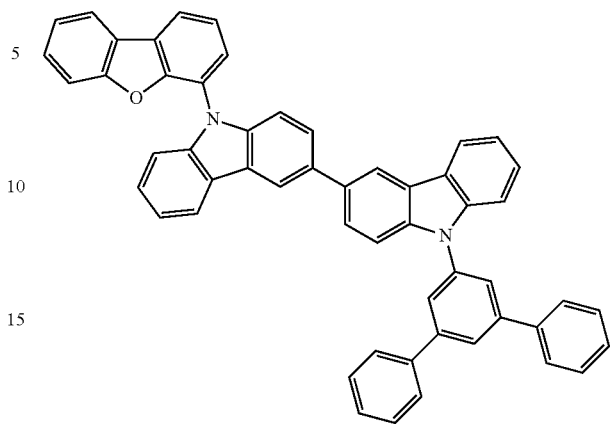
B-56
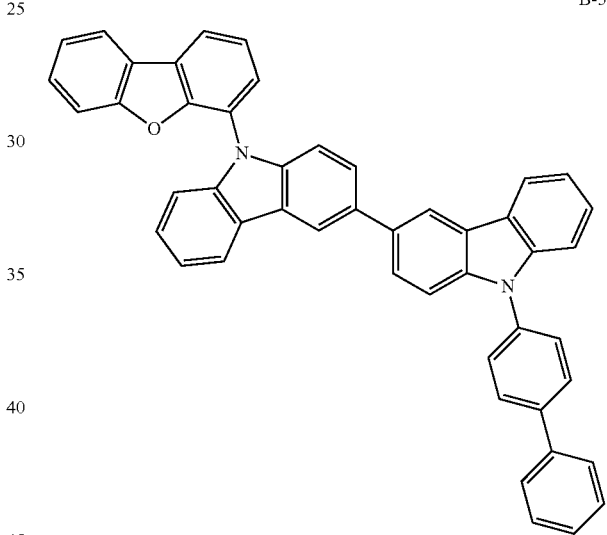
B-57
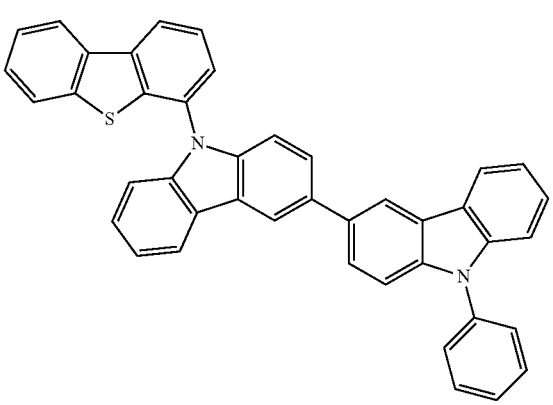

B-58
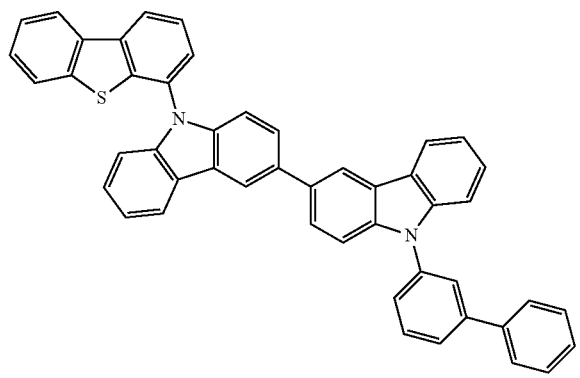
B-59
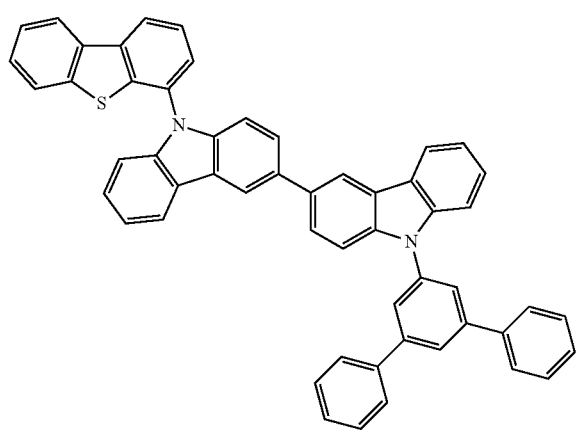
B-60
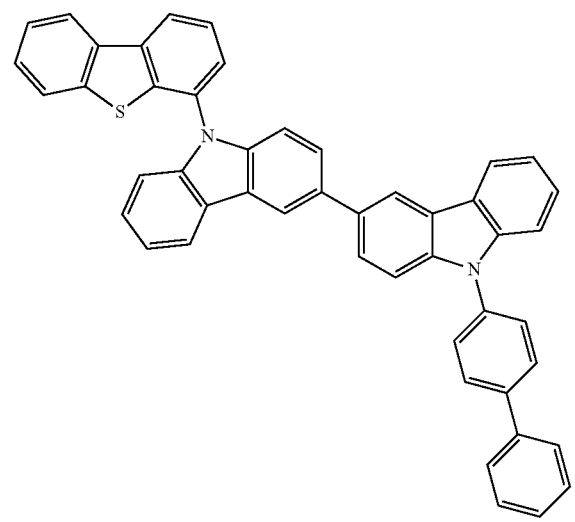
B-61
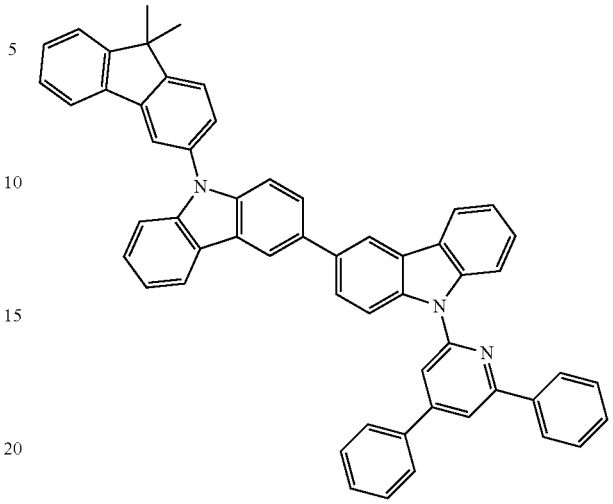
B-62
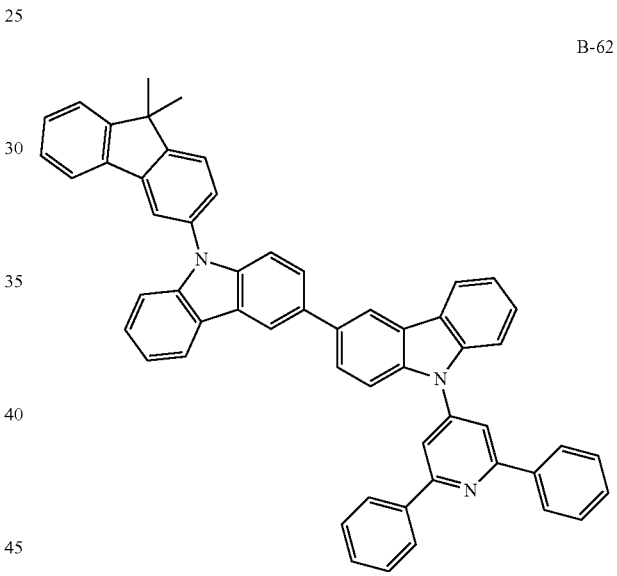
B-63
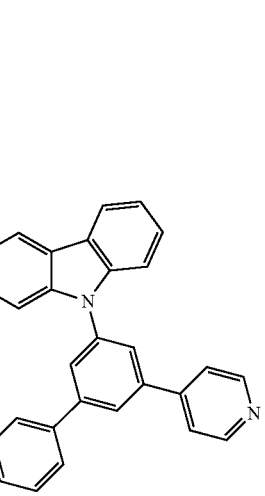

B-64
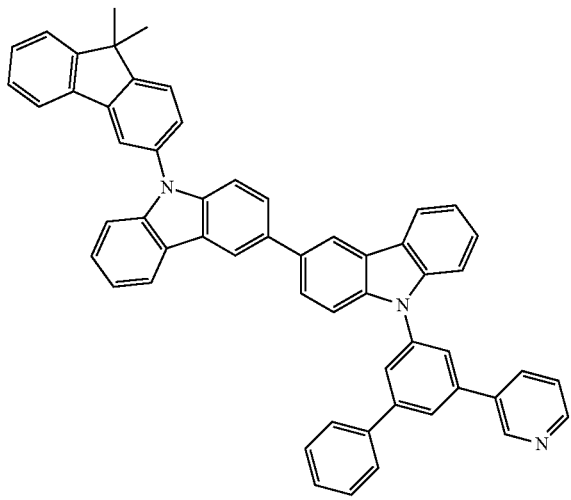
B-67
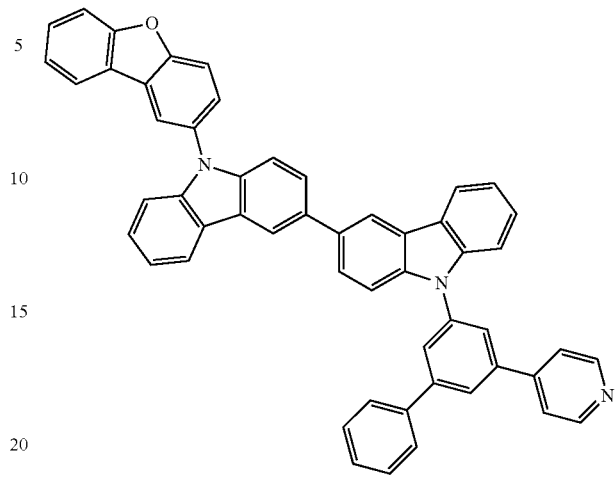
B-65
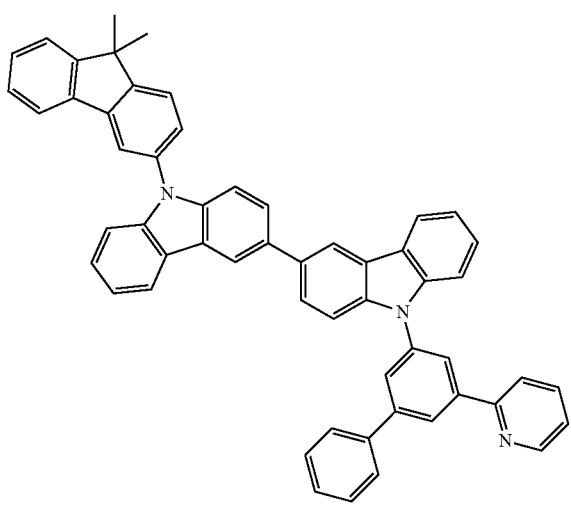
B-68
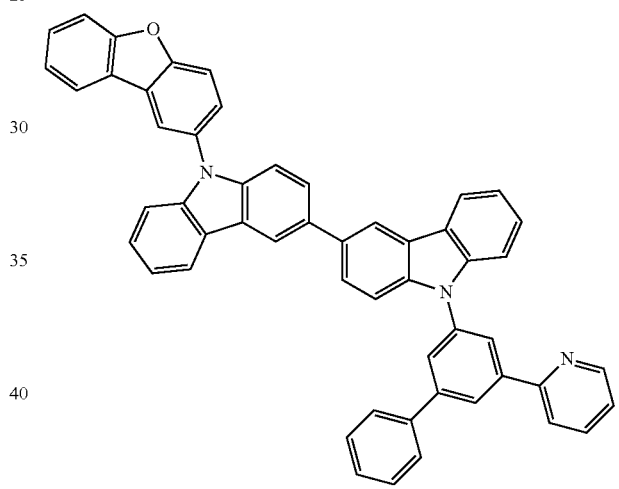
B-66
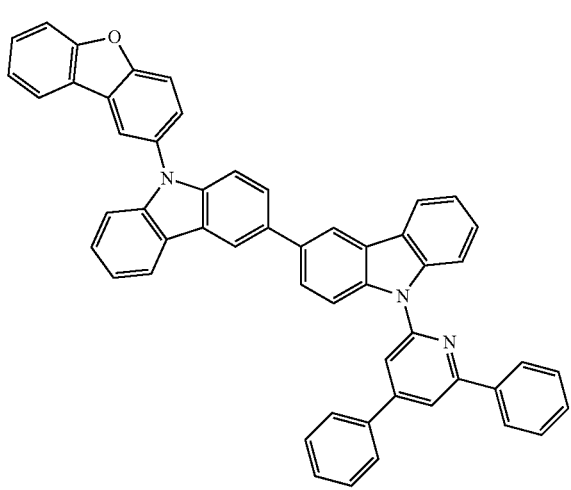
B-69
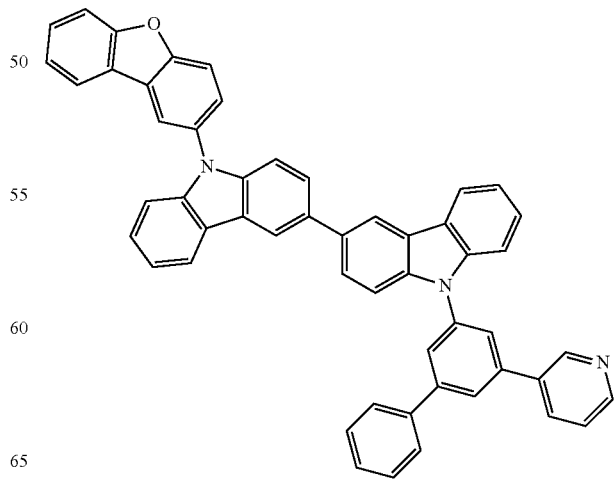

-continued
B-70
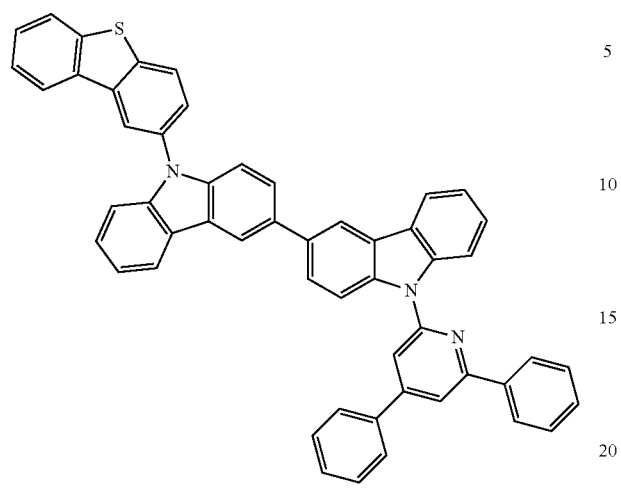
B-71
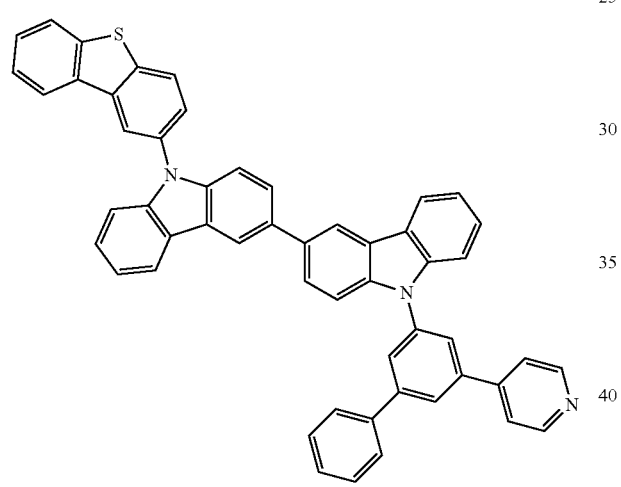
B-72
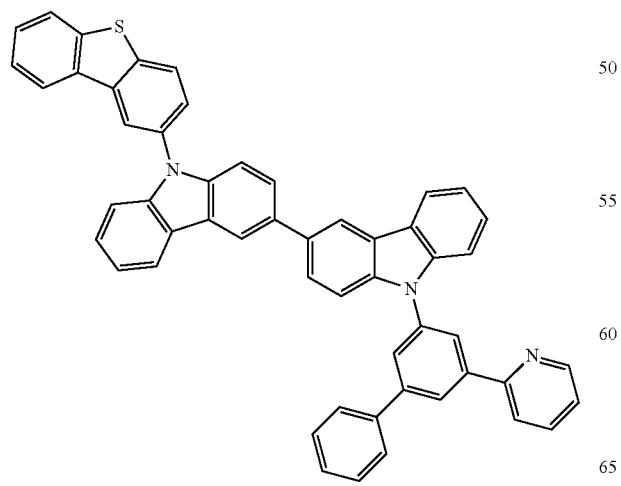
-continued
B-73
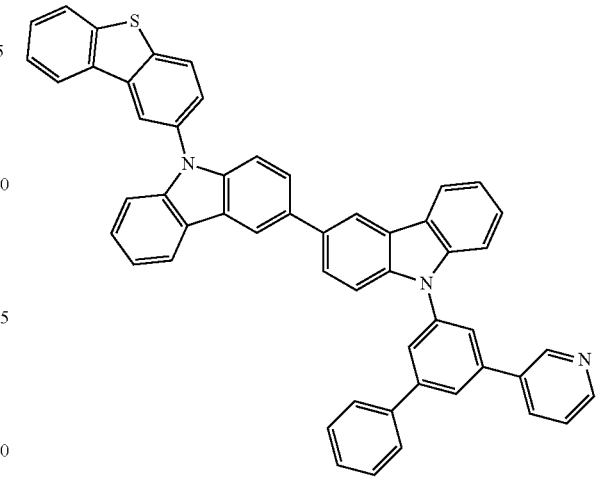
B-74
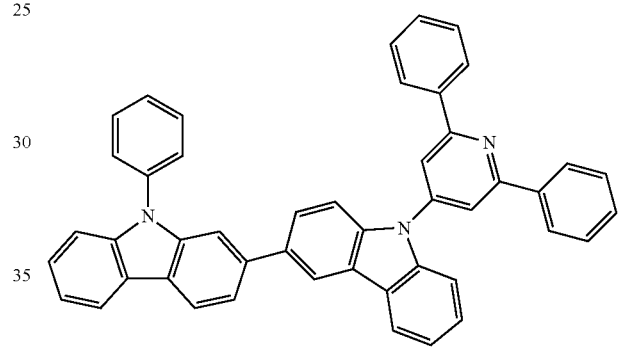
B-75
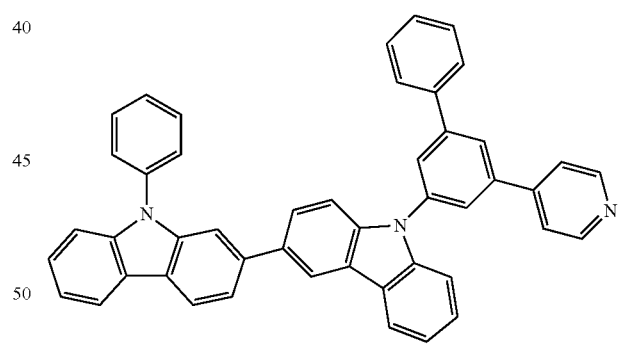
B-76
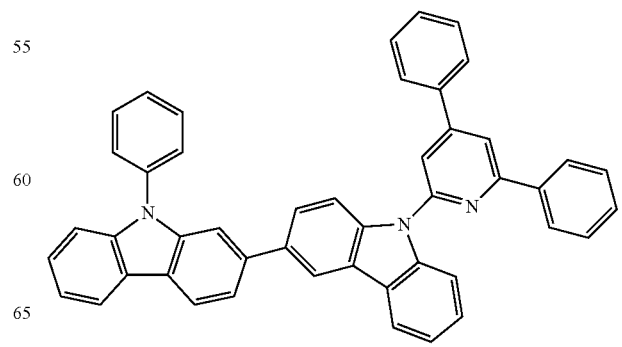

B-77
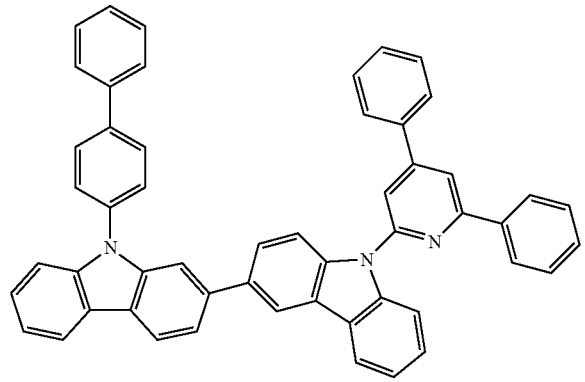
B-78
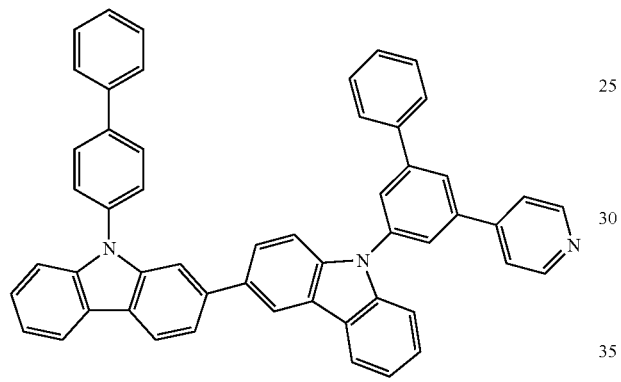
B-79
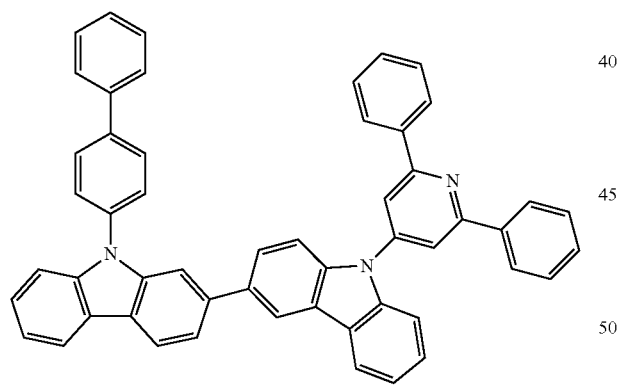
B-80
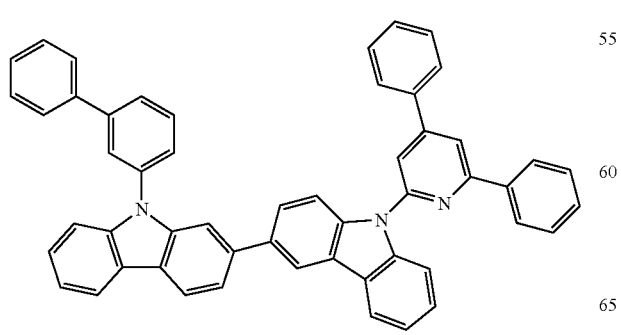
B-81
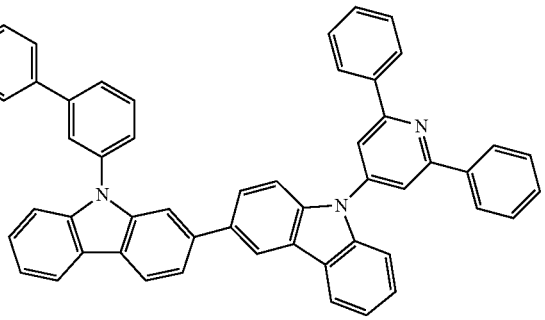
B-82
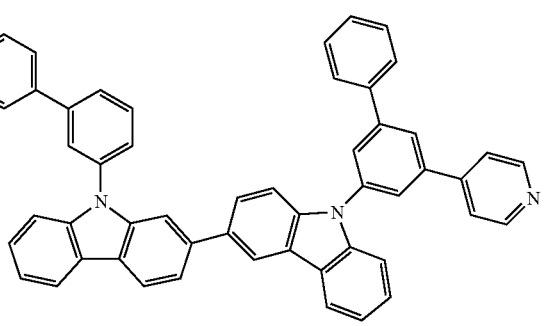
B-83
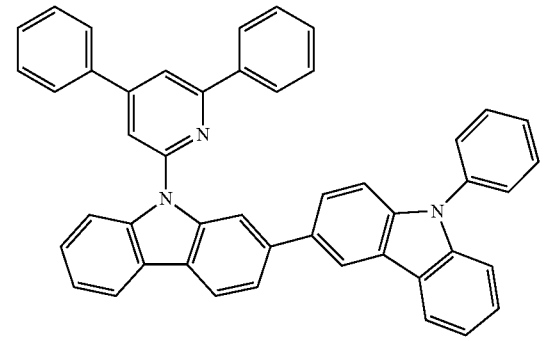
B-84
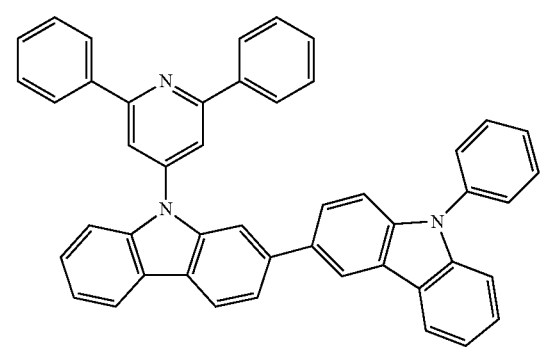

B-85
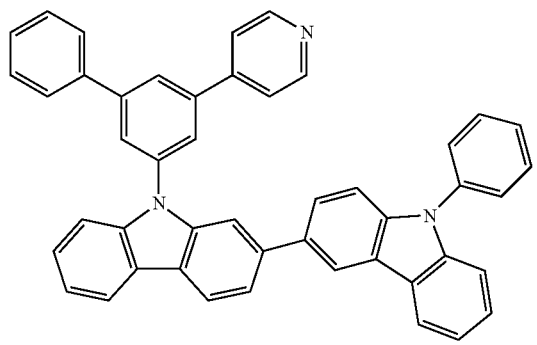
B-86
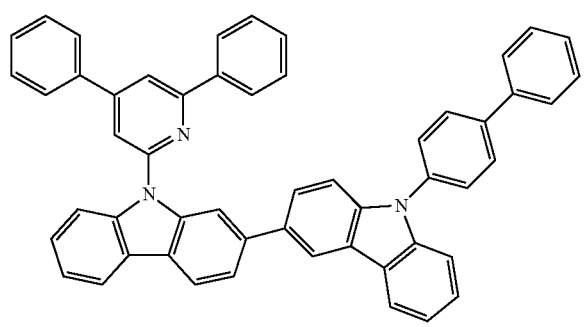
B-87
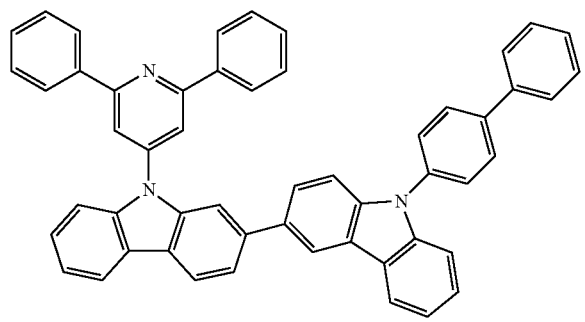
B-88
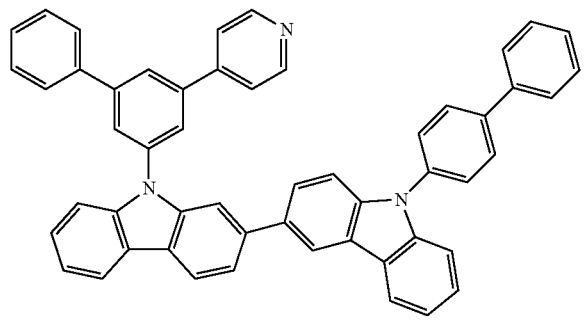
B-89
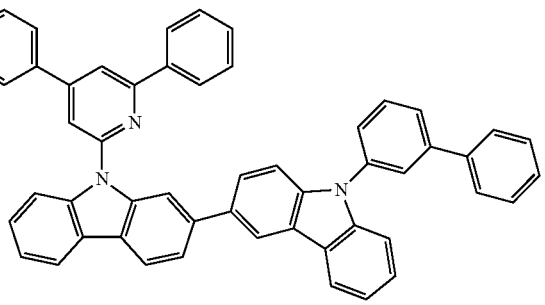
B-90
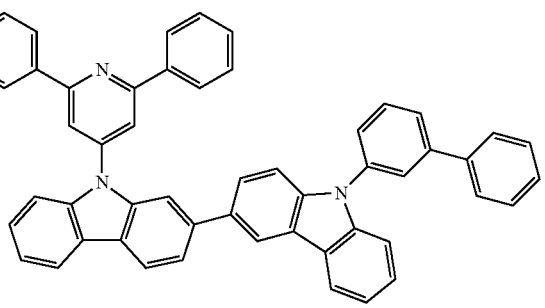
B-91
B-92
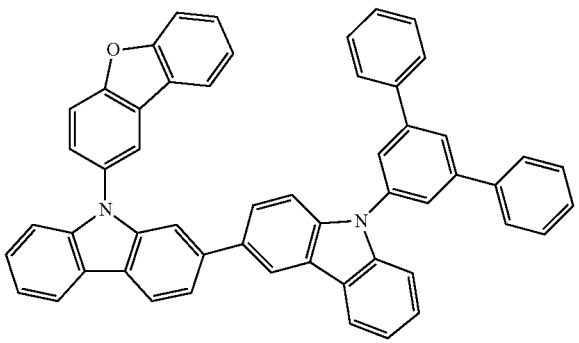

B-93
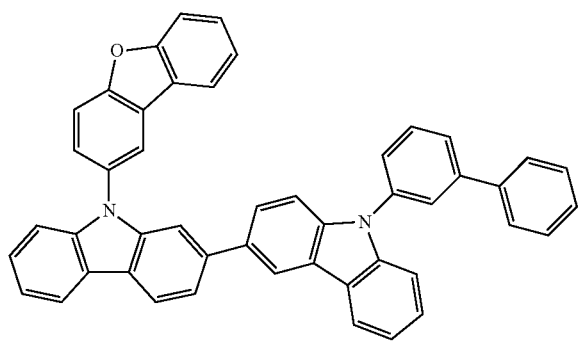
B-97
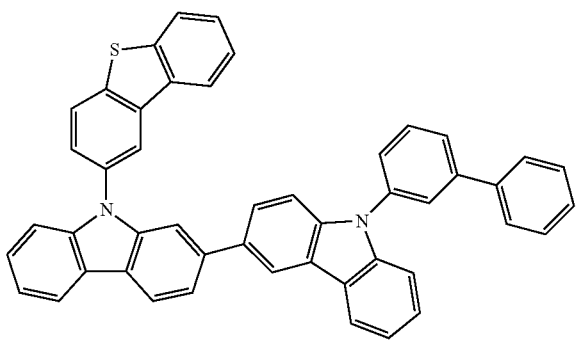
B-94
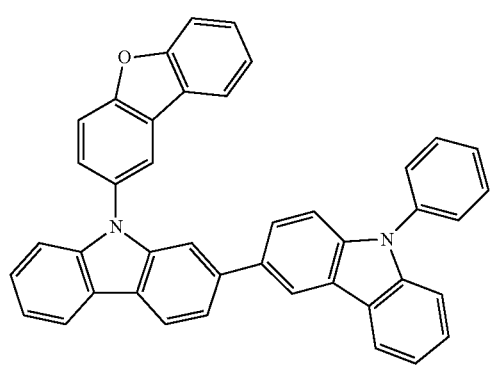
B-98
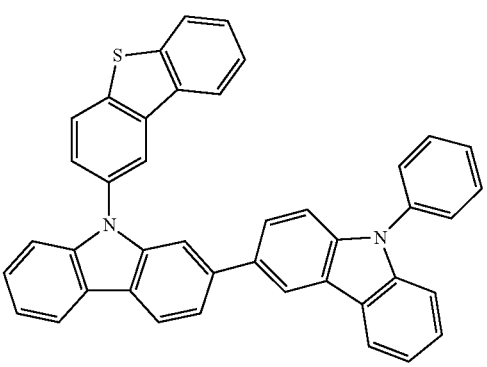
B-95
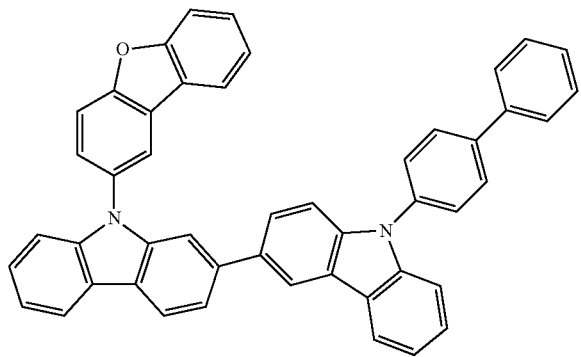
B-99
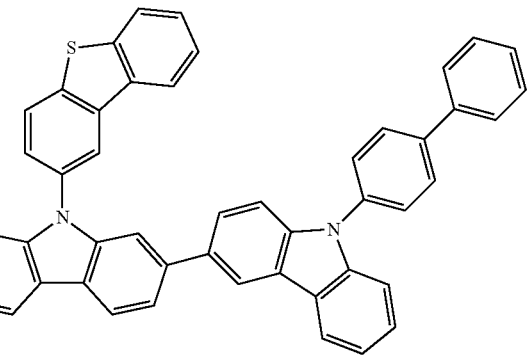
B-96
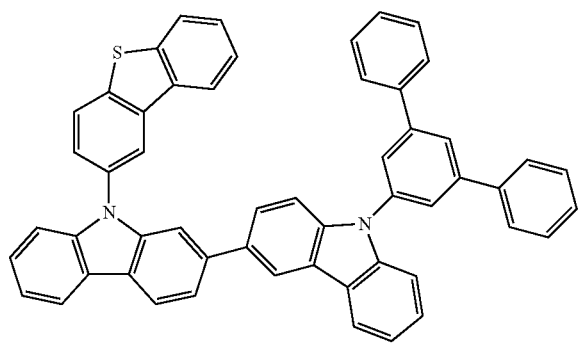
B-100
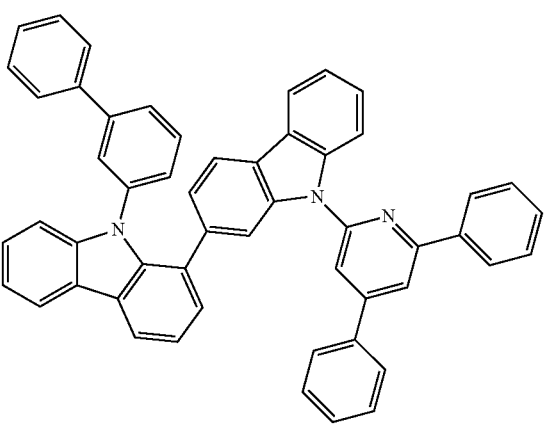

-continued
B-101
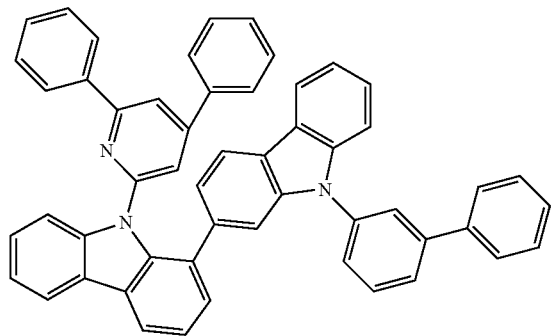
B-105
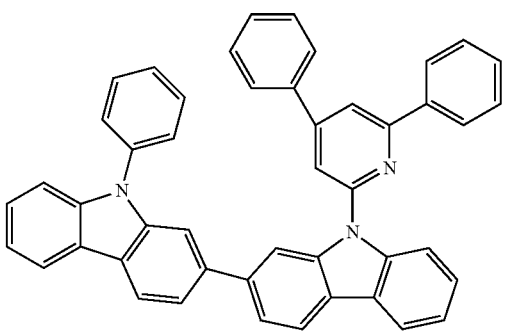
B-102
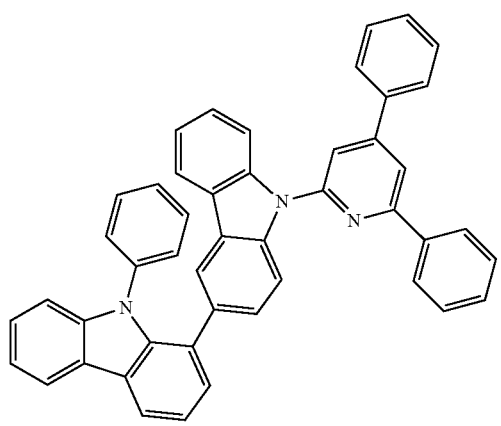
B-106
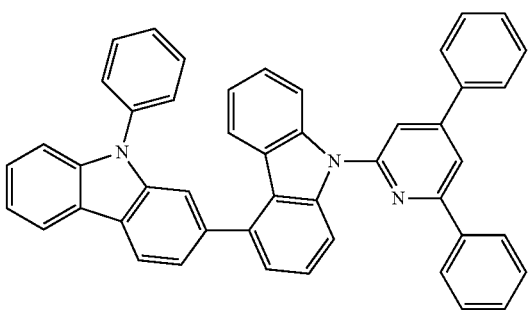
B-103
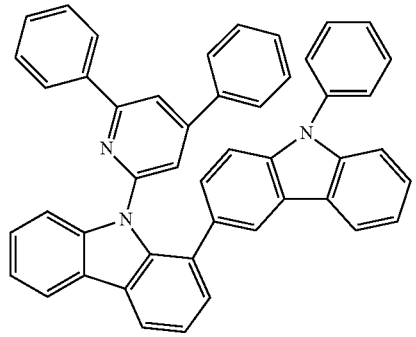
B-107
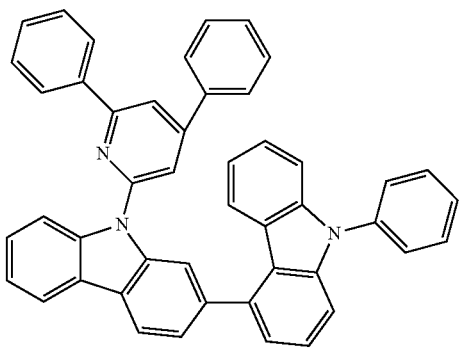
B-104
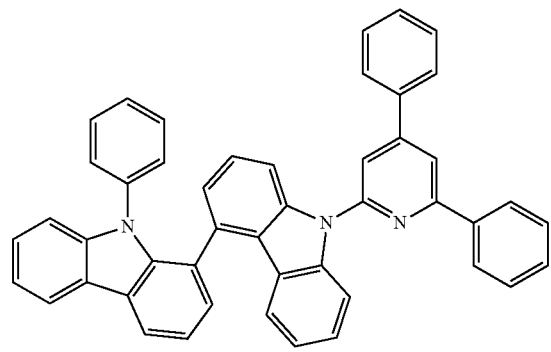
B-108
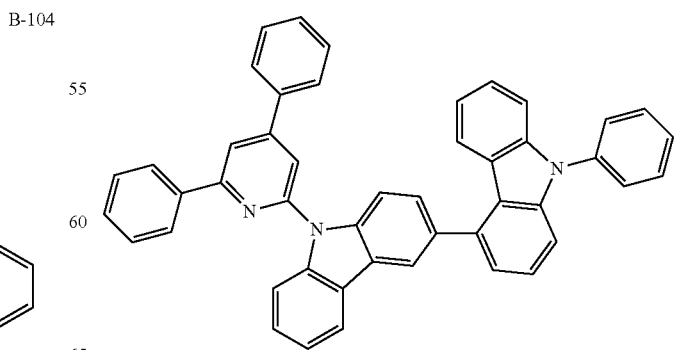

B-109
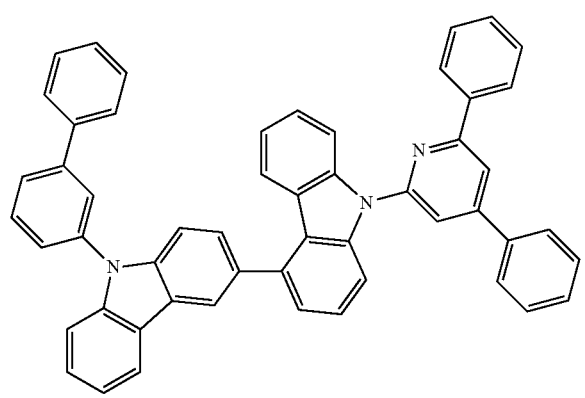
B-110
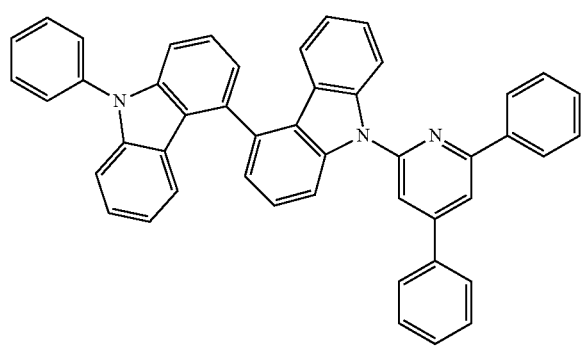
B-111
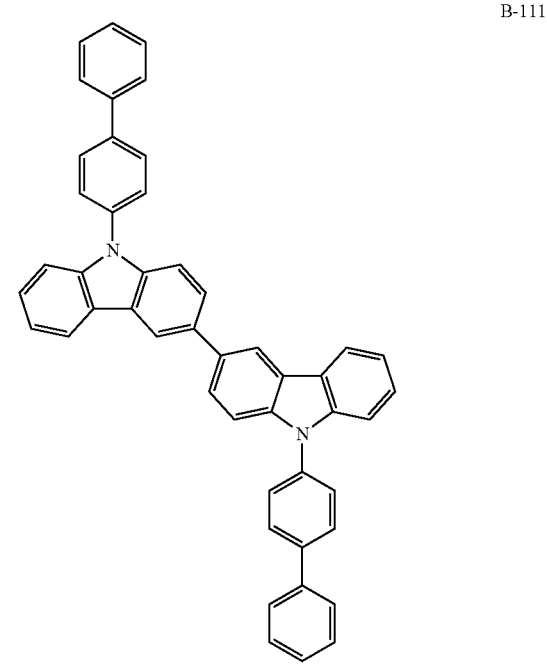
B-112
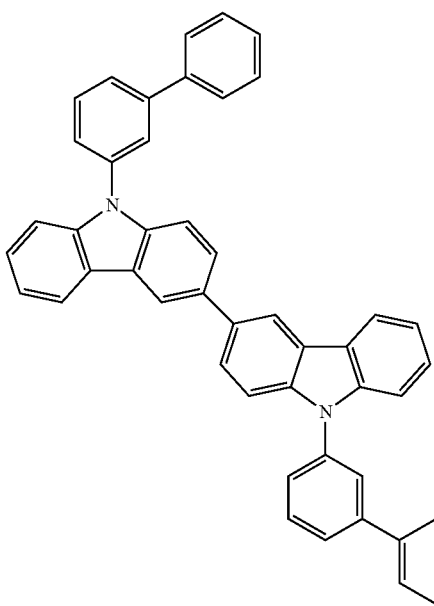
B-113
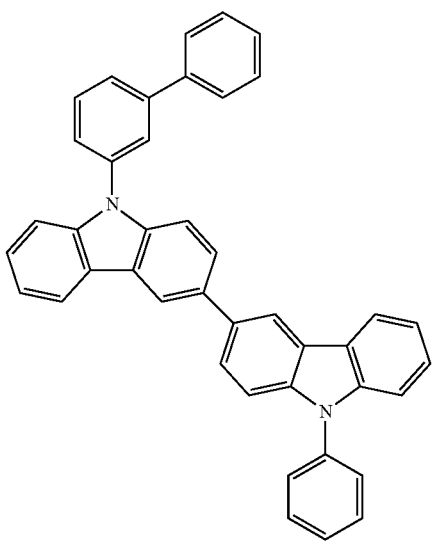
C-10
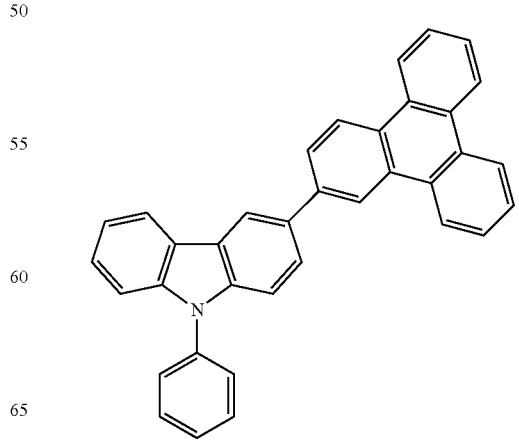

-continued
C-11
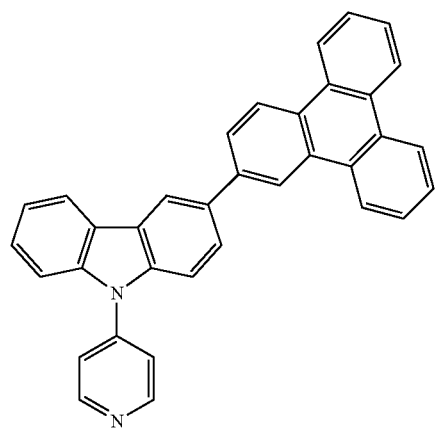
C-12
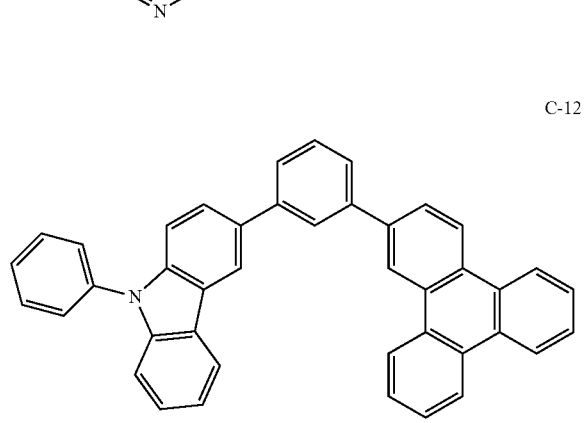
C-13
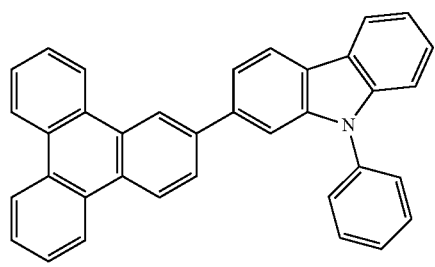
C-14
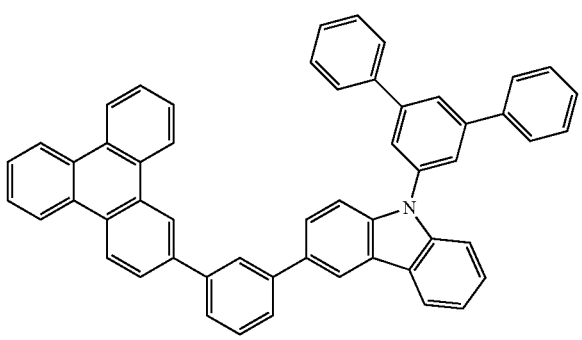
-continued
C-15
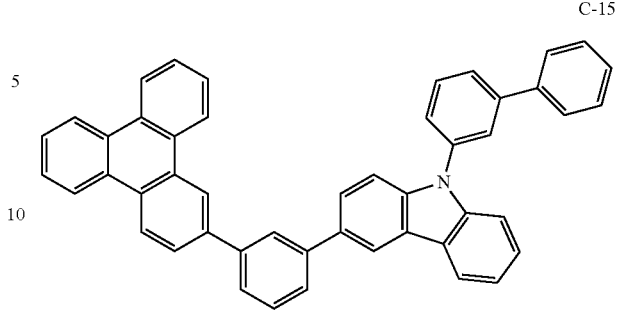
C-16
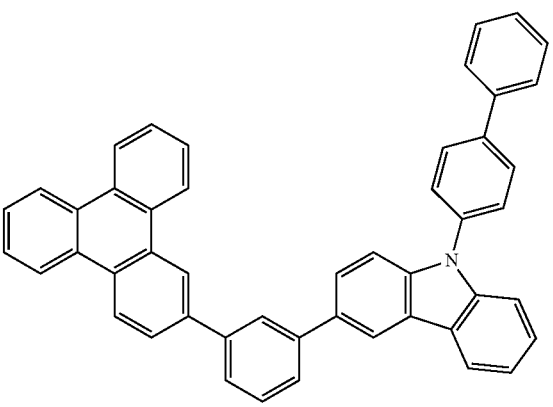
C-17
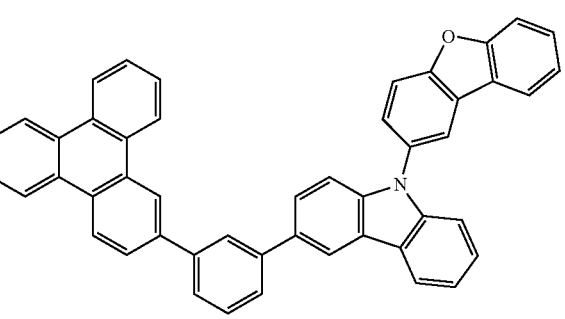
C-18
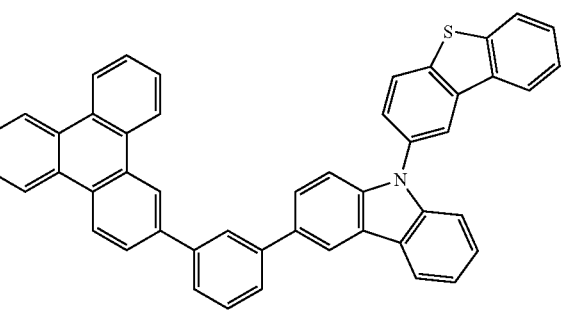

-continued
C-19
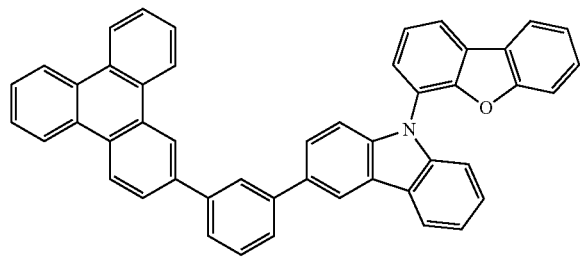
C-20
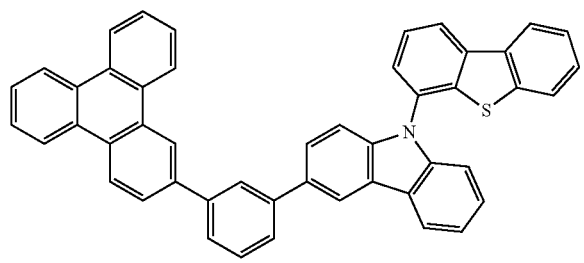
C-21
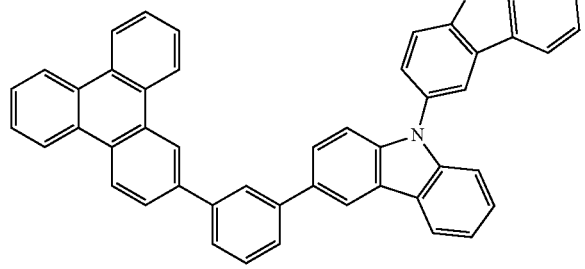
C-22
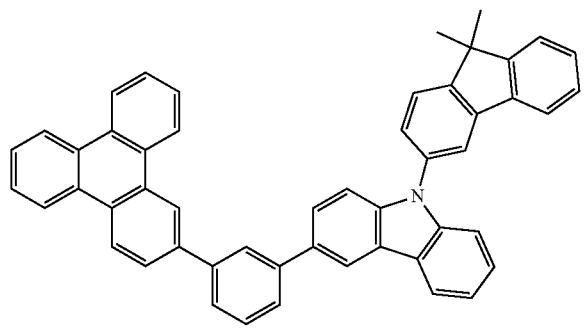
-continued
C-23
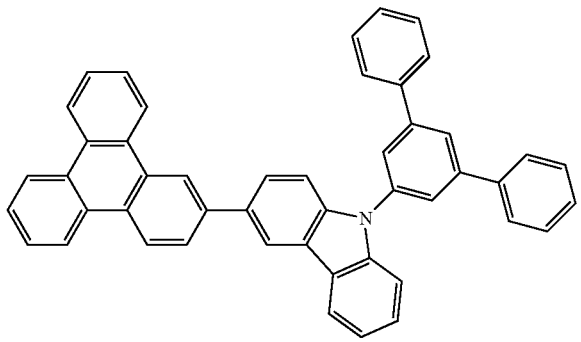
C-24
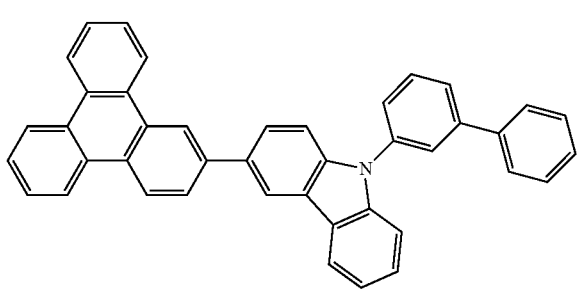
C-25
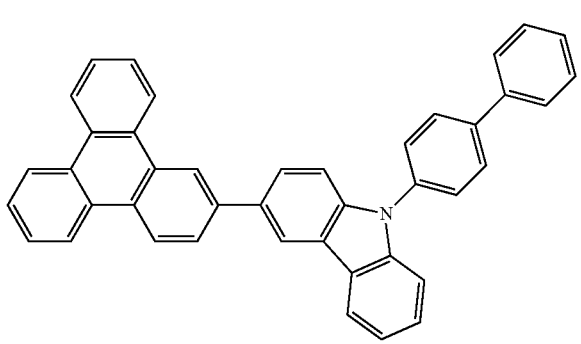
C-26
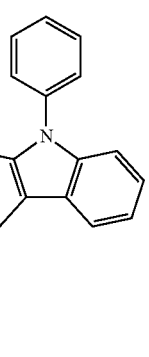

C-27
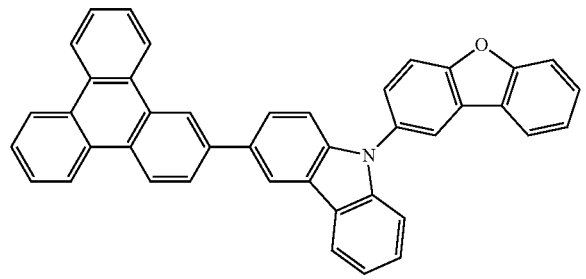
C-28
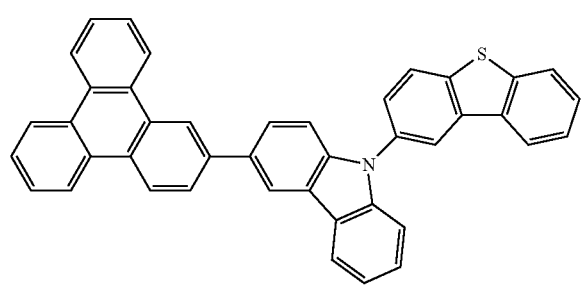
C-29
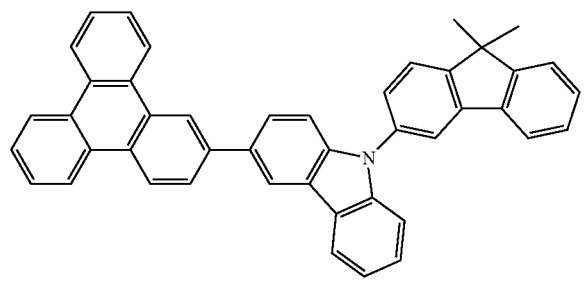
C-30
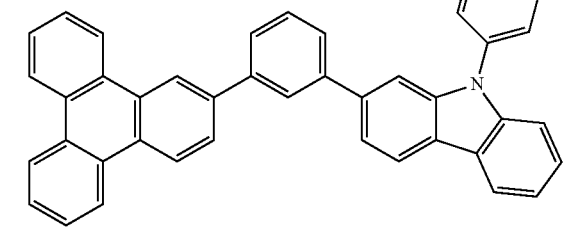
C-31
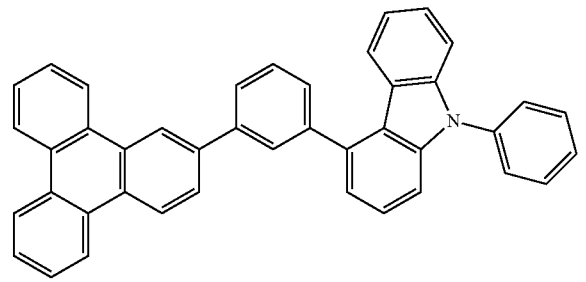
C-32
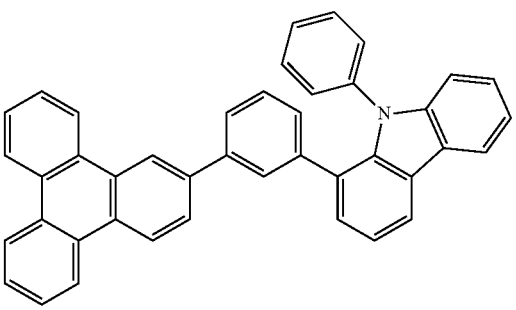
C-33
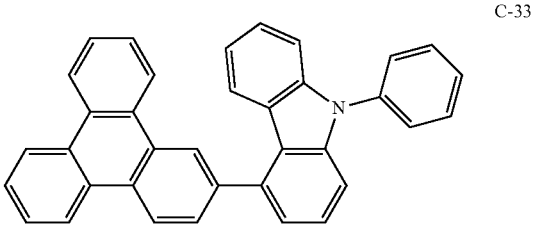
D-10
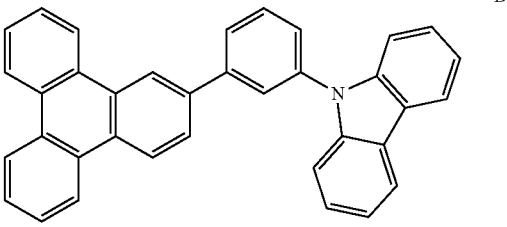
D-11
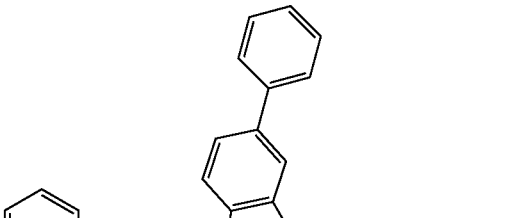
D-12
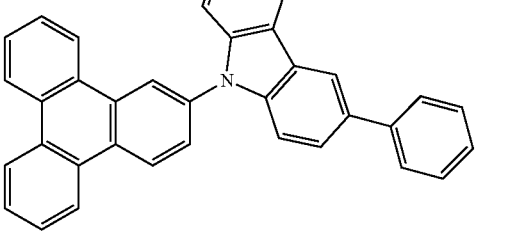

D-13
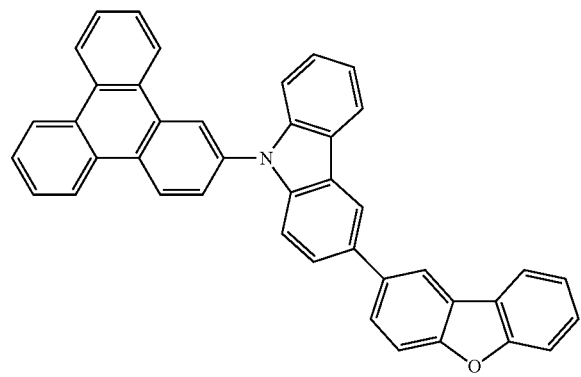
D-14
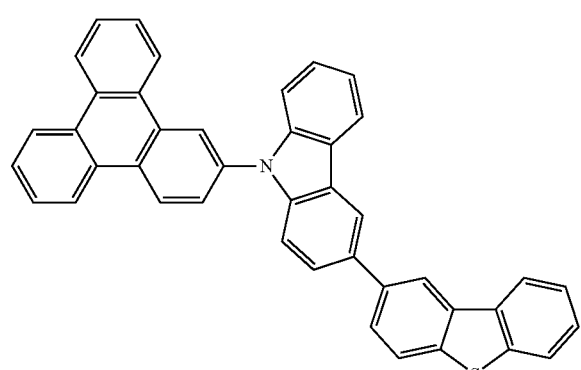
D-15
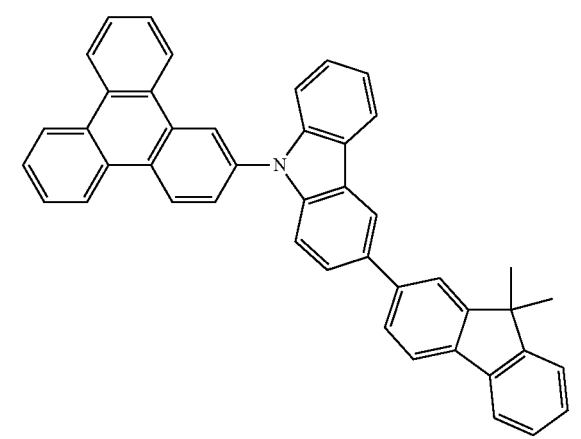
D-16
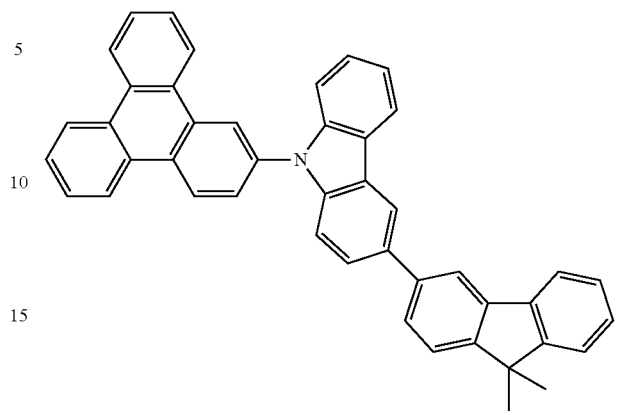
D-17
D-18
D-19
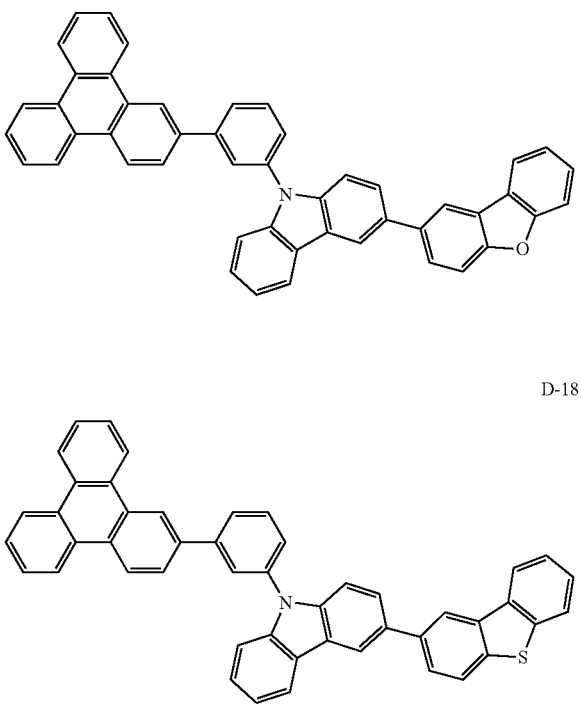

D-20
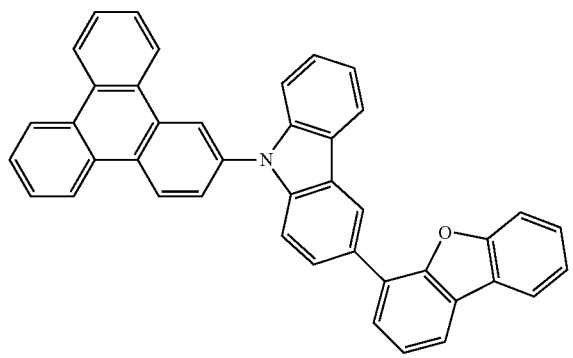
D-21
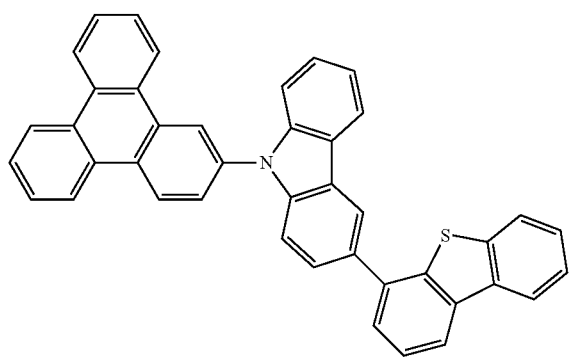
D-22
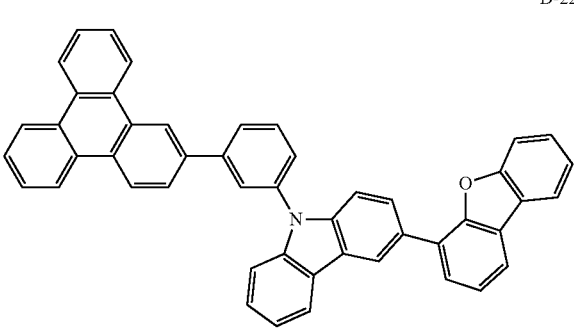
D-23
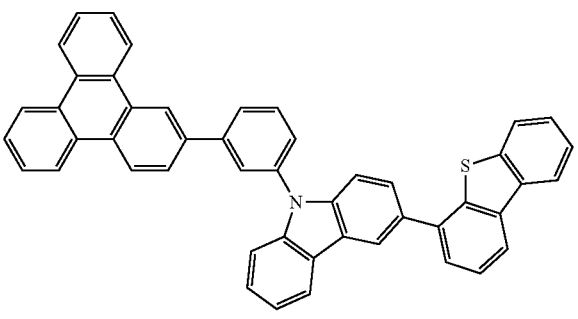
D-24
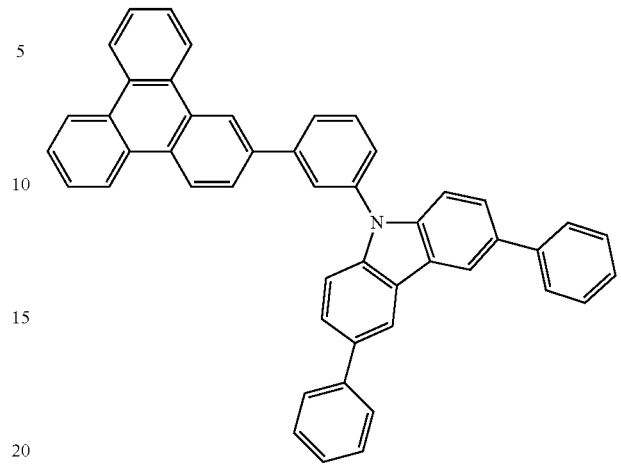
D-25
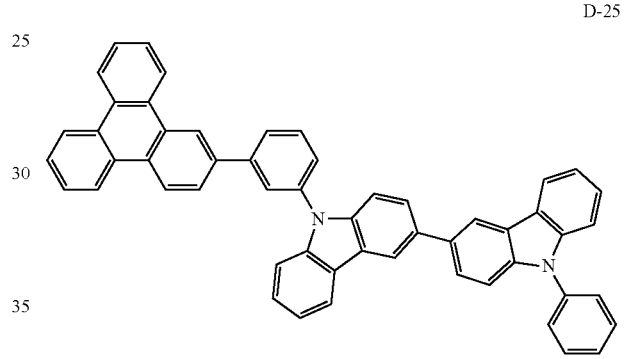
D-26
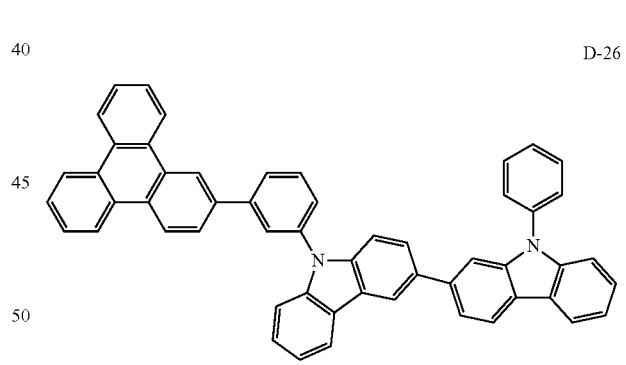
D-27
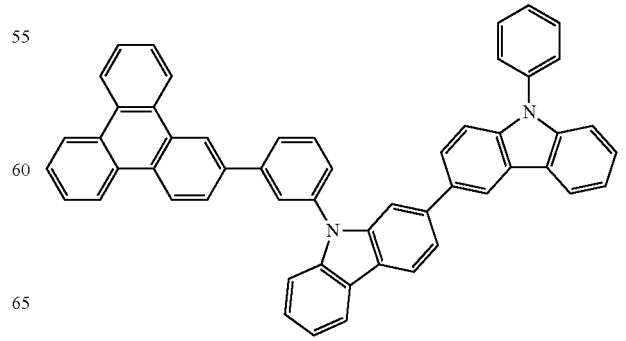

D-28

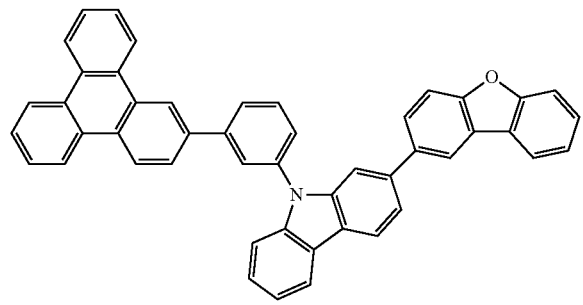

D-29

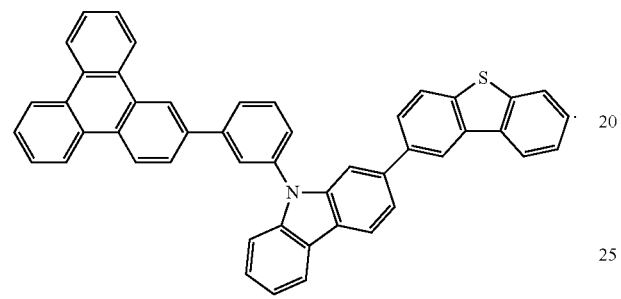

In one embodiment, the first host and the third host may be identical to each other, and the second host and the fourth host may be identical to each other.

In one embodiment, the dopant included in the doping layer may include a phosphorescent dopant.

In one embodiment, the dopant included in the doping layer may be selected from Compounds E-1 to E-31, but embodiments of the present disclosure are not limited thereto:

E-1

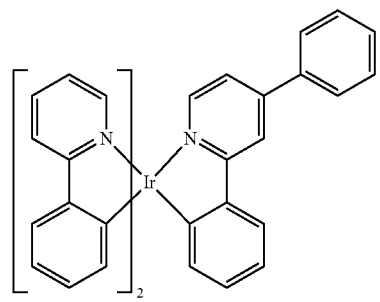

E-2

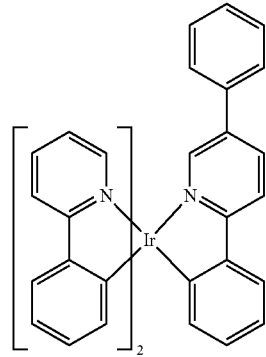

E-3

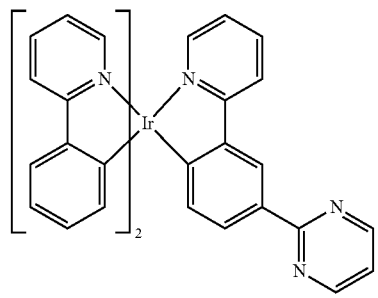

E-4

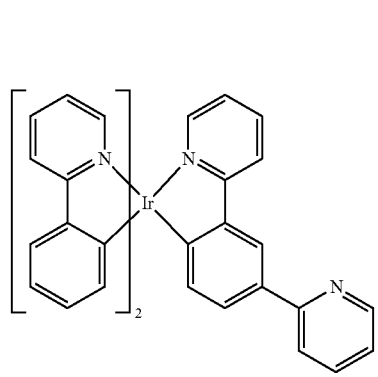

E-5

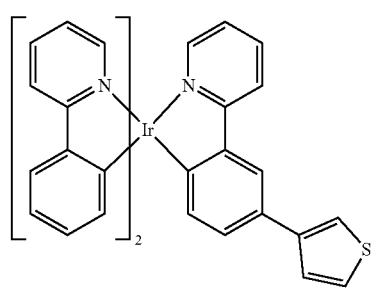

E-6

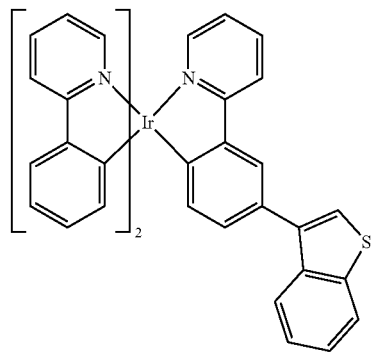

E-7

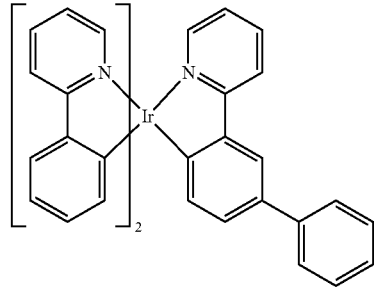

E-8
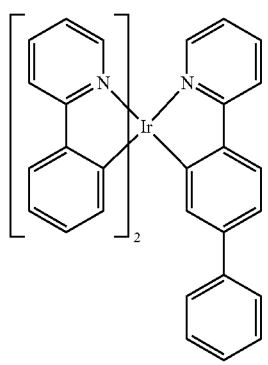
E-9
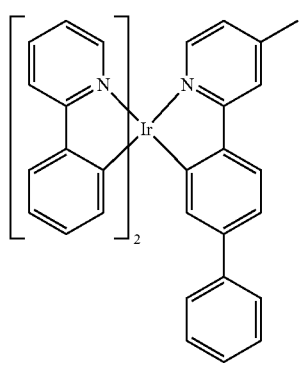
E-10
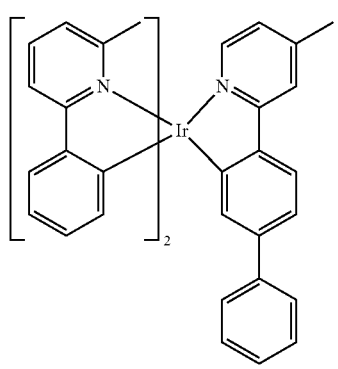
E-11
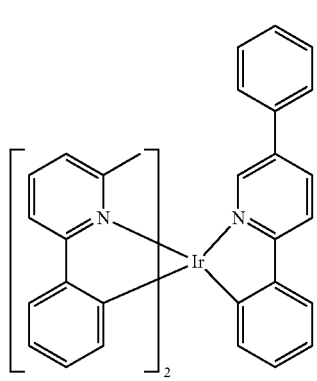
E-12
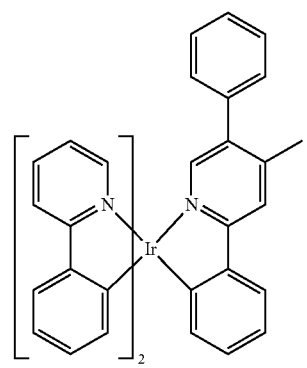
E-13
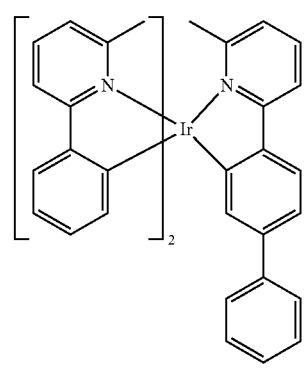
E-14
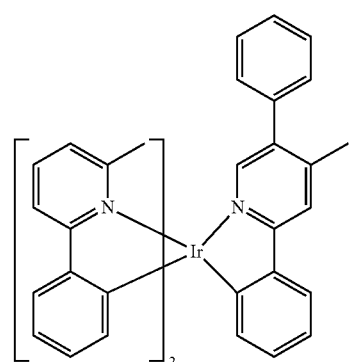
E-15
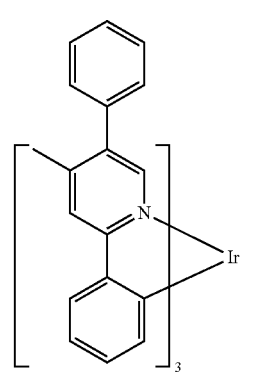

E-16 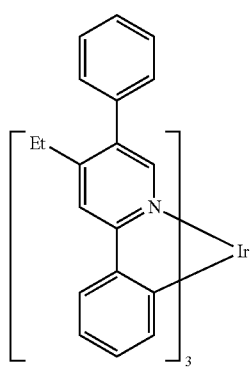
E-17 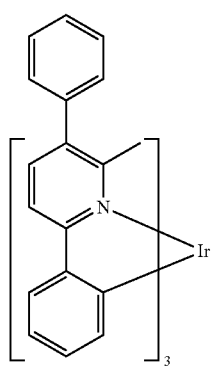
E-18 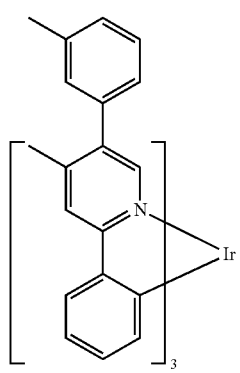
E-19 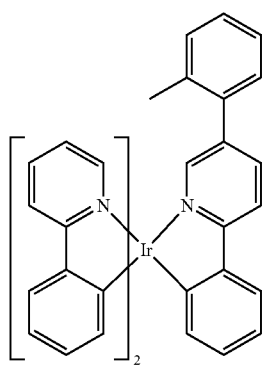
E-20 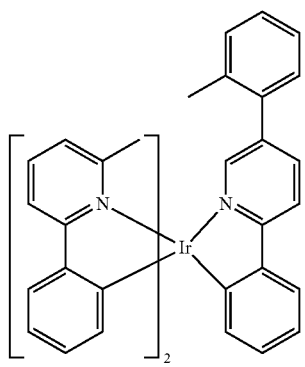
E-21 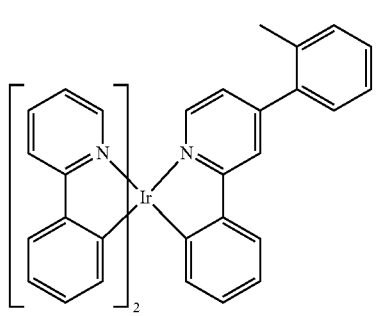
E-22 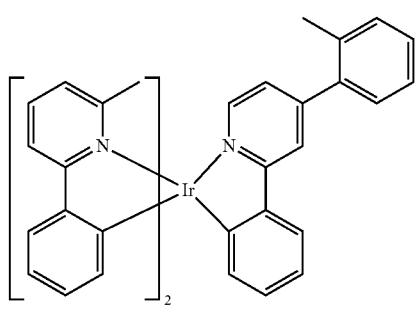
E-23 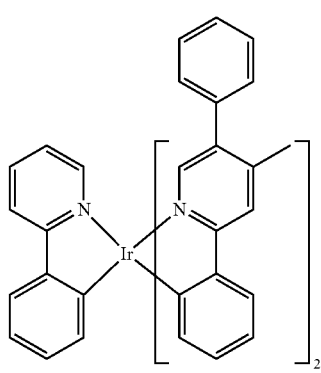

E-24
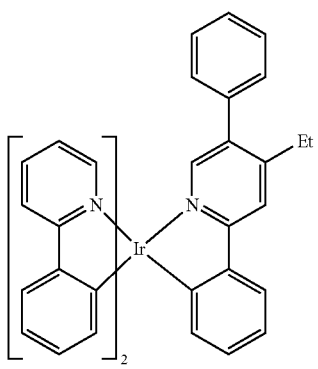

E-25
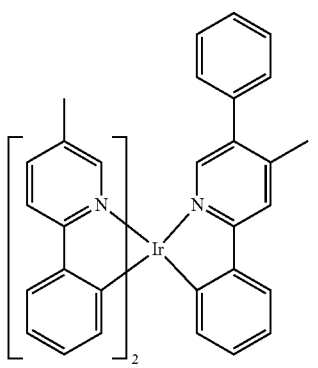

E-26
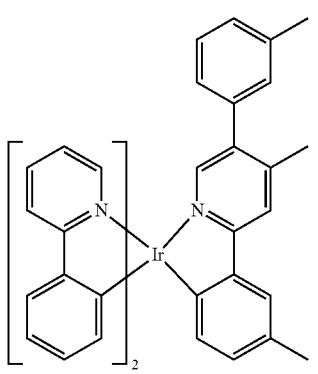

E-27
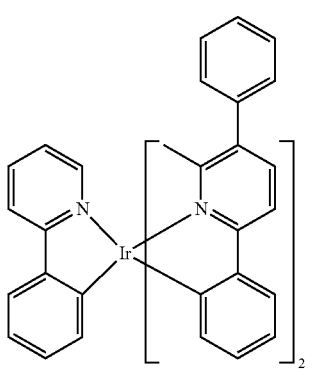

E-28
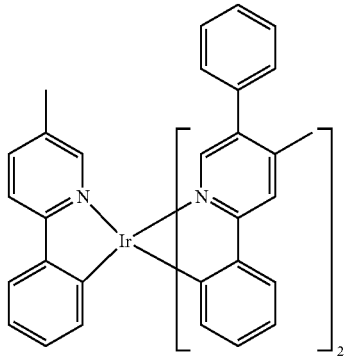

E-29
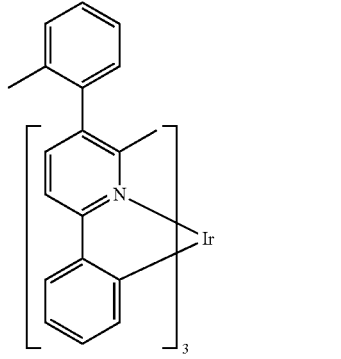

E-30
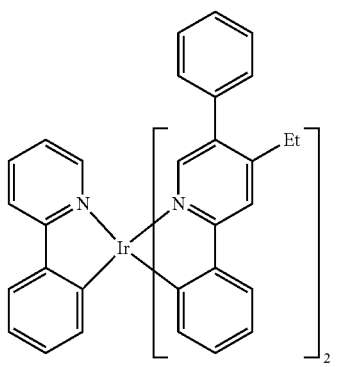

E-31
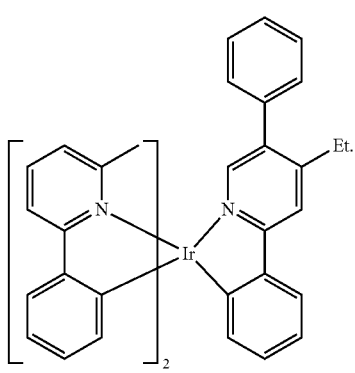

In Compounds E-1 to E-31, "Et" indicates an ethyl group.

In one embodiment, the first electrode may be an anode, the second electrode may be a cathode, and the organic layer may further include a hole transport region, which is disposed between the first electrode and the emission layer, and an electron transport region, which is disposed between the emission layer and the second electrode, wherein the hole transport region may include a hole injection layer, a hole transport layer, an emission auxiliary layer, an electron blocking layer, or any combination thereof, and the electron transport region may include a buffer layer, a hole blocking layer, an electron control layer, an electron transport layer, an electron injection layer, or any combination thereof.

In one embodiment, the non-doping layer may be disposed at least one of between the hole transport region and the doping layer and between the electron transport region and the doping layer.

In one embodiment, the non-doping layer may include a first non-doping layer and a second non-doping layer, wherein the first non-doping layer may be disposed between the hole transport region and the doping layer, and the second non-doping layer may be disposed between the electron transport region and the doping layer.

In one embodiment, the doping layer may include a first doping layer and a second doping layer, wherein the first doping layer may be disposed toward the first electrode, and the second doping layer may be disposed toward the second electrode.

In one embodiment, the non-doping layer may be disposed at least one of between the hole transport region and the first doping layer, between the electron transport region and the second doping layer, and between the first doping layer and the second doping layer.

In one or more embodiments, the doping layer may include a first doping layer and a second doping layer, and the non-doping layer may include a first non-doping layer, a second non-doping layer, and a third non-doping layer, wherein the first doping layer may be disposed toward the first electrode, the second doping layer may be disposed toward the second electrode, the first non-doping layer may be disposed between the hole transport region and the first doping layer, the second non-doping layer may be disposed between the electron transport region and the second doping layer, and the third non-doping layer may be disposed between the first doping layer and the second doping layer.

In one embodiment, a thickness of the non-doping layer may be in a range from about 5 Å to about 100 Å, but embodiments of the present disclosure are not limited thereto. The non-doping layer may directly contact the doping layer.

In one embodiment, the emission layer may emit green light, but embodiments of the present disclosure are not limited thereto.

An electronic apparatus includes the organic light-emitting device and a thin film transistor, wherein the first electrode of the organic light-emitting device is electrically coupled to (e.g., electrically connected to) at least one of a source electrode and a drain electrode of the thin film transistor.

The term "organic layer," as used herein, refers to a single layer and/or a plurality of layers disposed between the first electrode and the second electrode of the organic light-emitting device. A material included in the "organic layer" is not limited to an organic material.

Description of FIG. 1

FIG. 1 is a schematic view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

First Electrode 110

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for a first electrode may be selected from materials with a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

Organic Layer 150

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

[Hole Transport Region in Organic Layer 150]

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/ electron blocking layer structure, wherein for each structure, constituting layers are sequentially stacked from the first electrode 110 in this stated order, but the structure of the hole transport region is not limited thereto.

The hole transport region may include at least one selected from m-MTDATA, TDATA, 2-TNATA, NPB (NPD), P-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly (4-styrenesulfonate) (PEDOT/PSS), polyaniline/camphor sulfonic acid (PANI/CSA), polyaniline/poly(4-styrene-sulfonate) (PANI/PSS), a compound represented by Formula 201, and a compound represented by Formula 202:
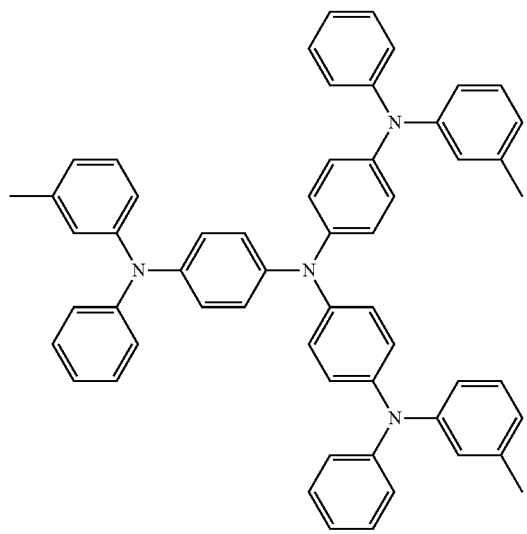
m-MTDATA
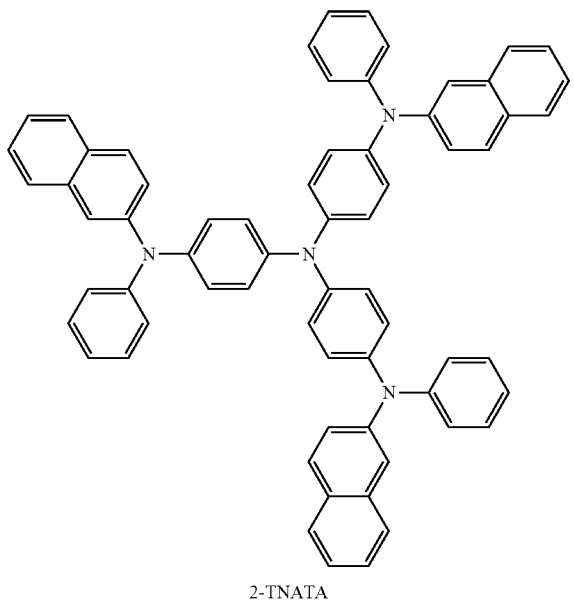
2-TNATA
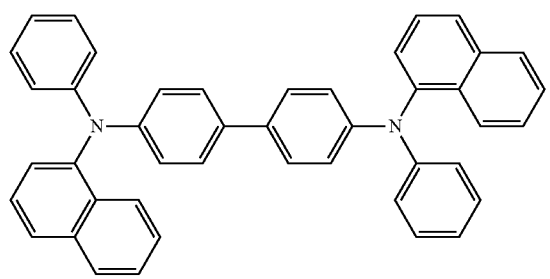
NPB
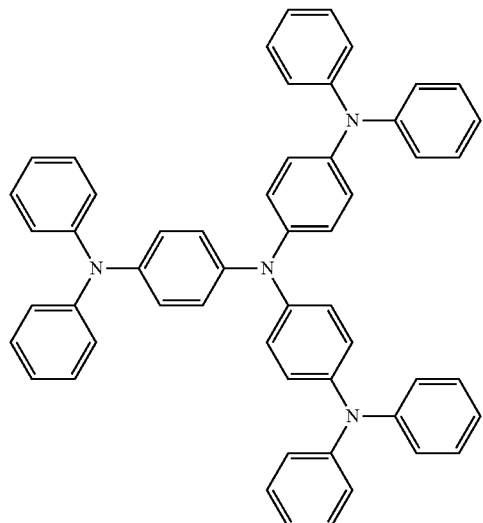
TDATA
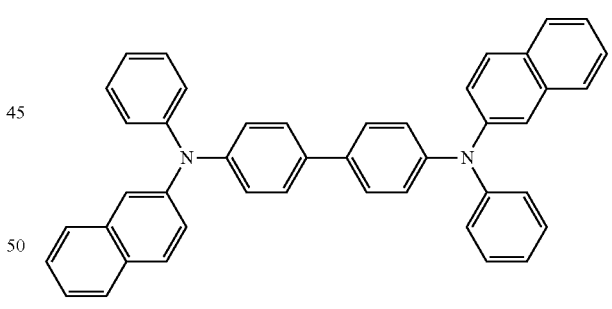
β–NPB
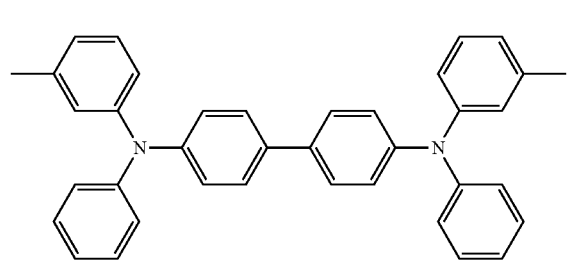
TPD -continued

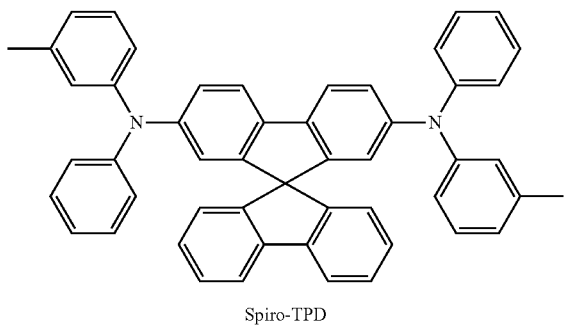

Spiro-TPD

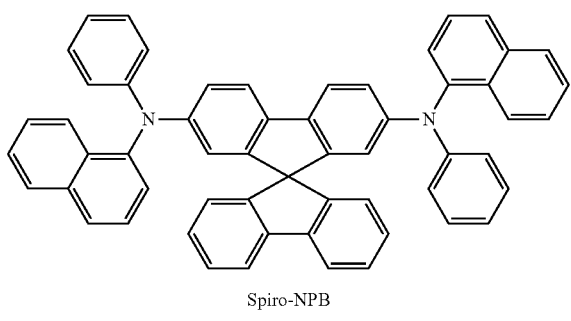

Spiro-NPB

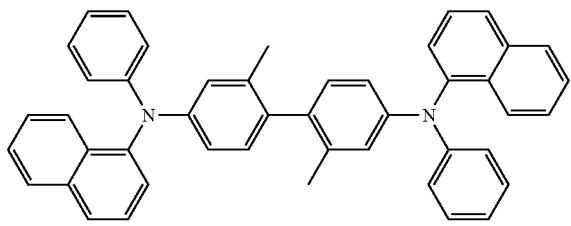

methylated NPB

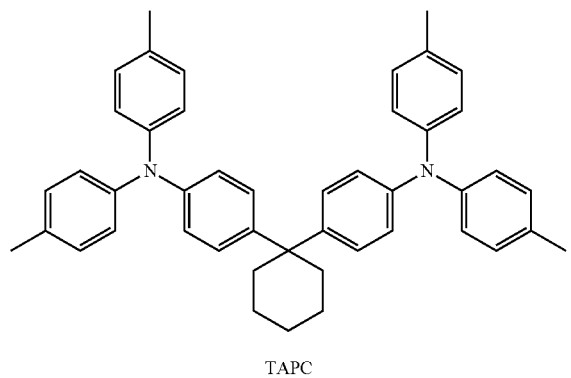

TAPC

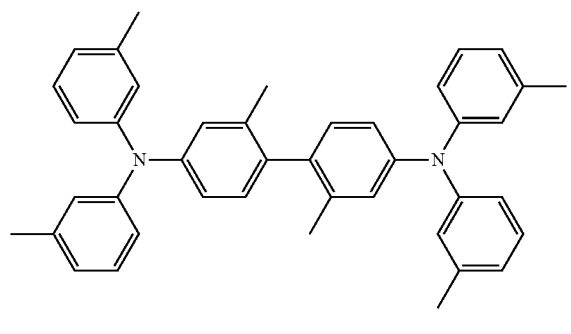

HMTPD

-continued

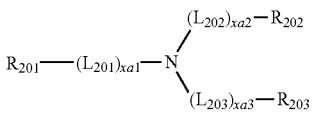

Formula 201

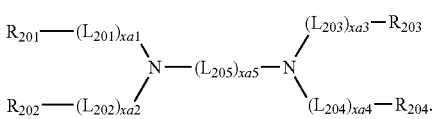

Formula 202

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently an integer of 0 to 3, xa5 may be an integer of 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, $R_{201}$ and $R_{202}$ in Formula 202 may optionally be linked via a single bond, a dimethyl-methylene group, or a diphenyl-methylene group, $R_{203}$ and $R_{204}$ in Formula 202 may optionally be linked via a single bond, a dimethyl-methylene group, or a diphenyl-methylene group.

In one embodiment, in Formulae 201 and 202, $L_{201}$ to $L_{205}$ may each independently be selected from: a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may be the same as described above.

In one or more embodiments, in Formula 201, at least one selected from $R_{201}$ to $R_{203}$ may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In one or more embodiments, in Formula 202, i) $R_{201}$ and $R_{202}$ may be linked via a single bond, and/or ii) $R_{203}$ and $R_{204}$ may be linked via a single bond.

In one or more embodiments, at least one selected from $R_{201}$ to $R_{204}$ in Formula 202 may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

The compound represented by Formula 201 may be represented by Formula 201A:

Formula 201A

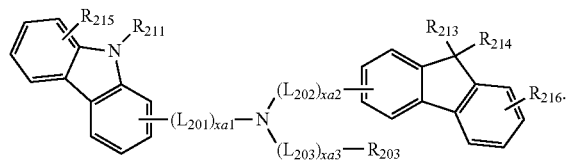

For example, the compound represented by Formula 201 may be represented by Formula 201A(1), but embodiments of the present disclosure are not limited thereto:

Formula 201A(1)

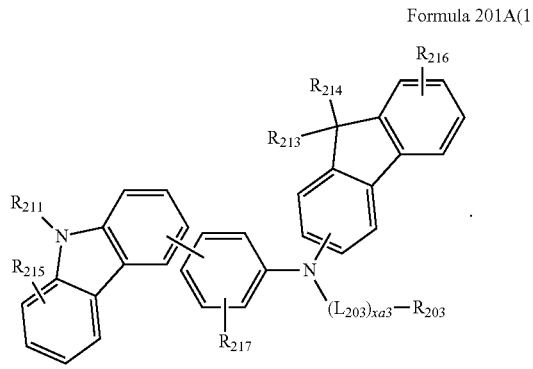

In one embodiment, the compound represented by Formula 201 may be represented by Formula 201A-1, but embodiments of the present disclosure are not limited thereto:

Formula 201A-1

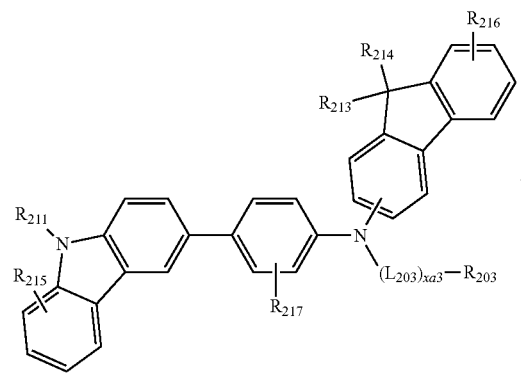

In one embodiment, the compound represented by Formula 202 may be represented by Formula 202A:

Formula 202A

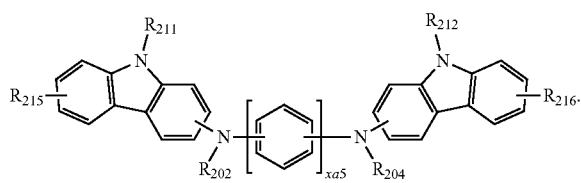

In one or more embodiments, the compound represented by Formula 202 may be represented by Formula 202A-1:

Formula 202A-1

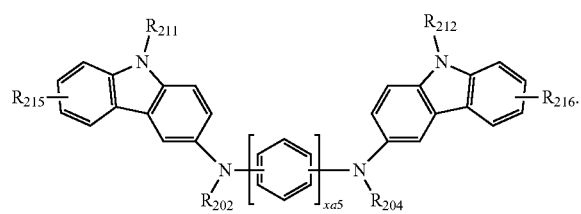

In Formulae 201A, 201A(1), 201A-1, 202A, and 202A-1, $L_{201}$ to $L_{203}$, xa1 to xa3, xa5, and $R_{202}$ to $R_{204}$ may each be the same as described above, $R_{211}$ and $R_{212}$ may be the same as described in connection with $R_{203}$, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments of the present disclosure are not limited thereto:

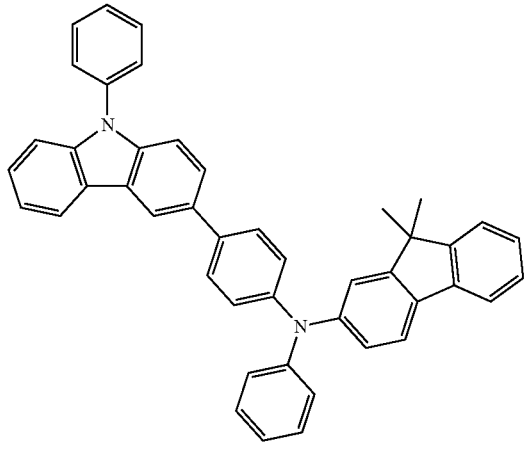

HT1

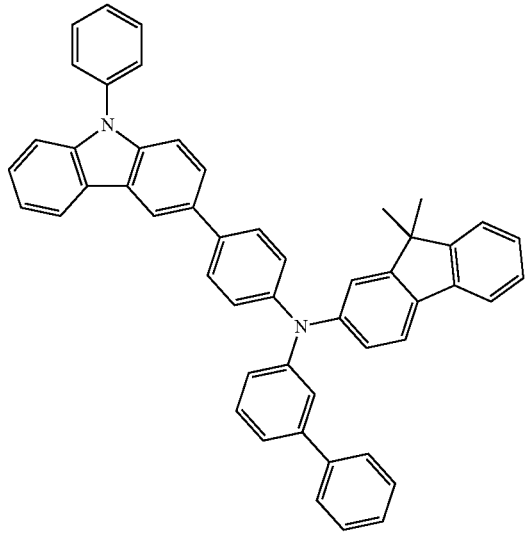

HT2

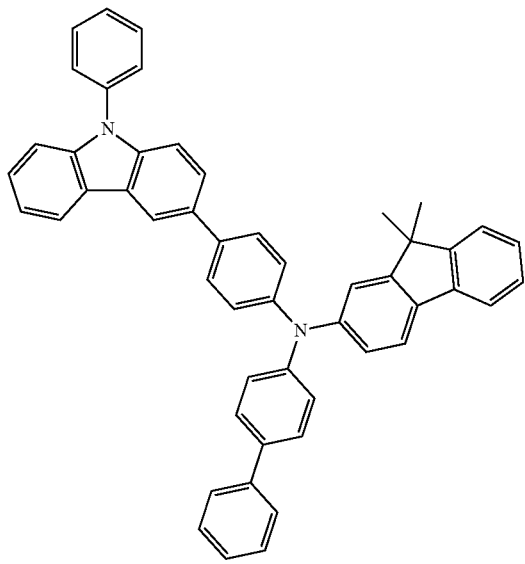

HT3

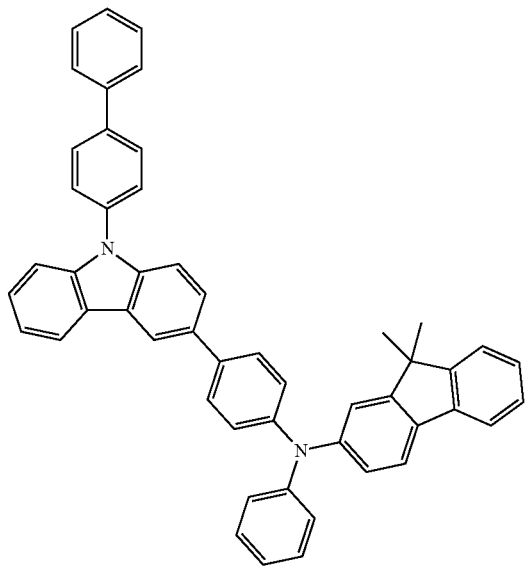

HT4

-continued
HT5
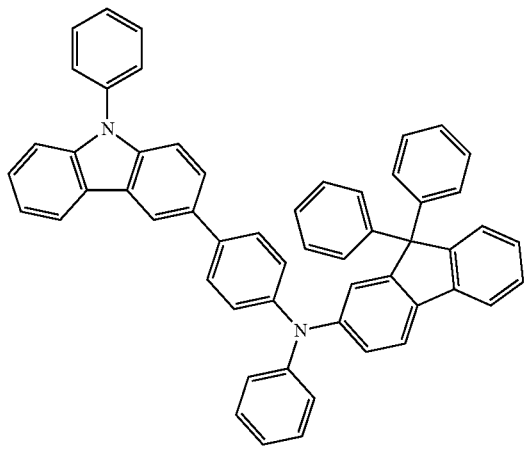
HT6
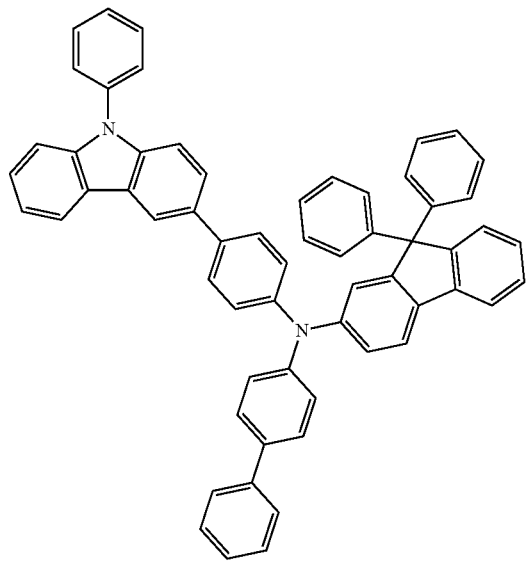
HT7
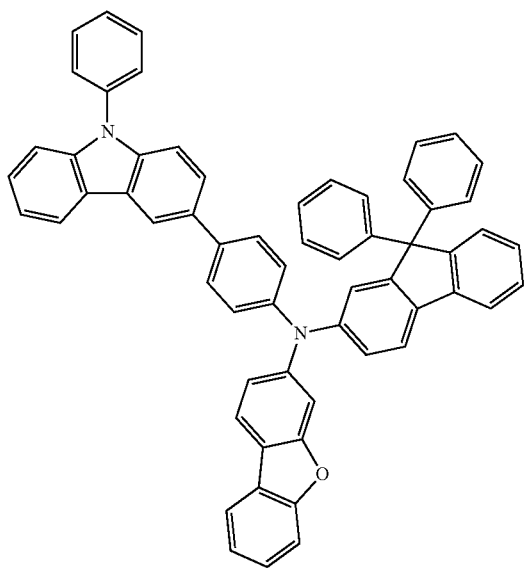
HT8
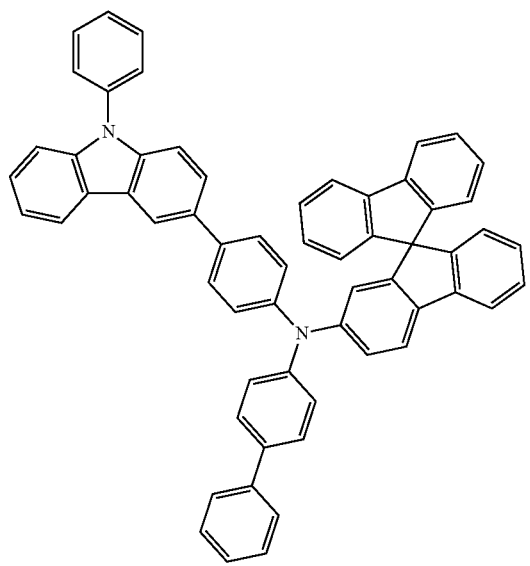

-continued
HT9
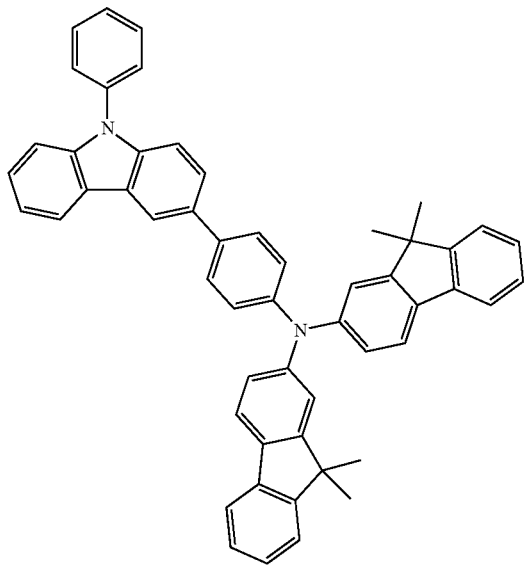
HT10
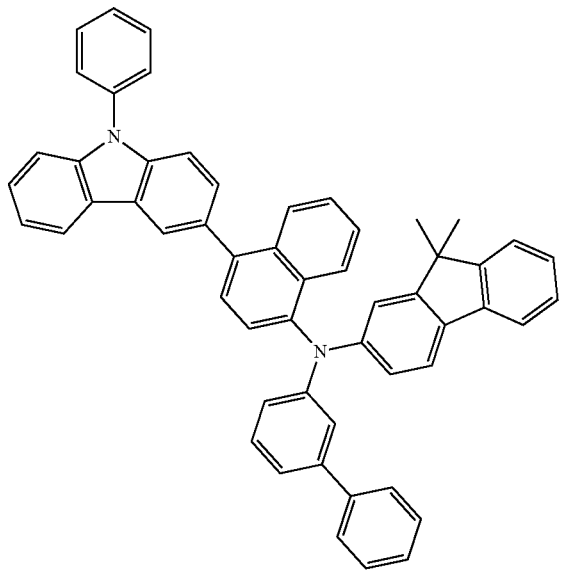
HT11
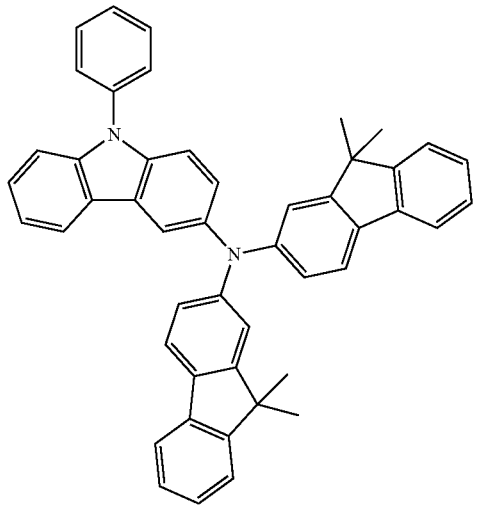
HT12
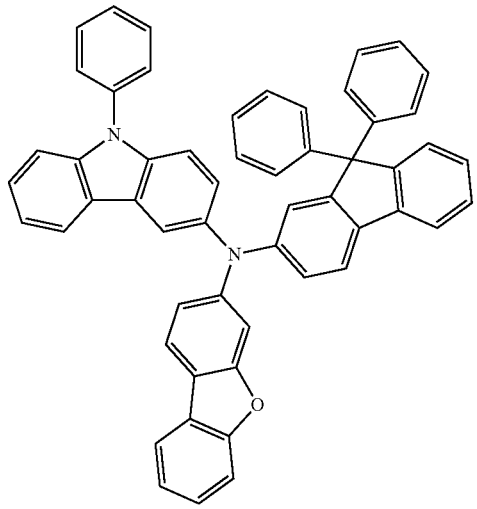

-continued
HT13
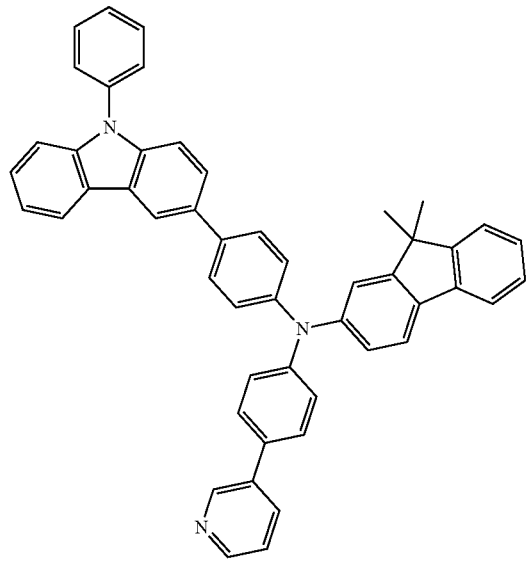
HT14
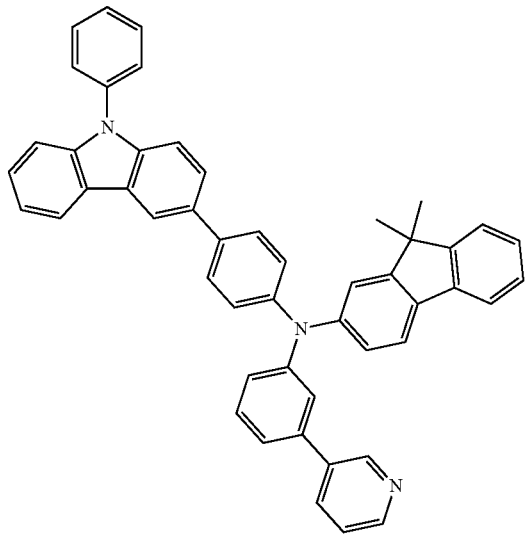
HT15
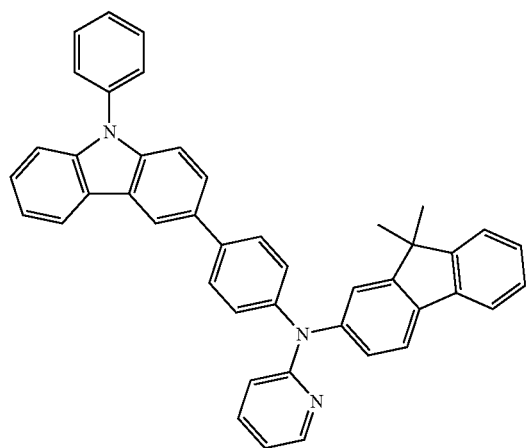
HT16
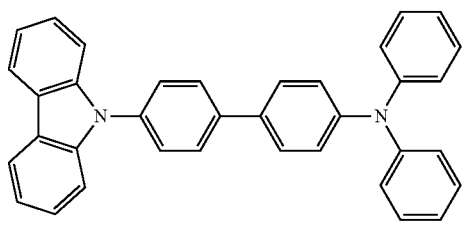
HT17
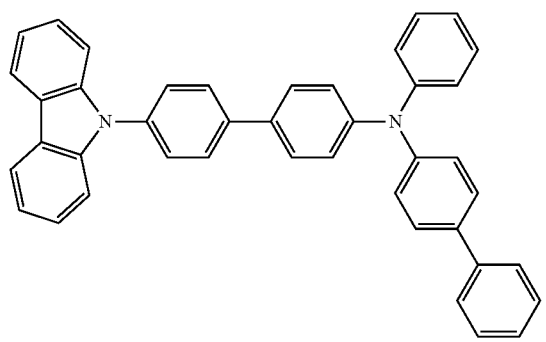
HT18
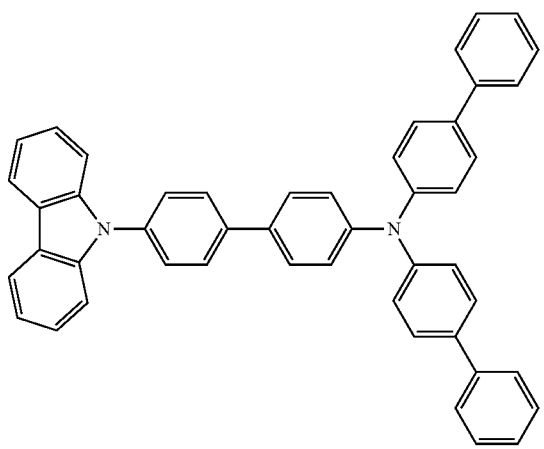

-continued
HT19
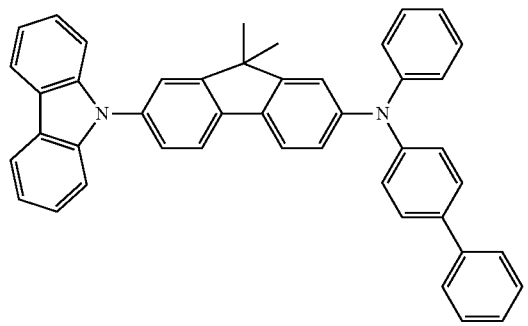
HT20
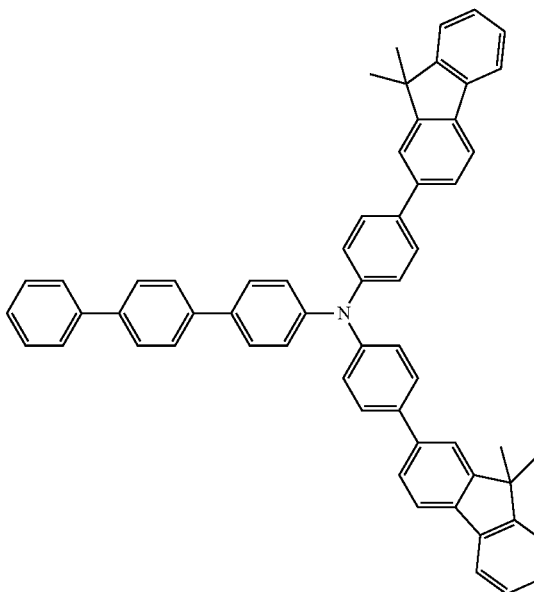
HT21
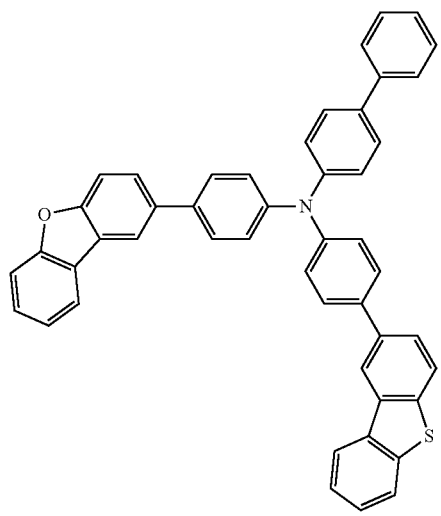
HT22
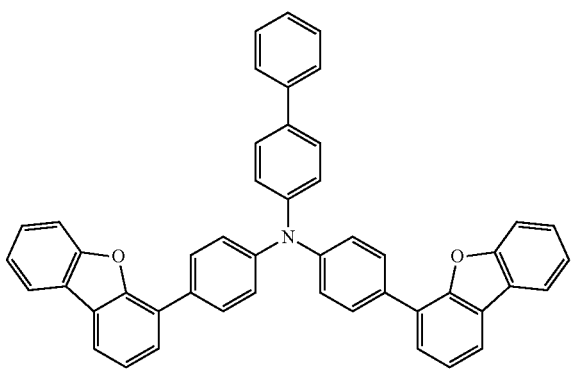
HT23
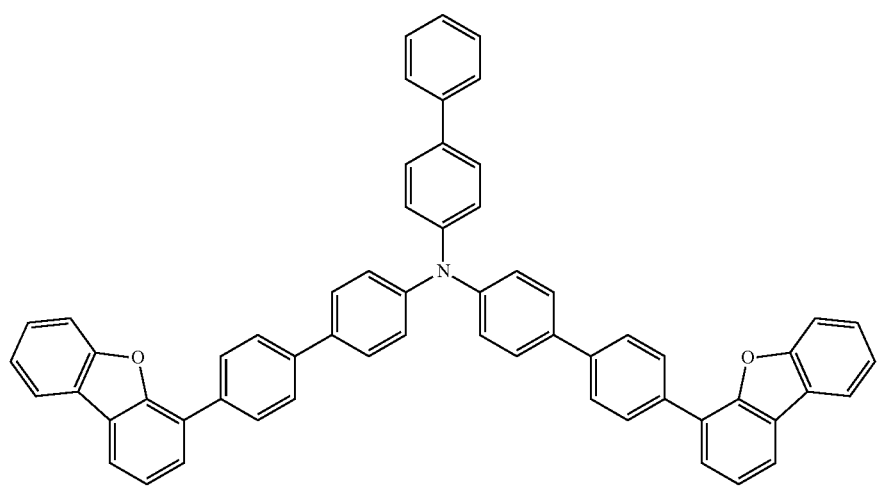

-continued
HT24
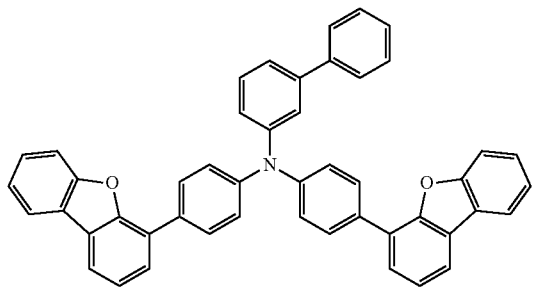
HT25
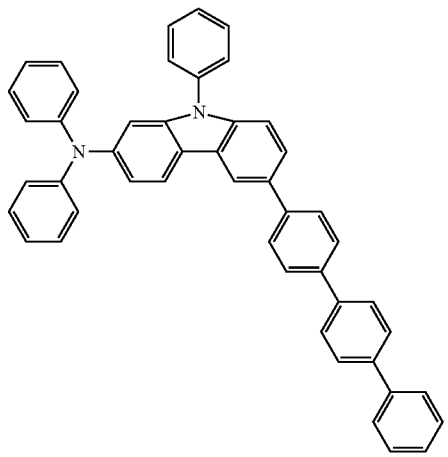
HT26
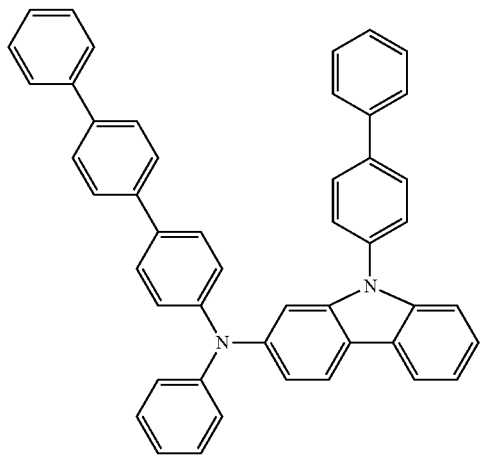
HT27
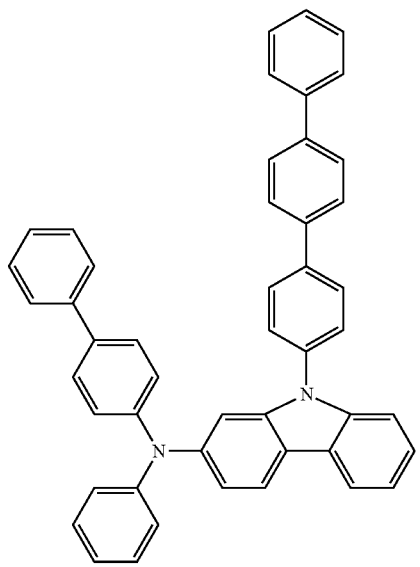
HT28
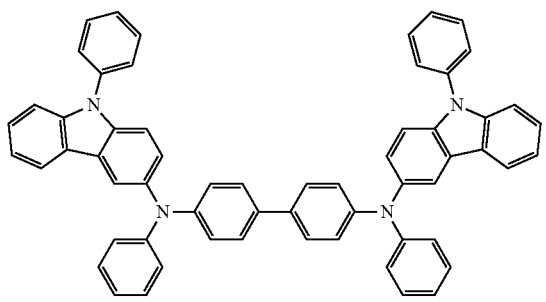
HT29
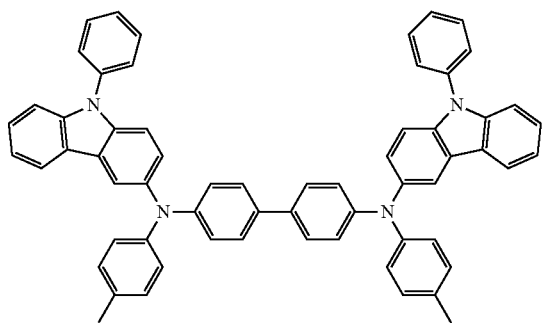

-continued
HT30
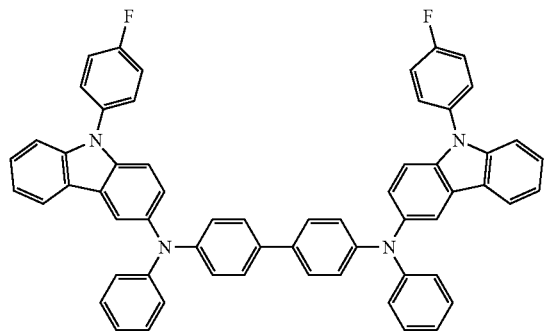
HT31
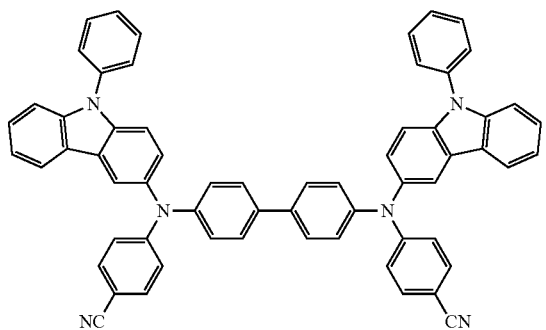
HT32
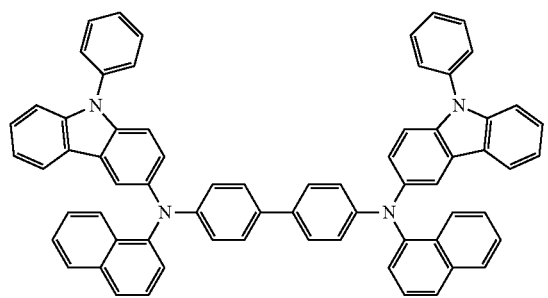
HT33
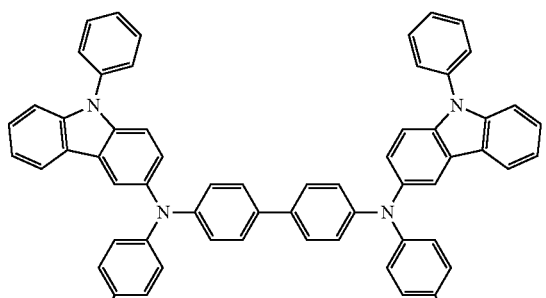
HT34
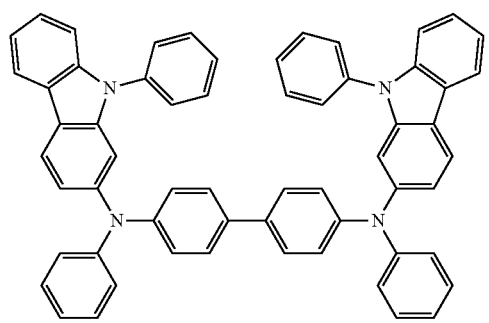
HT35
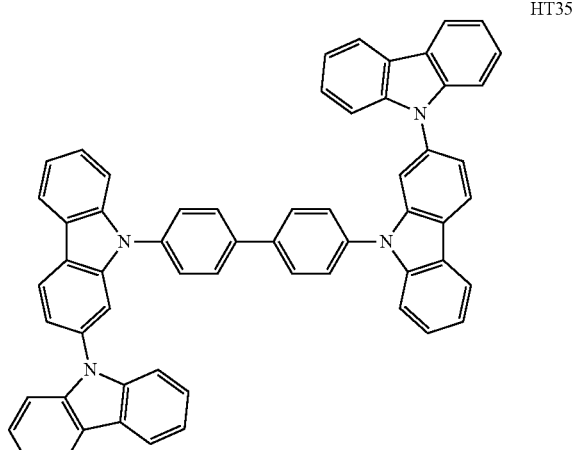
HT36
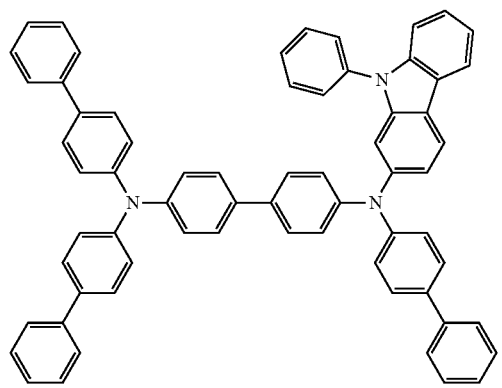
HT37
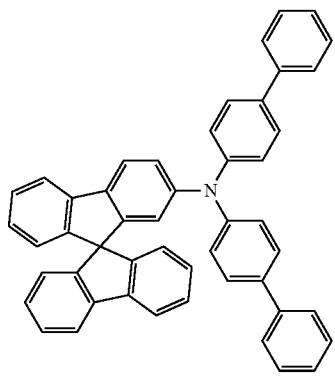

-continued

HT38
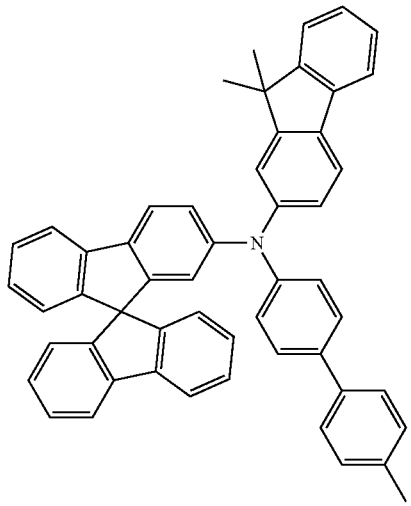

HT39
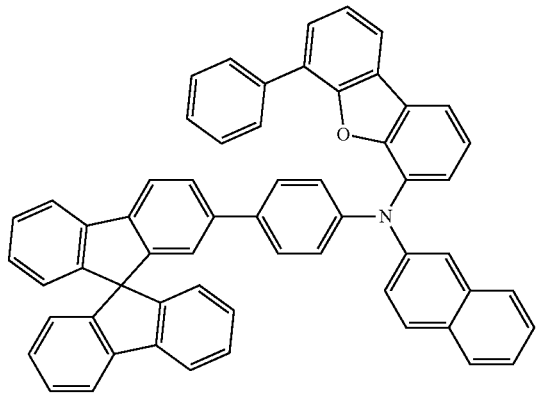

A thickness of the hole transport region may be in a range of about 100 Å to about 10,000 Å, for example, about 100 Å to about 1,000 Å. When the hole transport region includes at least one selected from a hole injection layer and a hole transport layer, the thickness of the hole injection layer may be in a range of about 100 Å to about 9,000 Å, and for example, about 100 Å to about 1,000 Å, and the thickness of the hole transport layer may be in a range of about 50 Å to about 2,000 Å, and for example, about 100 Å to about 1500 Å. When the thicknesses of the hole transport region, the hole injection layer, and the hole transport layer are within these ranges, suitable or satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

p-Dopant

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, the p-dopant may have a lowest unoccupied molecular orbital (LUMO) level of about −3.5 eV or less.

The p-dopant may include at least one selected from a quinone derivative, a metal oxide, and a cyano group-containing compound, but embodiments of the present disclosure are not limited thereto.

For example, the p-dopant may be selected from:
a quinone derivative such as tetracyanoquinodimethane (TCNQ) and 2,3,5,6-tetrafluoro-7,7,8,8-tetracyanoquinodimethane (F4-TCNQ);
a metal oxide, such as a tungsten oxide and a molybdenum oxide;

1,4,5,8,9,12-hexaazatriphenylene-hexacarbonitrile (HAT-CN); and
a compound represented by Formula 221,
but embodiments of the present disclosure are not limited thereto:

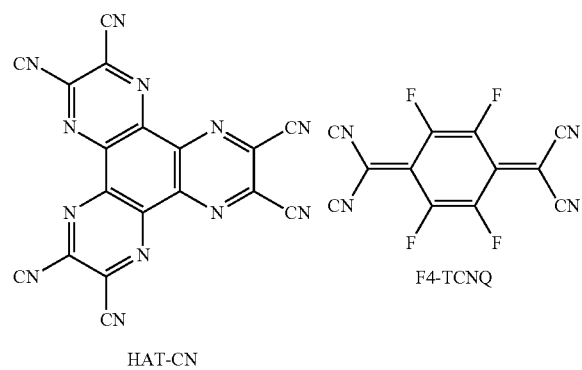

HAT-CN

F4-TCNQ

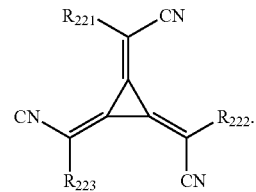

Formula 221

In Formula 221,
$R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one embodiment, at least one selected from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in Organic Layer 150

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescent dopant and a fluorescent dopant.

In the emission layer, an amount of a dopant may be in a range of about 0.01 parts to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

[Host in Emission Layer]

In one or more embodiments, the host may include a compound represented by Formula 301:

Formula 301

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer of 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), xb21 may be an integer of 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one embodiment, in Formula 301, $Ar_{301}$ may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In Formula 301, when xb11 is two or more, two or more of $Ar_{301}$(s) may be linked via a single bond.

In one or more embodiments, the compound represented by Formula 301 may be represented by Formula 301-1 or 301-2:

Formula 301-1

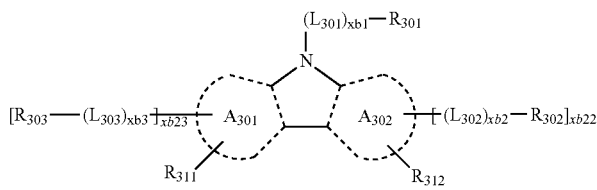

Formula 301-2

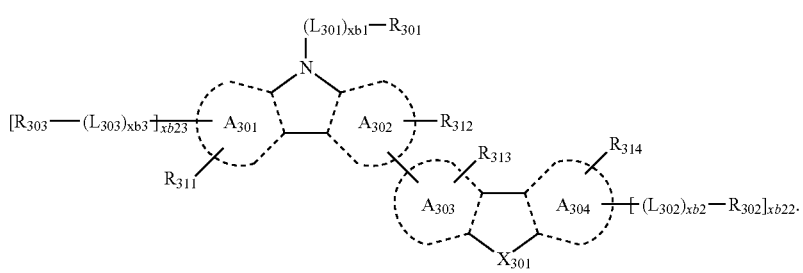

In Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-$[(L_{304})_{xb4}$-$R_{304}]$, $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si$(Q_{31})(Q_{32})(Q_{33})$, —N$(Q_{31})(Q_{32})$, —B$(Q_{31})(Q_{32})$, —C(=O)$(Q_{31})$, —S(=O)$_2(Q_{31})$, and —P(=O)$(Q_{31})(Q_{32})$, xb22 and xb23 may each independently be 0, 1, or 2, $L_{301}$, xb1, $R_{301}$, and $Q_{31}$ to $Q_{33}$ may be the same as described above, $L_{302}$ to $L_{304}$ may each independently be the same as described in connection with $L_{301}$, xb2 to xb4 may each independently be the same as described in connection with xb1, and $R_{302}$ to $R_{304}$ may each independently be the same as described in connection with $R_{301}$.

For example, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may be the same as described above.

In one embodiment, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may be the same as described above.

In one embodiment, the host may include an alkaline earth metal complex.

For example, the host may be selected from a Be complex (for example, Compound H55), an Mg complex, and a Zn complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:

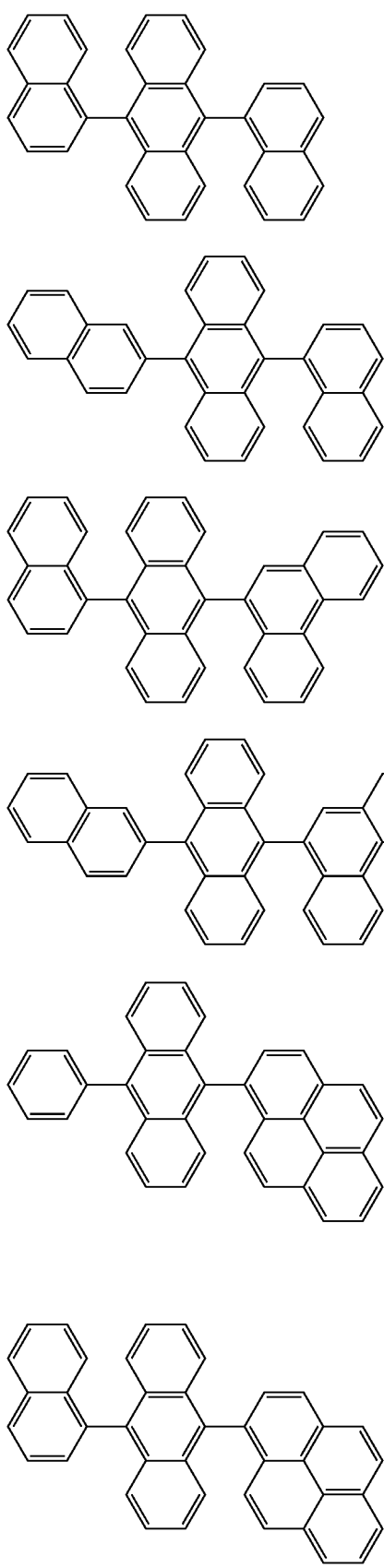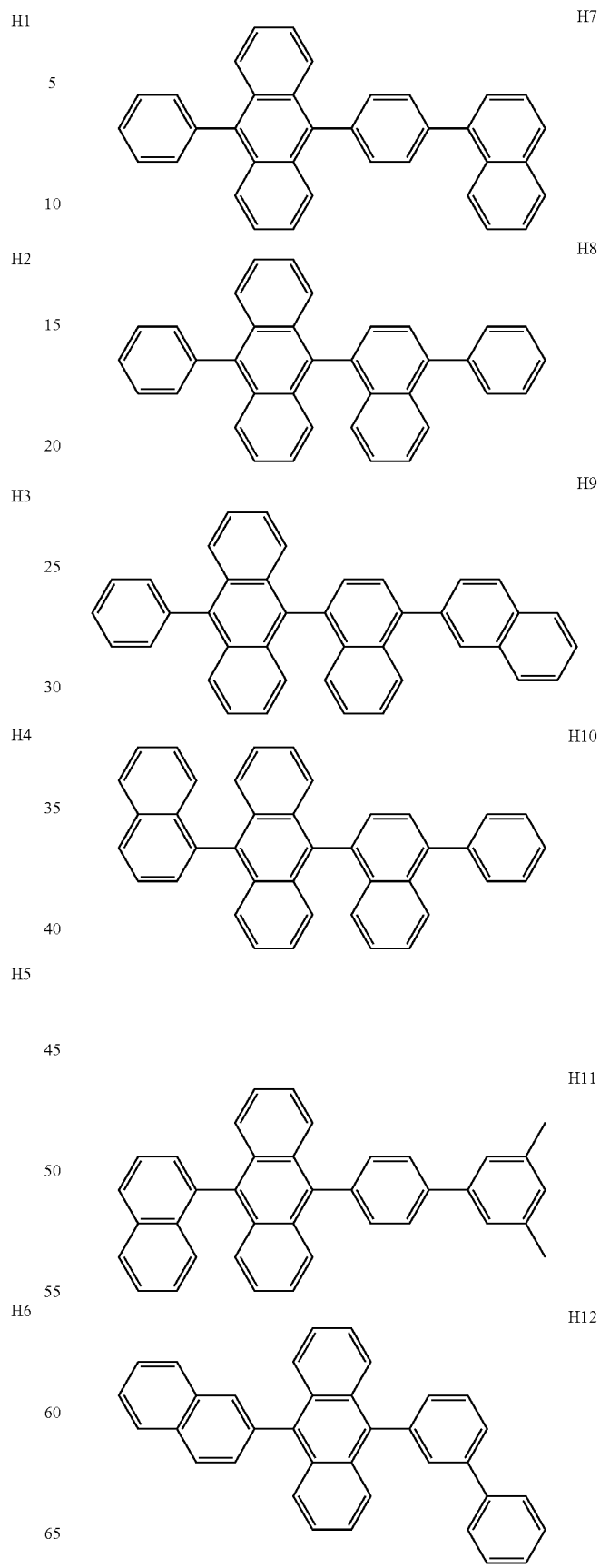

H13
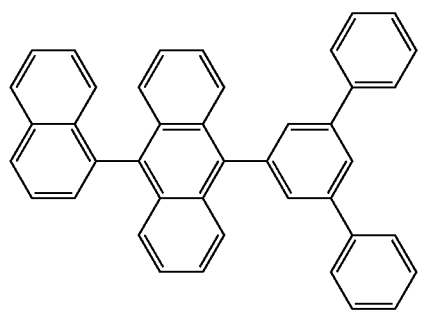
H14
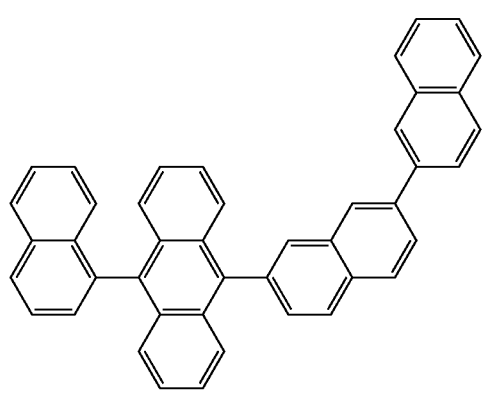
H15
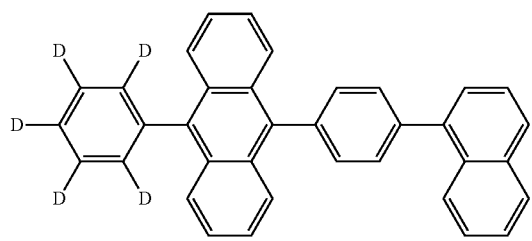
H16
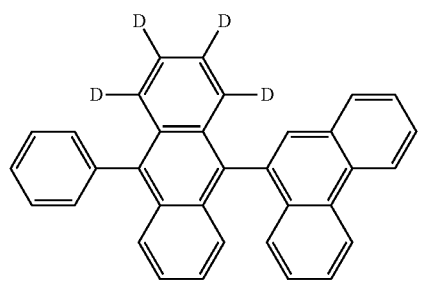
H17
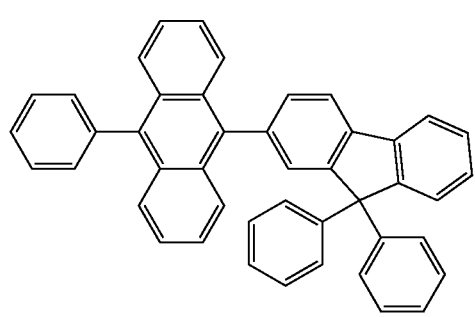
H18
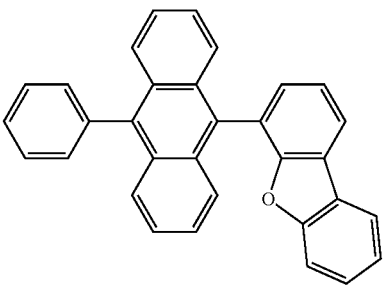
H19
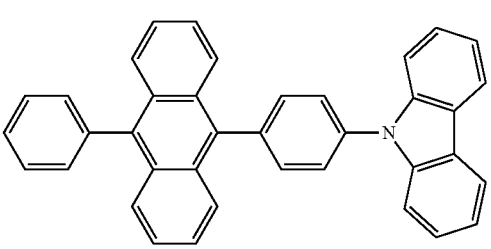
H20
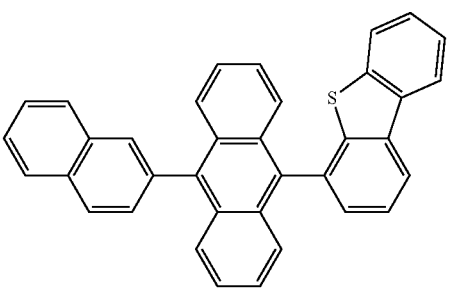
H21
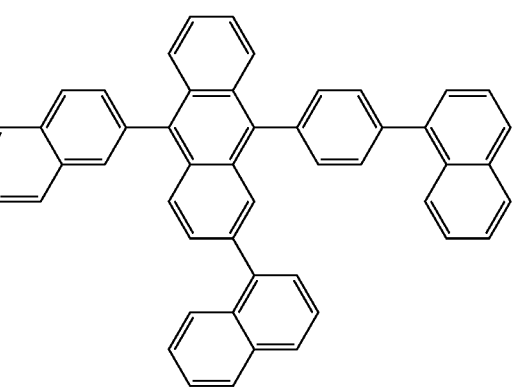
H22
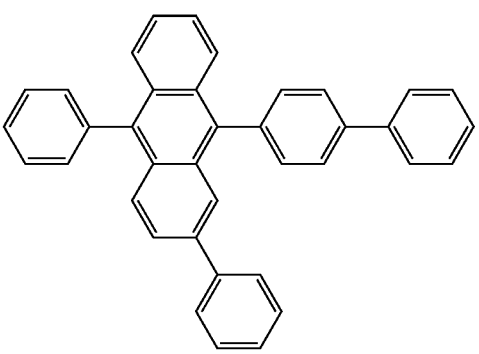

H23
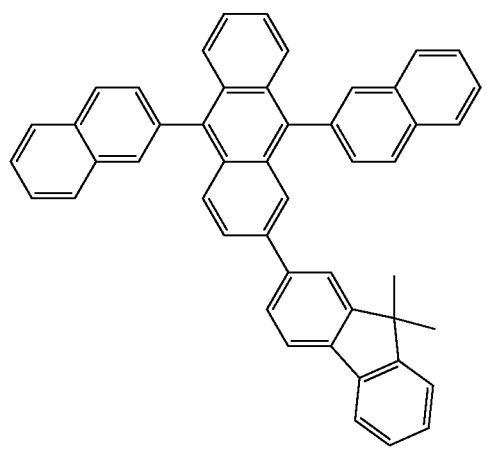
H24
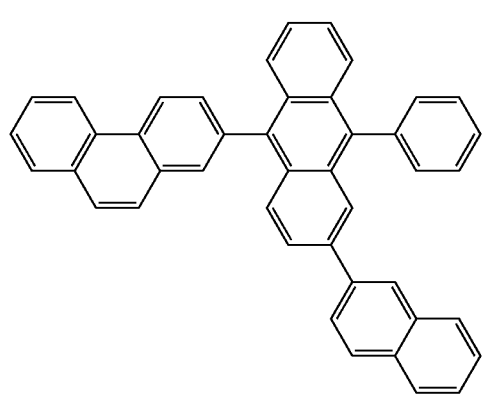
H25
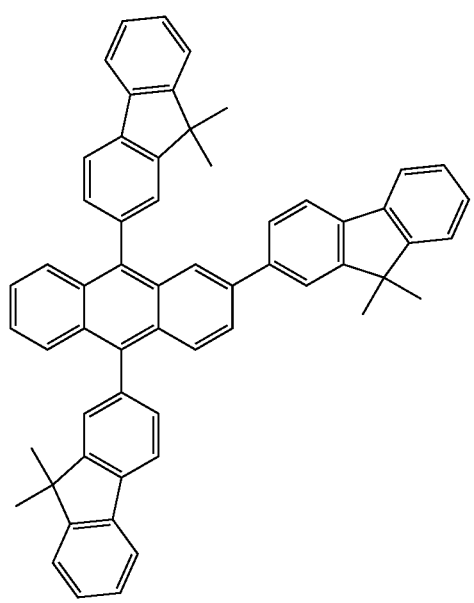
H26
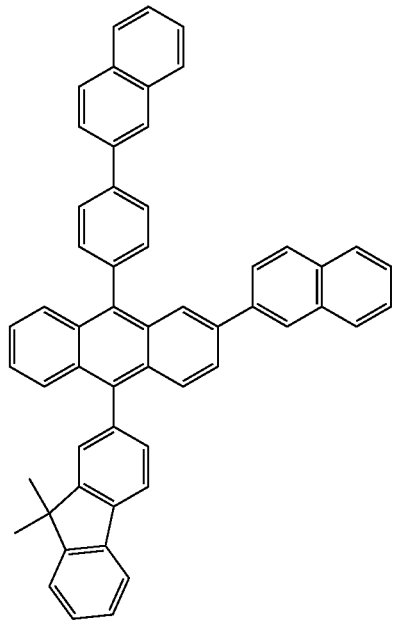
H27
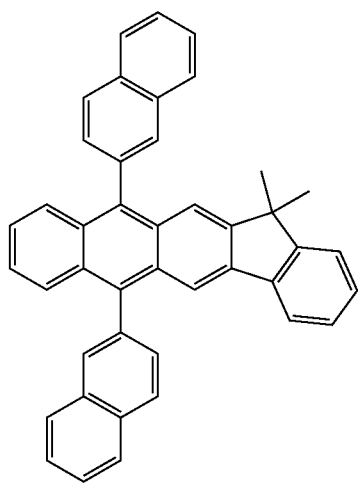
H28
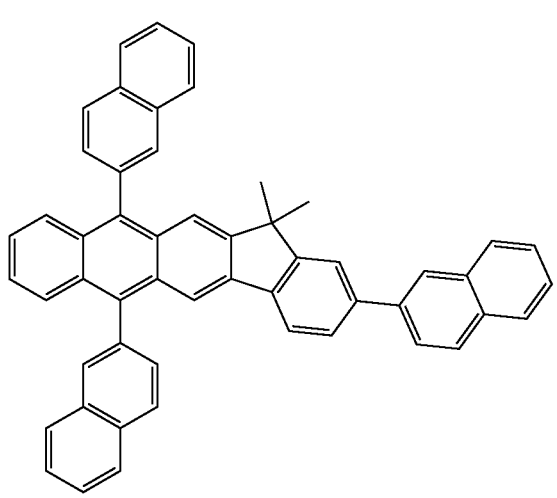

-continued
H29
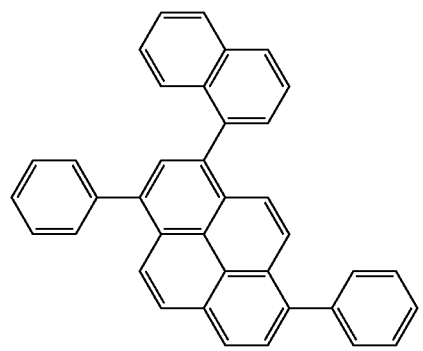
H30
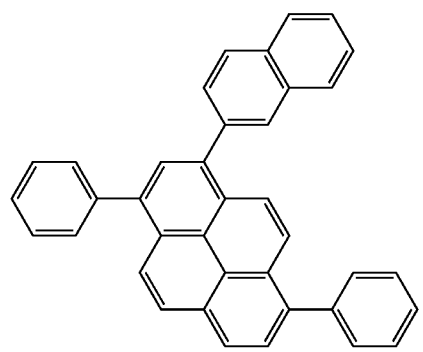
H31
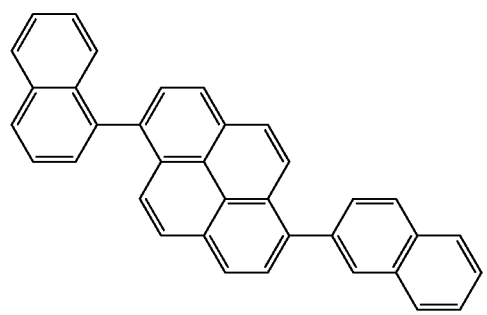
H32
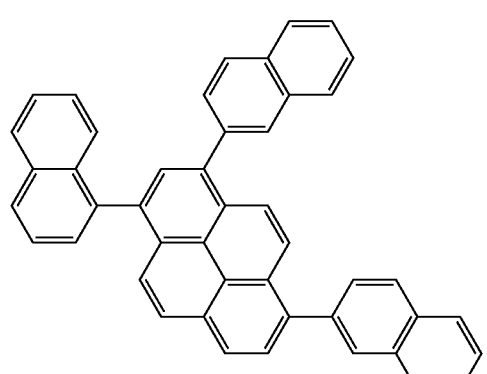
H33
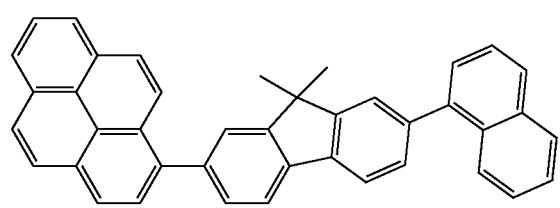
-continued
H34
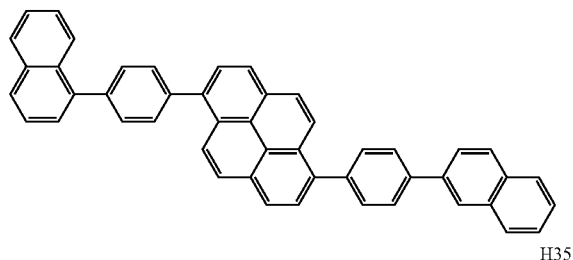
H35
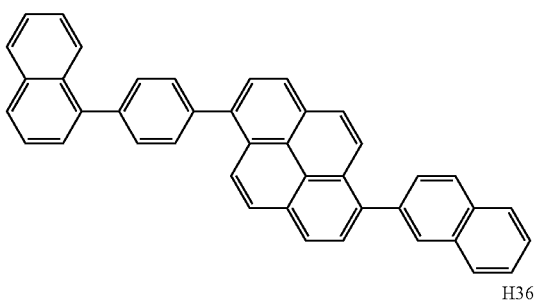
H36
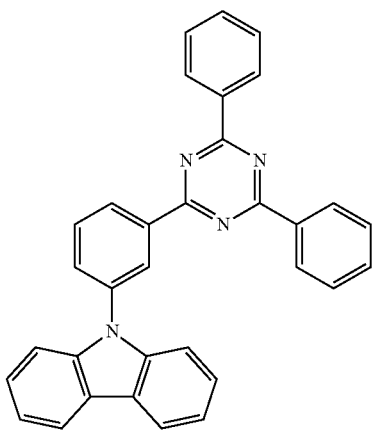
H37
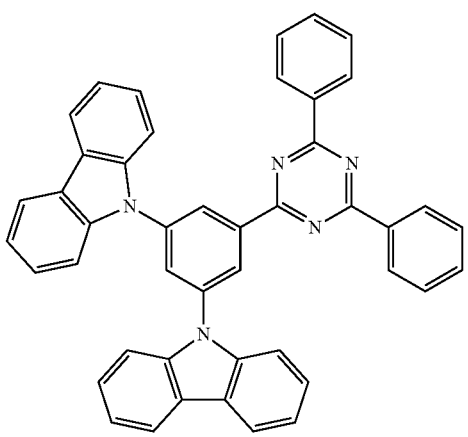
H38
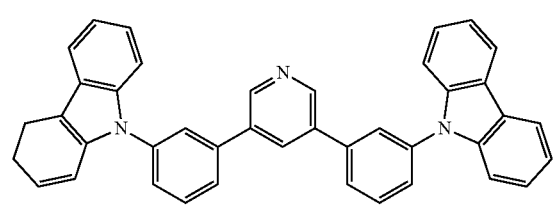

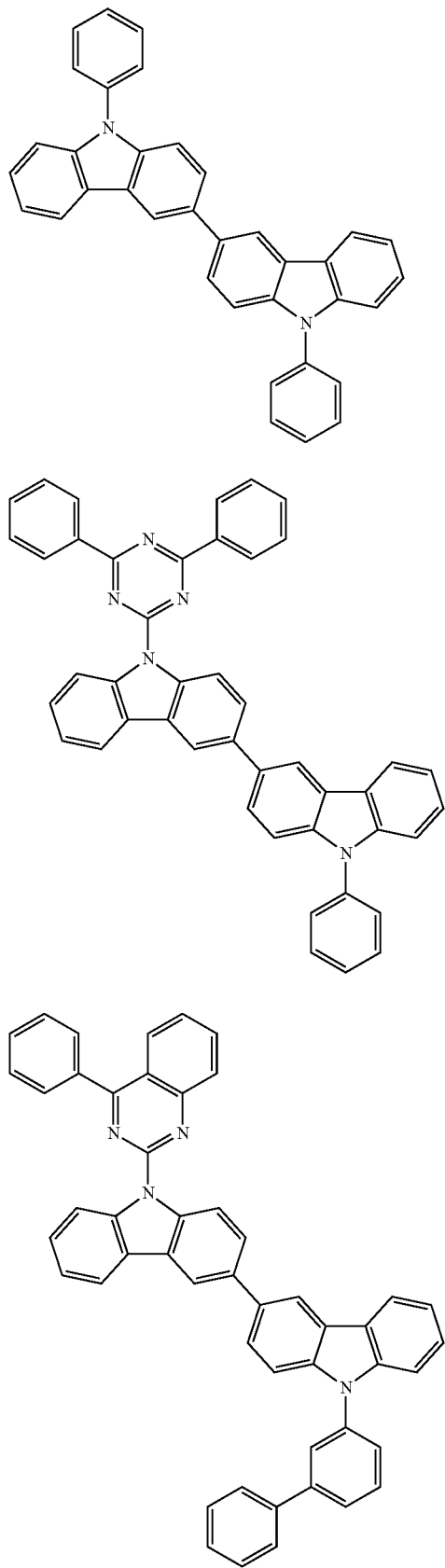
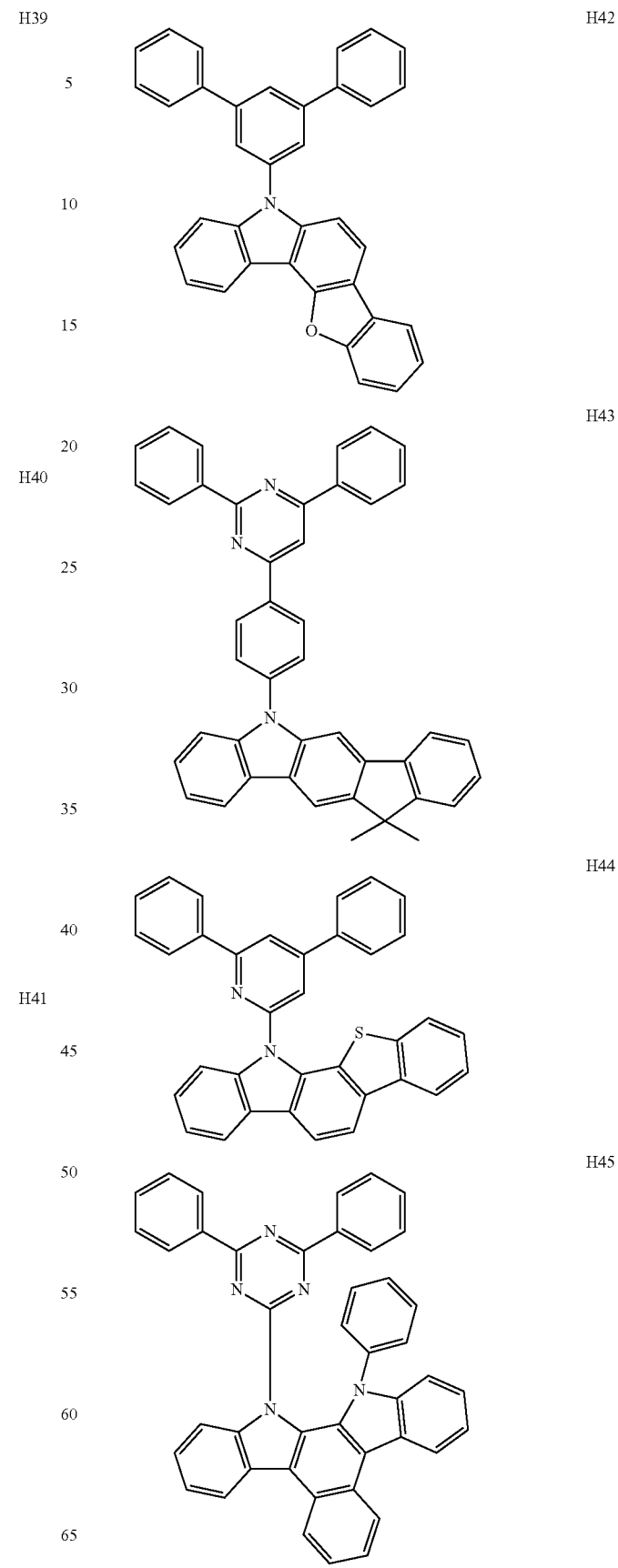

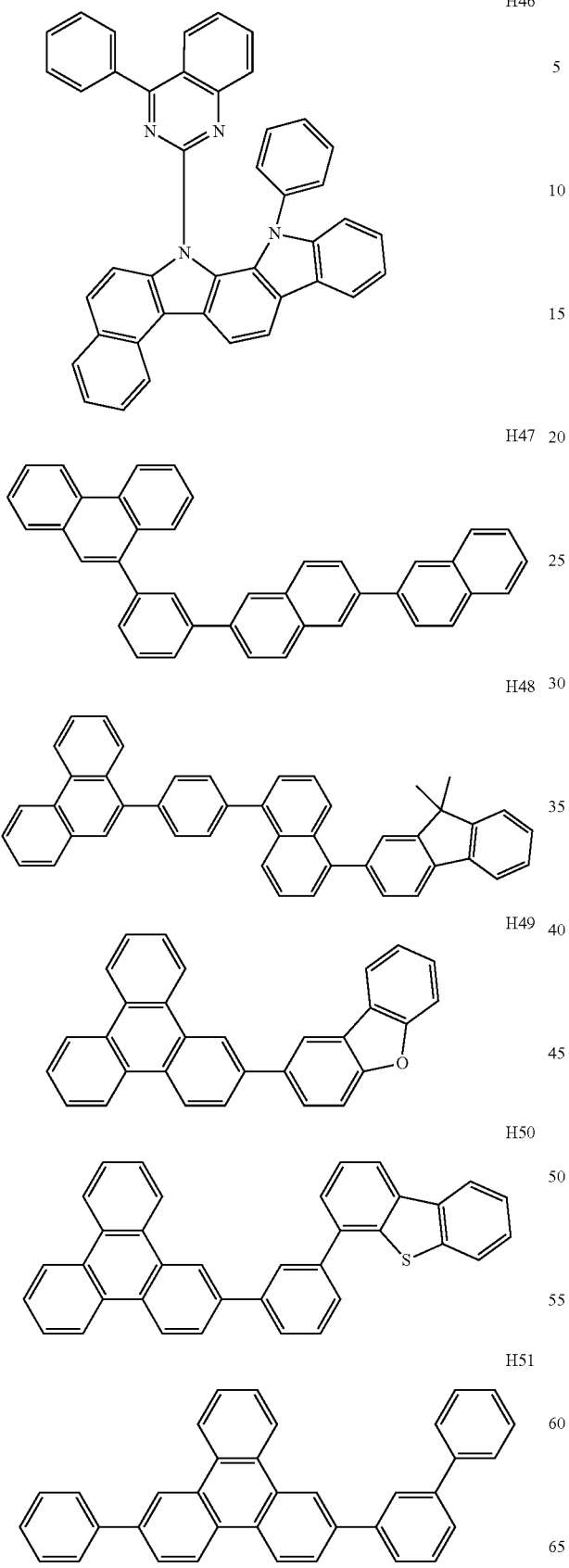
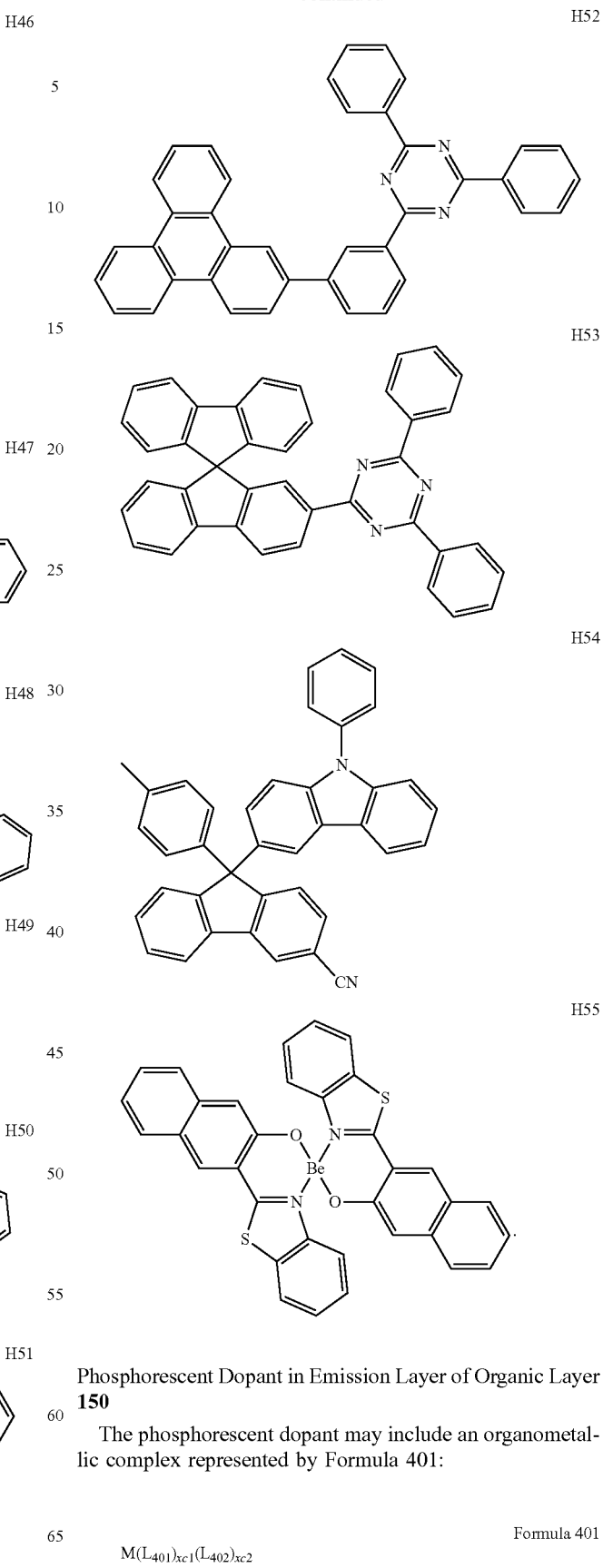
Phosphorescent Dopant in Emission Layer of Organic Layer 150
The phosphorescent dopant may include an organometallic complex represented by Formula 401:
$$M(L_{401})_{xc1}(L_{402})_{xc2}$$
Formula 401

Formula 402

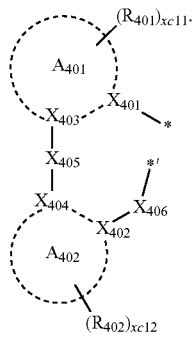

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from a ligand represented by Formula 402, and xc1 may be 1, 2, or 3. When xc1 two or more, two or more of $L_{401}(S)$ may be identical to or different from each other, $L_{402}$ may be an organic ligand, xc2 may be an integer of 0 to 4. When xc2 is two or more, two or more of $L_{402}(S)$ may be identical to or different from each other, $X_{401}$ to $X_{404}$ may each independently be N or C, $X_{401}$ and $X_{403}$ may be linked via a single bond or a double bond, and $X_{402}$ and $X_{404}$ may be linked via a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—O($Q_{411}$)=C($Q_{412}$)-*', *—C($Q_{411}$)=*', or *=C=*', wherein $Q_{411}$ and $Q_{412}$ may each independently hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer of 0 to 10, and

* and *' in Formula 402 each indicate a binding site to M of Formula 401.

In one embodiment, in Formula 402, $A_{401}$ and $A_{402}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be N and $X_{402}$ may be C, or ii) $X_{401}$ and $X_{402}$ may be both N.

In one or more embodiments, in Formula 402, $R_{401}$ and $R_{402}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantyl group, a norbornanyl group, and a norbornenyl group;

a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments of the present disclosure are not limited thereto.

In one or more embodiments, in Formula 401, when xc1 is two or more, two $A_{401}$(s) among a plurality of $L_{401}$(s) may optionally be linked via a linking group, $X_{407}$, or two $A_{402}$(s) may optionally be linked via a linking group, $X_{408}$ (see Compounds PD1 to PD4 and PD7). $X_{407}$ and $X_{408}$ may each independently be a single bond, *—O—*', *—S—*', *—C(=O)—*', *—N($Q_{413}$)-*', *—C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group or a naphthyl group), but embodiments of the present disclosure are not limited thereto.

In Formula 401, $L_{402}$ may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and phosphorus (for example, phosphine and phosphite), but embodiments of the present disclosure are not limited thereto.

In one embodiment, the phosphorescent dopant may be, for example, selected from Compounds PD1 to PD25, but embodiments of the present disclosure are not limited thereto:

PD1

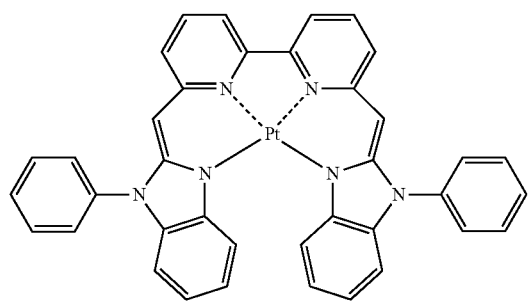

PD2

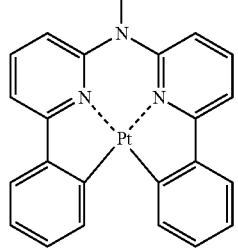

PD3

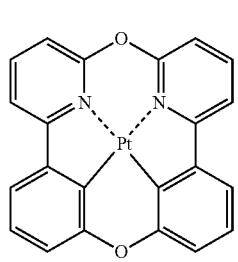

PD4

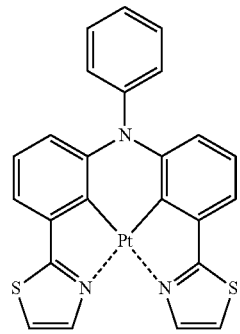

PD5

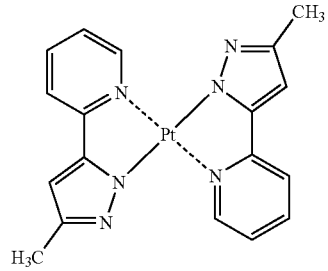

PD6

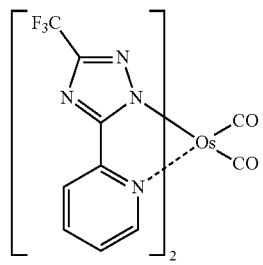

PD7

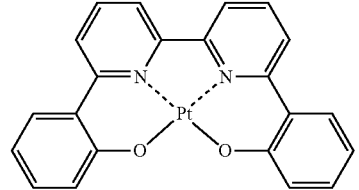

PD8

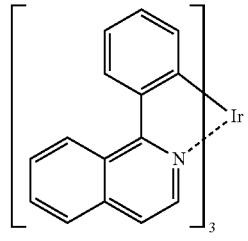

PD9

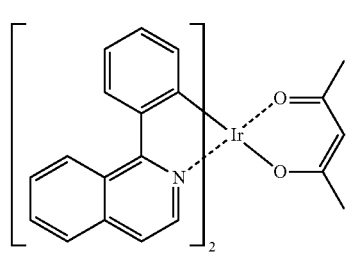

PD10 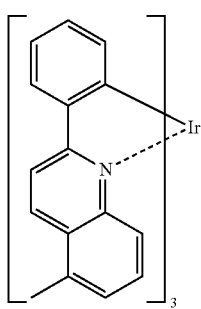
PD11 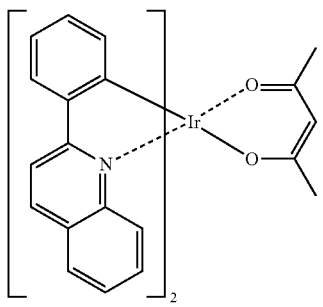
PD12 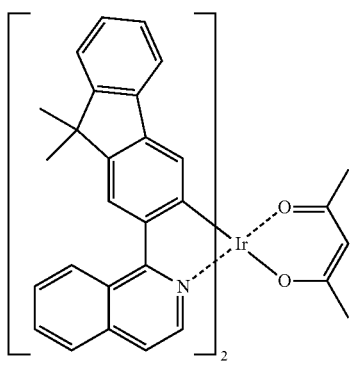
PD13 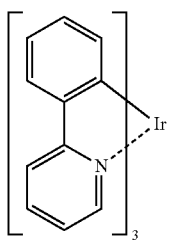
PD14 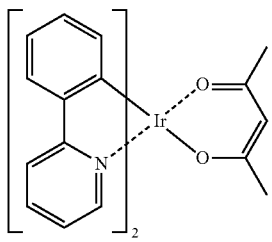
PD15 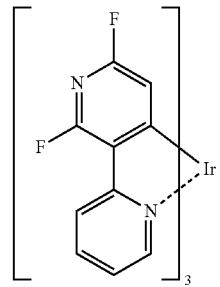
PD16 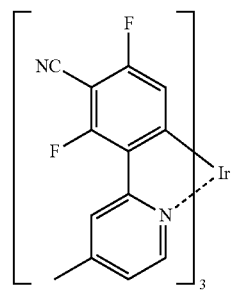
PD17 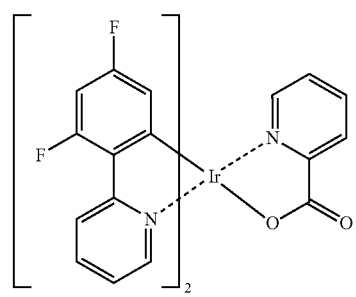
PD18 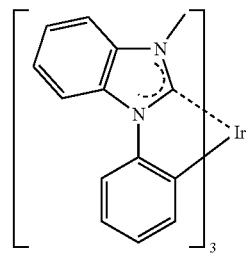
PD19 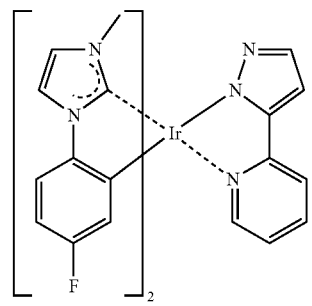

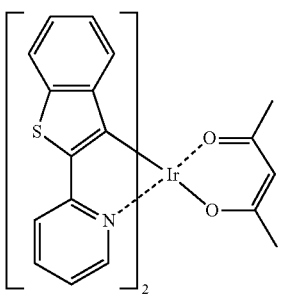
PD20

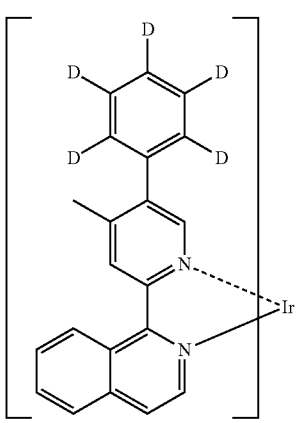
PD21

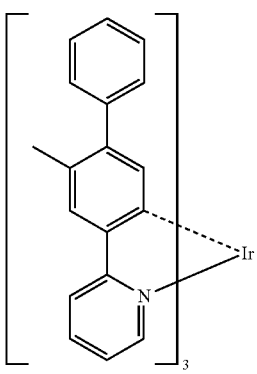
PD22

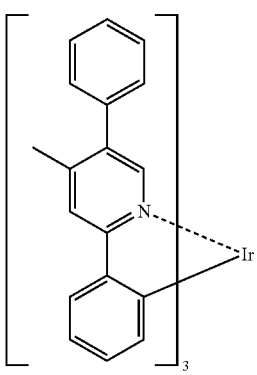
PD23

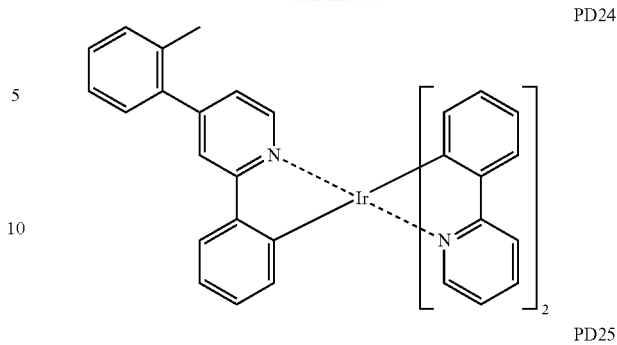
PD24

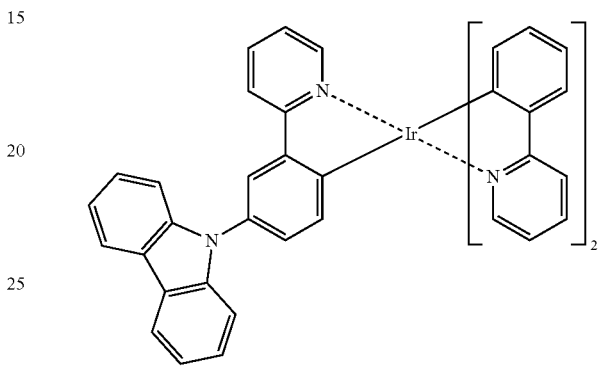
PD25

Fluorescent Dopant in Emission Layer

The fluorescent dopant may include an arylamine compound or a styrylamine compound.

The fluorescent dopant may include a compound represented by Formula 501:

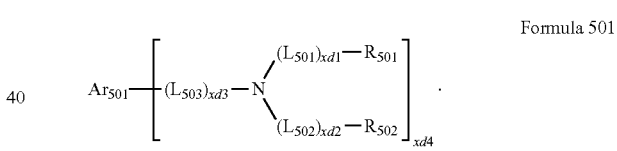
Formula 501

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer of 1 to 6.

In one embodiment, in Formula 501, $Ar_{501}$ may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, in Formula 501, $L_{501}$ to $L_{503}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, in Formula 501, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescent dopant may be selected from Compounds FD1 to FD22:

FD1
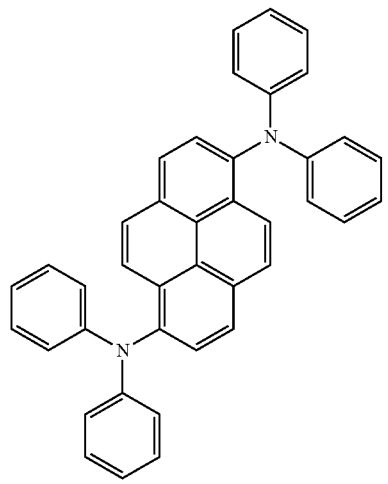
FD2
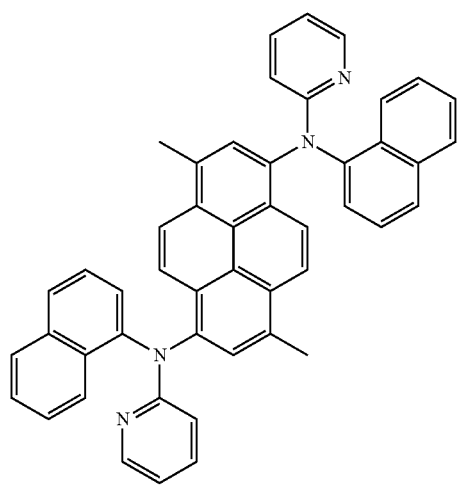
FD3
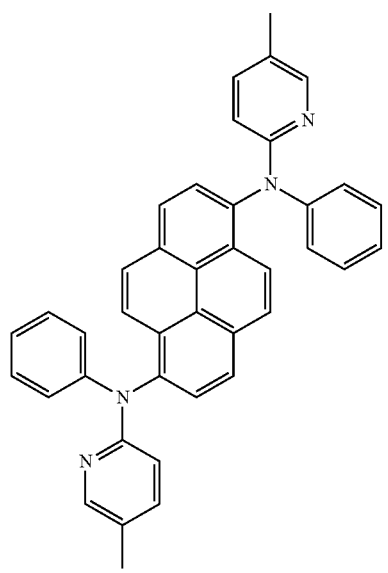
FD4
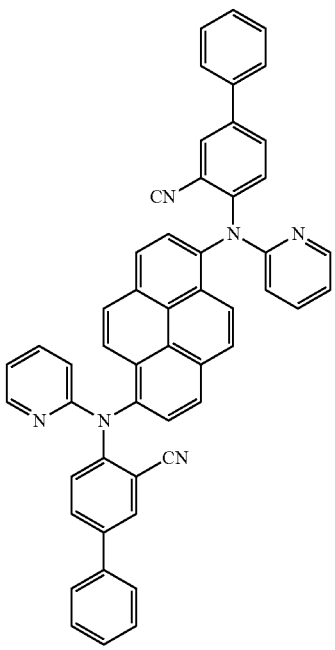
FD5
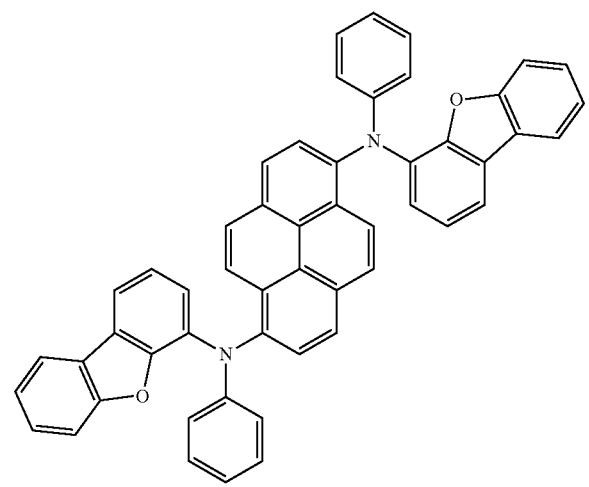
FD6
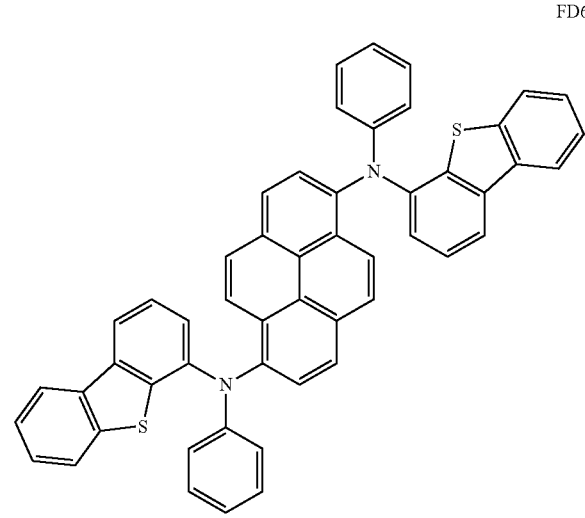

-continued
FD7
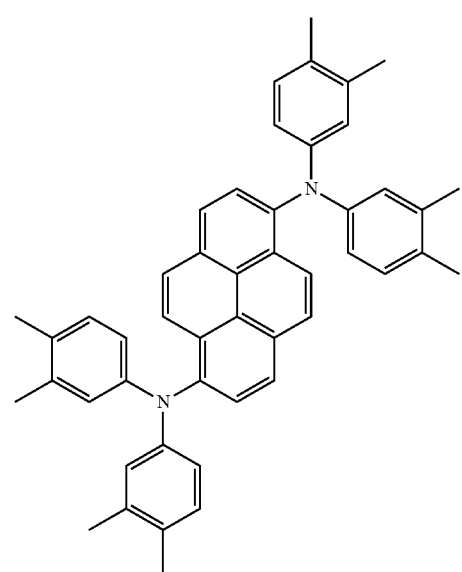
FD8
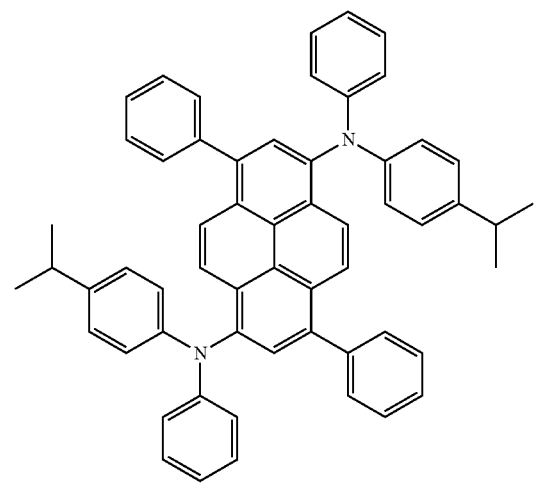
FD9
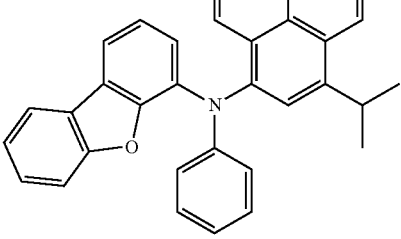
FD10
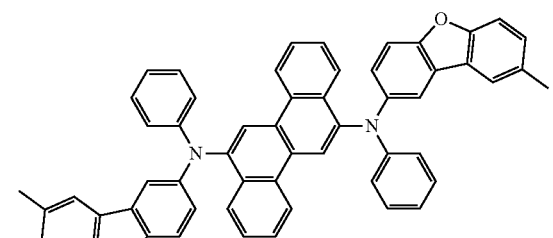
FD11
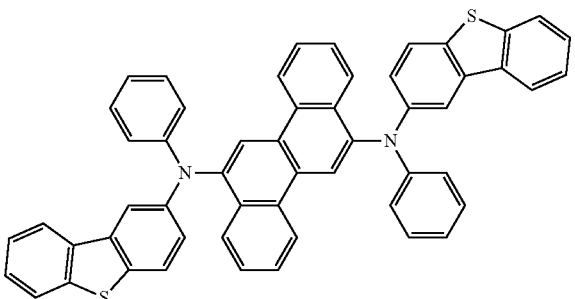
FD12
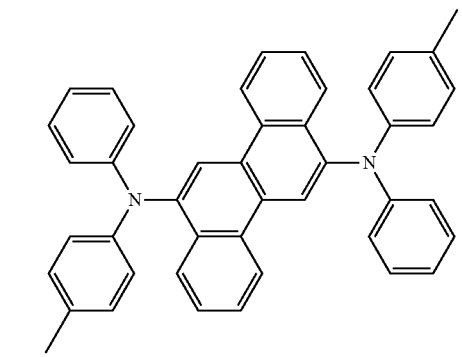
FD13
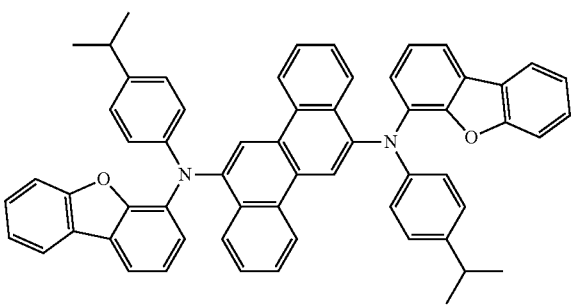
FD14
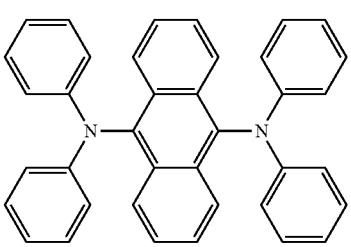

FD15
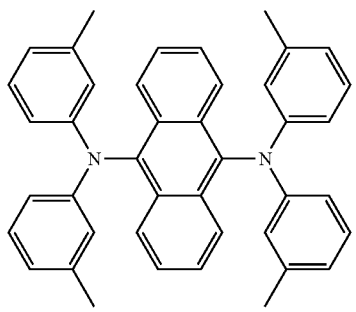
FD16
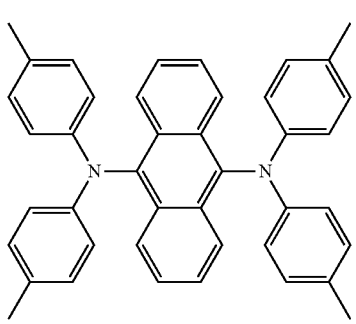
FD17
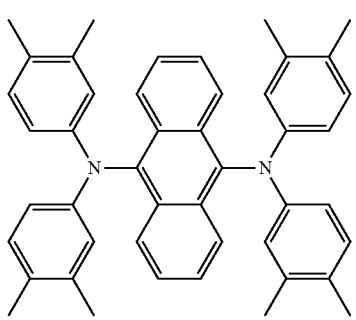
FD18
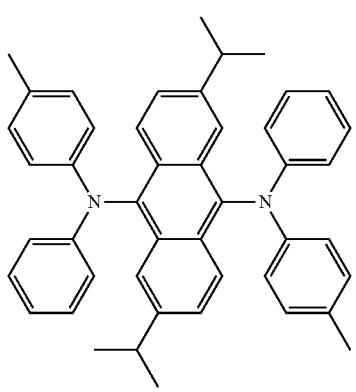
FD19
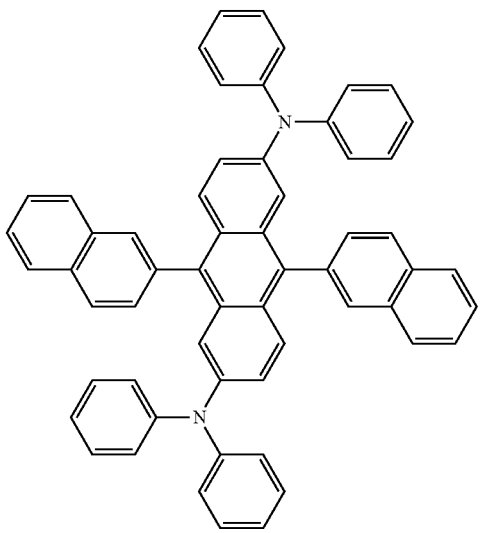
FD20
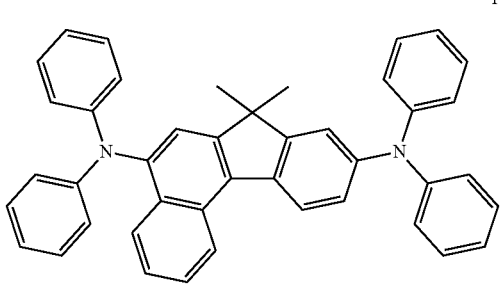
FD21
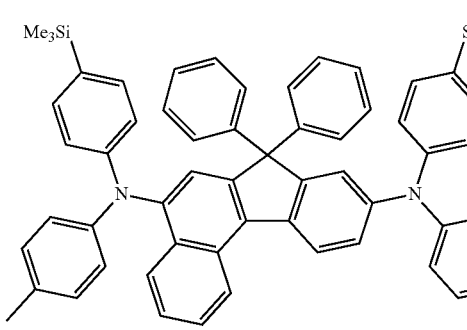
FD22
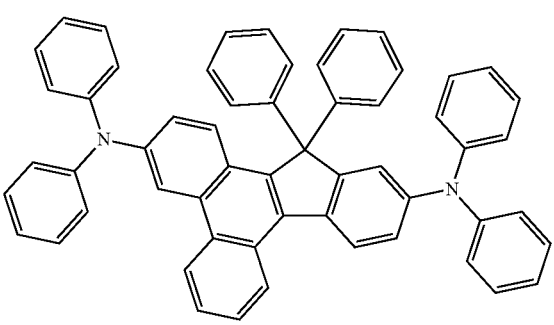
In one or more embodiments, the fluorescent dopant may be selected from the following compounds, but embodiments of the present disclosure are not limited thereto:

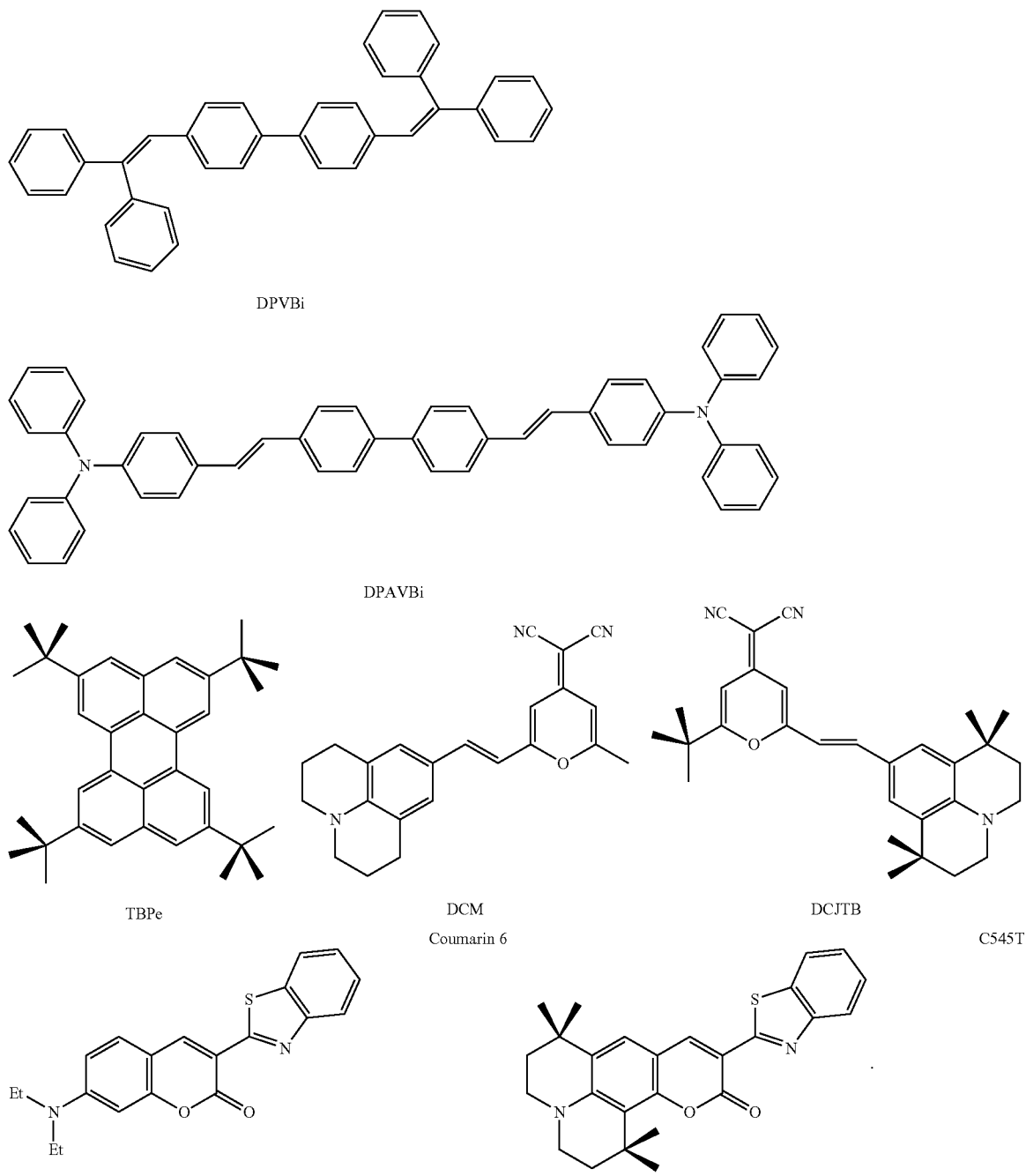

Electron Transport Region in Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

The electron transport region (for example, a buffer layer, a hole blocking layer, an electron control layer, or an electron transport layer in the electron transport region) may include a metal-free compound containing at least one π electron-depleted nitrogen-containing ring.

The term "π electron-depleted nitrogen-containing ring," as used herein, indicates a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other (e.g., combined together), or iii) a heteropolycyclic group in which at least one of 5-membered to 7-membered heteromonocyclic groups, each having at least one *—N=*' moiety, is condensed with (e.g., combined with) at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, and an azacarbazole, but are not limited thereto.

For example, the electron transport region may include a compound represented by Formula 601:

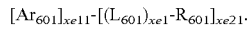   Formula 601

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one of $Ar_{601}$(s) in the number of xe11 and $R_{601}$(s) in the number of xe21 may include the π electron-depleted nitrogen-containing ring.

In one embodiment, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more $Ar_{601}$(s) may be linked via a single bond.

In one or more embodiments, $Ar_{601}$ in Formula 601 may be an anthracene group.

In one or more embodiments, a compound represented by Formula 601 may be represented by Formula 601-1:

Formula 601-1

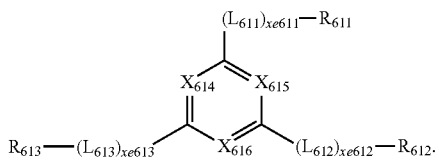

In Formula 601-1, $X_{614}$ may be N or $C(R_{614})$, $X_{615}$ may be N or $C(R_{615})$, and $X_{616}$ may be N or $C(R_{616})$, wherein at least one selected from $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, in Formulae 601 and 601-1, $L_{601}$ and $L_{611}$ to $L_{613}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formulae 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$), and —P(=O)(Q$_{601}$)(Q$_{602}$), and Q$_{601}$ and Q$_{602}$ may be the same as described above.

The electron transport region may include at least one compound selected from Compounds ET1 to ET36, but embodiments of the present disclosure are not limited thereto:

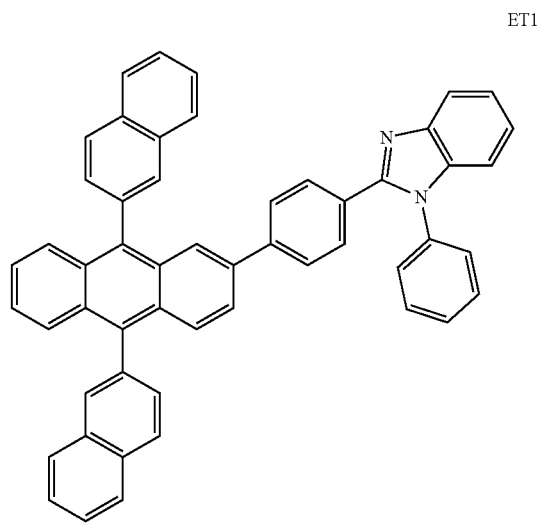

ET1

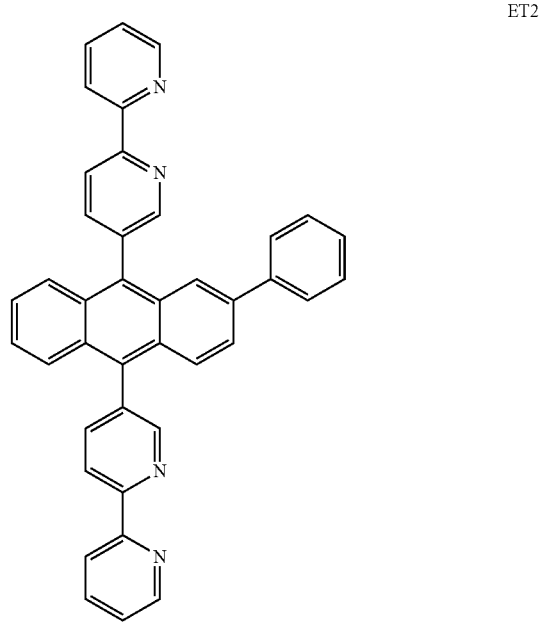

ET2

-continued
ET3
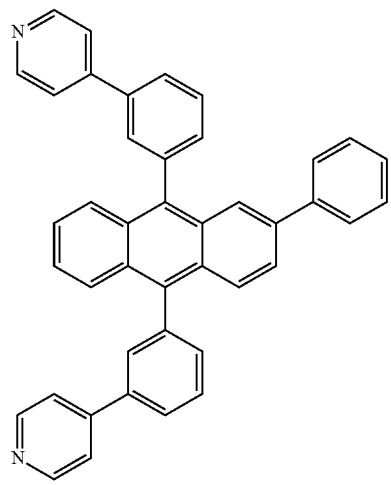
ET4
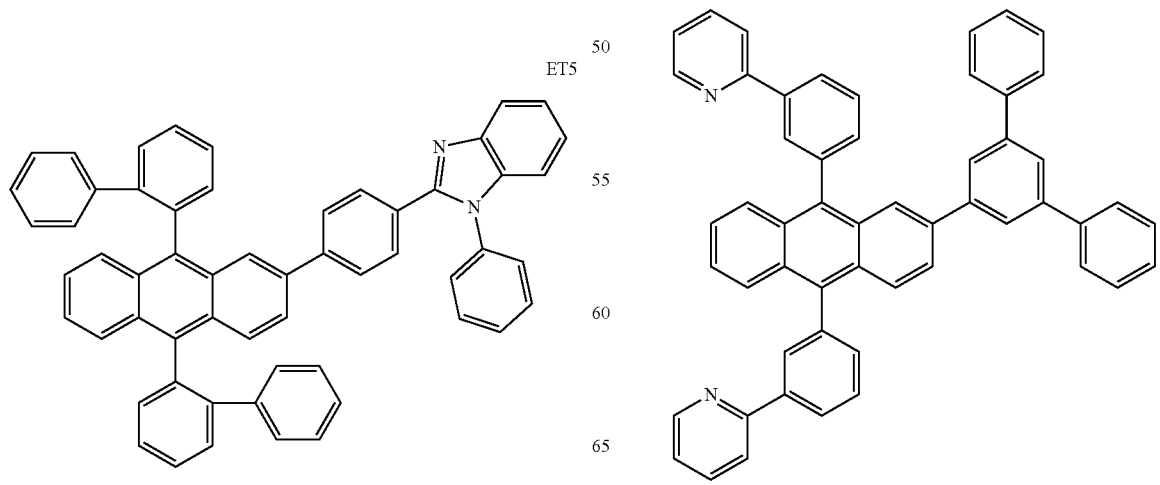
ET5
ET6
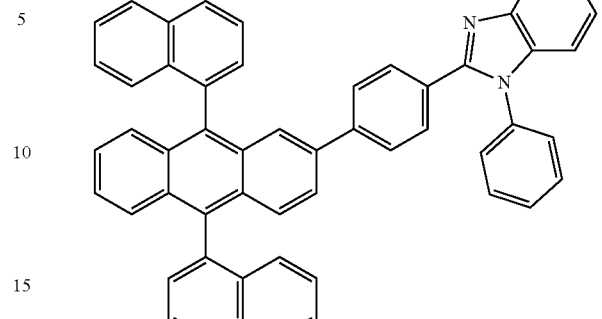
ET7
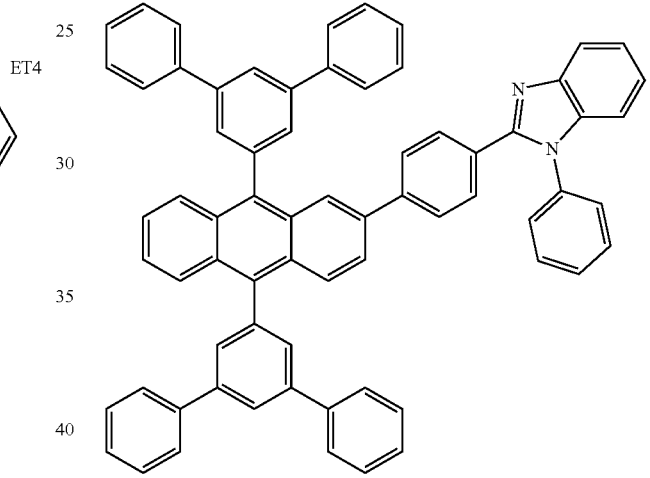
ET8

199
-continued
ET9
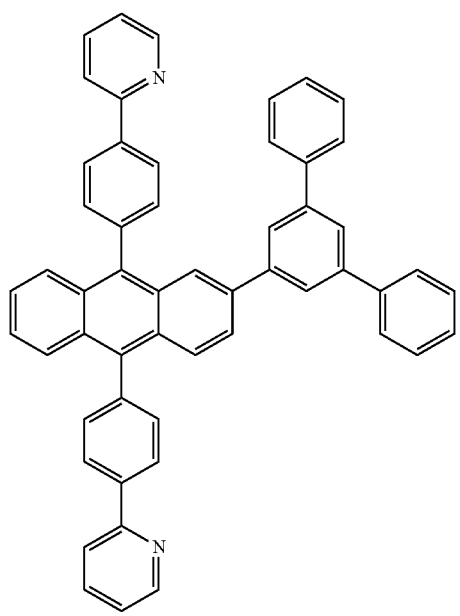
ET10
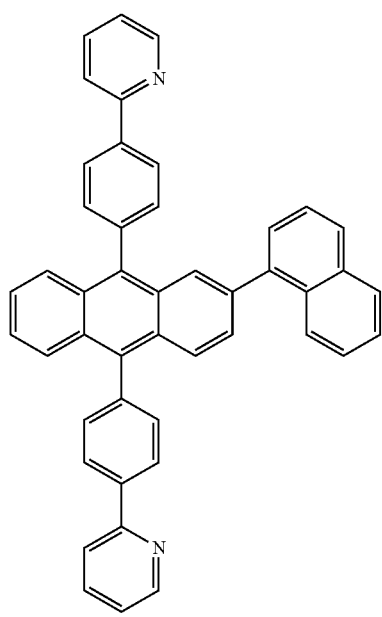
200
-continued
ET11
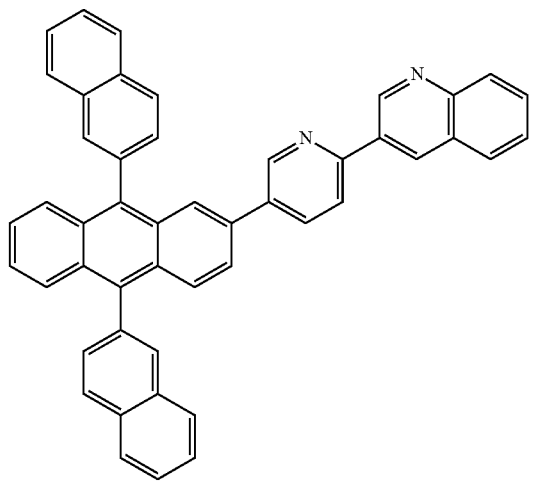
ET12
ET13
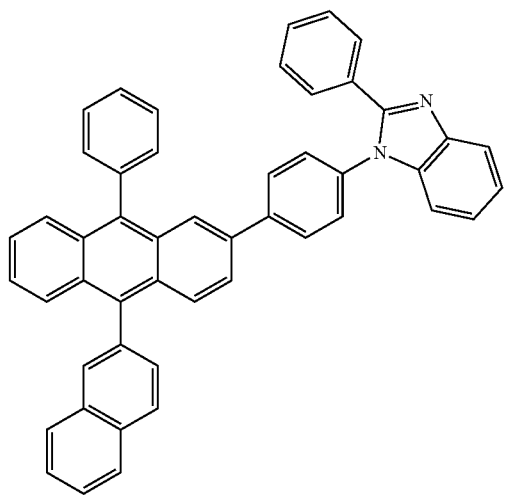

ET14
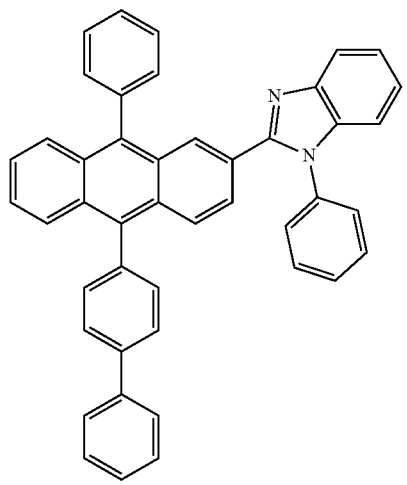
ET15
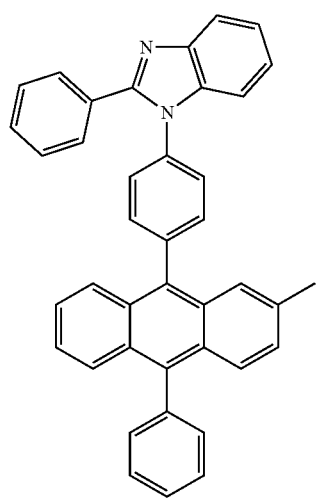
ET16
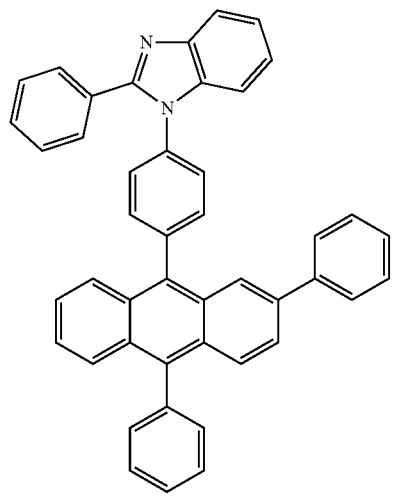
ET17
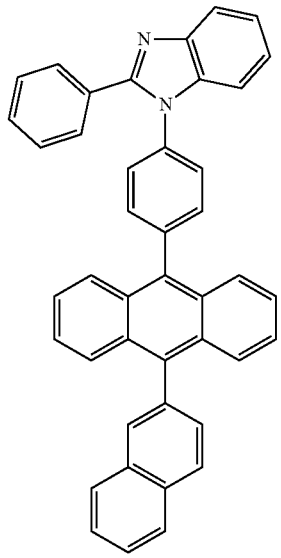
ET18
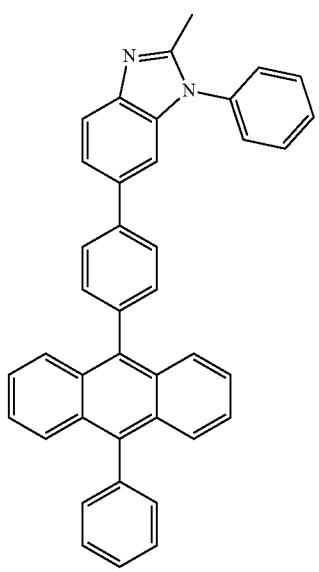
ET19
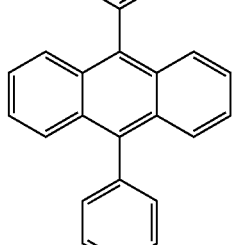

ET20
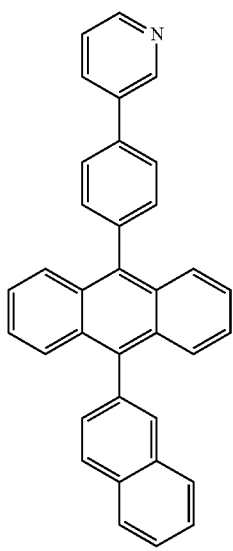
ET21
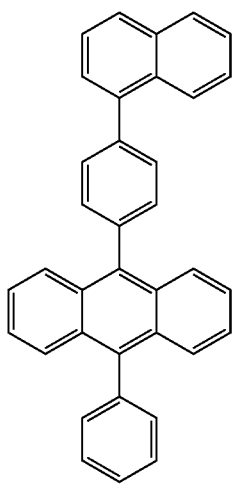
ET22
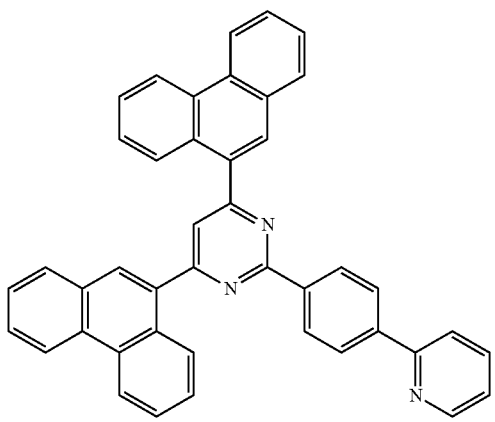
ET23
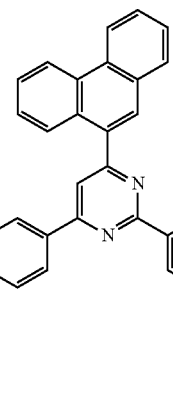
ET24
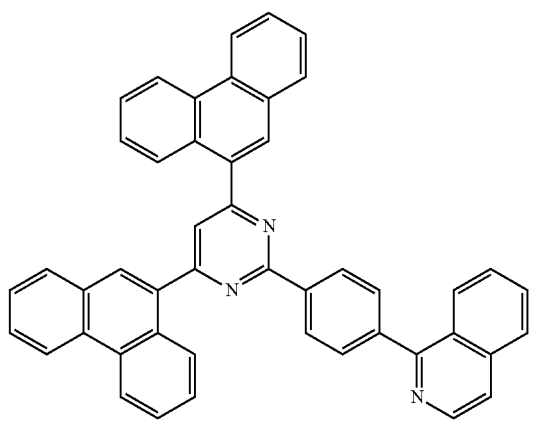
ET25
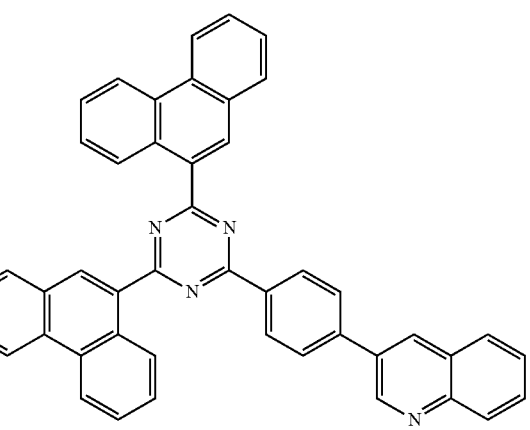

ET26
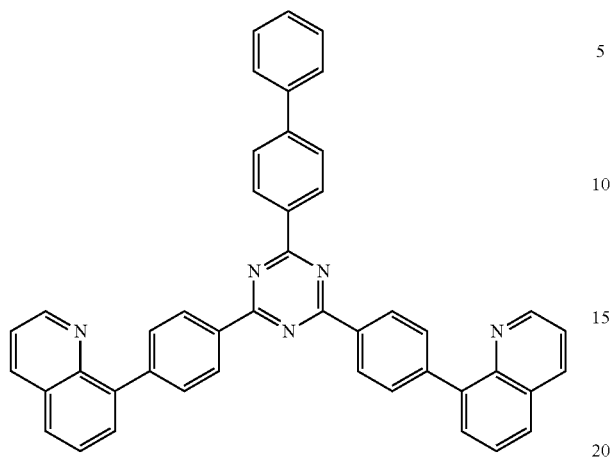
ET27
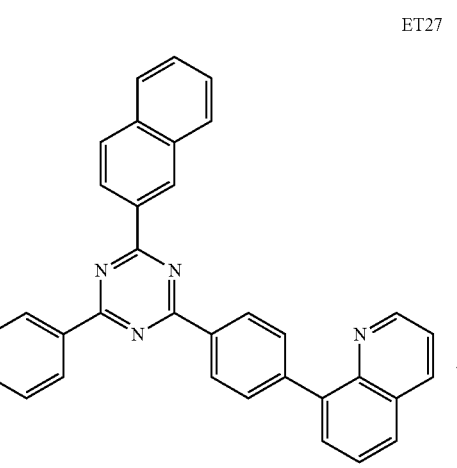
ET28
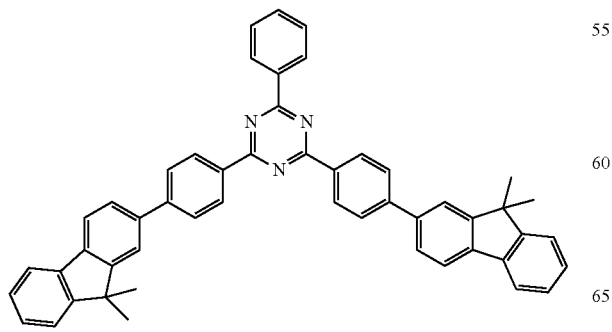
ET29
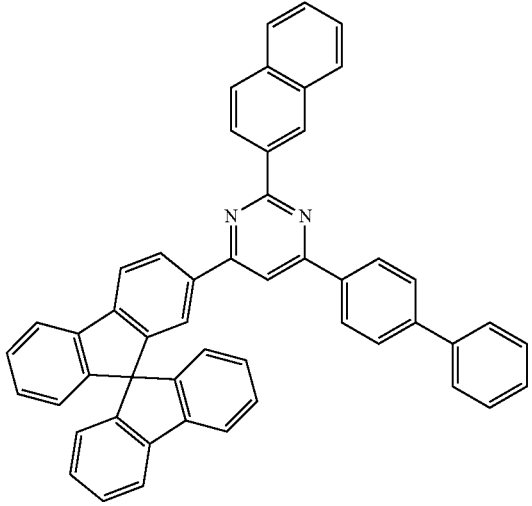
ET30
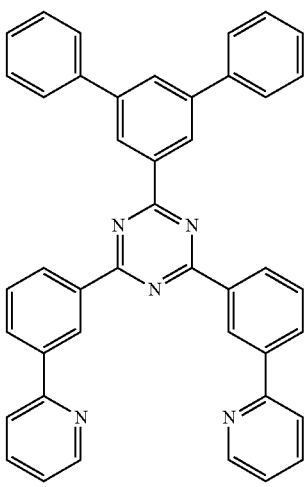
ET31
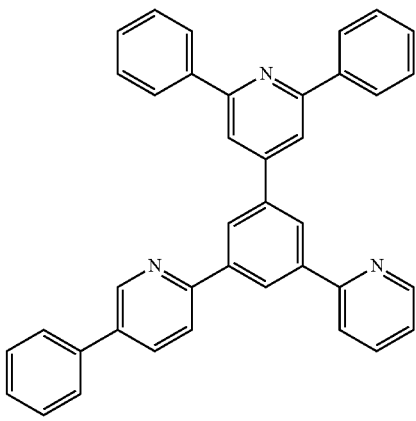

ET32
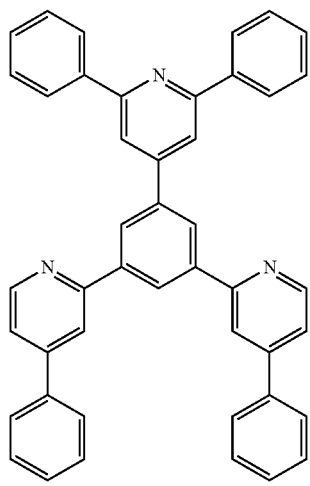
ET33
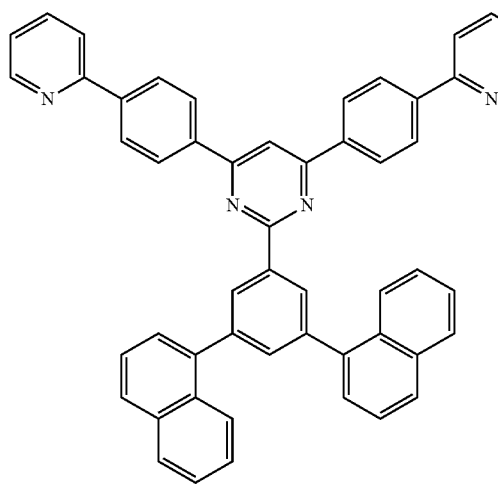
ET34
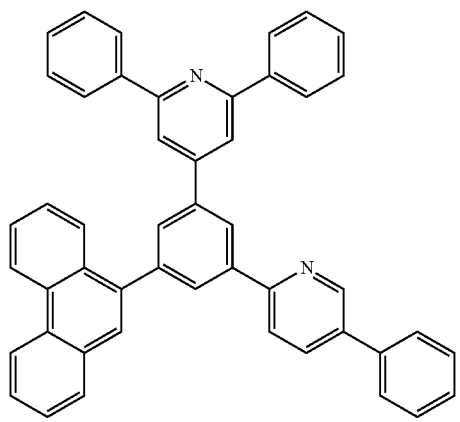
ET35
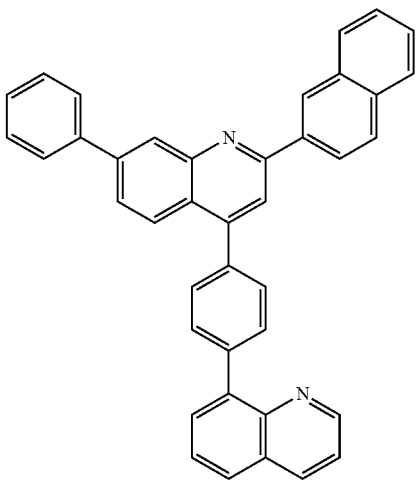
ET36
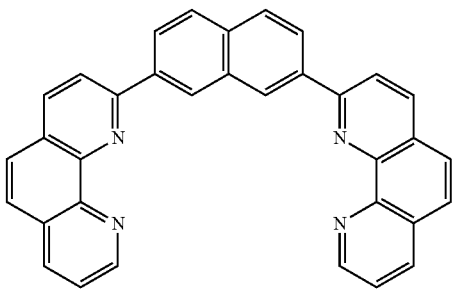
In one or more embodiments, the electron transport region may include at least one compound selected from 2,9-dimethyl-4,7-diphenyl-1,10-phenanthroline (BCP), 4,7-diphenyl-1,10-phenanthroline (Bphen), Alq$_3$, BAlq, 3-(biphenyl-4-yl)-5-(4-tert-butylphenyl)-4-phenyl-4H-1,2,4-triazole (TAZ), and NTAZ
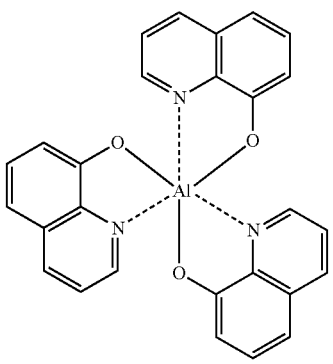
Alq$_3$

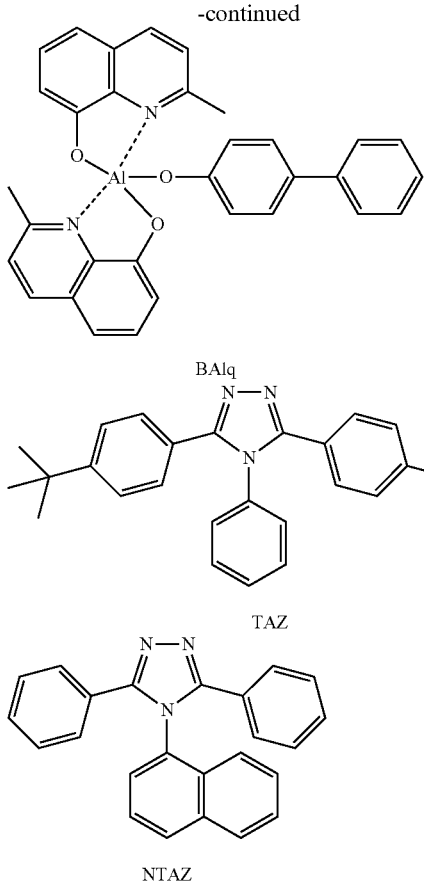

BAlq

TAZ

NTAZ

Thicknesses of the buffer layer, the hole blocking layer, and the electron control layer may each be in a range of about 20 Å to about 1,000 Å, for example, about 30 Å to about 300 Å. When the thicknesses of the buffer layer, the hole blocking layer, and the electron control layer are within these ranges, the electron transport region may have excellent hole blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described above, the electron transport layer may have excellent electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy phenyloxadiazole, a hydroxy phenylthiadiazol, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) or ET-D2:

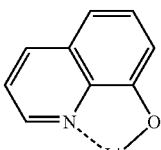

ET-D1

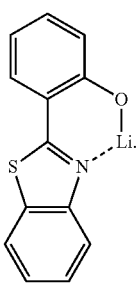

ET-D2

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs. In one embodiment, the alkali metal may be Li, Na, or Cs. In one or more embodiments, the alkali metal may be Li or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, or KI. In one embodiment, the alkali metal compound may be selected from LiF, $Li_2O$, NaF, LiI, NaI, CsI, and KI, but embodiments of the present disclosure are not limited thereto.

The alkaline earth-metal compound may be selected from alkaline earth-metal oxides, such as BaO, SrO, CaO, $Ba_xSr_{1-x}O$ (0<x<1), or $Ba_xCa_{1-x}O$ (0<x<1). In one embodiment, the alkaline earth-metal compound may be selected from BaO, SrO, and CaO, but embodiments of the present disclosure are not limited thereto.

The rare earth metal compound may be selected from $YbF_3$, $ScF_3$, $Sc_2O_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazol, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may consist of an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have suitable or satisfactory electron injection characteristics without a substantial increase in driving voltage.

Second Electrode 190

The second electrode 190 may be disposed on the organic layer 150 having such a structure. The second electrode 190 may be a cathode which is an electron injection electrode, and in this regard, a material for forming the second electrode 190 may be selected from metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

Layers constituting the hole transport region, an emission layer, and layers constituting the electron transport region may be formed in a certain region by using one or more suitable methods selected from vacuum deposition, spin coating, casting, Langmuir-Blodgett deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100 to about 500° C., vacuum degree of about $10^{-8}$ torr to about $10^{-3}$ torr, and a deposition rate of about 0.01 Å/sec to about 100 Å/sec depending on the material to be included in each layer to be formed, and the structure of each layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C., depending on the material to be included in each layer to be formed, and the structure of each layer to be formed.

Description of FIG. 2

FIG. 2 is a schematic view of an organic light-emitting device 20 according to an embodiment.

The organic light-emitting device 20 of FIG. 2 includes the first electrode 110, the second electrode 190 facing the first electrode 110, and an emission layer 151 between the first electrode 110 and the second electrode 190. The emission layer 151 includes a first non-doping layer (151-ND1), a doping layer (151-D), and a second non-doping layer (151-ND2). The first non-doping layer 151-ND1 and second non-doping layer (151-ND2) are each a dopant-free layer, and may include the third host and fourth host. The doping layer 151-D is a dopant-containing layer, and may include the first host, the second host, and the dopant.

A hole transport region 120 may be disposed between the first electrode 110 and the emission layer 151, and an electron transport region 170 may be disposed between the second electrode 190 and the emission layer 151.

Description of FIG. 3

FIG. 3 is a schematic view of an organic light-emitting device 30 according to an embodiment.

The organic light-emitting device 30 of FIG. 3 includes the first electrode 110, the second electrode 190 facing the first electrode 110, and the emission layer 151 between the first electrode 110 and the second electrode 190. The emission layer 151 includes the first non-doping layer 151-ND1, a first doping layer (151-D1), the second non-doping layer 151-ND2, a second doping layer (151-D2), and a third non-doping layer (151-ND3). The first non-doping layer 151-ND1, the second non-doping layer 151-ND2, and the third non-doping layer 151-ND3 are each a dopant-free layer, and may each include the third host and fourth host. The first doping layer 151-D1 and the second doping layer 151-D2 are each a dopant-containing layer, and may include the first host, the second host, and the dopant.

The hole transport region 120 may be disposed between the first electrode 110 and the emission layer 151, and the electron transport region 170 may be disposed between the second electrode 190 and the emission layer 151.

The first doping layer 151-D1 may be disposed toward the first electrode 110, and the second doping layer 151-D2 may be disposed toward the second electrode 190.

The first non-doping layer 151-ND1 may be disposed between the hole transport region 120 and the first doping layer 151-D1. The second non-doping layer 151-ND2 may be disposed between the electron transport region 170 and the second doping layer 151-D2. The third non-doping layer 151 ND-3 may be disposed between the first doping layer 151-D1 and the second doping layer 151-D2.

General Definition of Some of the Substituents

The term "$C_1$-$C_{60}$ alkyl group," as used herein, refers to a linear or branched aliphatic saturated hydrocarbon monovalent group having 1 to 60 carbon atoms, and examples thereof may include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a hydrocarbon group having at least one double bond at a main chain (e.g., in the middle) or at a terminus of the $C_2$-$C_{60}$ alkyl group, and examples thereof may include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a hydrocarbon group having at least one carbon-carbon triple bond at a main chain (e.g., in the middle) or at a terminus of the $C_2$-$C_{60}$ alkyl group, and examples thereof may include an ethynyl group, and a propynyl group. The term "$C_2$-$C_{60}$ alkynylene group," as used herein, refers to a divalent group having substantially the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon monocyclic group having 3 to 10 carbon atoms, and examples thereof may include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent monocyclic group having at least one heteroatom selected from N, O, Si, P, and S as a ring-forming atom and 1 to 10 carbon atoms, and examples thereof may include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms and at least one double bond in the ring thereof and no aromaticity (e.g., the ring and/or group is not aromatic), and examples thereof may include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent monocyclic group that has at least one heteroatom selected from N, O, Si, P, and S as a ring-forming atom, 1 to 10 carbon atoms, and at least one double bond in its ring. Non-limiting examples of the $C_1$-$C_{10}$ heterocycloalkenyl group may include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and the term "$C_6$-$C_{60}$ arylene group," as used herein, refers to a divalent group having a carbocyclic aromatic system having 6 to 60 carbon atoms. Non-limiting examples of the $C_6$-$C_{60}$ aryl group may include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other (e.g., combined together).

The term "$C_1$-$C_{60}$ heteroaryl group," as used herein, refers to a monovalent group having a heterocyclic aromatic system that has at least one heteroatom selected from N, O, Si, P, and S as a ring-forming atom, in addition to 1 to 60 carbon atoms. The term "$C_1$-$C_{60}$ heteroarylene group," as used herein, refers to a divalent group having a carbocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group may include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be condensed with each other (e.g., combined together).

The term "$C_6$-$C_{60}$ aryloxy group," as used herein, refers to —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

The term "monovalent non-aromatic condensed polycyclic group," as used herein, refers to a monovalent group (for example, having 8 to 60 carbon atoms) having two or more rings condensed with each other (e.g., combined together), only carbon atoms as ring-forming atoms, and no aromaticity in its entire molecular structure (e.g., the entire molecule is not aromatic). An example of the monovalent non-aromatic condensed polycyclic group may be a fluorenyl group. The term "divalent non-aromatic condensed polycyclic group," as used herein, refers to a divalent group having substantially the same structure as the monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other (e.g., combined together), at least one heteroatom selected from N, O, Si, P, and S, other than carbon atoms, as a ring-forming atom, and no aromaticity in its entire molecular structure (e.g., the entire molecule is not aromatic). An example of the monovalent non-aromatic condensed heteropolycyclic group may be a carbazolyl group. The term "divalent non-aromatic condensed heteropolycyclic group," as used herein, refers to a divalent group having substantially the same structure as the monovalent non-aromatic condensed heteropolycyclic group.

The term "$C_5$-$C_{60}$ carbocyclic group," as used herein, refers to a monocyclic or polycyclic group having 5 to 60 carbon atoms in which the ring-forming atoms are only carbon atoms. The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group," as used herein, refers to a group having substantially the same structure as the $C_1$-$C_{60}$ carbocyclic group, except that as a ring-forming atom, at least one heteroatom selected from N, O, Si, P, and S is used in addition to carbon (the number of carbon atoms may be in a range of 1 to 60).

At least one substituent selected from the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, substituted divalent non-aromatic condensed polycyclic group, substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph," as used herein, refers to a phenyl group, the term "Me," as used herein, refers to a methyl group, the term "Et," as used herein, refers to an ethyl group, the term "ter-Bu" or "But," as used herein, refers to a tert-butyl group, and the term "OMe," as used herein, refers to a methoxy group.

The term "biphenyl group," as used herein, refers to "a phenyl group substituted with a phenyl group." In other words, the "biphenyl group" is a substituted phenyl group having a $C_6$-$C_{60}$ aryl group as a substituent.

The term "terphenyl group," as used herein, refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

* and *' used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The wording "B was used instead of A" used in describing Synthesis Examples refers to that an identical (or substantially identical) molar equivalent of B was used in place of A.

EXAMPLES (1) Synthesis of Compound 1-1

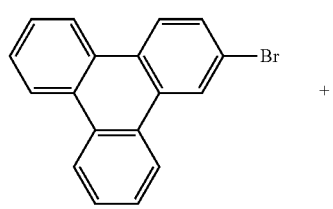

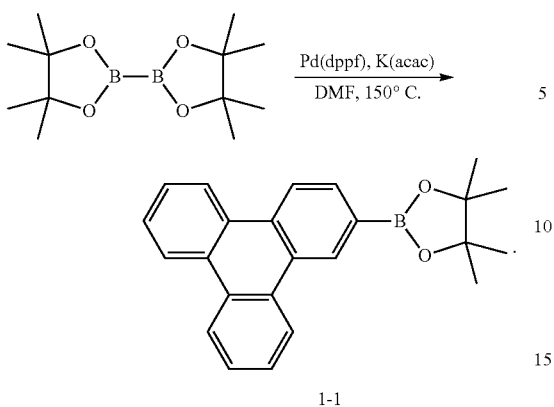

1-1

100 g (326 mmol) of 2-bromotriphenylene was dissolved in 1 L of dimethylformamide (DMF) under a nitrogen condition, and 99.2 g (391 mmol) of bis(pinacolato)diboron, 2.66 g (3.26 mmol) of (1,1'-bis(diphenylphosphine)ferrocene)dichloropalladium (II), and 80 g (815 mmol) of potassium acetate were added thereto. The mixed solution was refluxed by heating at a temperature of 150° C. for 5 hours. After the reaction was completed, water was added to the reaction solution. The mixture of the resulting reaction solution was then filtered, and dried in a vacuum oven. The residue obtained therefrom was separated and purified by flash column chromatography to obtain 113 g (98%) of Compound 1-1.

HRMS (70 eV, EI+): m/z calcd for $C_{24}H_{23}BO_2$: 354.1791, found: 354.

Elemental Analysis: C, 81%; H, 7%

Synthesis Example 2: Synthesis of Compound A-1

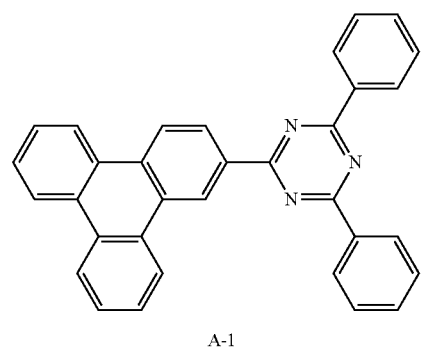

A-1

20 g (56.5 mmol) of Compound 1-1 was dissolved in 0.2 L of tetrahydrofuran (THF) under a nitrogen condition (a nitrogen atmosphere), and 15.1 g (56.5 mmol) of 2-chloro-4,6-diphenyl-1,3,5-triazine and 0.65 g (0.57 mmol) of tetrakis(triphenylphosphine)palladium were added thereto. The mixed solution was then stirred. 19.5 g (141 mmol) of potassium carbonate saturated in water was added thereto, and refluxed by a heating process performed thereon at a temperature of 80° C. for 20 hours. After the reaction was completed, water was added to the reaction solution, and an extraction process was performed thereon by using dichloromethane (DCM). Moisture in the extraction was dried by using anhydrous magnesium sulfate ($MgSO_4$), and the resulting mixture was then filtered and concentrated under reduced pressure. The residue obtained therefrom was separated and purified by flash column chromatography to obtain 22.1 g (85%) of Compound A-1.

HRMS (70 eV, EI+): m/z calcd for $C_{33}H_{21}N_3$: 459.1735, found: 459.

Elemental Analysis: C, 86%; H, 5%

Synthesis Example 3: Synthesis of Compound A-2

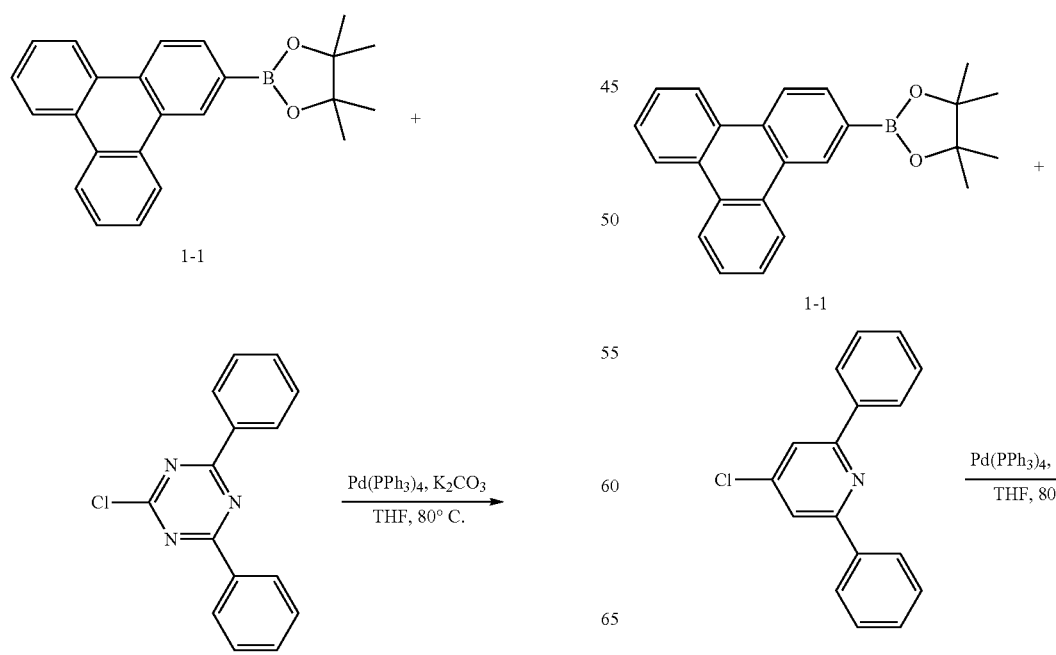

-continued

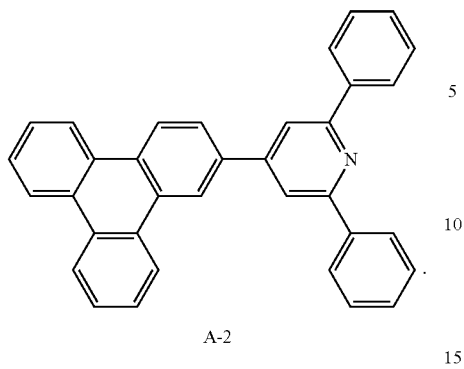

A-2

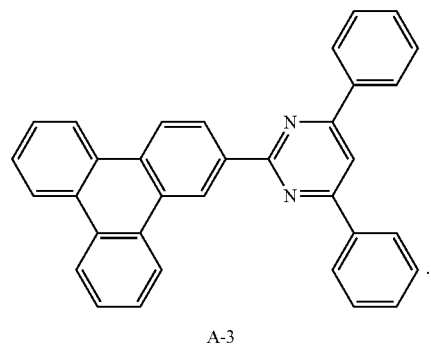

A-3

20 g (56.5 mmol) of Compound 1-1 was dissolved in 0.2 L of THF under a nitrogen condition, and 14.5 g (56.5 mmol) of 4-chloro-2,6-diphenylpyridine and 0.65 g (0.57 mmol) of tetrakis(triphenylphosphine)palladium were added thereto. The mixed solution was then stirred. 19.5 g (141 mmol) of potassium carbonate saturated in water was added to the mixed solution, and refluxed by a heating process performed thereon at a temperature of 80° C. for 20 hours. After the reaction was completed, water was added to the reaction solution, and an extraction process was performed thereon by using DCM. Moisture in the extraction was dried by using anhydrous MgSO$_4$, and the resulting mixture was then filtered and concentrated under reduced pressure. The residue obtained therefrom was separated and purified by flash column chromatography to obtain Compound A-2.

Synthesis Example 4: Synthesis of Compound A-3

20 g (56.5 mmol) of Compound 1-1 was dissolved in 0.2 L of THF under a nitrogen condition, and, and 15.1 g (56.5 mmol) of 2-chloro-4,6-diphenylpyrimidine and 0.65 g (0.57 mmol) of tetrakis(triphenylphosphine)palladium were added thereto. The mixed solution was then stirred. 19.5 g (141 mmol) of potassium carbonate saturated in water was added thereto, and refluxed by a heating process performed thereon at a temperature of 80° C. for 20 hours. After the reaction was completed, water was added to the reaction solution, and an extraction process was performed thereon by using DCM. Moisture in the extraction was dried by using anhydrous MgSO$_4$, and the resulting mixture was then filtered and concentrated under reduced pressure. The residue obtained therefrom was separated and purified by flash column chromatography to obtain Compound A-3.

Synthesis Example 5: Synthesis of Compound B-10

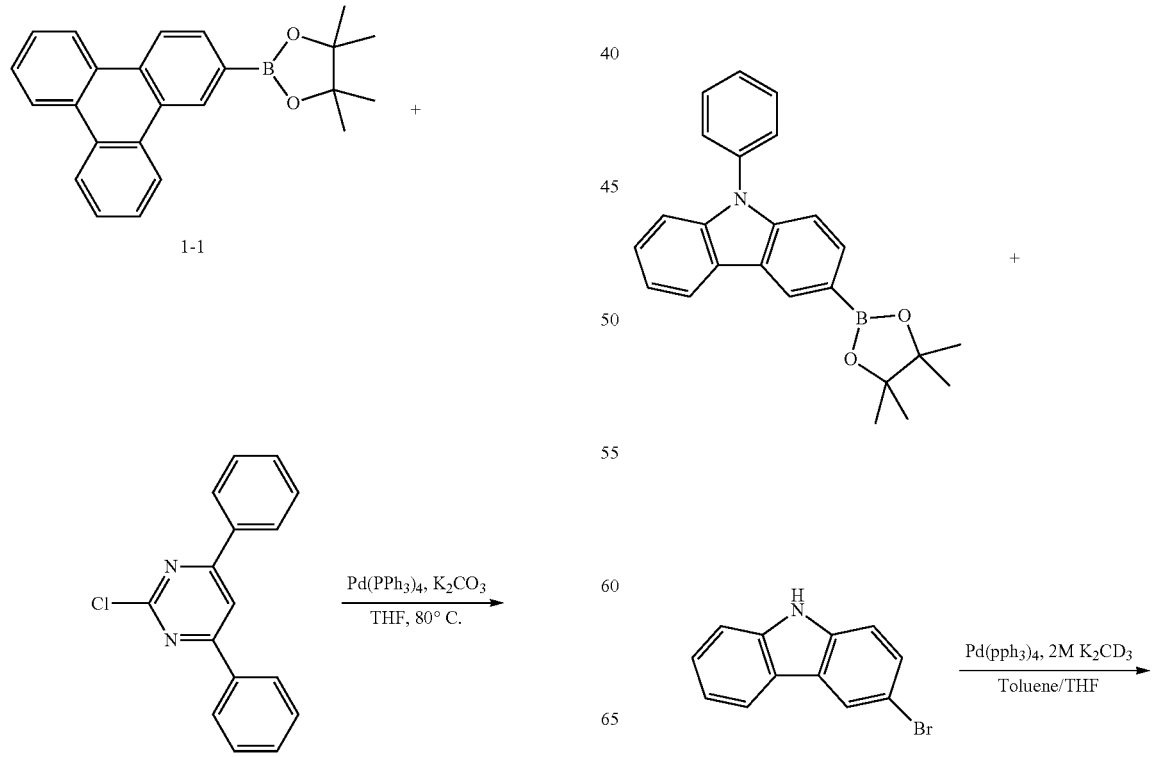

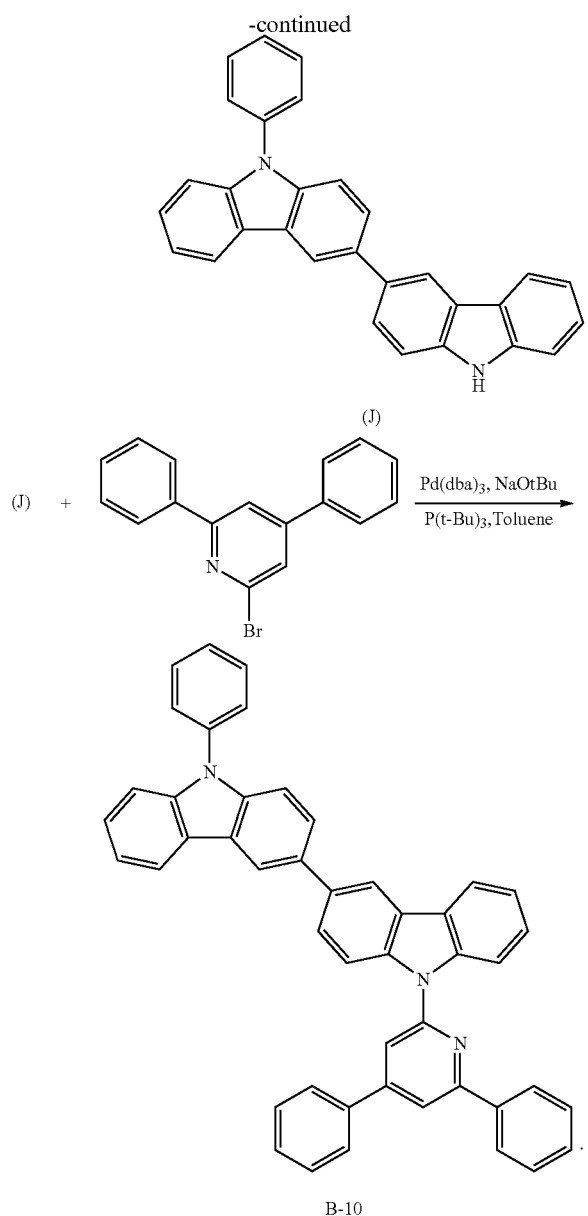

B-10

Step 1: Synthesis of Compound J 26.96 g (81.4 mmol) of N-phenyl carbazole-3-boronic acid pinacolato and 23.96 g (97.36 mmol) of 3-bromocarbazole were mixed with a mixture of 230 mL of tetrahydrofuran and 100 mL of 2M-potassium carbonate aqueous solution. Then, the mixed solution was refluxed by heating for 12 hours in a nitrogen atmosphere. After the reaction was completed, methanol was poured into the reaction product. Solids produced therefrom were filtered, and then, the filtrate was dissolved again in chlorobenzene, and activated carbon and anhydrous MgSO$_4$ were added thereto. The mixed solution was then stirred. After a filtration process was performed thereon, the resulting product was subjected to recrystallization by using chlorobenzene and methanol to obtain 22.6 g (yield: 68%) of Compound J.

HRMS (70 eV, EI+): m/z calcd for C30H20N2: 408.16, found: 408.

Elemental Analysis: C, 88%; H, 5%

Step 2: Synthesis of Compound B-10

22.42 g (54.88 mmol) of Compound J, 20.43 g (65.85 mmol) of 2-bromo-4,6-diphenylpyridine, and 7.92 g (82.32 mmol) of sodium tert-butoxide were dissolved in 400 ml of toluene, and then, 1.65 g (1.65 mmol) of tris(dibenzylideneacetone)dipalladium(0) (Pd(dba)$_3$) and 1.78 g (4.39 mmol) of tri-tert-butylphosphine were added thereto dropwise. The mixed solution was refluxed by heating for 12 hours in a nitrogen atmosphere at a temperature of 110° C. After the reaction was completed, methanol was poured into the reaction product. Solids produced therefrom were filtered, and then, the filtrate was dissolved again in chlorobenzene, and activated carbon and anhydrous MgSO$_4$ were added thereto. The mixed solution was then stirred. After a filtration process was performed thereon, the resulting product was subjected to recrystallization by using chlorobenzene and methanol to obtain 28.10 g (yield: 80%) of Compound B-10.

HRMS (70 eV, EI+): m/z calcd for C47H31N3: 637.25, found: 637.

Elemental Analysis: C, 89%; H, 5%

Synthesis Example 6: Synthesis of Compound B-11

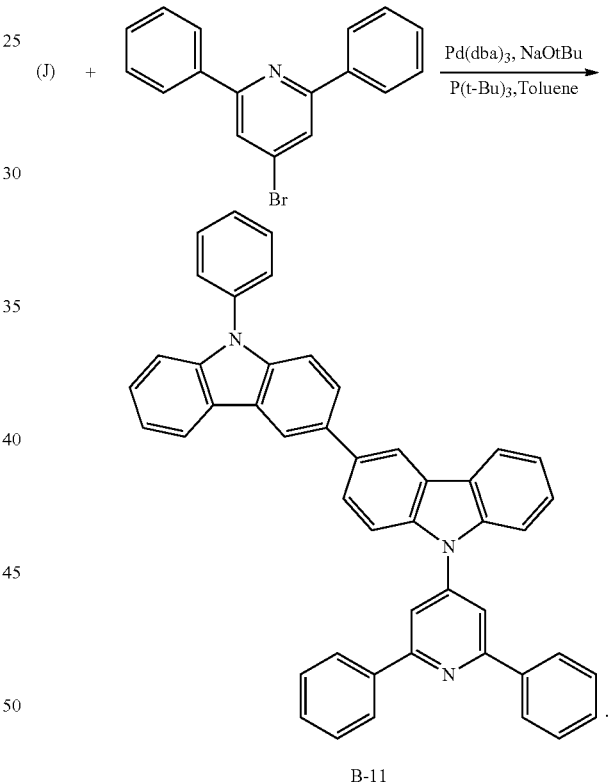

B-11

22.42 g (54.88 mmol) of Compound J, 20.43 g (65.85 mmol) of 4-bromo-2,6-diphenylpyridine, and 7.92 g (82.32 mmol) of sodium tert-butoxide were dissolved in 400 ml of toluene, and then, 1.65 g (1.65 mmol) of tris(dibenzylideneacetone)dipalladium(0) (Pd(dba)$_3$) and 1.78 g (4.39 mmol) of tri-tert-butylphosphine were added thereto dropwise. The mixed solution was refluxed by heating for 12 hours in a nitrogen atmosphere at a temperature of 110° C. After the reaction was completed, methanol was poured into the reaction product. Solids produced therefrom were filtered, and then, the filtrate was dissolved again in chlorobenzene, and activated carbon and anhydrous MgSO$_4$ were added thereto. The mixed solution was then stirred. After a filtration process was performed thereon, the resulting product was subjected to recrystallization by using chlorobenzene and methanol to obtain 28.10 g (yield: 80%) of Compound B-11.

HRMS (70 eV, EI+): m/z calcd for C47H31N3: 637.25, found: 637.

Elemental Analysis: C, 89%; H, 5%

Example 1

As a substrate and an ITO anode, a Corning 30 Ω/cm² (300 Å) ITO glass substrate was cut to a size of 50 mm×50 mm×0.5 mm, sonicated with isopropyl alcohol and pure water each for 10 minutes, and then, cleaned by exposure to ultraviolet rays and ozone for 10 minutes. Then, the ITO glass substrate was mounted on a vacuum deposition apparatus.

Compound HT1 and Compound 221 were vacuum deposited on the ITO anode formed on the ITO glass substrate at a weight ratio of 97:3 to form a hole injection layer having a thickness of 100 Å, and Compound HT1 was vacuum deposited thereon to form a hole transport layer having a thickness of 600 Å, thereby forming a hole transport region.

Compound A-1 (as the third host) and Compound B-10 (as the fourth host) were co-deposited at a weight ratio of 50:50 on the hole transport region to form a first non-doping layer having a thickness of 30 Å. Compound A-1 (as the first host), Compound B-10 (as the second host), and Compound PD13 (as the dopant) were co-deposited on the first non-doping layer at a weight ratio of 46:46:8 to form a doping layer having a thickness of 340 Å. Compound A-1 (as the third host) and Compound B-10 (as the fourth host) were co-deposited on the doping layer at a weight ratio of 50:50 to form a second non-doping layer having a thickness of 30 Å, thereby forming an emission layer.

Compounds ET1 and ET-D1 were deposited on the emission layer at a weight ratio of 50:50 to form an electron transport layer having a thickness of 300 Å, and Al was vacuum deposited on the electron transport layer to form a cathode having a thickness of 1,200 Å, thereby manufacturing an organic light-emitting device.

221

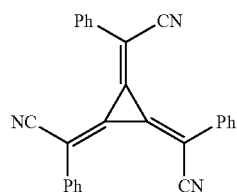

PD13

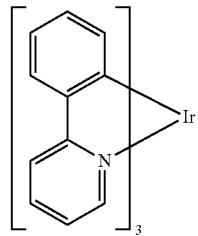

ET1

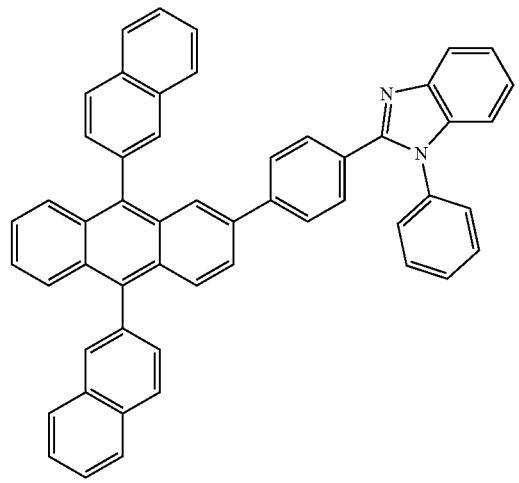

ET-D1

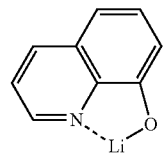

HT1

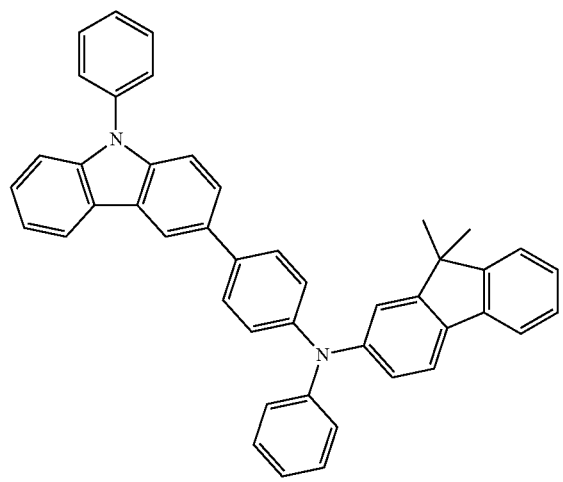

Example 2

An organic light-emitting device was manufactured substantially in the same manner as in Example 1, except that Compound A-2 was used instead of Compound A-1 in forming an emission layer.

Example 3

An organic light-emitting device was manufactured substantially in the same manner as in Example 1, except that Compound B-11 was used instead of Compound B-10 in forming an emission layer.

Example 4

An organic light-emitting device was manufactured substantially in the same manner as in Example 1, except that Compound A-3 was used instead of Compound A-1 in forming an emission layer.

Example 5

An organic light-emitting device was manufactured substantially in the same manner as in Example 1, except that, in forming an emission layer, Compound A-3 was used instead of Compound A-1 and Compound B-11 was used instead of Compound B-10.

Comparative Example 1

An organic light-emitting device was manufactured substantially in the same manner as in Example 1, except that, in forming an emission layer, Compound A-1 and Compound B-10 were used to form an emission layer having a thickness of 400 Å.

Comparative Example 2

An organic light-emitting device was manufactured substantially in the same manner as in Example 1, except that a non-doping layer was not formed in forming an emission layer.

Comparative Example 3

An organic light-emitting device was manufactured substantially in the same manner as in Example 1, except that, in forming an emission layer, Compound A-1 (as the third host) was used to form a non-doping layer, and Compound A-1 (as the first host) and a dopant were used to form a doping layer.

Comparative Example 4

An organic light-emitting device was manufactured substantially in the same manner as in Example 1, except that, in forming an emission layer, Compound B-10 (as the fourth host) was used to form a non-doping layer, and Compound B-10 (as the second host) and a dopant were used to form a doping layer.

Comparative Example 5

An organic light-emitting device was manufactured substantially in the same manner as in Example 1, except that, in forming an emission layer, Compound RH1 was used to form a non-doping layer, and Compound RH1 (as the host) and Compound RD1 (as the dopant) were used to form a doping layer:

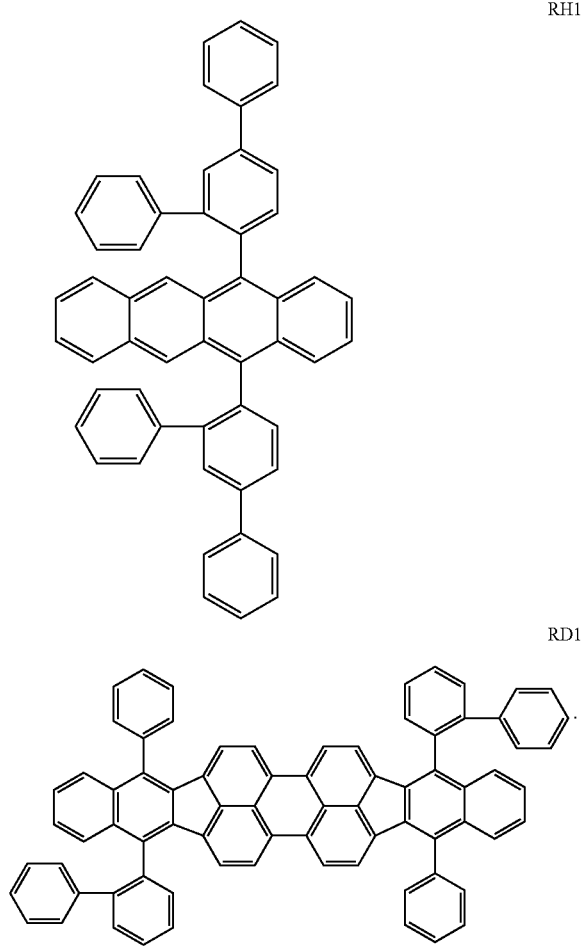

The driving voltage, current density, and efficiency of the organic light-emitting devices manufactured according to Examples 1 to 5 and Comparative Examples 1 to 5 were measured by using a Keithley SMU 236 and a luminance meter PR650, and results thereof are shown in Table 1.

TABLE 1

| | Doping layer | | | Non-doping layer | | Driving | Current | |
|---|---|---|---|---|---|---|---|---|
| | First host | Second host | Dopant | Third host | Fourth host | voltage (V) | density (mA/cm$^2$) | Efficiency (cd/A) |
| Example 1 | A-1 | B-10 | PD13 | A-1 | B-10 | 2.3 | 10 | 62.8 |
| Example 2 | A-2 | B-10 | PD13 | A-2 | B-10 | 2.5 | 10 | 61.8 |
| Example 3 | A-1 | B-11 | PD13 | A-1 | B-11 | 2.4 | 10 | 60.7 |
| Example 4 | A-3 | B-10 | PD13 | A-3 | B-10 | 2.8 | 10 | 59.8 |
| Example 5 | A-3 | B-11 | PD13 | A-3 | B-11 | 2.6 | 10 | 58.4 |
| Comparative Example 1 | — | — | — | A-1 | B-10 | 6.8 | 10 | 15.0 |
| Comparative Example 2 | A-1 | B-10 | PD13 | — | — | 3.5 | 10 | 55.4 |
| Comparative Example 3 | A-1 | — | PD13 | A-1 | — | 8.2 | 10 | 21.6 |

TABLE 1-continued

|  | Doping layer | | | Non-doping layer | | Driving voltage (V) | Current density (mA/cm$^2$) | Efficiency (cd/A) |
| --- | --- | --- | --- | --- | --- | --- | --- | --- |
|  | First host | Second host | Dopant | Third host | Fourth host |  |  |  |
| Comparative Example 4 | — | B-10 | PD13 |  | B-10 | 3.8 | 10 | 45.1 |
| Comparative Example 5 | RH1 | — | RD1 | RH1 | — | 4.8 | 10 | 15.6 |

Referring to Table 1, it is confirmed that the organic light-emitting devices of Examples 1 to 5 had excellent driving voltage and efficiency, as compared with those of the organic light-emitting devices of Comparative Examples 1 to 5.

According to one or more embodiments, the organic light-emitting device may have a low driving voltage and a high efficiency concurrently (e.g., at the same time).

It should be understood that embodiments described herein should be considered in a descriptive sense only and not for purposes of limitation. Descriptions of features or aspects within each embodiment should typically be considered as available for other similar features or aspects in other embodiments.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more embodiments have been described with reference to the figures, it will be understood by those of ordinary skill in the art that various changes in form and details may be made therein without departing from the spirit and scope as defined by the following claims

What is claimed is:

1. An organic light-emitting device comprising:
a first electrode;
a second electrode facing the first electrode; and
an organic layer between the first electrode and the second electrode and comprising an emission layer,
wherein the emission layer comprises at least one doping layer and at least one non-doping layer,
the doping layer is thicker than the at least one non-doping layer,
the doping layer comprises a first host, a second host, and a dopant,
the non-doping layer comprises a third host and a fourth host, and does not comprise a dopant,
the first host and the third host are each independently represented by Formula 1, and
the second host and the fourth host are each independently represented by one selected from Formulae 2-1 to 2-3:

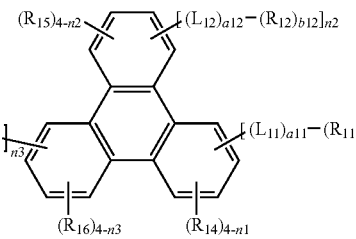

Formula 1

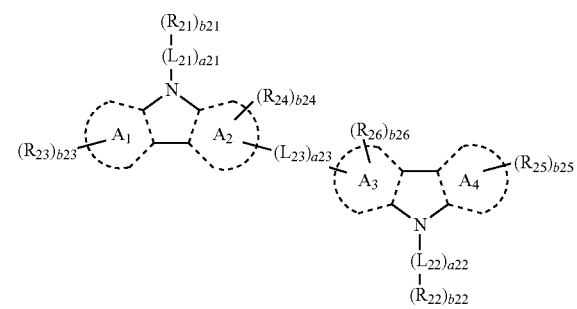

Formula 2-1

-continued

Formula 2-2

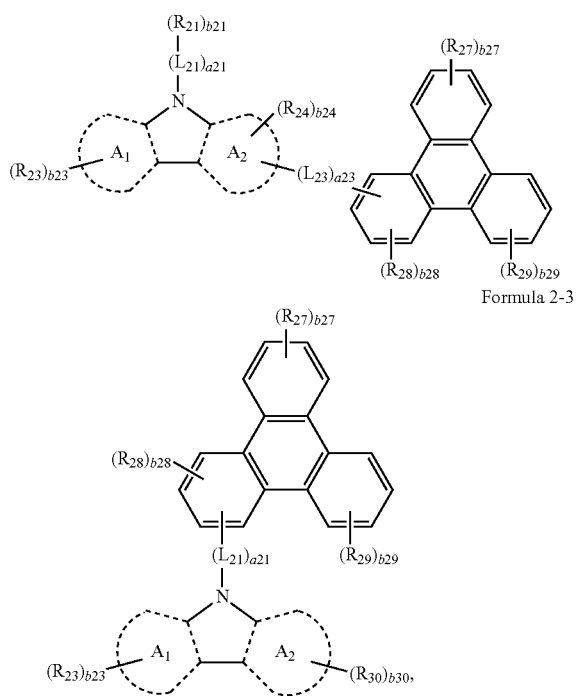

Formula 2-3 wherein, in Formulae 1 and 2-1 to 2-3,
n1 to n3 are each independently 0, 1, or 2,
the sum of n1, n2, and n3 is 1, 2, 3, 4, 5, or 6,
$L_{11}$ to $L_{13}$ and $L_{21}$ to $L_{23}$ are each independently selected from a single bond, a substituted or unsubstituted $C_5$-$C_{60}$ carbocyclic group, and a substituted or unsubstituted $C_1$-$C_{60}$ heterocyclic group,
a11 to a13 and a21 to a23 are each independently be 1, 2, 3, 4, or 5,
$A_1$ to $A_4$ are each independently selected from a $C_5$-$C_{60}$ carbocyclic group and a $C_1$-$C_{60}$ heterocyclic group,
$R_{11}$ to $R_{16}$ and $R_{21}$ to $R_{30}$ are each independently selected form hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —C(=O)($Q_1$), —N($Q_1$)($Q_2$), —P(=O)($Q_1$)($Q_2$), and —S(=O)$_2$($Q_1$)($Q_2$),
at least one selected from $R_{11}$ to $R_{13}$ is $R_{ET}$,
b11 to b3, b21 to b26, and b30 are each independently 1, 2, 3, 4, or 5,
b27 and b29 are each independently 1, 2, 3, or 4,
b28 is 1, 2, or 3,
$R_{ET}$ is selected form:
a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbolinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, and a pyrimidobenzothiophenyl group;
a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbolinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, and a pyrimidobenzothiophenyl group, each substituted with at least one selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a pyridinyl group, a pyrazinyl group, a pyrimidinyl group, a pyridazinyl group, a triazinyl group, —N($Q_{31}$)($Q_{32}$), —Si($Q_{31}$)($Q_{32}$)($Q_{33}$), and —B($Q_{31}$)($Q_{32}$); and
a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbolinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, and a pyrimidobenzothiophenyl group, each substituted with at least one selected from a phenyl group, a biphenyl group, a terphenyl group, and a naphthyl group that are each substituted with at least one selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a pyridinyl group, a pyrazinyl group, a pyrimidinyl group, a pyridazinyl group, a triazinyl group, —N($Q_{41}$)($Q_{42}$), —Si($Q_{41}$)($Q_{42}$)($Q_{43}$), and —B($Q_{41}$)($Q_{42}$), each of the substituents of the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, $Q_{31}$ to $Q_{33}$, and $Q_{41}$ to $Q_{43}$ are each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

2. The organic light-emitting device of claim 1, wherein the first host and the third host are each independently represented by Formula 1-1:

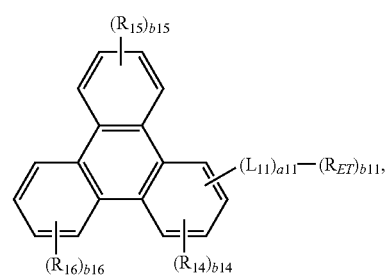

Formula 1-1 wherein, in Formula 1-1, $L_{11}$, a11, $R_{ET}$, $R_{14}$ to $R_{16}$, and b11 are the same as those described in connection with Formula 1, b14 is 1, 2, or 3, and b15 and b16 are each independently 1, 2, 3, or 4.

3. The organic light-emitting device of claim 1, wherein the first host and the third host are each independently represented by Formula 1-1A or 1-1B:

Formula 1-1A

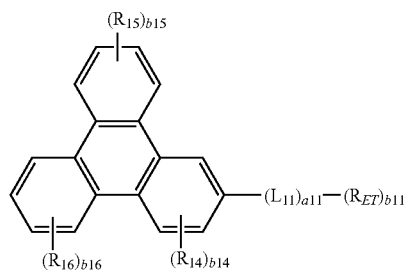

Formula 1-1B

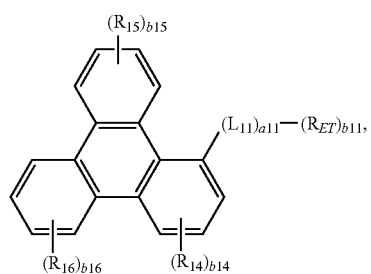

wherein, in Formulae 1-1A and 1-1B, $L_{11}$, a11, $R_{ET}$, $R_{14}$ to $R_{16}$, and b11 are the same as described in connection with Formula 1, b14 is 1, 2, or 3, and b15 and b16 are each independently 1, 2, 3, or 4.

4. The organic light-emitting device of claim 1, wherein $A_1$ to $A_4$ are each independently selected from a benzene group, a naphthalene group, a pyridine group, a pyrimidine group, a pyrazine group, and a pyridazine group.

5. The organic light-emitting device of claim 1, wherein the second host and the fourth host are each independently represented by one selected from Formulae 2-4 to 2-6:

Formula 2-4

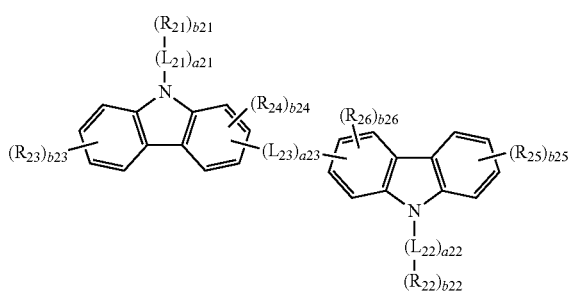

Formula 2-5

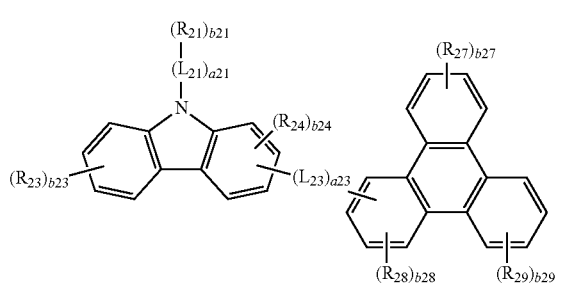

Formula 2-6

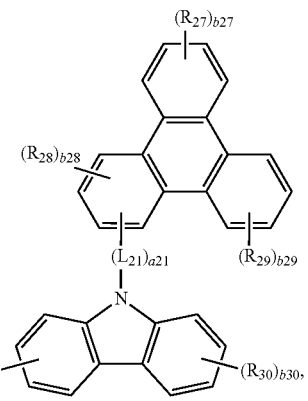

wherein, in Formulae 2-4 to 2-6, $L_{21}$ to $L_{23}$, a21 to a23, $R_{21}$ to $R_{30}$, b21, b22, and b27 to b29 are the same as described in connection with Formulae 2-1 to 2-3, b23, b25, and b30 are each independently 1, 2, 3, or 4, and b24 and b26 are each independently 1, 2, or 3.

6. The organic light-emitting device of claim 1, wherein $L_{11}$ to $L_{13}$ and $L_{21}$ to $L_{23}$ are each independently selected from a single bond and groups represented by Formulae 3-1 to 3-53:

3-1

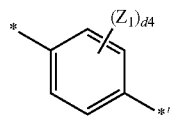

3-2

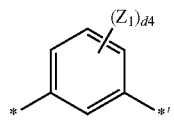

3-3

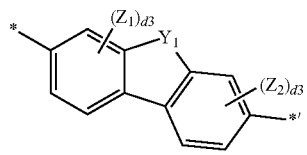

3-4

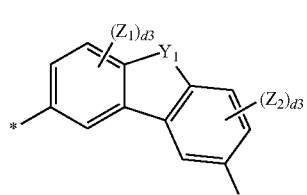

3-5

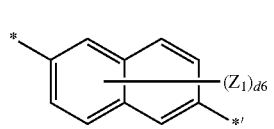

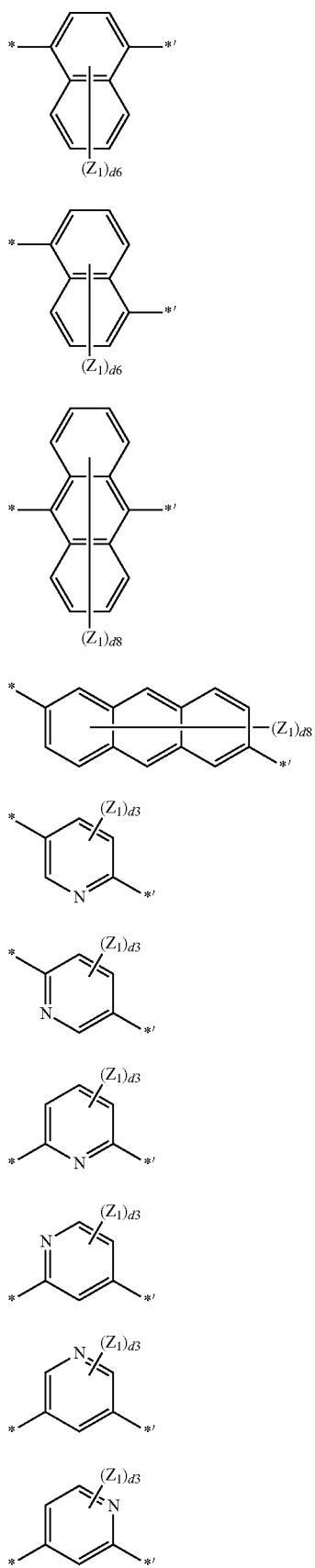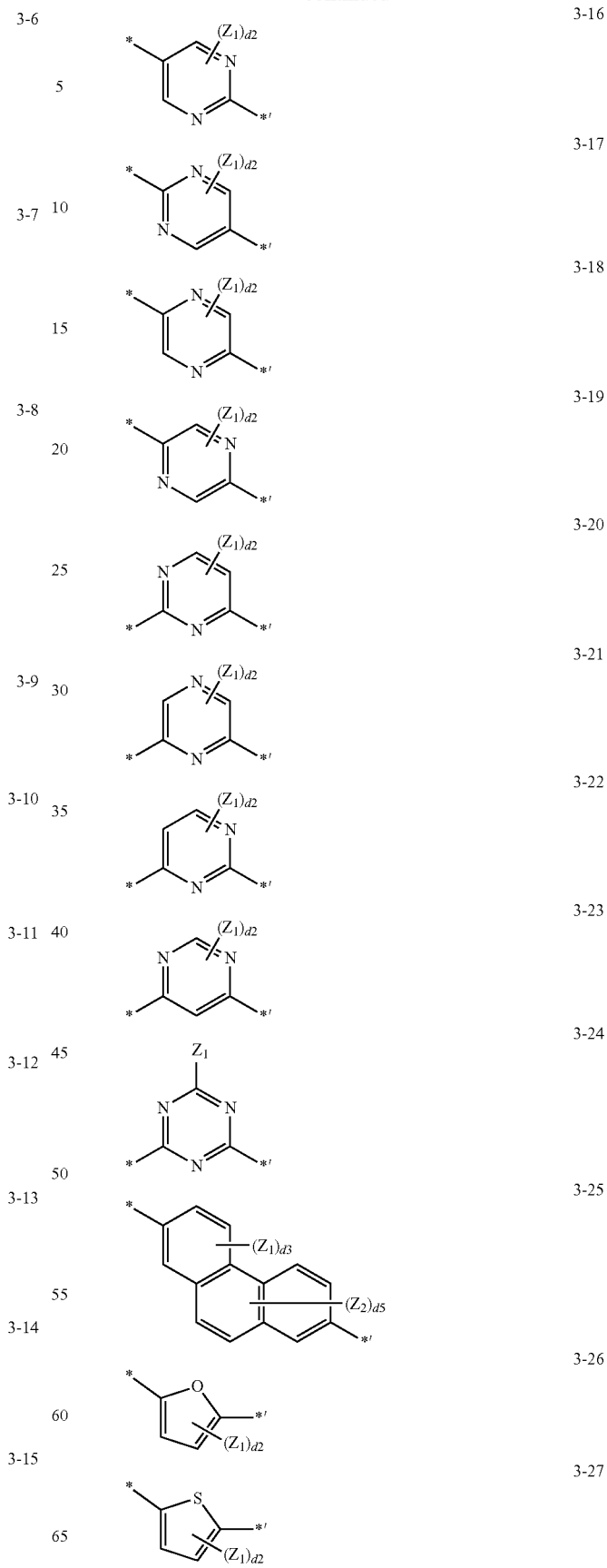

3-28
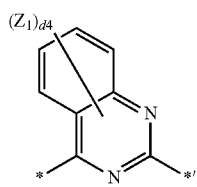
3-29
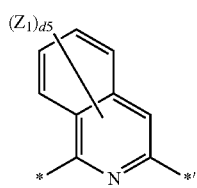
3-30
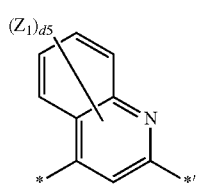
3-31
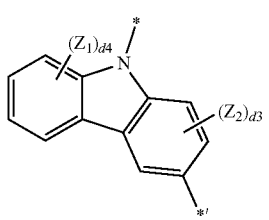
3-32
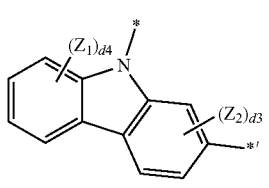
3-33
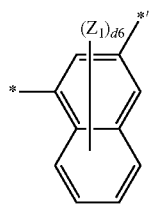
3-34
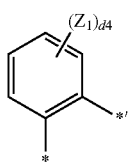
3-35
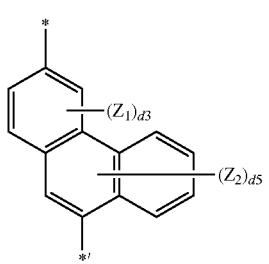
3-36
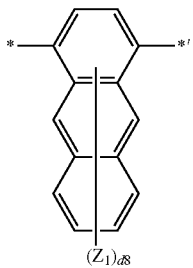
3-37
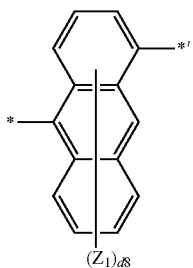
3-38
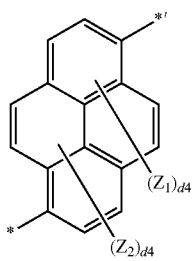
3-39
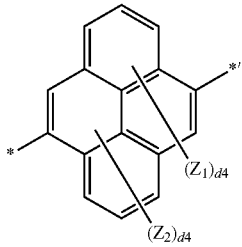
3-40
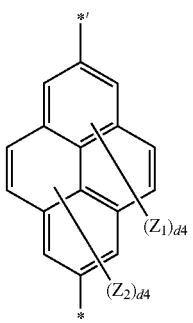

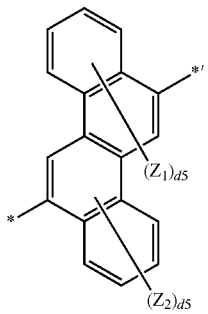 3-41

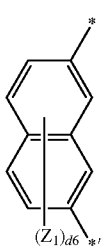 3-42

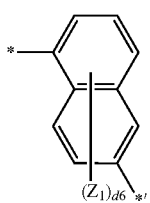 3-43

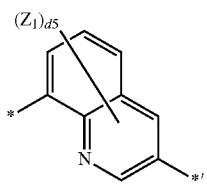 3-44

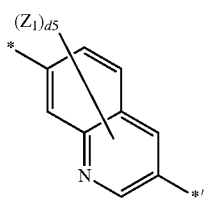 3-45

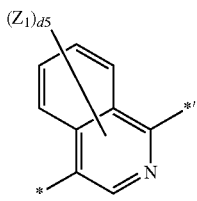 3-46

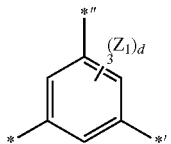 3-47

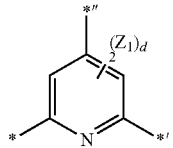 3-48

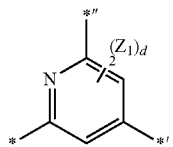 3-49

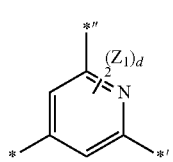 3-50

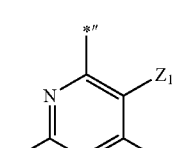 3-51

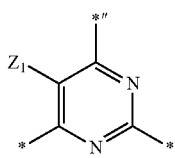 3-52

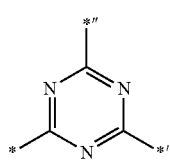 3-53 wherein, in Formulae 3-1 to 3-53, $Y_1$ is O, S, $C(Z_3)(Z_4)$, $N(Z_5)$, or $Si(Z_6)(Z_7)$, $Z_1$ to $Z_7$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, a dibenzothiophenyl group, —$N(Q_{31})(Q_{32})$, —$Si(Q_{31})(Q_{32})(Q_{33})$, and —$B(Q_{31})(Q_{32})$, d2 is an integer of 0 to 2, and when d2 is two, two $Z_1$(s) are identical to or different from each other, d3 is an integer of 0 to 3, and when d3 is two or more, two or more of $Z_1(s)$ are identical to or different from each other, and two or more of $Z_2(s)$ are identical to or different from each other, d4 is an integer of 0 to 4, and when d4 is two or more, two or more of $Z_1(s)$ are identical to or different from each other, and two or more of $Z_2(s)$ are identical to or different from each other, d5 is an integer of 0 to 5, and when d5 is two or more, two or more of $Z_1(s)$ are identical to or different from each other, and two or more of $Z_2(s)$ are identical to or different from each other, d6 is an integer of 0 to 6, and when d6 is two or more, two or more of $Z_1(s)$ are identical to or different from each other, d8 is an integer of 0 to 8, when d8 is two or more, two or more of $Z_1(s)$ are identical to or different from each other, and $Q_{31}$ to $Q_{33}$ are each independently selected from a $C_1$-$C_{20}$ alkyl group, a $C_1$-$C_{20}$ alkoxy group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, and

*, *', and *'' each indicate a binding site to a neighboring atom.

7. The organic light-emitting device of claim 1, wherein $R_{11}$ to $R_{13}$, $R_{21}$, and $R_{22}$ are each independently selected from groups represented by Formulae 5-1 to 5-81, wherein at least one selected from $R_{11}$ to $R_{13}$ is selected from groups represented by Formulae 5-21 to 5-79:

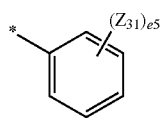

5-1

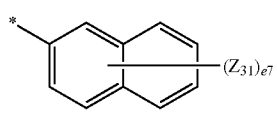

5-2

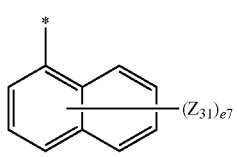

5-3

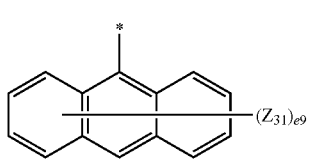

5-4

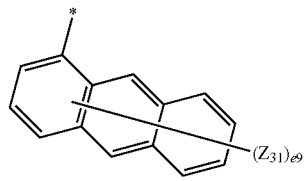

5-5

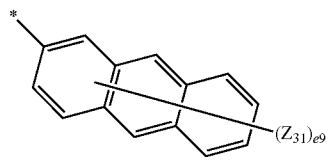

5-6

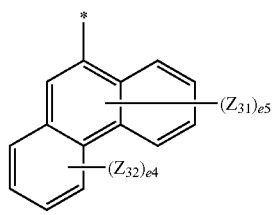

5-7

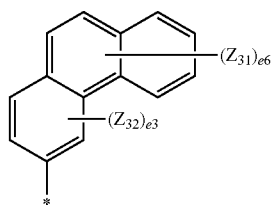

5-8

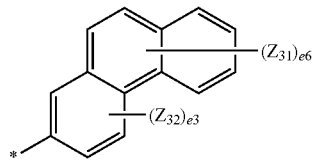

5-9

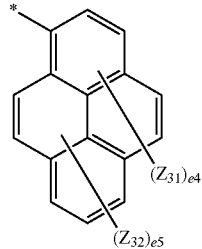

5-10

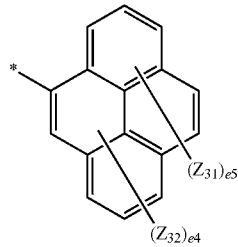

5-11

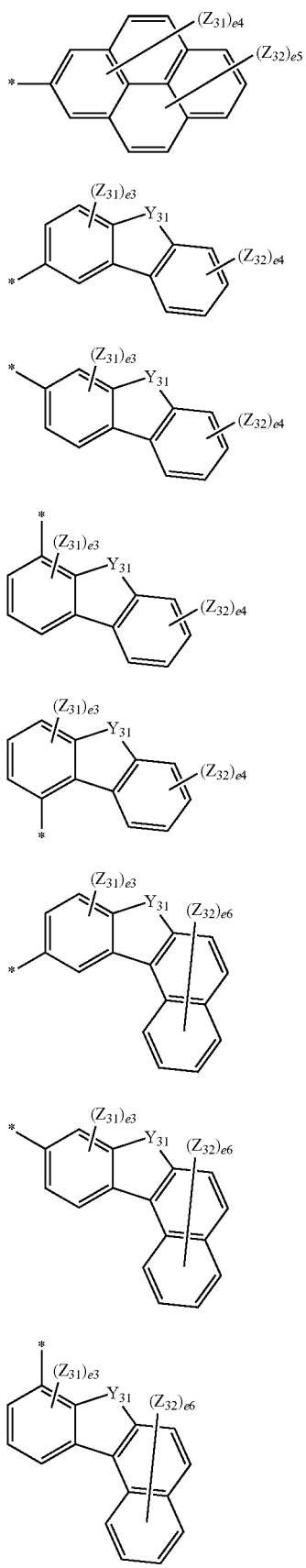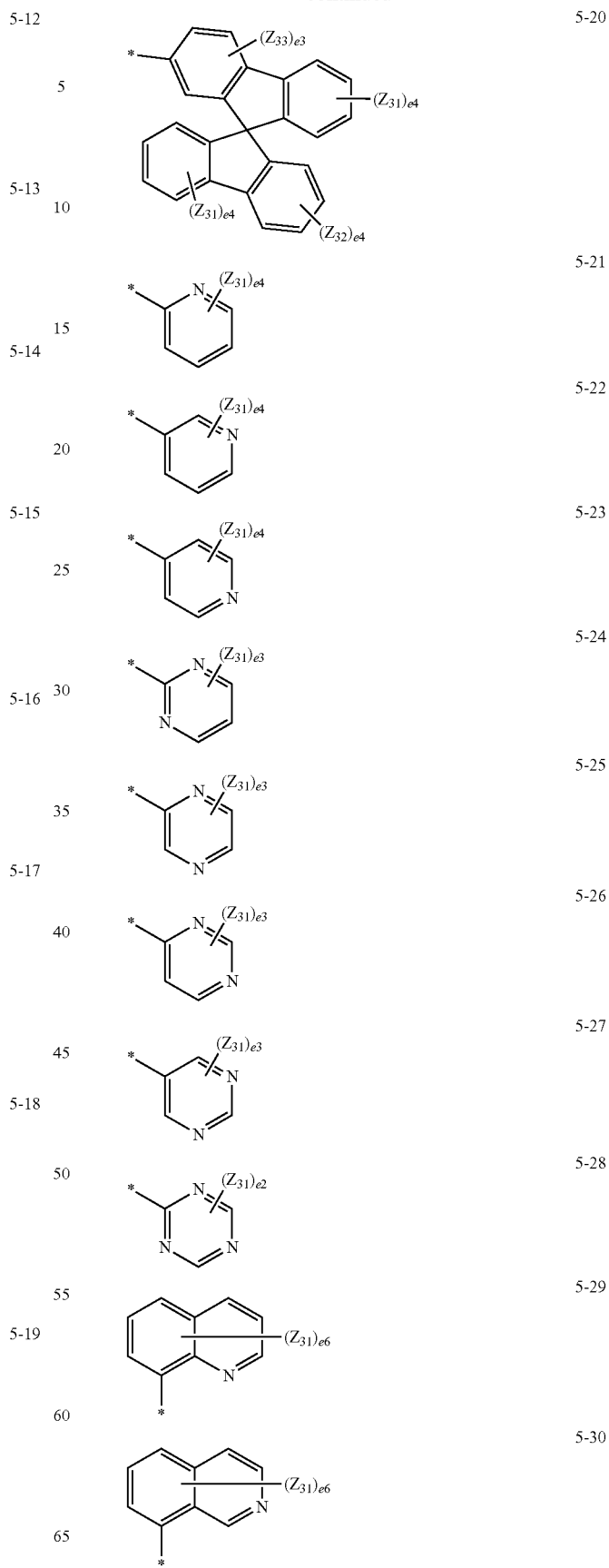

| | |
|---|---|
| 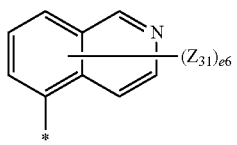 | 5-31 |
| 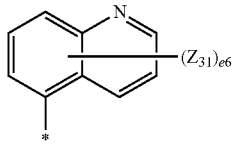 | 5-32 |
| 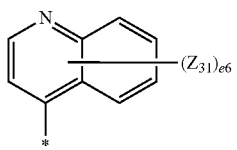 | 5-33 |
| 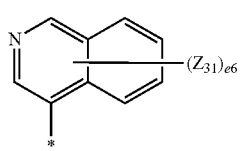 | 5-34 |
| 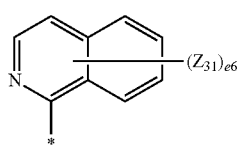 | 5-35 |
| 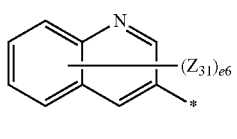 | 5-36 |
| 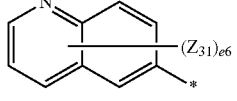 | 5-37 |
| 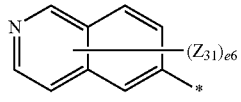 | 5-38 |
| 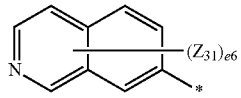 | 5-39 |
| 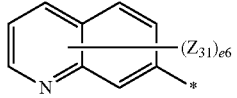 | 5-40 |
| 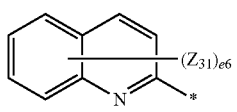 | 5-41 |
| 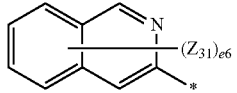 | 5-42 |
| | |
|---|---|
| 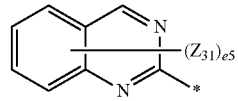 | 5-43 |
| 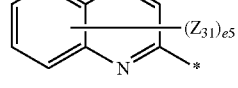 | 5-44 |
| 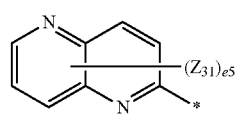 | 5-45 |
| 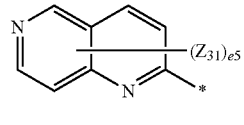 | 5-46 |
| 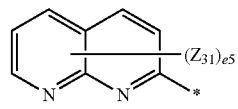 | 5-47 |
| 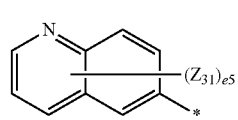 | 5-48 |
| 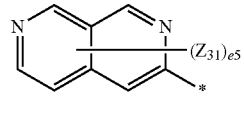 | 5-49 |
| 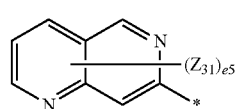 | 5-50 |
| 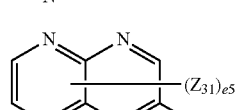 | 5-51 |
| 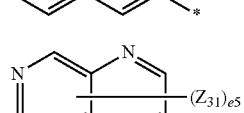 | 5-52 |
| 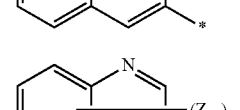 | 5-53 |
| 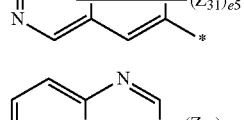 | 5-54 |
5-55
5-56

| | |
|---|---|
| 5-57 | 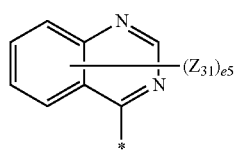 |
| 5-58 | 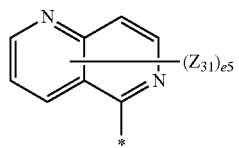 |
| 5-59 | 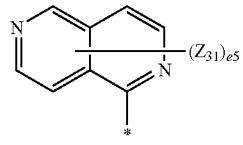 |
| 5-60 | 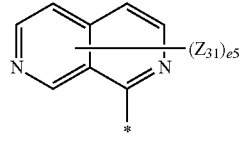 |
| 5-61 | 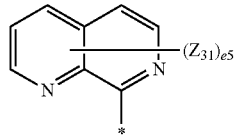 |
| 5-62 | 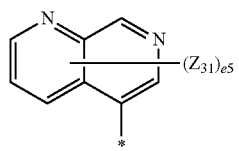 |
| 5-63 | 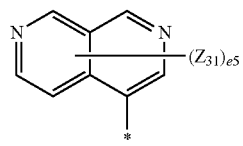 |
| 5-64 | 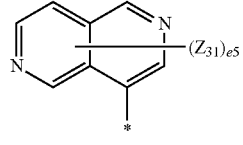 |
| 5-65 | 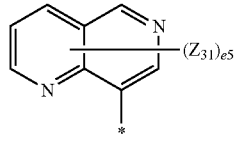 |
| 5-66 | 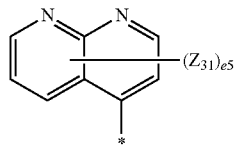 |
| | |
|---|---|
| 5-67 | 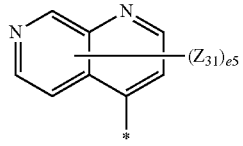 |
| 5-68 | 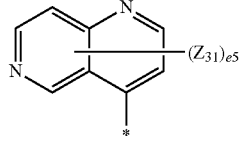 |
| 5-69 | 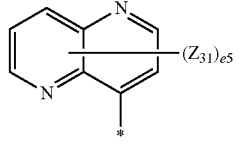 |
| 5-70 | 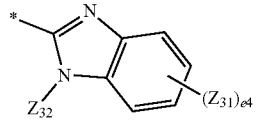 |
| 5-71 | 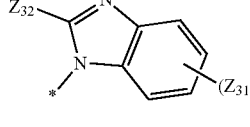 |
| 5-72 | 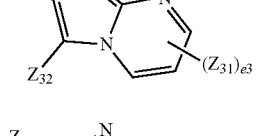 |
| 5-73 | 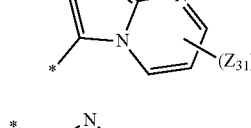 |
| 5-74 | 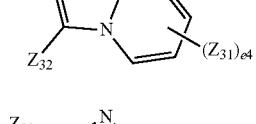 |
| 5-75 | 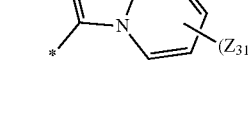 |
| 5-76 | 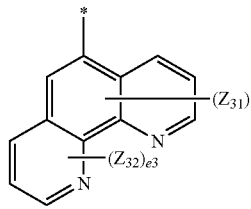 |

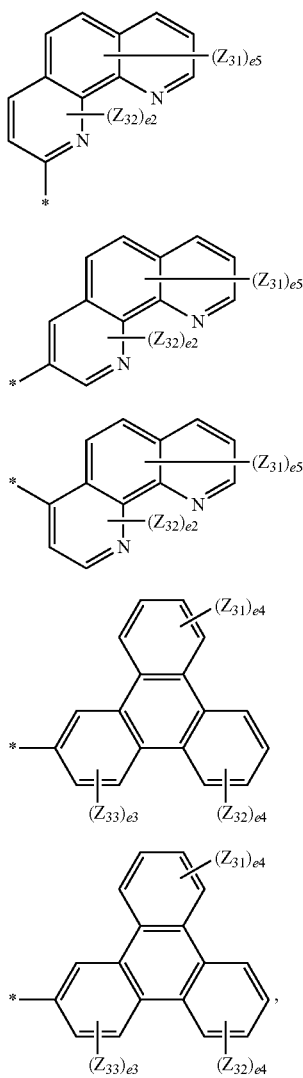

wherein, in Formulae 5-1 to 5-81, $Y_{31}$ is O, S, $C(Z_{33})(Z_{34})$, $N(Z_{35})$ or $Si(Z_{36})(Z_{37})$, $Z_{31}$ to $Z_{37}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, a dibenzothiophenyl group, —$N(Q_{31})(Q_{32})$, —$Si(Q_{31})(Q_{32})(Q_{33})$, and —$B(Q_{31})(Q_{32})$, e2 is an integer of 0 to 2, and when e2 is two, two $Z_{31}(5)$ are identical to or different from each other, and two $Z_{32}(5)$ are identical to or different from each other, e3 is an integer of 0 to 3, when e3 is two or more, two or more of $Z_{31}(s)$ are identical to or different from each other, two or more of $Z_{32}(s)$ are identical to or different from each other, and two or more of $Z_{33}(s)$ are identical to or different from each other, e4 is an integer of 0 to 4, and when e4 is two or more, two or more of $Z_{31}(s)$ are identical to or different from each other, and two or more of $Z_{32}(s)$ are identical to or different from each other, e5 is an integer of 0 to 5, and when e5 is two or more, two or more of $Z_{31}(s)$ are identical to or different from each other, and two or more of $Z_{32}(s)$ are identical to or different from each other, e6 is an integer of 0 to 6, and when e6 is two or more, two or more of $Z_{31}(s)$ are identical to or different from each other, and two or more of $Z_{32}(s)$ are identical to or different from each other, e7 is an integer of 0 to 7, and when e7 is two or more, two or more of $Z_{31}(s)$ are identical to or different from each other, e9 is an integer of 0 to 9, and when e9 is two or more, two or more of $Z_{31}(s)$ are identical to or different from each other, $Q_{31}$ to $Q_{33}$ are each independently selected from a $C_1$-$C_{20}$ alkyl group, a $C_1$-$C_{20}$ alkoxy group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, and

* indicates a binding site to a neighboring atom.

8. The organic light-emitting device of claim 1, wherein $R_{ET}$ is selected from:

a pyridinyl group, a pyrazinyl group, a pyrimidinyl group, a pyridazinyl group, and a triazinyl group;

a pyridinyl group, a pyrazinyl group, a pyrimidinyl group, a pyridazinyl group, and a triazinyl group, each substituted with at least one selected from deuterium, —F, —Cl, —Br, —I, a methyl group, an ethyl group, an n-propyl group, an isopropyl group, an n-butyl group, a sec-butyl group, an isobutyl group, a tert-butyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, a terphenyl group, a naphthyl group, a pyridinyl group, a pyrazinyl group, a pyrimidinyl group, a pyridazinyl group, a triazinyl group, —$N(Q_{31})(Q_{32})$, —$Si(Q_{31})(Q_{32})(Q_{33})$, and —$B(Q_{31})(Q_{32})$; and a pyridinyl group, a pyrazinyl group, a pyrimidinyl group, a pyridazinyl group, and a triazinyl group, each substituted with at least one selected from a phenyl group, a biphenyl group, a terphenyl group, and a naphthyl group that are each substituted with at least one selected from deuterium, —F, —Cl, —Br, —I, a methyl group, an ethyl group, an n-propyl group, an isopropyl group, an n-butyl group, a sec-butyl group, an isobutyl group, a tert-butyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, a terphenyl group, a naphthyl group, a pyridinyl group, a pyrazinyl group, a pyrimidinyl group, a pyridazinyl group, a triazinyl group, $-N(Q_{41})(Q_{42})$, $-Si(Q_{41})(Q_{42})(Q_{43})$, and $-B(Q_{41})(Q_{42})$, and $Q_{31}$ to $Q_{33}$ and $Q_{41}$ to $Q_{43}$ are each independently selected from a methyl group, an ethyl group, an n-propyl group, an isopropyl group, an n-butyl group, a sec-butyl group, an isobutyl group, a tert-butyl group, a phenyl group, a biphenyl group, a terphenyl group, and a naphthyl group.

9. The organic light-emitting device of claim 1, wherein:
$R_{14}$ to $R_{16}$ and $R_{23}$ to $R_{29}$ are each independently selected from hydrogen, deuterium, —F, a cyano group, a methyl group, an ethyl group, an n-propyl group, an isopropyl group, an n-butyl group, a sec-butyl group, an isobutyl group, a tert-butyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, a terphenyl group, a naphthyl group, $-Si(Q_1)(Q_2)(Q_3)$, $-B(Q_1)(Q_2)$, and $-N(Q_1)(Q_2)$, $R_{30}$ is selected from hydrogen, deuterium, —F, a cyano group, a methyl group, an ethyl group, an n-propyl group, an isopropyl group, an n-butyl group, a sec-butyl group, an isobutyl group, a tert-butyl group, a methoxy group, an ethoxy group, an n-propoxy group, an isopropoxy group, an n-butoxy group, a sec-butoxy group, an isobutoxy group, a tert-butoxy group, a phenyl group, a biphenyl group, a terphenyl group, a naphthyl group, a fluorenyl group, a 9,9-dimethylfluorenyl group, a dibenzofuranyl group, a dibenzothiophenyl group, a carbazolyl group, phenyl-substituted carbazolyl group, $-Si(Q_1)(Q_2)(Q_3)$, $-B(Q_1)(Q_2)$, and $-N(Q_1)(Q_2)$, $Q_1$ to $Q_3$ are each independently selected from a methyl group, an ethyl group, an n-propyl group, an isopropyl group, an n-butyl group, a sec-butyl group, an isobutyl group, a tert-butyl group, a phenyl group, a biphenyl group, a terphenyl group, and a naphthyl group.

10. The organic light-emitting device of claim 1, wherein the dopant comprises a phosphorescent dopant.

11. The organic light-emitting device of claim 1, wherein the first electrode is an anode, the second electrode is a cathode, and the organic layer further comprises a hole transport region between the first electrode and the emission layer, and an electron transport region between the emission layer and the second electrode,
wherein the hole transport region comprises a hole injection layer, a hole transport layer, an emission auxiliary layer, an electron blocking layer, or any combination thereof, and
the electron transport region comprises a hole blocking layer, an electron transport layer, an electron injection layer, or any combination thereof.

12. The organic light-emitting device of claim 11, wherein the non-doping layer is disposed at least one of between the hole transport region and the doping layer and between the electron transport region and the doping layer.

13. The organic light-emitting device of claim 11, wherein the non-doping layer comprises a first non-doping layer and a second non-doping layer,
wherein the first non-doping layer is disposed between the hole transport region and the doping layer, and
the second non-doping layer is disposed between the electron transport region and the doping layer.

14. The organic light-emitting device of claim 11, wherein the doping layer comprises a first doping layer and a second doping layer,
wherein the first doping layer is disposed toward the first electrode,
the second doping layer is disposed toward the second electrode, and
the non-doping layer is disposed at least one of between the hole transport region and the first doping layer, between the electron transport region and the second doping layer, and between the first doping layer and the second doping layer.

15. The organic light-emitting device of claim 11, wherein the doping layer comprises a first doping layer and a second doping layer, and the non-doping layer comprises a first non-doping layer, a second non-doping layer, and a third non-doping layer,
wherein the first doping layer is disposed toward the first electrode,
the second doping layer is disposed toward the second electrode,
the first non-doping layer is disposed between the hole transport region and the first doping layer,
the second non-doping layer is disposed between the electron transport region and the second doping layer, and
the third non-doping layer is disposed between the first doping layer and the second doping layer.

16. The organic light-emitting device of claim 1, wherein a thickness of the non-doping layer is in a range from about 5 to about 100 Å.

17. The organic light-emitting device of claim 1, wherein the non-doping layer directly contacts the doping layer.

18. The organic light-emitting device of claim 1, wherein:
the first host and the third host are identical to each other, and
and the second host and the fourth host are identical to each other.

19. The organic light-emitting device of claim 1, wherein the emission layer emits green light.

20. An electronic apparatus comprising:
the organic light-emitting device of claim 1; and
a thin film transistor,
wherein the first electrode of the organic light-emitting device is electrically coupled to one of a source electrode and a drain electrode of the thin film transistor.

* * * * *